US009988430B2

(12) United States Patent
Reedtz-Runge et al.

(10) Patent No.: US 9,988,430 B2
(45) Date of Patent: Jun. 5, 2018

(54) STABLE GLP-1 BASED GLP-1/GLUCAGON RECEPTOR CO-AGONISTS

(71) Applicant: Novo Nordisk A/S, Bagsvaerd (DK)

(72) Inventors: Steffen Reedtz-Runge, Bikeroed (DK); Ulrich Sensfuss, Vanloese (DK); Thomas Kruse, Herlev (DK); Jane Spetzler, Broenshoej (DK); Henning Thoegersen, Farum (DK); Christian W. Tornoee, Lyngby (DK); Jesper F. Lau, Farum (DK)

(73) Assignee: Novo Nordisk A/S, Bagsvaerd (DK)

( * ) Notice: Subject to any disclaimer, the term of this patent is extended or adjusted under 35 U.S.C. 154(b) by 0 days. days.

(21) Appl. No.: 14/879,428

(22) Filed: Oct. 9, 2015

(65) Prior Publication Data
US 2016/0102129 A1 Apr. 14, 2016

(30) Foreign Application Priority Data
Oct. 10, 2014 (EP) .................................. 14188421

(51) Int. Cl.
*A61K 38/26* (2006.01)
*C07K 14/605* (2006.01)
*A61K 38/00* (2006.01)

(52) U.S. Cl.
CPC ............ *C07K 14/605* (2013.01); *A61K 38/00* (2013.01)

(58) Field of Classification Search
CPC .............................. A61K 38/26; C07K 14/605
See application file for complete search history.

(56) References Cited

U.S. PATENT DOCUMENTS

| | | | |
|---|---|---|---|
| 2011/0082079 A1 | 4/2011 | Spetzler et al. | |
| 2012/0288511 A1 | 11/2012 | Dimarchi | |
| 2013/0157953 A1 | 6/2013 | Petersen et al. | |
| 2014/0088005 A1 | 3/2014 | Wieczorek et al. | |

FOREIGN PATENT DOCUMENTS

| | | |
|---|---|---|
| WO | 02/46227 A2 | 6/2002 |
| WO | 2008019143 A2 | 2/2008 |
| WO | 2009/030738 A1 | 3/2009 |
| WO | 2009/030771 A1 | 3/2009 |
| WO | 2011088837 A1 | 7/2011 |
| WO | 2011/117415 A1 | 9/2011 |
| WO | 2011/60633 A1 | 12/2011 |
| WO | 2013041678 A1 | 3/2013 |
| WO | 2015/124612 A1 | 8/2015 |

OTHER PUBLICATIONS

Cegla J. et al., Energy intake following infusion of glucagon and GLP-1: a double-blind crossover study, Endocrine Abstracts, 2013, 31.
Cho Min Y et al., Targeting the glucagon receptor family for diabetes and obesity therapy, Pharmacology & Therapeutics, 2012, vol. 135, No. 3, 247-278.
Clodfelter D. K. et al., Effects of Non-Covalent Self-Association on the Subcutaneous Absorption of a Therapeutic Peptide, Pharmaceutical Research, 1998, vol. 15, No. 2, 254-262.
Cohen M. A. et al., Oxyntomodulin Suppresses Appetite and Reduces Food Intake in Humans, The Journal of Clinical Endocrinology & Metabolism, 2003, vol. 88, No. 10, pp. 4696-4701.
Dakin C. L. et al., Oxyntomodulin Inhibits Food Intake in the Rat, Endocrinology, 2001, vol. 142, No. 10, pp. 4244-4250.
Day J. W. et al., A new glucagon and GLP-1 co-agonist eliminates obesity in rodents, Nature Chemical Biology, 2009, vol. 5, No. 10, pp. 749-757.
Day J. W. et al., Optimization of Co-Agonism at GLP-1 and Glucagon Receptors to Safely Maximize Weight Reduction in DIO-Rodents, PeptideScience, 2012, vol. 98, No. 5, pp. 443-450.
Donnelly D. et al., The structure and function of the glucagon-like peptide-1 receptor and; its ligands, British Journal of Pharmacology, 2012, vol. 166, No. 1, pp. 27-41.
Habegger K. M. et al., The metabolic actions of glucagon revisited, Endocrinology, 2010, vol. 6, pp. 689-697.
Hongxiang H. et al., Structure and function studies of glucagon-like peptide-1 (GLP-1): the designing of a novel pharmacological agent for the treatment of diabetes, Diabetes Metabolism Research and Reviews, 2005, vol. 21, No. 4, 313-331.
Jiang G. et al., Glucagon and regulation of glucose metabolism, American Journal of Physiology,Endocrinology and Metabolism, 2003, vol. 284, pp. E671-E678.
Moran T. H. et al., Gut peptides in the control of food intake, International Journal of Obesity, 2009, vol. 33, pp. S7-S10.
Pocai A. et al., Glucagon-Like Peptide 1/Glucagon Receptor Dual Agonism Reverses Obesity in Mice, Diabetes, 2009, vol. 58, pp. 2258-2266.
Pocai A., Unraveling oxyntomodulin, GLP1's enigmatic brother, Journal of Endocrinology, 2012, vol. 215, pp. 335-346.
Sherwin R. S. et al., Hyperglucagonemia and blood glucose regulation in normal, obese and diabetic subjects, The New England Journal of Medicine, 1976, vol. 294, No. 9, pp. 455-461.
Tan T. M. et al., Coadministration of Glucagon-Like Peptide-1 During Glucagon Infusion in Humans Results in Increased Energy Expenditure and Amelioration of Hyperglycemia, Diabetes, 2013, vol. 62, pp. 1131-1138.
Wynne K. et al., Subcutaneous Oxyntomodulin Reduces Body Weight in Overweight and Obese Subjects, A Double-Blind, Randomized, Controlled Trial, Diabetes, 2005, vol. 54, pp. 2390-2395.

*Primary Examiner* — Gyan Chandra
(74) *Attorney, Agent, or Firm* — Leon Y. Lum

(57) ABSTRACT

New GLP-1 derivatives, compositions thereof and their use in medicine.

29 Claims, 1 Drawing Sheet

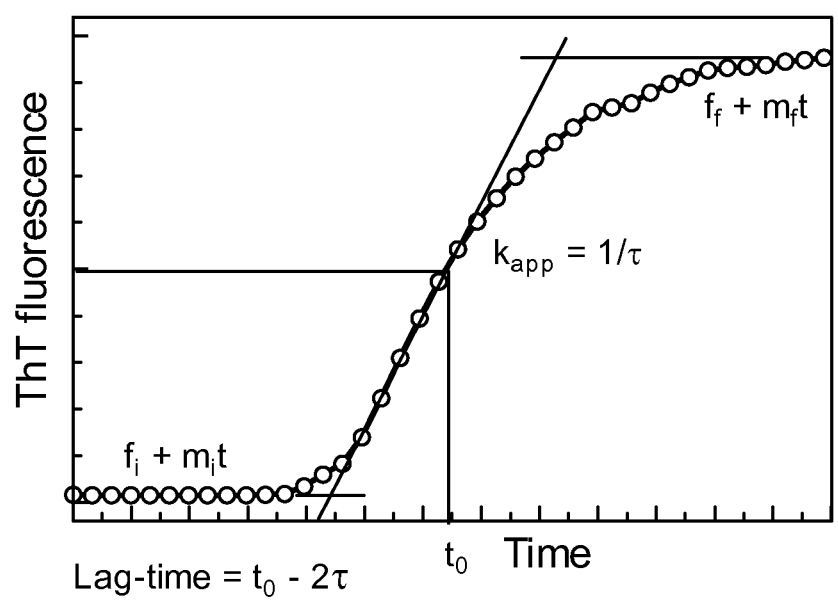

STABLE GLP-1 BASED GLP-1/GLUCAGON RECEPTOR CO-AGONISTS

The present invention relates to novel GLP-1 derivatives which are GLP-1/glucagon receptor co-agonists, compositions thereof, and their use in medicine.

CROSS-REFERENCE TO RELATED APPLICATIONS

This application claims priority under 35 U.S.C. § 119 to European Patent Application 14188421.3, filed Oct. 10, 2014; the contents of which are incorporated herein by reference.

SEQUENCE LISTING

The instant application contains a Sequence Listing which has been submitted in ASCII format via EFS-Web and is hereby incorporated by reference in its entirety. Said ASCII copy, created on Dec. 10, 2015, is named 140051_SeqListNEW_ST25.txt and is 22,372 bytes in size.

BACKGROUND

Numerous gastro-intestinal peptide hormones are involved in the regulation of food intake and energy homeostasis (e.g. CCK, GLP-1, PYY, ghrelin). Recently, also Oxyntomodulin (Oxm), a product from the proglucagon gene in intestinal L-cells was shown to have anorexigenic properties in both rodents and humans. A four week long clinical study in obese humans demonstrated that repeated subcutaneous administration of Oxm reduced food intake and caused a significant body weight loss. Since a specific Oxm receptor remains to be found, it has been suggested that many of the physiological effects are mediated through GLP-1 and glucagon receptor activation. Indeed, Oxm binds and activates both GLP-1 and glucagon receptors albeit with lower affinity and potency than the cognate ligands. Several recent papers have demonstrated the power of simultaneous GLP-1/glucagon receptor targeting by constructing dual agonists and comparing the weight lowering effect in DIO mice and knock-out mouse models. Treatment with a balanced GLP-1/glucagon receptor co-agonist resulted in robust reduction in body weight and fat mass, exceeding that of a pure GLP-1 receptor agonist, and with glucose control comparable to that of a GLP-1 receptor agonist. Improvements in plasma metabolic parameters including insulin, leptin, and adiponectin were more pronounced upon treatment with a GLP-1/glucagon receptor co-agonist than with a pure GLP-1 receptor agonist. In addition, GLP-1/glucagon receptor co-agonist-treatment increased fatty acid oxidation and reduced hepatic steatosis in DIO mice. In GLP-1- or glucagon receptor knock-out mice GLP-1/glucagon receptor co-agonists demonstrated a reduced, but still significant effect on body weight loss compared to wild-type animals thus supporting the hypothesis that simultaneous activation of the GLP-1 and glucagon receptors results in superior weight loss.

One physiological effect of glucagon receptor activation is to increase blood glucose levels by stimulating hepatic glycogenolysis and gluconeogenesis. Glucagon receptor activation has additionally been shown to increase energy expenditure and decrease food intake in both rodents and humans.

In a recent study 16 human volunteers were infused with glucagon, GLP-1, a combination of glucagon and GLP-1, or saline. The energy intake during the meal was significantly reduced (13%) in the combination group, but not affected when either hormone was given alone.

In another study, energy expenditure (EE) was measured after infusions of GLP-1, glucagon or the combination hereof into healthy human volunteers. The study showed that glucagon and the combination of glucagon and GLP-1 increased EE to a similar degree, while GLP-1 was without effect. Glucagon infusion was accompanied by a rise in plasma glucose levels, but co-infusion of GLP-1 in addition to glucagon rapidly reduced this excursion. The importance of GLP-1 receptor activity in preventing glucagon receptor-mediated hyperglycaemia in obese mice was further demonstrated using a family of GLP-1/glucagon receptor co-agonist peptides varying in murine receptor potency for the two receptors. The study indicated that a balanced GLP-1/glucagon receptor co-agonist peptide exhibited the optimal therapeutic profile for weight loss while mitigating the hyperglycaemic risk associated with glucagon receptor activation.

All together, these studies support the concept of a dual GLP-1 and glucagon agonism as a potential target for treatment of obesity.

The vast majority of GLP-1/glucagon receptor co-agonists have been obtained using glucagon or oxyntomodulin as starting point and GLP-1 activity has been improved by various amino acid mutations. Glucagon has a poor physical and chemical stability, and this is also observed for many glucagon based co-agonists.

Accordingly, a need remains for GLP-1/glucagon receptor co-agonists with improved stability, including improved chemical and physical stability.

SUMMARY

The invention relates to novel stable and protracted GLP-1 derivatives which are GLP-1/glucagon receptor co-agonists, compositions thereof, use of the GLP-1 derivatives in medicine, and to methods of treatment comprising administration of the GLP-1 derivatives to patients, including treatment of diabetes, obesity and related diseases and conditions.

In some embodiments the invention relates to GLP-1 derivatives comprising a polypeptide consisting of the amino acid sequence of Formula I (SEQ ID NO: 2):

```
Imp-X8-His-Gly-Thr-Phe-Thr-Ser-Asp-X16-Ser-X18-
Tyr-Leu-Glu-X22-X23-Ala-Ala-X26-X27-Phe-Ile-
Ala-Trp-Leu-X33-X34-X35-X36-X37 [I],
``` wherein
  X8 is Ala, Aib, Acb, or Gly;
  X16 is Val, Leu, Ile, or Tyr;
  X18 is Lys or Arg;
  X22 is Gly, Ala, Glu, Lys, Arg, Ser, or Aib;
  X23 is Gln, Arg, or Lys;
  X26 is Lys or Arg;
  X27 is Glu or Lys;
  X33 is Val, Leu, or Ile;
  X34 is Lys or Arg;
  X35 is Gly, Thr, Lys, or is absent;
  X36 is Ala, Gly, Lys, Ser, or is absent;
  X37 is Gly or is absent;
wherein said GLP-1 derivative further comprises a substituent comprising a lipophilic moiety and at least two negatively charged moieties, wherein one of said negatively charged moieties is distal of a lipophilic moiety;
wherein said polypeptide optionally comprises a C-terminal amide;
or a pharmaceutically acceptable salt and/or ester thereof.

In some embodiments the invention relates to a pharmaceutical composition comprising the GLP-1 derivative as defined in any one of the preceding claims and one or more pharmaceutically acceptable excipients.

In some embodiments the invention relates to a GLP-1 derivative as defined in any one of the preceding claims for use in medicine, such as for use in the treatment or prevention of obesity, hyperglycaemia, type 2 diabetes, impaired glucose tolerance, and/or type 1 diabetes.

In some embodiments the invention relates to intermediate products in the form of GLP-1 analogues as defined herein, or a pharmaceutically acceptable salt, amide or ester thereof.

BRIEF DESCRIPTION OF THE DRAWINGS

FIG. 1. Theoretical sigmoidal time course for ThT fluorescence emission during amyloid fibril formation.

DESCRIPTION

The present invention provides novel GLP-1 derivatives comprising amino acid substitutions and a substituent with negatively charged moieties which GLP-1 derivatives are GLP-1/glucagon receptor co-agonists. The term "GLP-1/glucagon receptor co-agonist" as used herein refers to an agonist which activates both the GLP-1 receptor and the glucagon receptor. Specifically, the GLP-1 derivatives of the invention comprise amino acid substitutions to desaminohistidine in position 7 and histidine in position 9 of the amino acid sequence of the GLP-1 derivatives which further comprising a substituent with at least two negative charges. In some embodiments references to amino acid positions in the GLP-1 derivative as used herein are relative to human GLP-1(7-37) wherein the N-terminal histidine is defined as position 7.

In some embodiments the GLP-1 derivative of the present invention activates better to the GLP-1 receptor than the glucagon receptor, i.e. the GLP-1 derivative has a ratio between its $EC_{50}$ value on the glucagon receptor and $EC_{50}$ on the GLP-1 receptor of more than 1. In some embodiments the GLP-1 derivative of the present invention binds better to the GLP-1 receptor than the glucagon receptor, i.e. the GLP-1 derivative has a ratio between its $IC_{50}$ value on the glucagon receptor and $IC_{50}$ on the GLP-1 receptor of more than 1. Receptor assays disclosed herein can be used for assessing such ratios.

The inventors have found that the GLP-1 derivatives of the present invention may have improved physical stability and improved chemical stability while retaining adequate aqueous solubility, receptor potency and receptor binding. In some embodiments the GLP-1 derivatives have improved physical stability (e.g. the GLP-1 derivatives show none or delayed fibrillation in an assay used to assess physical stability—examples of such assays are disclosed herein). Also, or alternatively, in some embodiments the GLP-1 derivatives have adequate aqueous solubility in a pH range acceptable for a pharmaceutical composition, such as at neutral pH or slightly basic pH. Also, or alternatively, in some embodiments the GLP-1 derivatives have improved chemical stability, e.g. the chemical degradation of the GLP-1 derivatives is reduced, for example in a liquid composition, such as a pharmaceutical composition. Also, or alternatively, in some embodiments the GLP-1 derivatives have improved pharmacokinetic properties, i.e., they have prolonged half-life in vivo, e.g. compared to human glucagon and/or human GLP-1. Also, or alternatively, in some embodiments the GLP-1 derivatives induce a significant reduction in body weight after s.c. administration. Assay (I) and (II) as described herein may be used to measure the activity and affinity, respectively, of the GLP-1 derivatives of the invention on the glucagon and GLP-1 receptors. The solubility of the GLP-1 derivatives of the invention at different pH values may be measured as described herein, see e.g. the Functional Properties section. The physical stability of the GLP-1 derivatives of the invention may be measured by the method as described in Assay (III) herein. The chemical stability the GLP-1 derivatives of the invention may be measured as described in Assay (V) herein. The half-life of the GLP-1 derivatives may be determined in a pharmacokinetic study in species, such as mice (e.g., using the method described in Assay (IV) herein), rats or in minipigs. The reduction in body weight caused by the GLP-1 derivatives of the invention may be measured by administration to DIO mice of the GLP-1 derivative of the invention and comparing its effect on body weight to administration of vehicle alone.

In some embodiments the GLP-1 derivative of the invention comprises a polypeptide consisting of the amino acid sequence of Formula I (SEQ ID NO: 2):

Imp-X8-His-Gly-Thr-Phe-Thr-Ser-Asp-X16-Ser-X18-

Tyr-Leu-Glu-X22-X23-Ala-Ala-X26-X27-Phe-Ile-

Ala-Trp-Leu-X33-X34-X35-X36-X37 [I], wherein
   X8 is Ala, Aib, Acb, or Gly;
   X16 is Val, Leu, Ile, or Tyr;
   X18 is Lys or Arg;
   X22 is Gly, Ala, Glu, Lys, Arg, Ser, or Aib;
   X23 is Gln, Arg, or Lys;
   X26 is Lys or Arg;
   X27 is Glu or Lys;
   X33 is Val, Leu, or Ile;
   X34 is Lys or Arg;
   X35 is Gly, Thr, Lys, or is absent;
   X36 is Ala, Gly, Lys, Ser, or is absent;
   X37 is Gly or is absent;
wherein said polypeptide comprises a substituent comprising a lipophilic moiety and at least two negatively charged moieties, wherein one of said negatively charged moieties is distal of a lipophilic moiety; or a pharmaceutically acceptable salt, amide and/or ester thereof.

In some embodiments the GLP-1 derivative of the invention comprises a polypeptide consisting of the amino acid sequence of Formula I (SEQ ID NO: 2):

Imp-X8-His-Gly-Thr-Phe-Thr-Ser-Asp-X16-Ser-X18-

Tyr-Leu-Glu-X22-X23-Ala-Ala-X26-X27-Phe-Ile-

Ala-Trp-Leu-X33-X34-X35-X36-X37 [I], wherein
   X8 is Ala, Aib, Acb, or Gly;
   X16 is Val, Leu, Ile, or Tyr;
   X18 is Lys or Arg;

X22 is Gly, Ala, Glu, Lys, Arg, Ser, or Aib;
X23 is Gln, Arg, or Lys;
X26 is Lys or Arg;
X27 is Glu or Lys;
X33 is Val, Leu, or Ile;
X34 is Lys or Arg;
X35 is Gly, Thr, Lys, or is absent;
X36 is Ala, Gly, Lys, Ser, or is absent;
X37 is Gly or is absent;
wherein said amino acid sequence comprises a lysine residue at one or more positions selected from the group consisting of position 22, 23, 27, 34, 35, and 36; and
wherein said polypeptide comprises a substituent comprising a lipophilic moiety and at least two negatively charged moieties, wherein one of said negatively charged moieties is distal of a lipophilic moiety, and wherein said substituent is attached at the epsilon position of a lysine residue at one of the amino acid positions selected from the group consisting of position 22, 23, 27, 34, 35, and 36;
or a pharmaceutically acceptable salt, amide and/or ester thereof.

GLP-1 Peptides and Analogues

The term "GLP-1 peptide" as used herein refers to human GLP-1, the sequence of which is included in the sequence listing as SEQ ID NO: 1 or an analogue thereof. The peptide consisting of the sequence of SEQ ID NO: 1 may also simply be referred to as "GLP-1" herein. In some embodiments as used herein the terms "human GLP-1" and "GLP-1" refers to HAEGTFTSDVSSYLEGQAAKEFIAWLVKGRG (SEQ ID NO: 1). In the sequence listing, the first amino acid residue of SEQ ID NO: 1 (histidine) is assigned no. 1. However, in what follows—according to established practice in the art—this histidine residue is referred to as no. 7, and subsequent amino acid residues are numbered accordingly, ending with glycine no. 37. Therefore, generally, any reference herein to an amino acid residue number or a position number of the GLP-1(7-37) sequence is to the sequence starting with His at position 7 and ending with Gly at position 37.

GLP-1 analogues of the derivatives of the invention may be described by reference to i) the number of the amino acid residue in native GLP-1(7-37) which corresponds to the amino acid residue which is changed (i.e., the corresponding position in native GLP-1), and to ii) the actual change.

In other words, a GLP-1 analogue is a GLP-1(7-37) peptide in which a number of amino acid residues have been changed when compared to native GLP-1(7-37) (SEQ ID NO: 1). These changes may represent, independently, one or more amino acid substitutions, additions, and/or deletions.

The term "GLP-1 analogue" as used herein refers to a peptide or a compound, which is a variant of GLP-1 (SEQ ID NO: 1). The amino acid sequence of Formula I herein is an example of a GLP-1 analogue. The terms "GLP-1 analogue" and "analogue" may be used interchangeably herein. The term "polypeptide" as used herein, e.g. in connection with the GLP-1 derivative such as "polypeptide of the GLP-1 derivative", may refer to the peptide consisting of the amino acid sequence of Formula I as defined herein.

GLP-1 analogues of the derivatives of the invention may be described by reference to i) the number of the amino acid residue in human GLP-1 (SEQ ID NO: 1) which corresponds to the amino acid residue which is modified (i.e. the corresponding position in GLP-1 (SEQ ID NO: 1)), and to ii) the actual modification. The following are non-limiting examples of suitable GLP-1 analogue nomenclature.

The GLP-1 analogue is a GLP-1 peptide with a number of modifications of amino acid residues when compared to human GLP-1 (SEQ ID NO: 1). These modifications may be one or more amino acid substitutions, additions, and/or deletions. For example, "[Imp7,His9]-GLP-1" or "[Imp7, His9]-GLP-1(7-37) peptide" (SEQ ID NO: 44) designates GLP-1 (SEQ ID NO: 1), wherein the amino acid in position 7 has been substituted with Imp and the amino acid in position 9 has been substituted with His. Similarly, "[Imp7, His9,des36-37]-GLP-1(7-35) peptide" or "[Imp7,His9, des36-37]-GLP-1" (SEQ ID NO: 45) designates GLP-1 (SEQ ID NO: 1), wherein the amino acid in position 7 has been substituted with Imp, and the amino acid in position 9 has been substituted with His, and the amino acids in positions 36 and 37 have been deleted.

Analogues "comprising" certain specified changes may comprise further changes, when compared to SEQ ID NO: 1. In a particular embodiment, the analogue "consists of" or "has" the specified changes.

As is apparent from the above examples, amino acid residues may be identified by their full name, their one-letter code, and/or their three-letter code. These three ways are fully equivalent. In some embodiments GLP-1 analogues and GLP-1 derivatives are drawn using standard one-letter or three-letter codes according to IUPAC-IUB nomenclature.

The expressions "position" or "corresponding position" may be used to characterise the site of change in a GLP-1 amino acid sequence by reference to human GLP-1 (SEQ ID NO: 1). The position, as well as the number of changes, are easily deduced, e.g. by simple handwriting and eyeballing.

The term "peptide", as e.g. used in the context of the GLP-1 analogues of the derivatives of the invention, refers to a compound which comprises a series of amino acids interconnected by amide (or peptide) bonds. The GLP-1 derivatives of the invention comprise at least five constituent amino acids connected by peptide bonds. In particular embodiments, the peptide a) comprises or b) consists of i) 28, ii) 29, iii) 30, or iv) 31 amino acids. In a still further particular embodiment the peptide consists of amino acids interconnected by peptide bonds.

Amino acids are molecules comprising an amino group and a carboxylic acid group. The term "amino acid" as used herein includes coded amino acids (amongst those the 20 standard amino acids), as well as non-coded amino acids. Coded amino acids are those which are encoded by the genetic code (IUPAC Table 1 section 3AA-1, www-.chem.qmul.ac.uk/iupac/AminoAcid/AA1n2.html#AA1).
Non-coded amino acids are either not found in native (e.g. human) peptides and/or proteins or not produced by standard cellular machinery (e.g., they may have been subject to post-translational modification). Non-limiting examples of non-coded amino acids are Aib (alpha-aminoisobutyric acid), des-amino-histidine (3-(imidazol-4-yl)propionic acid, alternative name imidazopropionic acid, abbreviated Imp), as well as the D-isomers of the coded amino acids. Herein, Imp is defined as an amino acid although it does not comprise an amino group.

Herein, all amino acids of the peptide (e.g. the GLP-1 analogue or GLP-1 derivative) for which the optical isomer is not stated are to be understood to mean the L-isomer (unless otherwise specified).

The GLP-1 derivative may comprise a total of up to 15 amino acid modifications (for example one or more additions, one or more deletions and/or one or more substitutions) in the polypeptide as compared to human GLP-1 (SEQ ID NO: 1). In some embodiments the GLP-1 derivative comprises a polypeptide comprising 3-15 amino acid residue modifications, such as substitutions, additions or deletions, as compared to human GLP-1 (SEQ ID NO: 1). In some embodiments the GLP-1 derivative comprises a polypeptide comprising up to 14, such as up to 13 or up to 12, amino acid residue modifications, such as substitutions, additions or deletions, as compared to human GLP-1 (SEQ ID NO: 1). In some embodiments the GLP-1 derivative comprises a polypeptide comprising up to 11, such as up to 10 or up to 9, amino acid residue modifications, such as substitutions, additions or deletions, as compared to human GLP-1 (SEQ ID NO: 1). In some embodiments the GLP-1 derivative comprises a polypeptide comprising up to 8, such as up to 7 or up to 6, amino acid residue modifications, such as substitutions, additions or deletions, as compared to human GLP-1 (SEQ ID NO: 1). In some embodiments the GLP-1 derivative comprises a polypeptide comprising up to 5, such as up to 4 or up to 3, amino acid residue modifications, such as substitutions, additions or deletions, as compared to human GLP-1 (SEQ ID NO: 1).

In some embodiments the polypeptide of the GLP-1 derivative consists of the amino acid sequence of Formula I (SEQ ID NO: 2):

```
Imp-X8-His-Gly-Thr-Phe-Thr-Ser-Asp-X16-Ser-X18-

Tyr-Leu-Glu-X22-X23-Ala-Ala-X26-X27-Phe-Ile-

Ala-Trp-Leu-X33-X34-X35-X36-X37 [I],
``` wherein
 X8 is Ala, Aib, Acb, or Gly;
 X16 is Val, Leu, Ile, or Tyr;
 X18 is Lys or Arg;
 X22 is Gly, Ala, Glu, Lys, Arg, Ser, or Aib;
 X23 is Gln, Arg, or Lys;
 X26 is Lys or Arg;
 X27 is Glu or Lys;
 X33 is Val, Leu, or Ile;
 X34 is Lys or Arg;
 X35 is Gly, Thr, Lys, or is absent;
 X36 is Ala, Gly, Lys, Ser, or is absent—X36 may alternatively be the native Arg residue;
 X37 is Gly or is absent.

In some embodiments the polypeptide comprises a C-terminal acid group, such as a carboxylic acid group. In some embodiments the polypeptide comprises a C-terminal amide.

In some embodiments X8 is Ala, Aib, Acb; X22 is Ala or Glu; X35 is Gly or Thr; and/or X36 is Gly or is absent.

In some embodiments X8 is Ala, Aib, Acb, or Gly. In some embodiments X8 is Ala, Aib or Acb.

In some embodiments X16 is Val, Leu, Ile, or Tyr.

In some embodiments X18 is Lys or Arg.

In some embodiments X22 is Gly, Ala, Glu, Lys, Arg, Ser, or Aib. In some embodiments X22 is Gly, Ala, or Glu. In some embodiments X22 is Lys, Arg, Ser, or Aib. In some embodiments X22 is Ala or Glu.

In some embodiments X23 is Gln, Arg, or Lys.
In some embodiments X26 is Lys or Arg.
In some embodiments X27 is Glu or Lys.
In some embodiments X33 is Val, Leu, or Ile.
In some embodiments X34 is Lys or Arg.
In some embodiments X35 is Gly, Thr, Lys, or is absent. In some embodiments X35 is Gly or Thr.
In some embodiments X36 is Ala, Gly, Lys, Ser, or is absent. In some embodiments X36 is Ala, Gly, or Lys. In some embodiments X36 is Gly or is absent.

In some embodiments if X35 is absent, then X36 and X37 are also absent. In some embodiments if X35 is absent, then X36 and X37 are also absent, and said GLP-1 derivative comprises a C-terminal carboxylic acid group.

In some embodiments if X36 is absent, then X37 is also absent. In some embodiments if X36 is absent, then X37 is also absent, and said GLP-1 derivative comprises a C-terminal carboxylic amide.

The abbreviations used in the present context have the following meanings:

| Three-letter code | One-letter code | Description |
|---|---|---|
| Acb | n/a* | 1-Aminocyclobutancarboxylic acid |
| Acpr | n/a | 1-Aminocyclopropanecarboxylic acid |
| Ado | n/a | (structure) |
| Aib | n/a | 2-Aminoisobutyric acid |
| Ala | A | Alanine |
| Asn | N | Asparagine |
| Asp | D | Aspartic acid |
| Arg | R | Arginine |
| Cit | n/a | Citrulline |
| Cys | C | Cysteine |
| Gln | Q | Glutamine |
| Glu | E | Glutamic acid |
| γGlu | n/a | (structure) |
| Gly | G | Glycine |
| His | H | Histidine |
| Hyp | n/a | 4-hydroxyproline |
| Ile | I | Isoleucine |
| Imp | n/a | (structure) |
| Leu | L | Leucine |
| Lys | K | Lysine |
| Met | M | Methionine |
| Orn | n/a | Ornithine |
| Phe | F | Phenylalanine |
| Pro | P | Proline |
| Ser | S | Serine |
| Thr | T | Threonine |
| Tyr | Y | Tyrosine |
| Trp | W | Tryptophan |
| Val | V | Valine |

*"n/a" means not available.

Amino acid abbreviations beginning with D-followed by a three letter code, such as D-Ser, D-His and so on, refer to the D-enantiomer of the corresponding amino acid, for example D-serine, D-histidine and so on.

GLP-1 Derivatives

The invention relates to GLP-1 derivatives which are derivatives of GLP-1 analogues. The term "derivative" as used herein in the context of a GLP-1 analogue means a chemically modified GLP-1 analogue in which one or more substituents have been covalently attached to the GLP-1 analogue. The term "substituent" as used herein, means a chemical moiety or group replacing a hydrogen atom. The derivative may comprise one or more modifications selected from amides, carbohydrates, alkyl groups, acyl groups, esters and the like.

In some embodiments the substituent is covalently attached via an amino acid residue in said polypeptide at one of the amino acid positions selected from the group consisting of position 22, 23, 27, 34, 35, and 36. In some embodiments the substituent is attached at the epsilon position of a lysine residue in said polypeptide at one of the amino acid positions selected from the group consisting of position 22, 23, 27, 34, 35, and 36.

In some embodiments the GLP-1 derivative comprises a substituent comprising a lipophilic moiety and at least two negatively charged moieties, wherein one of said negatively charged moieties is distal of a lipophilic moiety, and wherein said substituent is attached at the epsilon position of a lysine residue in one of the amino acid positions selected from the group consisting of 22, 23, 27, 34, 35, and 36 in the polypeptide consisting of the amino acid sequence of Formula I.

The term "lipophilic moiety" as used herein, means an aliphatic or cyclic hydrocarbon moiety with more than 6 and less than 30 carbon atoms, wherein said hydrocarbon moiety may comprise additional substituents.

The term "negatively charged moiety" as used herein, means a negatively chargeable chemical moiety, such as, but not limited to an amino acid moiety (e.g. Glu, γGlu, Asp or beta-Asp, a carboxylic acid, sulphonic acid or a tetrazole moiety). The number of negatively charged moieties may be determined at physiological pH (pH 7.4). The negatively charged moiety may be a carboxylic acid group.

In some embodiments the substituent is attached to the amino acid residue at a position of the polypeptide consisting of the amino acid sequence of Formula I selected from the group consisting of position 22, 23, 27, 34, 35, and 36. In some embodiments the substituent is attached to an amino acid residue at position 34 or position 35 in the polypeptide consisting of the amino acid sequence of Formula I.

In some embodiments the substituent is attached at the epsilon nitrogen of a lysine residue at a position selected from the group consisting of position 22, 23, 27, 34, 35, and 36 in the polypeptide consisting of the amino acid sequence of Formula I. In some embodiments the substituent is attached at the epsilon nitrogen of a lysine residue a position at position 34 and position 35 in the polypeptide consisting of the amino acid sequence of Formula I.

In some embodiments the substituent comprises at least two negatively charged moieties. In some embodiments the substituent comprises three, four or five negatively charged moieties. In some embodiments the substituent comprises three or four negatively charged moieties. In some embodiments the substituent comprises between two and ten negatively charged moieties.

In some embodiments the substituent binds non-covalently to albumin.

In some embodiments the substituent is negatively charged at physiological pH, such as pH 7.0-8.2, pH 7.0-7.7, or pH 7.2-7.5, or such as pH 7.4.

In some embodiments the substituent comprises Formula II:

$$Z_1\text{—}Z_2\text{—}Z_3\text{—}Z_4\text{—}Z_5\text{—}Z_6\text{—}Z_7\text{—}Z_8\text{—}Z_9\text{—}Z_{10}\text{—} \quad [\text{II}],$$

wherein $Z_1$ comprises Formula IIa:

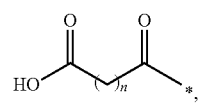

[IIa]

wherein in Formula IIa n is 6-20, and the symbol * represents the attachment point to the nitrogen of the neighbouring group;

wherein $Z_2$, $Z_3$, $Z_4$, $Z_5$, $Z_6$, $Z_7$, $Z_8$, $Z_9$, and $Z_{10}$ individually are absent or are amino acids selected from the group consisting of Glu, γGlu, Gly, Ser, Ala, Thr, Ado; and wherein $Z_1\text{—}Z_2\text{—}Z_3\text{—}Z_4\text{—}Z_5\text{—}Z_6\text{—}Z_7\text{—}Z_8\text{—}Z_9\text{—}Z_{10}$ together comprises at least two negatively charged moieties.

In some embodiments the substituent is attached at the side chain of an amino acid residue, such as at the epsilon position of a lysine residue in the polypeptide of the GLP-1 derivative.

In some embodiments $Z_1$ consists of Formula IIa:

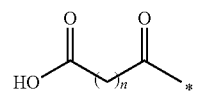

[IIa]

wherein n is an integer in the range of from 12 to 18. In some embodiments n in Formula IIa is 12, 14, 16 or 18. In some embodiments n in Formula IIa is 16 (i.e. $Z_1$ is 17-carboxyheptadecanoyl).

In some embodiments, in Formula II, $Z_2\text{—}Z_3\text{—}Z_4\text{—}Z_5\text{—}Z_6\text{—}Z_7\text{—}Z_8\text{—}Z_9\text{—}Z_{10}\text{—}$ is a linker, wherein each of $Z_2$, $Z_3$, $Z_4$, $Z_5$, $Z_6$, $Z_7$, $Z_8$, $Z_9$, and $Z_{10}$ individually are any one of the following amino acid residues: Glu, γGlu, Gly, Ser, Ala, Thr and/or Ado; or one or more of residues $Z_2$, $Z_3$, $Z_4$, $Z_5$, $Z_6$, $Z_7$, $Z_8$, $Z_9$, and $Z_{10}$ are absent; provided, however, that at least two of residues $Z_2$, $Z_3$, $Z_4$, $Z_5$, $Z_6$, $Z_7$, $Z_8$, $Z_9$, and $Z_{10}$ are present; and wherein $Z_1\text{—}Z_2\text{—}Z_3\text{—}Z_4\text{—}Z_5\text{—}Z_6\text{—}Z_7\text{—}Z_8\text{—}Z_9\text{—}Z_{10}\text{—}$ together comprises at least two negatively charged moieties. In some embodiments $Z_2$, $Z_3$, $Z_4$, $Z_5$, $Z_6$, $Z_7$, $Z_8$, $Z_9$, and $Z_{10}$ are individually represented by any one of the following amino acid residues: Glu, γGlu, Gly, Ser, and/or Ado; or one or more of $Z_2$, $Z_3$, $Z_4$, $Z_5$, $Z_6$, $Z_7$, $Z_8$, $Z_9$, and $Z_{10}$ are absent; provided, however, that at least two of $Z_2$, $Z_3$, $Z_4$, $Z_5$, $Z_6$, $Z_7$, $Z_8$, $Z_9$, and $Z_{10}$ are present. In some embodiments $Z_2$, $Z_3$, $Z_4$, $Z_5$, $Z_6$, $Z_7$, $Z_8$, $Z_9$, and $Z_{10}$ are individually represented by any one of the following amino acid residues: γGlu and/or Ado; or one or more of $Z_2$, $Z_3$, $Z_4$, $Z_5$, $Z_6$, $Z_7$, $Z_8$, $Z_9$, and $Z_{10}$ are absent; provided, however, that at least two of $Z_2$, $Z_3$, $Z_4$, $Z_5$, $Z_6$, $Z_7$, $Z_8$, $Z_9$, and $Z_{10}$ are present. In some embodiments at least three of $Z_2$, $Z_3$, $Z_4$, $Z_5$, $Z_6$, $Z_7$, $Z_8$, $Z_9$, and $Z_{10}$ are present. In some embodiments at least four of $Z_2$, $Z_3$, $Z_4$, $Z_5$, $Z_6$, $Z_7$, $Z_8$, $Z_9$, and $Z_{10}$ are present. In some embodiments at least five of $Z_2$, $Z_3$, $Z_4$, $Z_5$, $Z_6$, $Z_7$, $Z_8$, $Z_9$, and $Z_{10}$ are present. In some embodiments at least six of $Z_2$, $Z_3$, $Z_4$, $Z_5$, $Z_6$, $Z_7$, $Z_8$, $Z_9$, and $Z_{10}$ are present. In some embodiments $Z_2\text{—}Z_3\text{—}Z_4\text{—}Z_5\text{—}Z_6\text{—}Z_7\text{—}Z_8\text{—}Z_9\text{—}Z_{10}\text{—}$ is selected from the group consisting of: γGlu-γGlu-Ado-Ado-, γGlu-γGlu-Ado-Ado-γGlu-, γGlu-γGlu-Ado-γGlu-γGlu-, γGlu-γGlu-Ado-γGlu-Ado-γGlu-Ado-γGlu-, γGlu-γGlu-Ser-Gly-, γGlu-γGlu-Ser-Gly-Glu-Ser-Gly-, γGlu-γGlu-γGlu-Ado-Ado-, γGlu-γGlu-γGlu-γGlu-, γGlu-Ado-Ado-, γGlu-Ado-Ado- γGlu-γGlu-, and Gly-Ser-Glu-Gly-Ser-γGlu-γGlu-. In some embodiments $Z_2$—$Z_3$—$Z_4$—$Z_5$—$Z_6$—$Z_7$—$Z_8$—$Z_9$—$Z_{10}$— is γGlu-γGlu-Ado-Ado-. In some embodiments $Z_2$—$Z_3$—$Z_4$—$Z_5$—$Z_6$—$Z_7$—$Z_8$—$Z_9$—$Z_{10}$— is γGlu-γGlu-Ado-Ado-γGlu-. In some embodiments $Z_2$—$Z_3$—$Z_4$—$Z_5$—$Z_6$—$Z_7$—$Z_8$—$Z_9$—$Z_{10}$— is γGlu-γGlu-Ado-γGlu-γGlu-. In some embodiments $Z_2$—$Z_3$—$Z_4$—$Z_5$—$Z_6$—$Z_7$—$Z_8$—$Z_9$—$Z_{10}$— is γGlu-γGlu-Ado-γGlu-Ado-γGlu-Ado-γGlu-. In some embodiments $Z_2$—$Z_3$—$Z_4$—$Z_5$—$Z_6$—$Z_7$—$Z_8$—$Z_9$—$Z_{10}$— is γGlu-γGlu-Ser-Gly-. In some embodiments $Z_2$—$Z_3$—$Z_4$—$Z_5$—$Z_6$—$Z_7$—$Z_8$—$Z_9$—$Z_{10}$— is γGlu-γGlu-Ser-Gly-Glu-Ser-Gly-. In some embodiments $Z_2$—$Z_3$—$Z_4$—$Z_5$—$Z_6$—$Z_7$—$Z_8$—$Z_9$—$Z_{10}$— is γGlu-γGlu-γGlu-Ado-Ado-. In some embodiments $Z_2$—$Z_3$—$Z_4$—$Z_5$—$Z_6$—$Z_7$—$Z_8$—$Z_9$—$Z_{10}$— is γGlu-γGlu-γGlu-γGlu-. In some embodiments $Z_2$—$Z_3$—$Z_4$—$Z_5$—$Z_6$—$Z_7$—$Z_8$—$Z_9$—$Z_{10}$— is γGlu-Ado-Ado-. In some embodiments $Z_2$—$Z_3$—$Z_4$—$Z_5$—$Z_6$—$Z_7$—$Z_8$—$Z_9$—$Z_{10}$— is γGlu-Ado-Ado-γGlu-γGlu-. In some embodiments $Z_2$—$Z_3$—$Z_4$—$Z_5$—$Z_6$—$Z_7$—$Z_8$—$Z_9$—$Z_{10}$— is Gly-Ser-Glu-Gly-Ser-γGlu-γGlu-.

In some embodiments the lipophilic moiety (e.g. $Z_1$) comprises an alkyl group of at least 12 carbon atoms, such as 12-20 carbon atoms or 14-18 carbon atoms, or such as 16 carbon atoms.

In some embodiments the substituent is covalently attached to the side chain of an amino acid, such as the nitrogen atom of the side chain of a lysine.

In some embodiments the substituent is selected from the group consisting of:

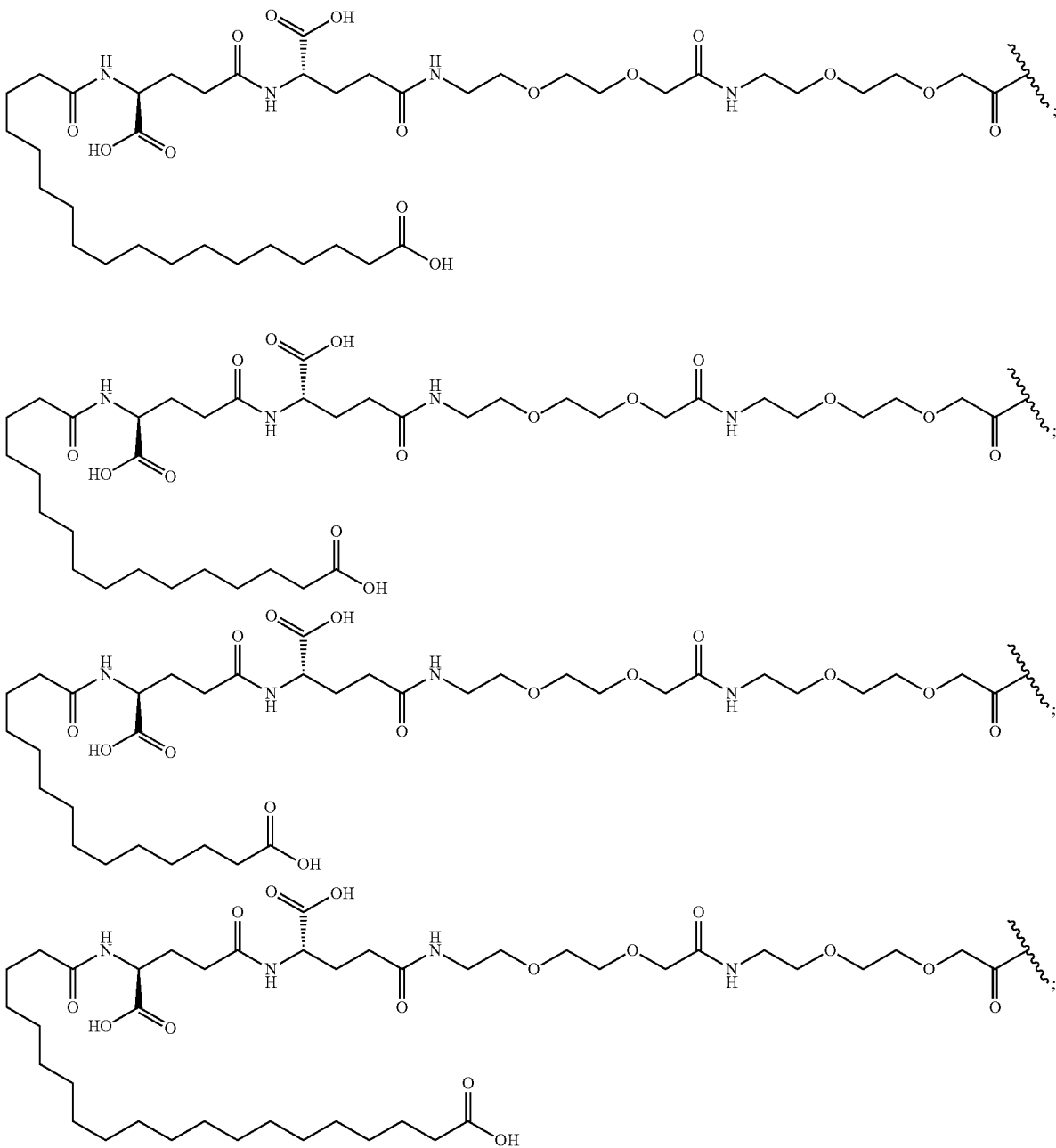

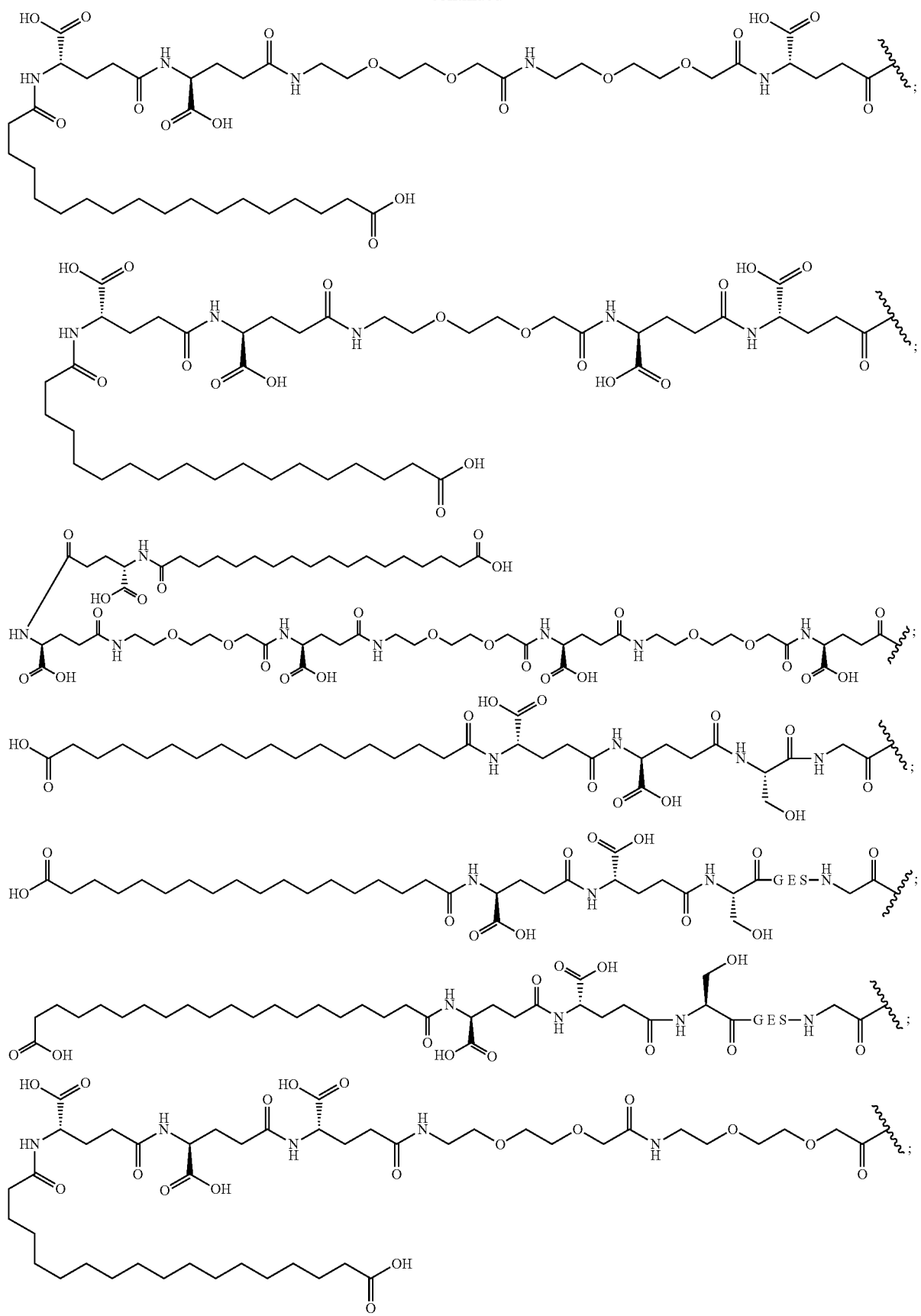

-continued

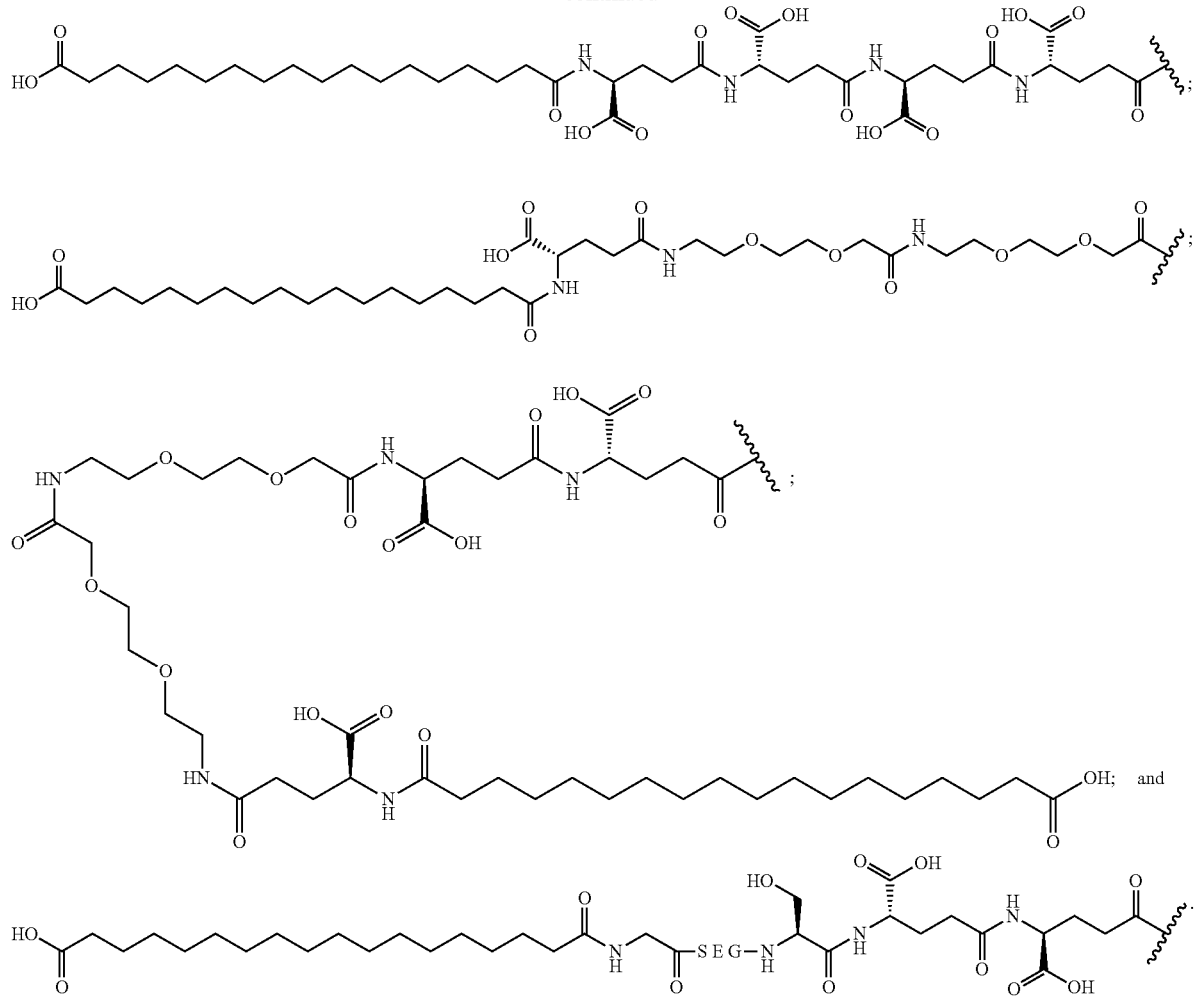

The substituent may be covalently attached to the polypeptide of the GLP-1 derivative, i.e. to the amino acid sequence consisting of Formula I, via the carbonyl group marked with a waved line in the structural formula of said substituent.

In some embodiments the GLP-1 derivative is N$^{\epsilon 35}$-[2-[[(2S)-2-[[(2S)-4-carboxy-2-[[2-[[(2S)-2-[[(4S)-4-carboxy-4-[[(4S)-4-carboxy-4-(17-carboxyheptadecanoylamino)butanoyl]amino]butanoyl]amino]-3-hydroxypropanoyl]amino]acetyl]amino]butanoyl]amino]-3-hydroxypropanoyl]amino]acetyl]-[Imp7,Acb8,His9,Tyr16,Lys18,Glu22,Arg26,Leu33,Lys35]-GLP-1-(7-35)-peptide amide (SEQ ID NO: 3)

(Chem. 1)

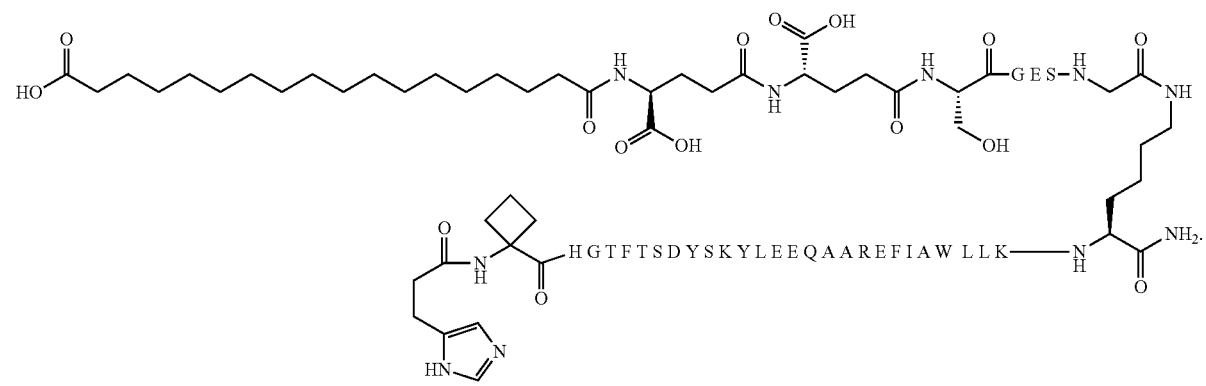

In some embodiments the GLP-1 derivative is N$^{\varepsilon 35}$-[2-[[(2S)-2-[[(2S)-4-carboxy-2-[[2-[[(2S)-2-[[(4S)-4-carboxy-4-[[(4S)-4-carboxy-4-(17-carboxyheptadecanoylamino)butanoyl]amino]butanoyl]amino]-3-hydroxypropanoyl]amino]acetyl]amino]butanoyl]amino]-3-hydroxypropanoyl]amino]acetyl]-[Imp7,Acb8,His9,Lys18,Glu22,Arg26,Leu33,Lys35]-GLP-1-(7-35)-peptide amide (SEQ ID NO: 4)

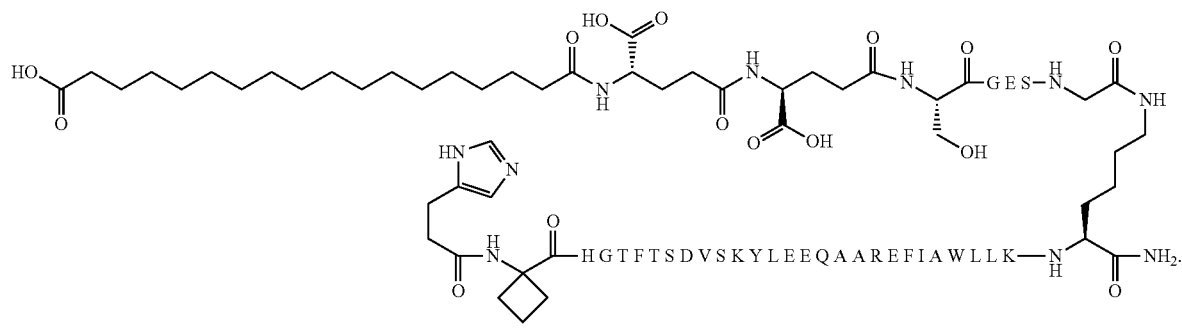

(Chem. 2)

In some embodiments the GLP-1 derivative is N$^{\varepsilon 34}$-[2-[[(2S)-2-[[(2S)-4-carboxy-2-[[2-[[(2S)-2-[[(4S)-4-carboxy-4-[[(4S)-4-carboxy-4-(17-carboxyheptadecanoylamino)butanoyl]amino]butanoyl]amino]-3-hydroxypropanoyl]amino]acetyl]amino]butanoyl]amino]-3-hydroxypropanoyl]amino]acetyl]-[Imp7,Aib8,His9,Lys18,Glu22,Arg26,Leu33,Thr35]-GLP-1-(7-35)-peptide amide (SEQ ID NO: 5)

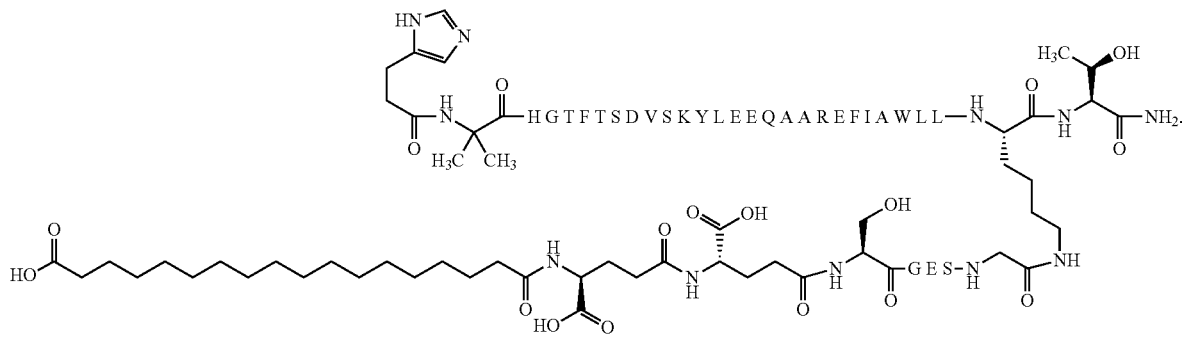

(Chem. 3)

In some embodiments the GLP-1 derivative is N$^{\varepsilon 34}$-[2-[[(2S)-2-[[(4S)-4-carboxy-4-[[(4S)-4-carboxy-4-(17-carboxyheptadecanoylamino)butanoyl]amino]butanoyl]amino]-3-hydroxypropanoyl]amino]acetyl]-[Imp7,Aib8,His9,Lys18,Glu22,Arg26,Leu33,Thr35]-GLP-1-(7-35)-peptide amide (SEQ ID NO: 5)

(Chem. 4)

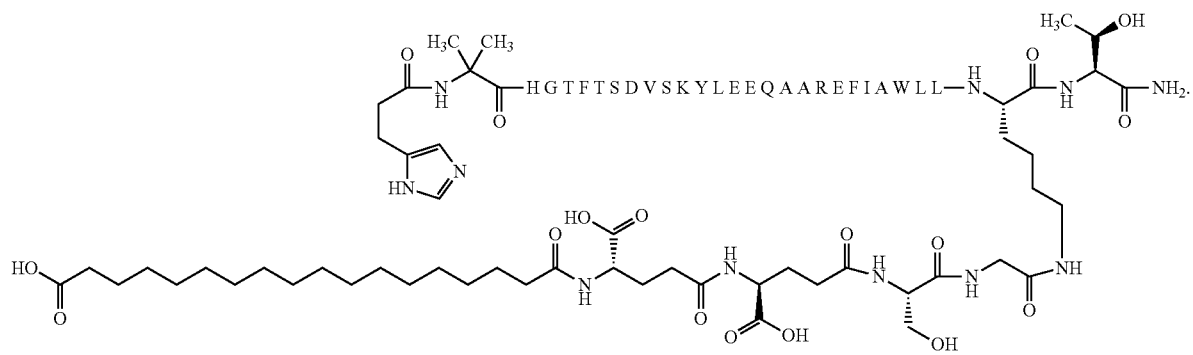

In some embodiments the GLP-1 derivative is $N^{\varepsilon 34}$-[2-[2-[2-[[2-[2-[2-[[(4S)-4-carboxy-4-[[(4S)-4-carboxy-4-(17-carboxyheptadecanoylamino)butanoyl]amino]butanoyl]amino]ethoxy]ethoxy]acetyl]amino]ethoxy]ethoxy]acetyl]-[Imp7,Aib8,His9,Lys18,Glu22,Arg26,Leu33,Thr35]-GLP-1-(7-35)-peptide amide (SEQ ID NO: 5)

(Chem. 5)

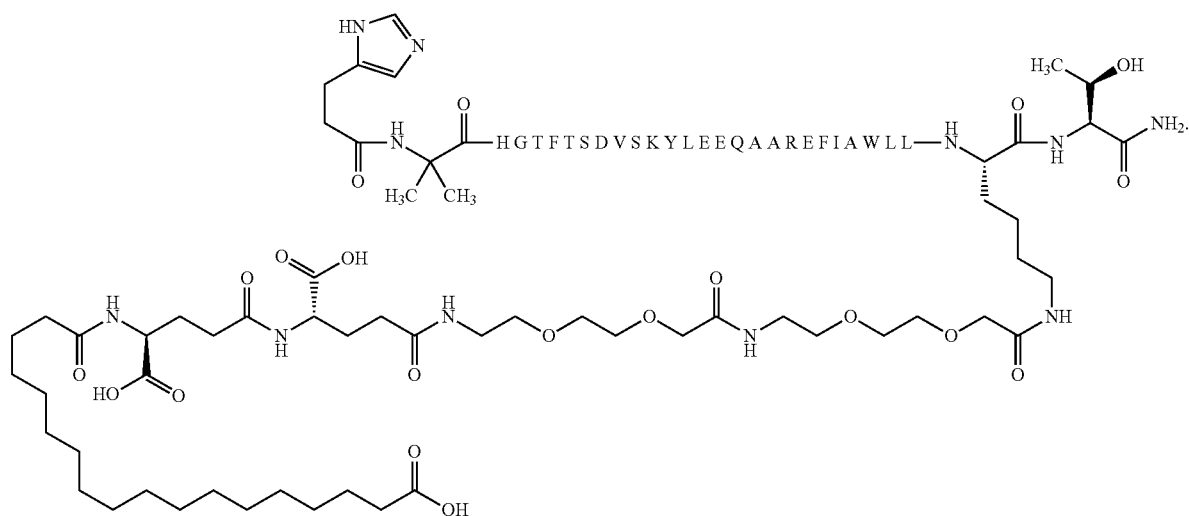

In some embodiments the GLP-1 derivative is $N^{\varepsilon 34}$-[(4S)-4-carboxy-4-[[(4S)-4-carboxy-4-[[(4S)-4-carboxy-4-[[(4S)-4-carboxy-4-(17-carboxyheptadecanoylamino)butanoyl]amino]butanoyl]amino]butanoyl]amino]butanoyl]-[Imp7,Aib8,His9,Lys18,Glu22,Arg26,Leu33,Thr35]-GLP-1-(7-35)-peptide amide (SEQ ID NO: 5)

(Chem. 6)

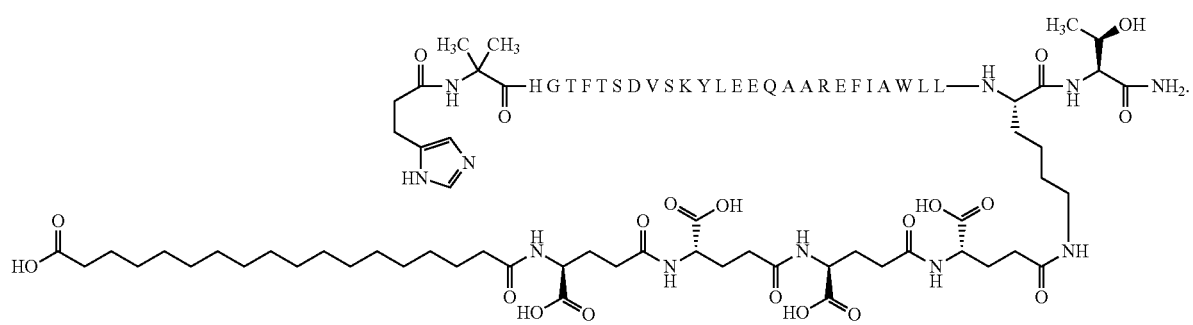

In some embodiments the GLP-1 derivative is N^{ε34}-[2-[[(2S)-2-[[(2S)-4-carboxy-2-[[2-[[(2S)-2-[[(4S)-4-carboxy-4-[[(4S)-4-carboxy-4-(17-carboxyheptadecanoylamino)butanoyl]amino]butanoyl]amino]-3-hydroxypropanoyl]amino]acetyl]amino]butanoyl]amino]-3-hydroxypropanoyl]amino]acetyl]-[Imp7,Aib8,His9,Arg18,Glu22,Arg26,Leu33,Thr35]-GLP-1-(7-35)-peptide amide (SEQ ID NO: 7)

(Chem. 7)

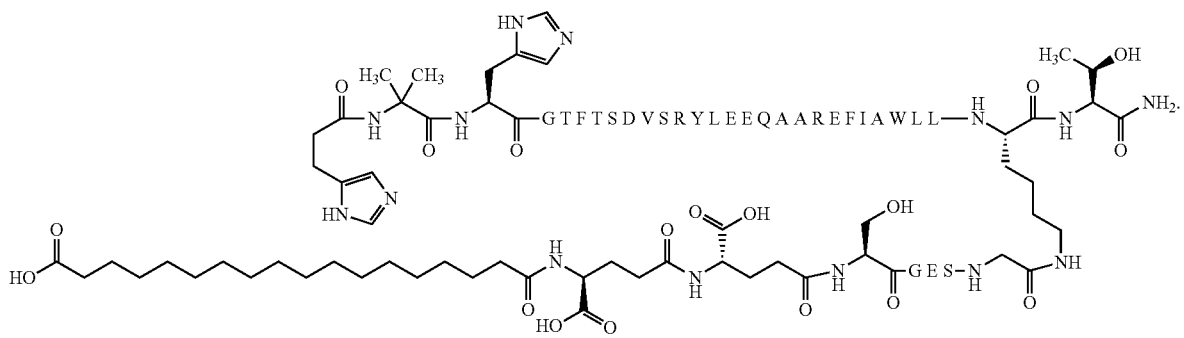

In some embodiments the GLP-1 derivative is N^{ε34}-[2-[[(2S)-2-[[(2S)-4-carboxy-2-[[2-[[(2S)-2-[[(4S)-4-carboxy-4-[[(4S)-4-carboxy-4-(17-carboxyheptadecanoylamino)butanoyl]amino]butanoyl]amino]-3-hydroxypropanoyl]amino]acetyl]amino]butanoyl]amino]-3-hydroxypropanoyl]amino]acetyl]-[Imp7,Aib8,His9,Arg18,Arg26,Leu33,Thr35]-GLP-1-(7-35)-peptide amide (SEQ ID NO: 8)

(Chem. 8)

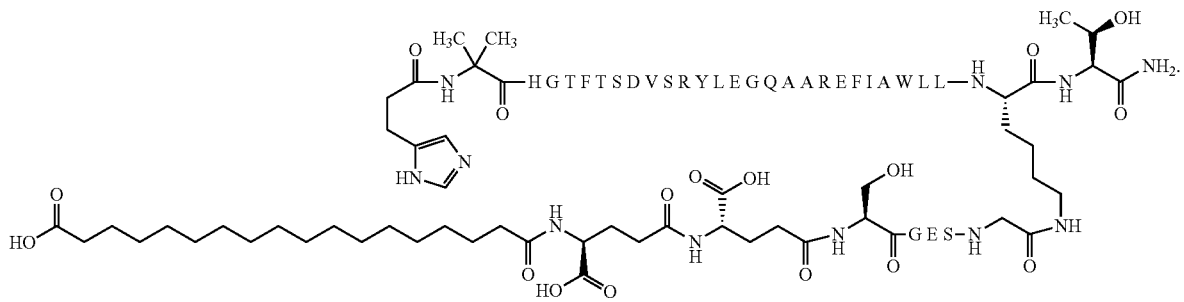

In some embodiments the GLP-1 derivative is N^{ε34}-[2-[[(2S)-2-[[(2S)-4-carboxy-2-[[2-[[(2S)-2-[[(4S)-4-carboxy-4-[[(4S)-4-carboxy-4-(17-carboxyheptadecanoylamino)butanoyl]amino]butanoyl]amino]-3-hydroxypropanoyl]amino]acetyl]amino]butanoyl]amino]-3-hydroxypropanoyl]amino]acetyl]-[Imp7,Acb8,His9,Lys18,Glu22,Arg26,Leu33,Thr35]-GLP-1-(7-35)-peptide amide (SEQ ID NO: 9)

(Chem. 9)

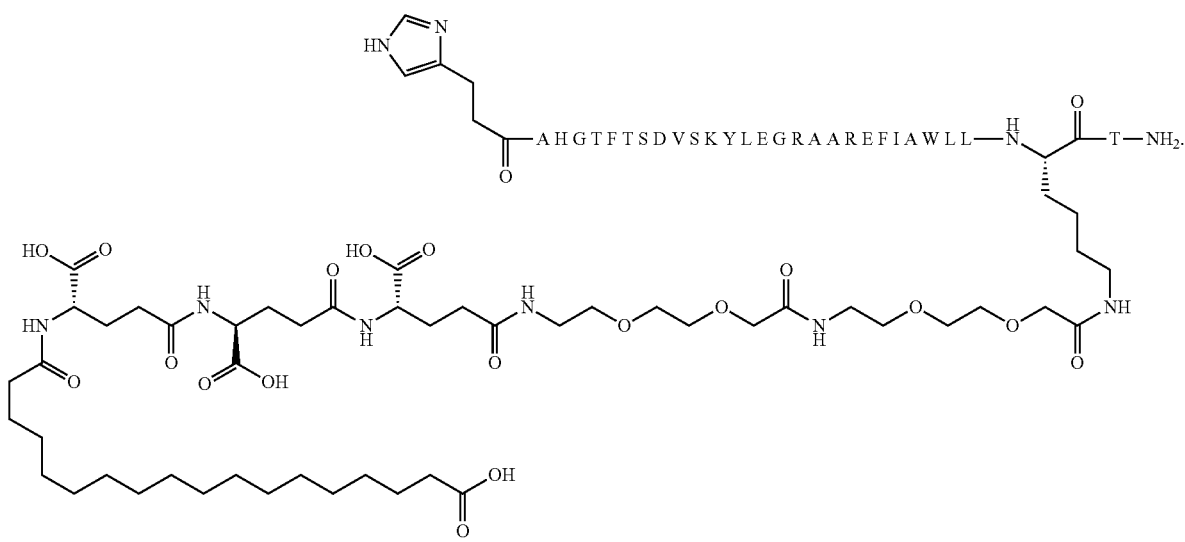

In some embodiments the GLP-1 derivative is $N^{\varepsilon 34}$-[2-[2-[2-[[2-[2-[2-[[(4S)-4-carboxy-4-[[(4S)-4-carboxy-4-[[(4S)-4-carboxy-4-(17-carboxyheptadecanoylamino)butanoyl]amino]butanoyl]amino]butanoyl]amino]ethoxy]ethoxy]acetyl]amino]ethoxy]ethoxy]acetyl]-[Imp7,His9,Lys18,Arg23,Arg26,Leu33,Thr35]-GLP-1-(7-35)-peptide amide (SEQ ID NO: 10)

(Chem. 10)

In some embodiments the GLP-1 derivative is $N^{\varepsilon 34}$-[2-[2-[2-[[2-[2-[2-[[(4S)-4-carboxy-4-[[(4S)-4-carboxy-4-[[(4S)-4-carboxy-4-(17-carboxyheptadecanoylamino)butanoyl]amino]butanoyl]amino]butanoyl]amino]ethoxy]ethoxy]acetyl]amino]ethoxy]ethoxy]acetyl]-[Imp7,His9,Lys18,Arg23,Arg26,Leu33,Gly36]-GLP-1-(7-37)-peptide (SEQ ID NO: 38)

(Chem. 11)

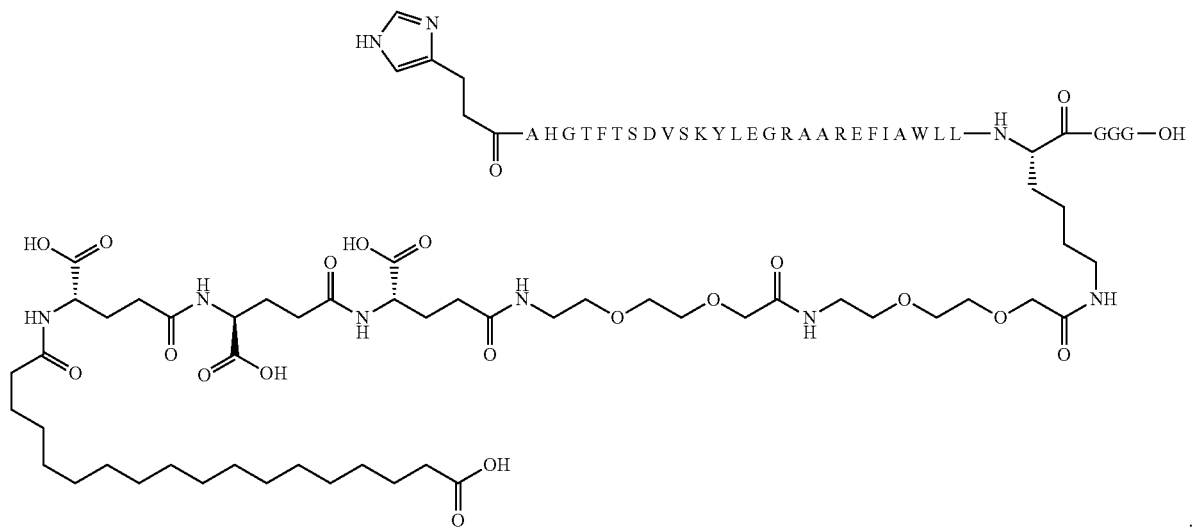

In some embodiments the GLP-1 derivative is N$^{\varepsilon 34}$-[2-[2-[2-[[2-[2-[2-[[(4S)-4-carboxy-4-(17-carboxyheptadecanoylamino)butanoyl]amino]ethoxy]ethoxy]acetyl]amino]ethoxy]ethoxy]acetyl]-[Imp7,Aib8,His9,Lys18,Glu22,Arg26,Leu33,Thr35]-GLP-1-(7-35)-peptide amide (SEQ ID NO: 5)

(Chem. 12)

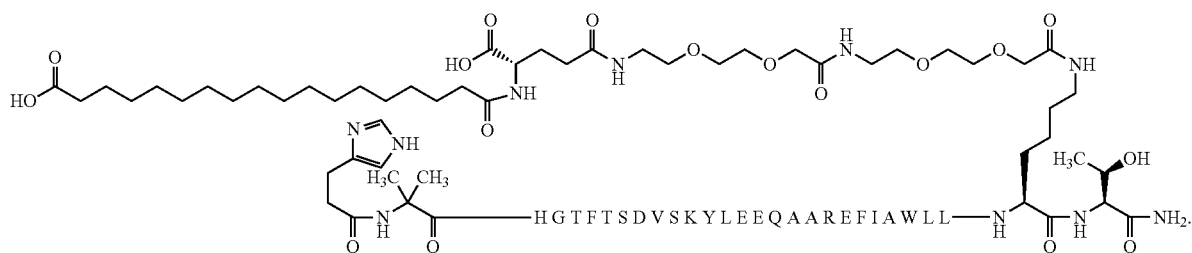

In some embodiments the GLP-1 derivative is N$^{\varepsilon 22}$-[(4S)-4-carboxy-4-[[(4S)-4-carboxy-4-[[2-[2-[2-[[2-[2-[2-[[(4S)-4-carboxy-4-(17-carboxyheptadecanoylamino)butanoyl]amino]ethoxy]ethoxy]acetyl]amino]ethoxy]ethoxy]acetyl]amino]butanoyl]amino]butanoyl]-[Imp7,Aib8,His9,Lys18,Lys22,Arg26,Leu33,Gly36]-GLP-1-(7-37)-peptide (SEQ ID NO: 39)

(Chem. 13)

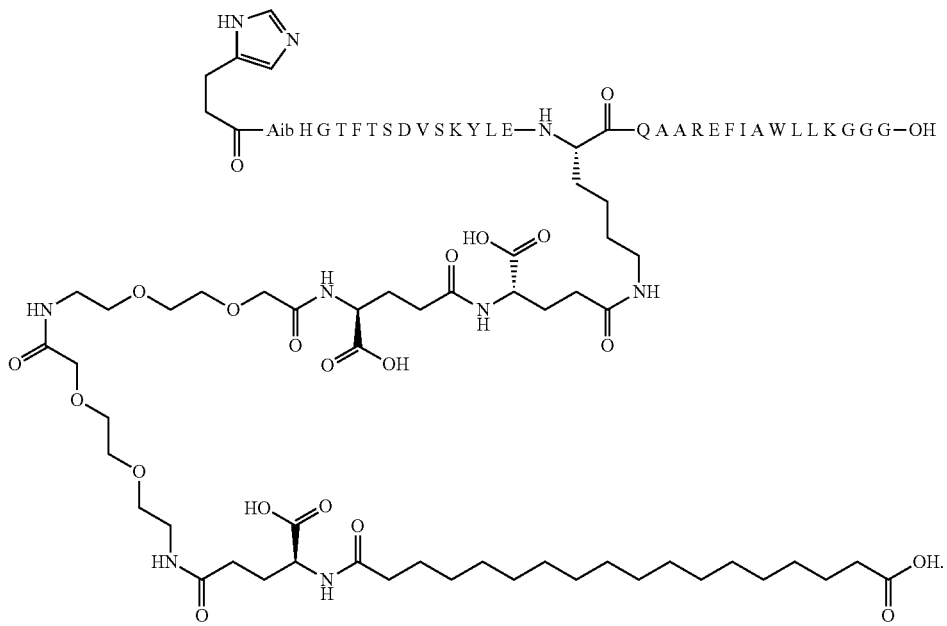

In some embodiments the GLP-1 derivative is $N^{\varepsilon 36}$-[2-[[(2S)-2-[[(2S)-4-carboxy-2-[[2-[[(2S)-2-[[(4S)-4-carboxy-4-[[(4S)-4-carboxy-4-(17-carboxyheptadecanoylamino)butanoyl]amino]butanoyl]amino]-3-hydroxypropanoyl]amino]acetyl]amino]butanoyl]amino]-3-hydroxypropanoyl]amino]acetyl]-[Imp7,Aib8,His9,Tyr16,Lys18,Glu22,Arg26,Leu33,Lys36]-GLP-1-(7-37)-peptide (SEQ ID NO: 13)

(Chem. 14)

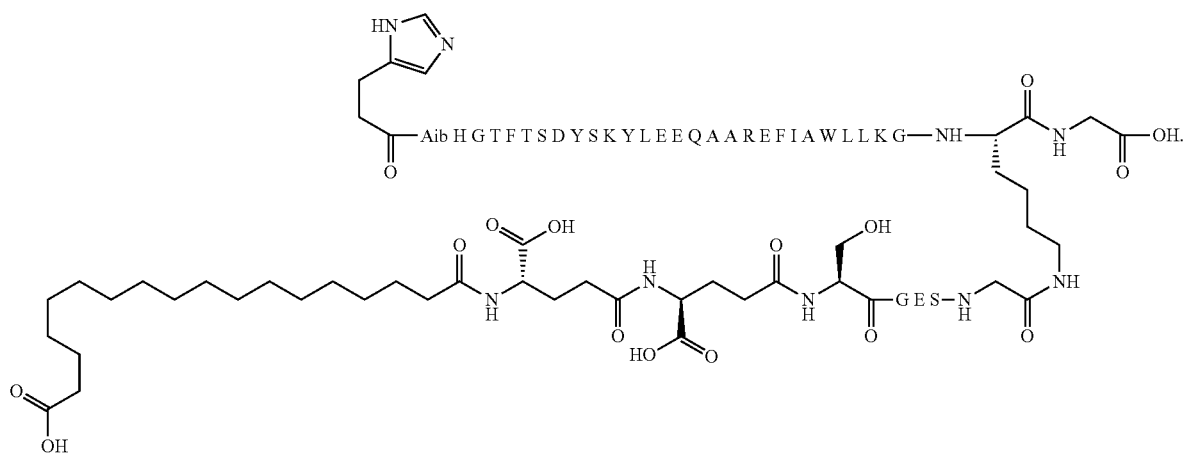

In some embodiments the GLP-1 derivative is $N^{\varepsilon 23}$-[2-[2-[2-[[2-[2-[2-[[(4S)-4-carboxy-4-(17-carboxyheptadecanoylamino)butanoyl]amino]ethoxy]ethoxy]acetyl]amino]ethoxy]ethoxy]acetyl]-[Imp7,Aib8,His9,Lys18,Lys23,Arg26,Leu33,Thr35]-GLP-1-(7-35)-peptide amide (SEQ ID NO: 14)

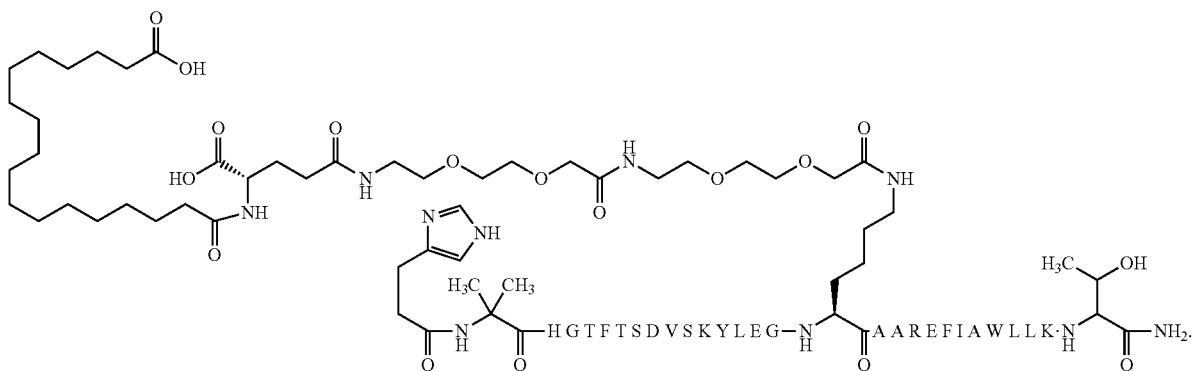

(Chem. 15)

In some embodiments the GLP-1 derivative is $N^{\varepsilon 23}$-[2-[2-[2-[[2-[2-[2-[[(4S)-4-carboxy-4-(17-carboxyheptadecanoylamino)butanoyl]amino]ethoxy]ethoxy]acetyl]amino]ethoxy]ethoxy]acetyl]-[Imp7,Aib8,His9,Tyr16,Lys18,Lys23,Arg26,Leu33,Thr35]-GLP-1-(7-35)-peptide amide (SEQ ID NO: 15)

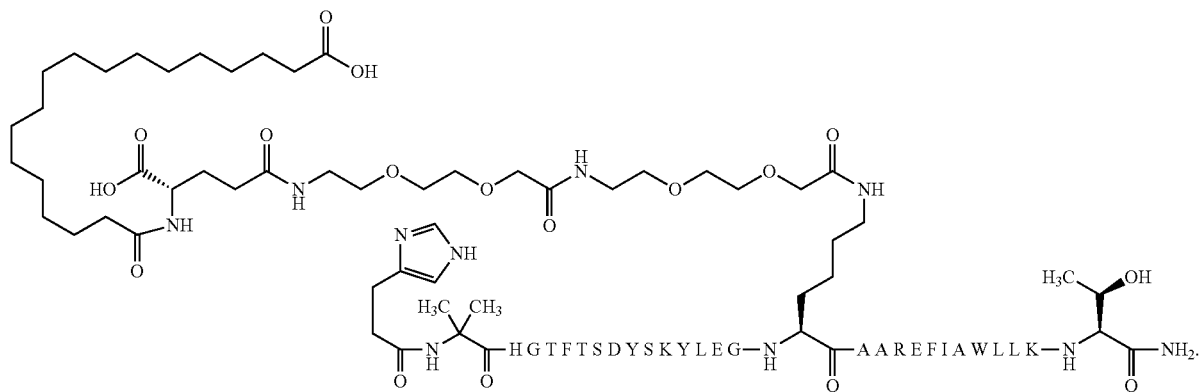

(Chem. 16)

In some embodiments the GLP-1 derivative is $N^{\varepsilon 34}$-[2-[2-[2-[[2-[2-[2-[[(4S)-4-carboxy-4-[[(4S)-4-carboxy-4-[[(4S)-4-carboxy-4-(17-carboxyheptadecanoylamino)butanoyl]amino]butanoyl]amino]butanoyl]amino]ethoxy]ethoxy]acetyl]amino]ethoxy]ethoxy]acetyl]-[Imp7,His9,Arg18,Arg23,Arg26,Leu33]-GLP-1-(7-34)-peptide (SEQ ID NO: 40)

(Chem. 17)

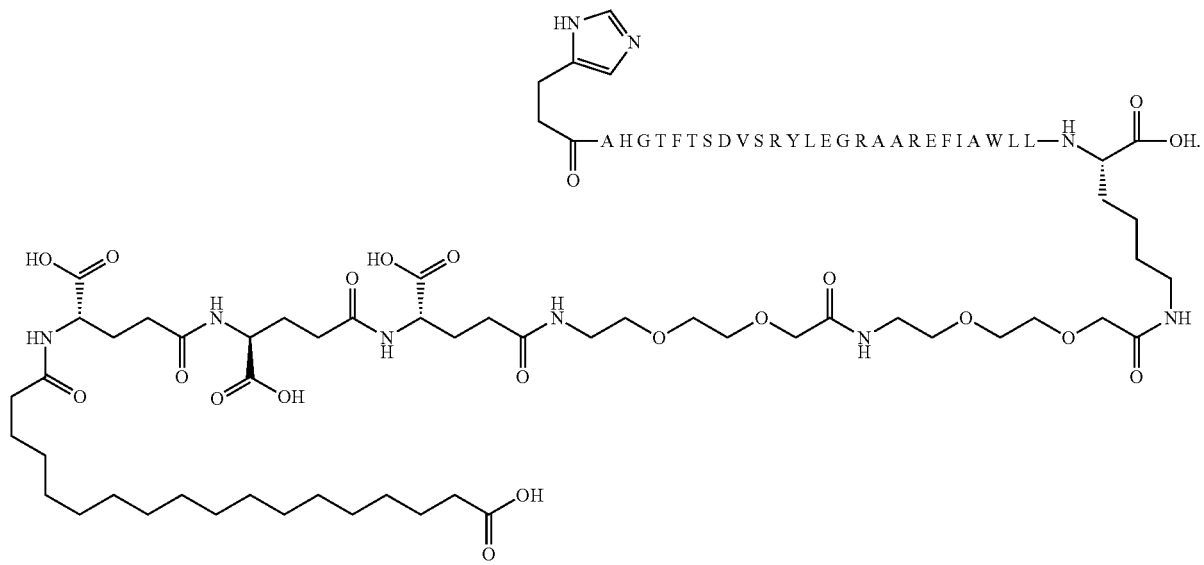

In some embodiments the GLP-1 derivative is $N^{\varepsilon 27}$-[2-[2-[2-[[2-[2-[2-[[(4S)-4-carboxy-4-[[(4S)-4-carboxy-4-[[(4S)-4-carboxy-4-(17-carboxyheptadecanoylamino)butanoyl]amino]butanoyl]amino]butanoyl]amino]ethoxy]ethoxy]acetyl]amino]ethoxy]ethoxy]acetyl]-[Imp7,His9,Arg18,Glu22,Arg26,Lys27,Leu33,Arg34]-GLP-1-(7-34)-peptide (SEQ ID NO: 17)

(Chem. 18)

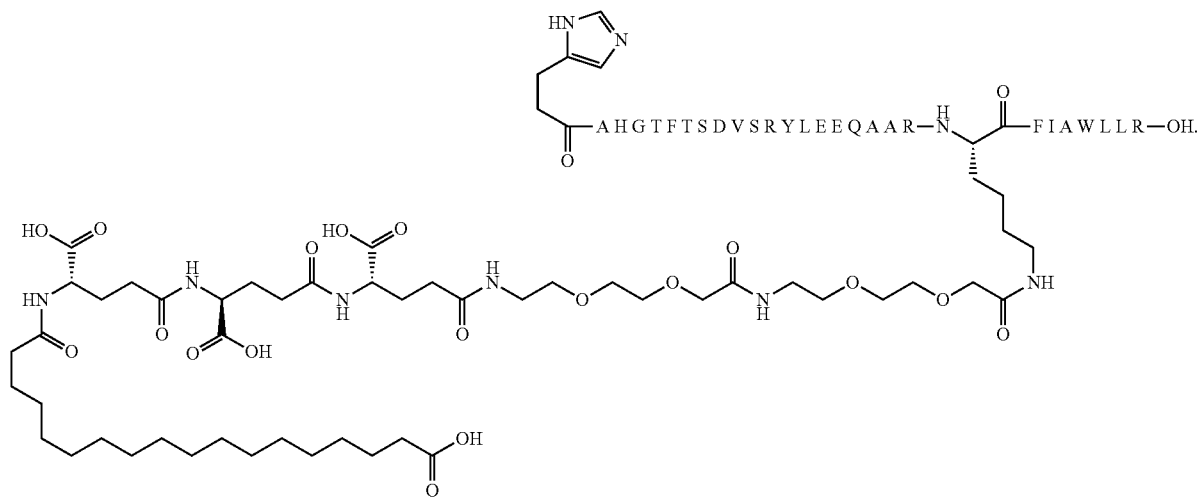

In some embodiments the GLP-1 derivative is $N^{\varepsilon 27}$-[2-[2-[2-[[2-[2-[2-[[(4S)-4-carboxy-4-[[(4S)-4-carboxy-4-[[(4S)-4-carboxy-4-(17-carboxyheptadecanoylamino)butanoyl]amino]butanoyl]amino]butanoyl]amino]ethoxy]ethoxy]oxy]acetyl]amino]ethoxy]ethoxy]acetyl]-[Imp7,Aib8,His9,Arg18,Glu22,Arg26,Lys27,Leu33,Arg34]-GLP-1-(7-34)-peptide (SEQ ID NO: 41)

(Chem. 19)

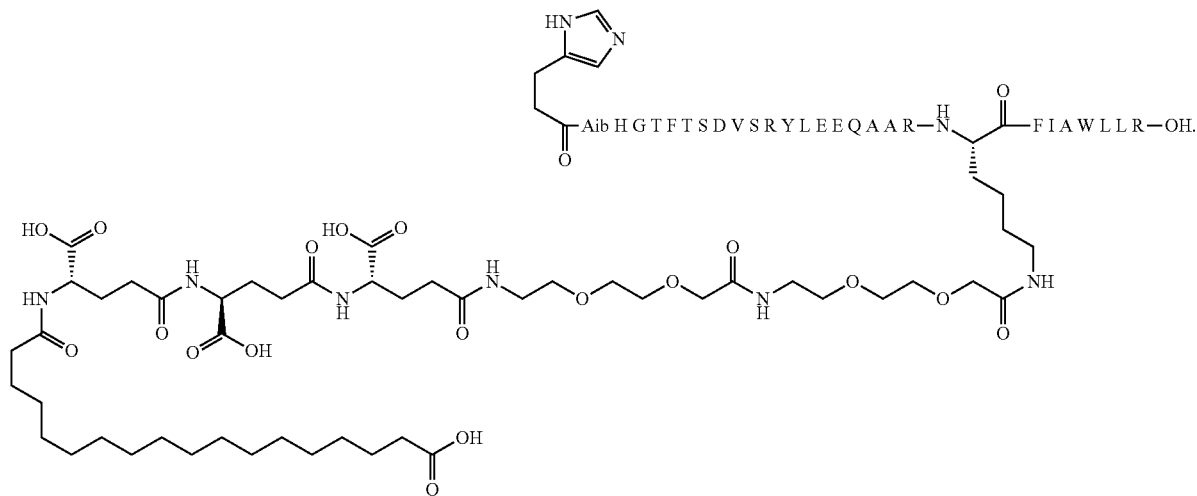

In some embodiments the GLP-1 derivative is $N^{\varepsilon 34}$-[2-[[(2S)-2-[[(2S)-4-carboxy-2-[[2-[[(2S)-2-[[(4S)-4-carboxy-4-[[(4S)-4-carboxy-4-(17-carboxyheptadecanoylamino)butanoyl]amino]butanoyl]amino]-3-hydroxypropanoyl]amino]acetyl]amino]butanoyl]amino]-3-hydroxypropanoyl]amino]acetyl]-[Imp7,Acb8,His9,Lys18,Arg23,Arg26,Leu33,Thr35]-GLP-1-(7-35)-peptide amide (SEQ ID NO: 19)

(Chem. 20)

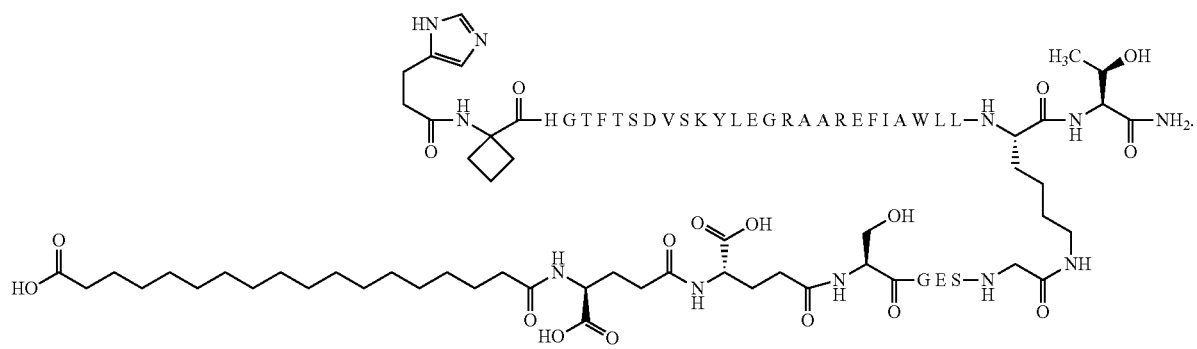

In some embodiments the GLP-1 derivative is $N^{\varepsilon 35}$-[(4S)-4-carboxy-4-[[2-[2-[2-[[(4S)-4-carboxy-4-[[2-[2-[2-[[(4S)-4-carboxy-4-[[2-[2-[2-[[(4S)-4-carboxy-4-[[(4S)-4-carboxy-4-(17-carboxyheptadecanoylamino)butanoyl]amino]butanoyl]amino]ethoxy]ethoxy]acetyl]amino]butanoyl]amino]ethoxy]ethoxy]acetyl]amino]butanoyl]amino]ethoxy]ethoxy]acetyl]amino]butanoyl]-[Imp7,Acb8,His9,Tyr16,Lys18,Glu22,Arg26,Leu33,Lys35]-GLP-1-(7-35)-peptide amide (SEQ ID NO: 3)

(Chem. 21)

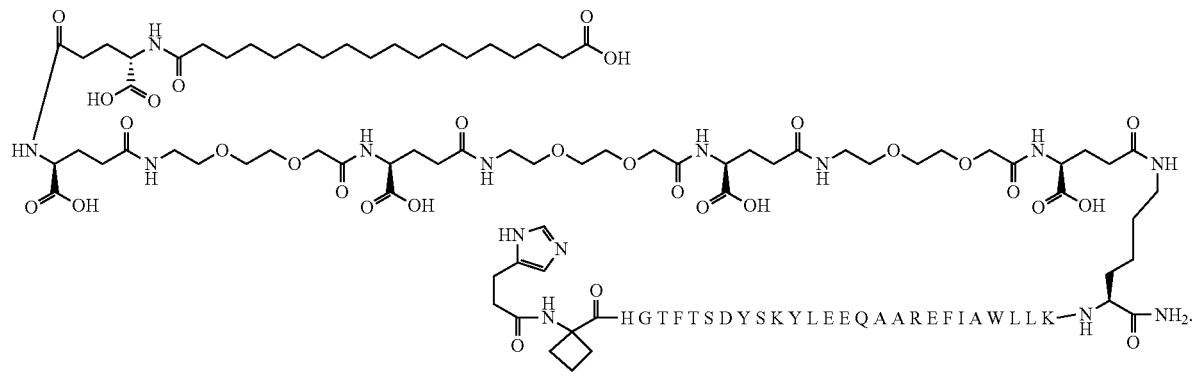

In some embodiments the GLP-1 derivative is $N^{\varepsilon 35}$-[(4S)-4-carboxy-4-[[2-[2-[2-[[(4S)-4-carboxy-4-[[2-[2-[2-[[(4S)-4-carboxy-4-[[2-[2-[2-[[(4S)-4-carboxy-4-[[(4S)-4-carboxy-4-(17-carboxyheptadecanoylamino)butanoyl]amino]butanoyl]amino]ethoxy]ethoxy]acetyl]amino]butanoyl]amino]ethoxy]ethoxy]acetyl]amino]butanoyl]amino]ethoxy]ethoxy]acetyl]amino]butanoyl]-[Imp7,Acb8,His9,Tyr16,Arg18,Glu22,Arg26,Leu33,Arg34,Lys35]-GLP-1-(7-35)-peptide amide (SEQ ID NO: 20)

(Chem. 22)

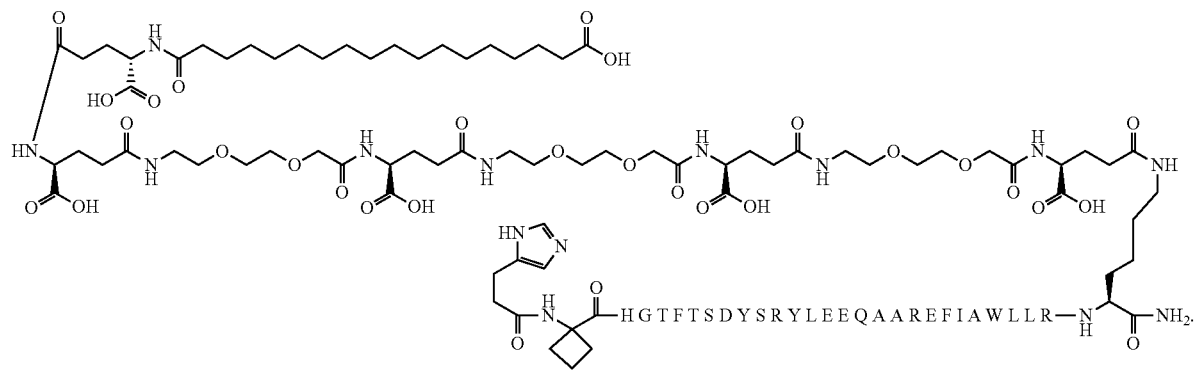

In some embodiments the GLP-1 derivative is $N^{\varepsilon 35}$-[(4S)-4-carboxy-4-[[2-[2-[2-[[(4S)-4-carboxy-4-[[2-[2-[2-[[(4S)-4-carboxy-4-[[2-[2-[2-[[(4S)-4-carboxy-4-[[(4S)-4-carboxy-4-(17-carboxyheptadecanoylamino)butanoyl]amino]butanoyl]amino]ethoxy]ethoxy]acetyl]amino]butanoyl]amino]ethoxy]ethoxy]acetyl]amino]butanoyl]amino]ethoxy]ethoxy]acetyl]amino]butanoyl]-[Imp7,Acb8,His9,Tyr16,Lys18,Arg22,Arg26,Leu33,Lys35]-GLP-1-(7-35)-peptide amide (SEQ ID NO: 21)

(Chem. 23)

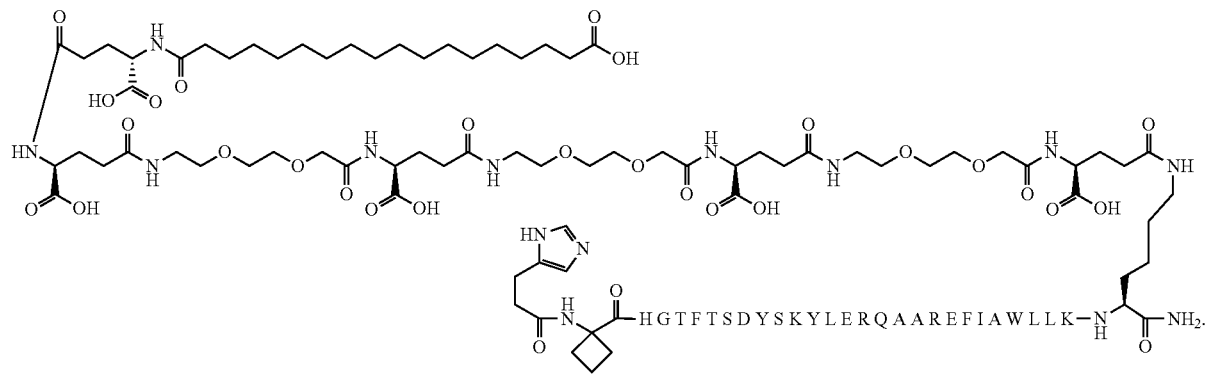

In some embodiments the GLP-1 derivative is $N^{\epsilon 35}$-[(4S)-4-carboxy-4-[[2-[2-[2-[[(4S)-4-carboxy-4-[[2-[2-[2-[[(4S)-4-carboxy-4-[[2-[2-[2-[[(4S)-4-carboxy-4-[[(4S)-4-carboxy-4-(17-carboxyheptadecanoylamino)butanoyl]amino]butanoyl]amino]ethoxy]ethoxy]acetyl]amino]butanoyl]amino]ethoxy]ethoxy]acetyl]amino]butanoyl]amino]ethoxy]ethoxy]acetyl]amino]butanoyl]-[Imp7,Acb8,His9,Tyr16,Lys18,Arg22,Arg23,Arg26,Leu33, Lys35]-GLP-1-(7-35)-peptide amide (SEQ ID NO: 22)

(Chem. 24)

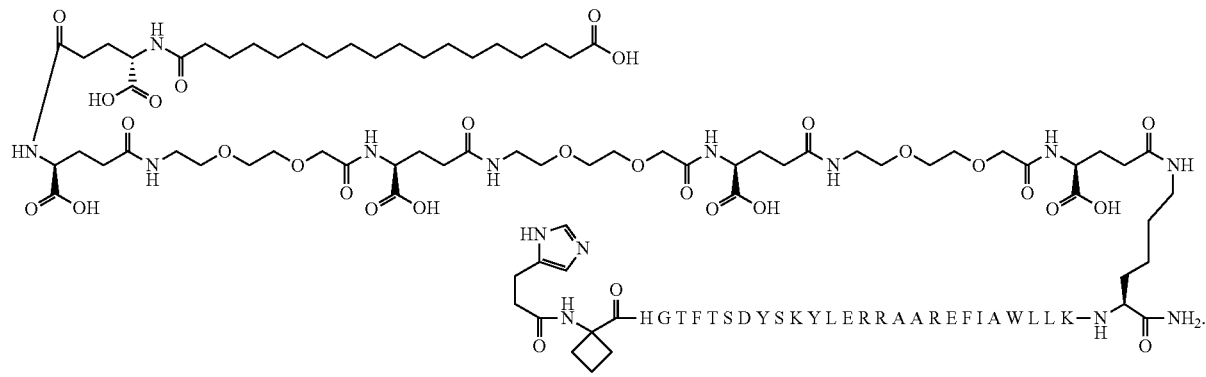

In some embodiments the GLP-1 derivative is $N^{\epsilon 34}$-[2-[[(2S)-2-[[(2S)-4-carboxy-2-[[2-[[(2S)-2-[[(4S)-4-carboxy-4-[[(4S)-4-carboxy-4-(17-carboxyheptadecanoylamino)butanoyl]amino]butanoyl]amino]-3-hydroxypropanoyl]amino]acetyl]amino]butanoyl]amino]-3-hydroxypropanoyl]amino]acetyl]-[Imp7,Aib8,His9,Lys18,Glu22,Arg26,Leu33,Thr35]-GLP-1-(7-35)-peptide (SEQ ID NO: 5)

(Chem. 25)

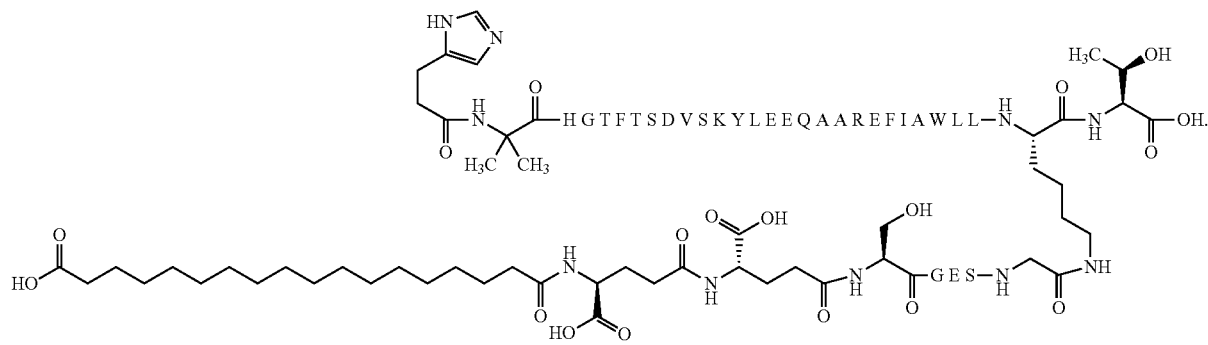

In some embodiments the GLP-1 derivative is $N^{\epsilon 35}$-[(4S)-4-carboxy-4-[[2-[2-[2-[[(4S)-4-carboxy-4-[[2-[2-[2-[[(4S)-4-carboxy-4-[[2-[2-[2-[[(4S)-4-carboxy-4-[[(4S)-4-carboxy-4-(17-carboxyheptadecanoylamino)butanoyl]amino]butanoyl]amino]ethoxy]ethoxy]acetyl]amino]butanoyl]amino]ethoxy]ethoxy]acetyl]amino]butanoyl]amino]ethoxy]ethoxy]acetyl]amino]butanoyl]-[Imp7,Acb8,His9,Tyr16,Lys18,Arg23,Arg26,Leu33,Lys35]-GLP-1-(7-35)-peptide amide (SEQ ID NO: 42)

(Chem. 26)

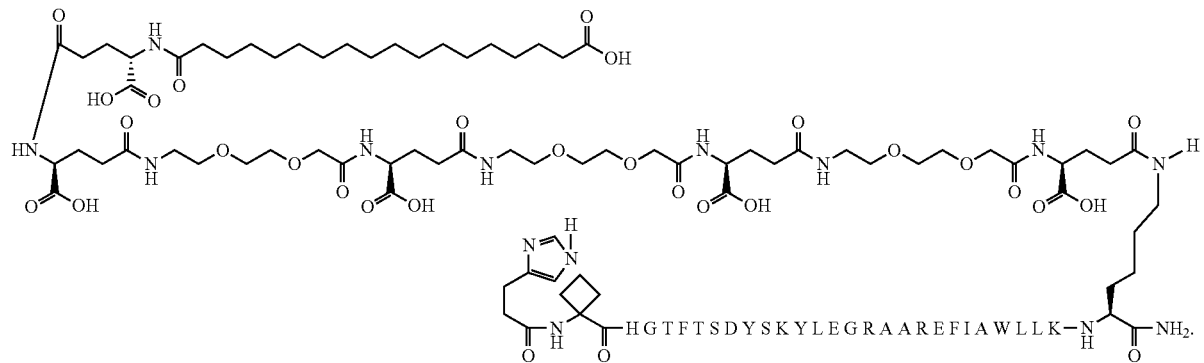

In some embodiments the GLP-1 derivative is N$^{\varepsilon 34}$-[(4S)-4-carboxy-4-[[(4S)-4-carboxy-4-[[(2S)-2-[[2-[[(2S)-4-carboxy-2-[[(2S)-2-[[2-(17-carboxyheptadecanoylamino)acetyl]amino]-3-hydroxypropanoyl]amino]butanoyl]amino]acetyl]amino]-3-hydroxypropanoyl]amino]butanoyl]amino]butanoyl]-[Imp7,Aib8,His9,Lys18,Glu22,Arg26,Leu33,Thr35]-GLP-1-(7-35)-peptide (SEQ ID NO: 5)

(Chem 27)

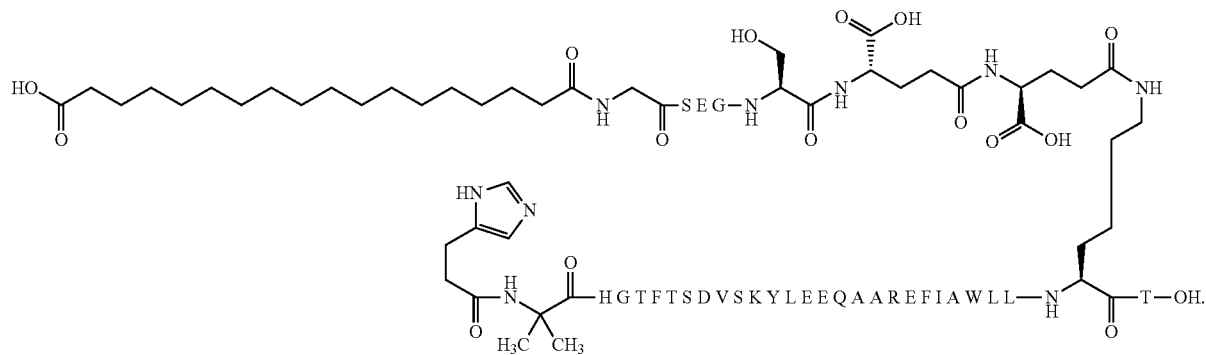

In some embodiments the GLP-1 derivative is N$^{\varepsilon 35}$-[(4S)-4-carboxy-4-[[2-[2-[2-[[(4S)-4-carboxy-4-[[2-[2-[2-[[(4S)-4-carboxy-4-[[2-[2-[2-[[(4S)-4-carboxy-4-[[(4S)-4-carboxy-4-(17-carboxyheptadecanoylamino)butanoyl]amino]butanoyl]amino]ethoxy]ethoxy]acetyl]amino]butanoyl]amino]ethoxy]ethoxy]acetyl]amino]butanoyl]amino]ethoxy]ethoxy]acetyl]amino]butanoyl]-[Imp7,Acb8,His9,Tyr16,Arg18,Arg23,Arg26,Leu33,Arg34,Lys35]-GLP-1-(7-35)-peptide amide (SEQ ID NO: 24)

(Chem. 28)

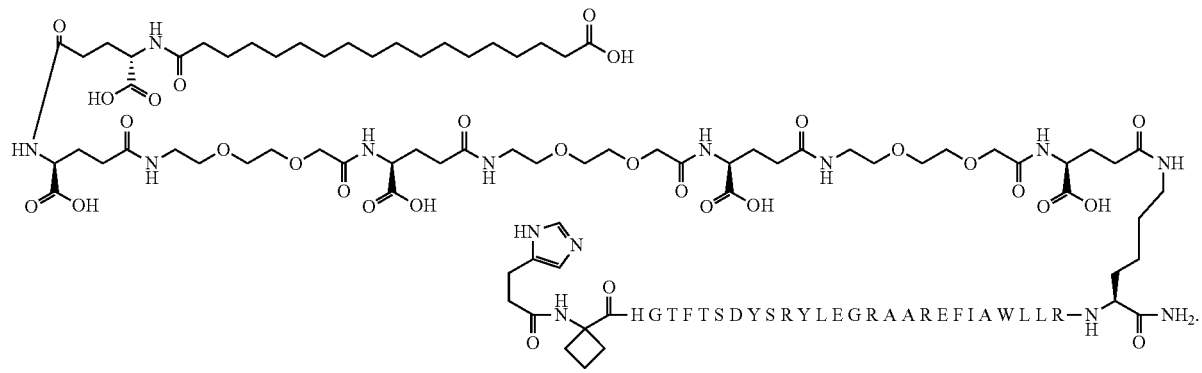

In some embodiments the GLP-1 derivative is $N^{\varepsilon 34}$-[2-[2-[2-[[2-[2-[2-[[(4S)-4-carboxy-4-[[(4S)-4-carboxy-4-[[(4S)-4-carboxy-4-(17-carboxyheptadecanoylamino)butanoyl]amino]butanoyl]amino]butanoyl]amino]ethoxy]ethoxy]acetyl]amino]ethoxy]ethoxy]acetyl]-[Imp7,Aib8,His9,Lys18,Glu22,Arg26,Leu33,Thr35]-GLP-1-(7-35)-peptide (SEQ ID NO: 5)

(Chem. 29)

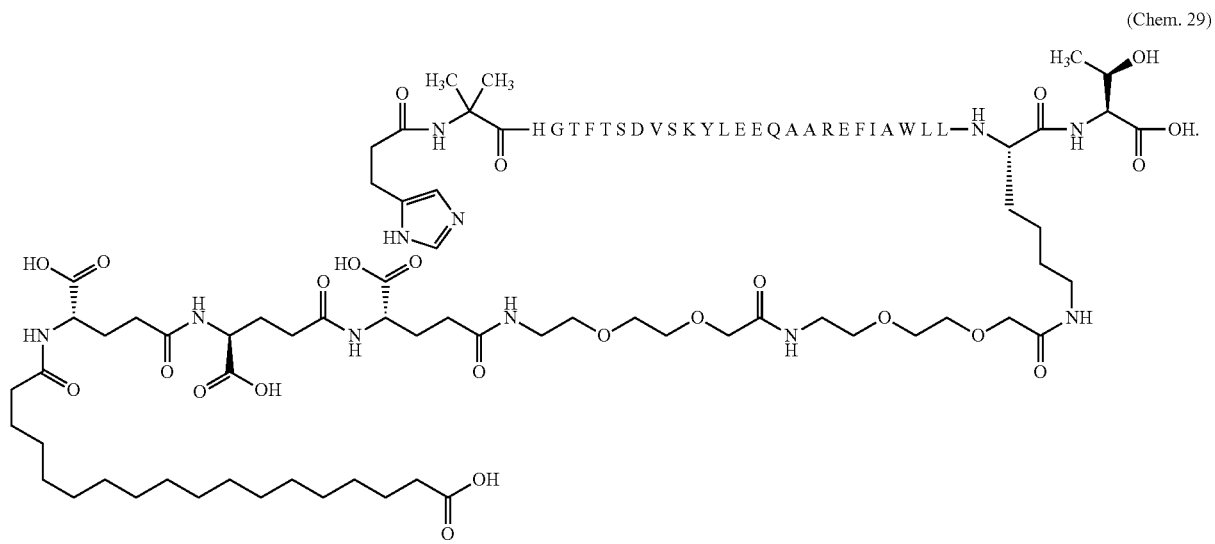

In some embodiments the GLP-1 derivative is $N^{\varepsilon 34}$-[2-[[(2S)-2-[[(2S)-4-carboxy-2-[[2-[[(2S)-2-[[(4S)-4-carboxy-4-[[(4S)-4-carboxy-4-(19-carboxynonadecanoylamino)butanoyl]amino]butanoyl]amino]-3-hydroxypropanoyl]amino]acetyl]amino]butanoyl]amino]-3-hydroxypropanoyl]amino]acetyl]-[Imp7,Aib8,His9,Lys18,Glu22,Arg26,Leu33,Thr35]-GLP-1-(7-35)-peptide amide (SEQ ID NO: 5)

(Chem. 30)

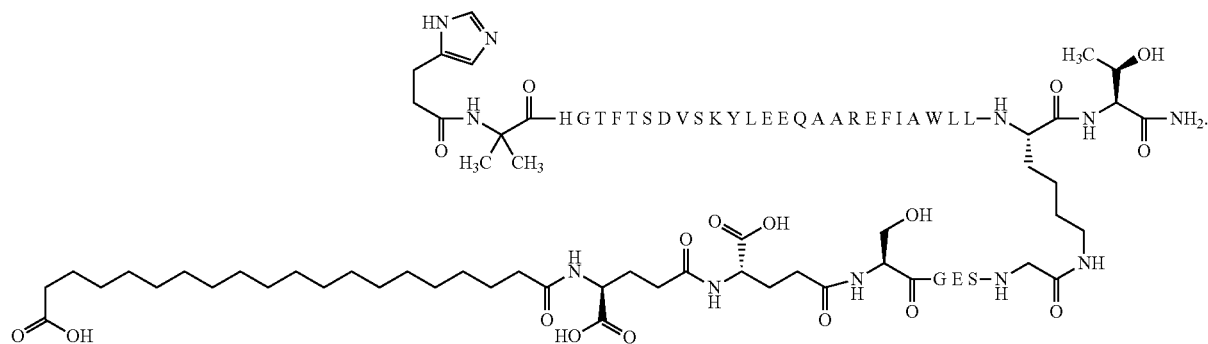

In some embodiments the GLP-1 derivative is $N^{\varepsilon 34}$-[(4S)-4-carboxy-4-[[2-[2-[2-[[2-[2-[2-[[(4S)-4-carboxy-4-[[(4S)-4-carboxy-4-(17-carboxyheptadecanoylamino)butanoyl]amino]butanoyl]amino]ethoxy]ethoxy]acetyl]amino]ethoxy]ethoxy]acetyl]amino]butanoyl]-[Imp7,Aib8,His9,Lys18,Ala22,Arg23,Arg26,Leu33,Gly36]-GLP-1-(7-37)-peptide (SEQ ID NO: 25)

(Chem. 31)

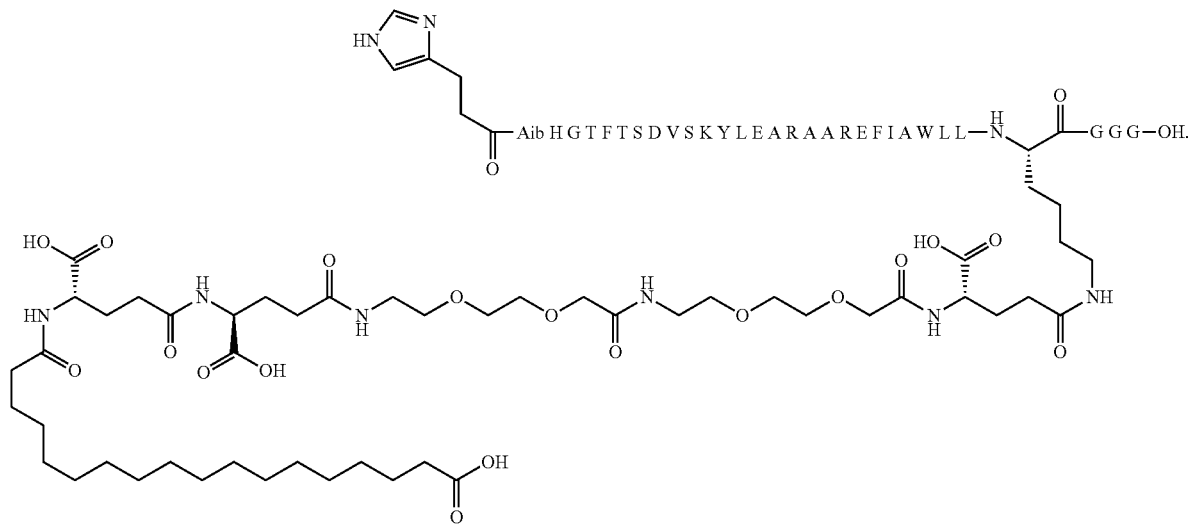

In some embodiments the GLP-1 derivative is $N^{\epsilon 22}$-[(4S)-4-carboxy-4-[[(4S)-4-carboxy-4-[[2-[2-[2-[[2-[2-[2-[[(4S)-4-carboxy-4-(17-carboxyheptadecanoylamino)butanoyl]amino]ethoxy]ethoxy]acetyl]amino]ethoxy]ethoxy]acetyl]amino]butanoyl]amino]butanoyl]-[Imp7,Acb8,His9,Lys18,Lys22,Arg23,Arg26,Leu33,Thr35]-GLP-1-(7-35)-peptide amide (SEQ ID NO: 26)

(Chem. 32)

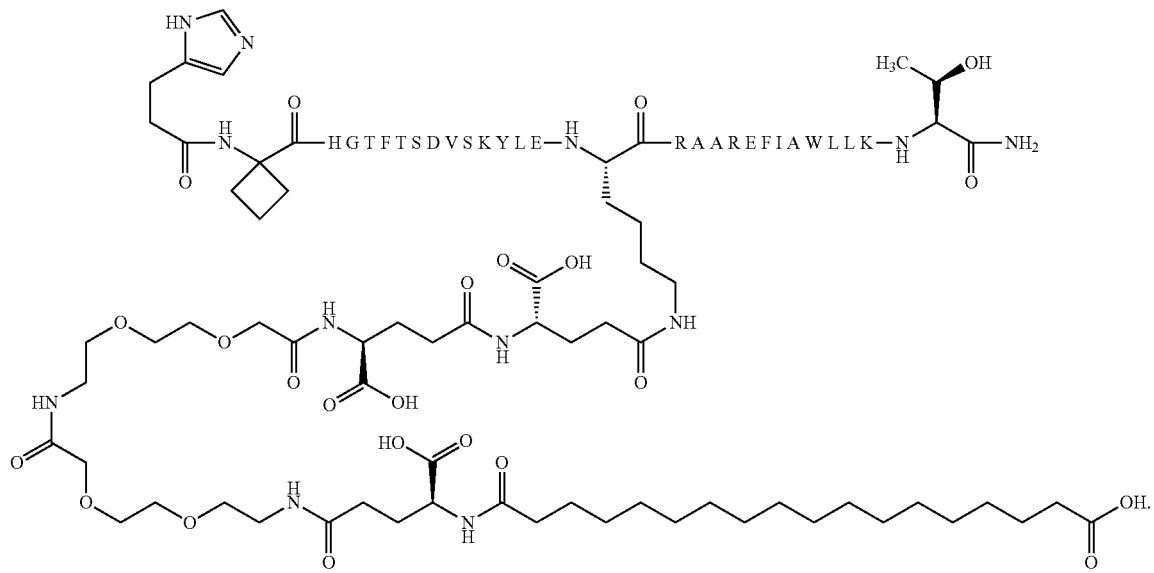

In some embodiments the GLP-1 derivative is $N^{\epsilon 22}$-[(4S)-4-carboxy-4-[[(4S)-4-carboxy-4-[[2-[2-[2-[[2-[2-[2-[[(4S)-4-carboxy-4-(17-carboxyheptadecanoylamino)butanoyl]amino]ethoxy]ethoxy]acetyl]amino]ethoxy]ethoxy]acetyl]amino]butanoyl]amino]butanoyl]-[Imp7,Acb8,His9,Lys18,Lys22,Arg26,Leu33,Thr35]-GLP-1-(7-35)-peptide amide (SEQ ID NO: 27)

(Chem. 33)

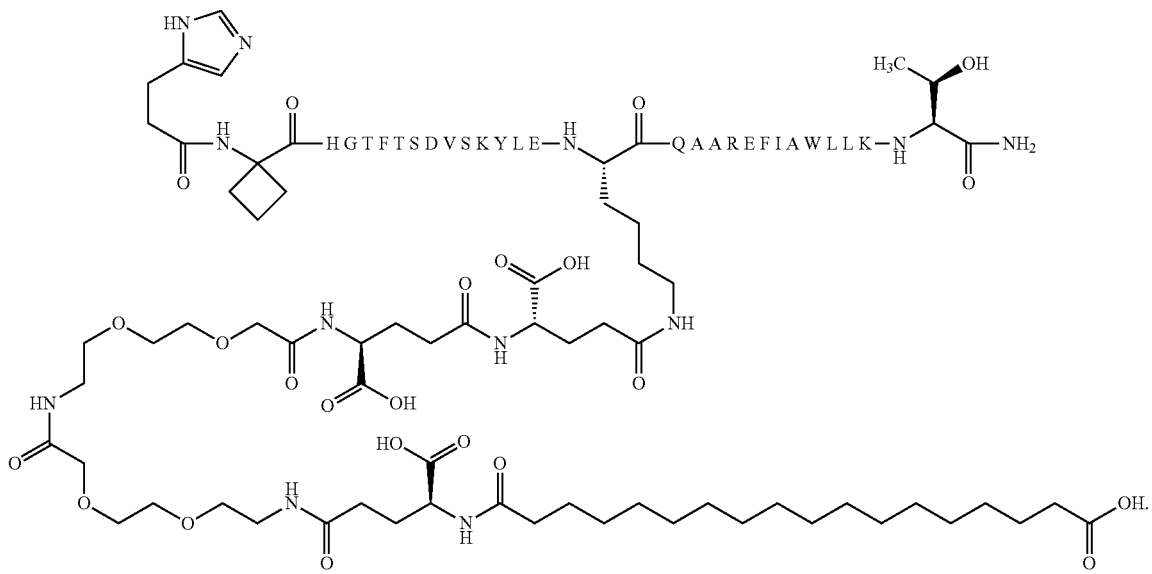

In some embodiments the GLP-1 derivative is N^ε34-[(4S)-4-carboxy-4-[[(4S)-4-carboxy-4-[[2-[2-[2-[[(4S)-4-carboxy-4-[[(4S)-4-carboxy-4-(17-carboxyheptadecanoylamino)butanoyl]amino]butanoyl]amino]ethoxy]ethoxy]acetyl]amino]butanoyl]amino]butanoyl]-[Imp7,Aib8,His9,Lys18,Ala22,Arg26,Leu33,Thr35]-GLP-1-(7-35)-peptide amide (SEQ ID NO: 28)

(Chem. 34)

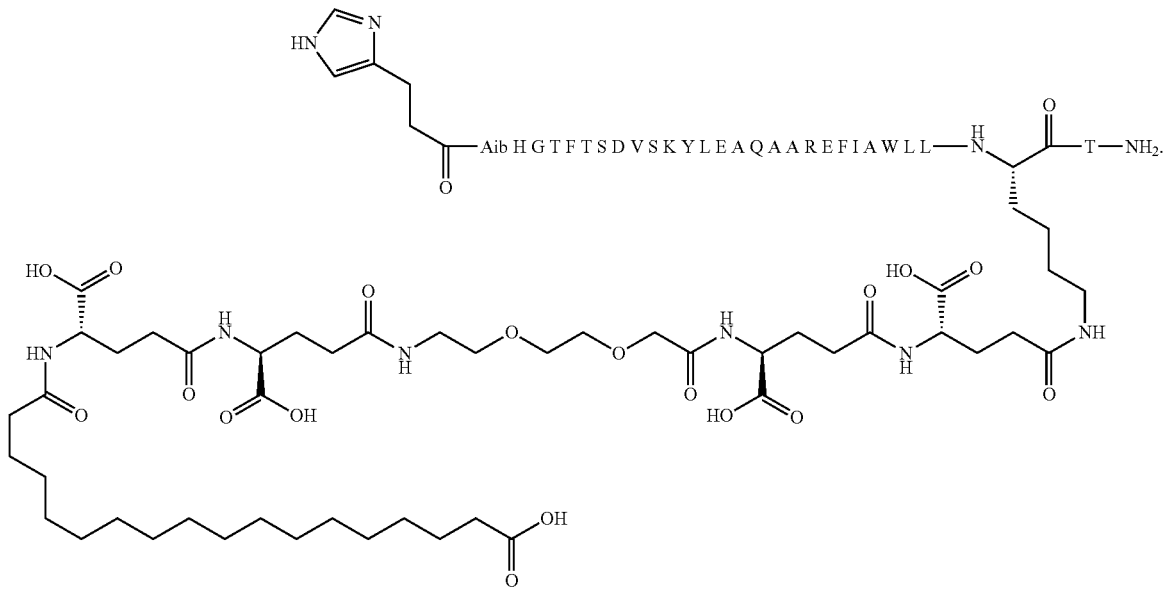

In some embodiments the GLP-1 derivative is N^ε34-[(4S)-4-carboxy-4-[[(4S)-4-carboxy-4-[[2-[2-[2-[[(4S)-4-carboxy-4-[[(4S)-4-carboxy-4-(17-carboxyheptadecanoylamino)butanoyl]amino]butanoyl]amino]ethoxy]ethoxy]acetyl]amino]butanoyl]amino]butanoyl]-[Imp7,Aib8,His9,Arg18,Arg23,Arg26,Leu33,Ala36]-GLP-1-(7-37)-peptide (SEQ ID NO: 29)

(Chem. 35)

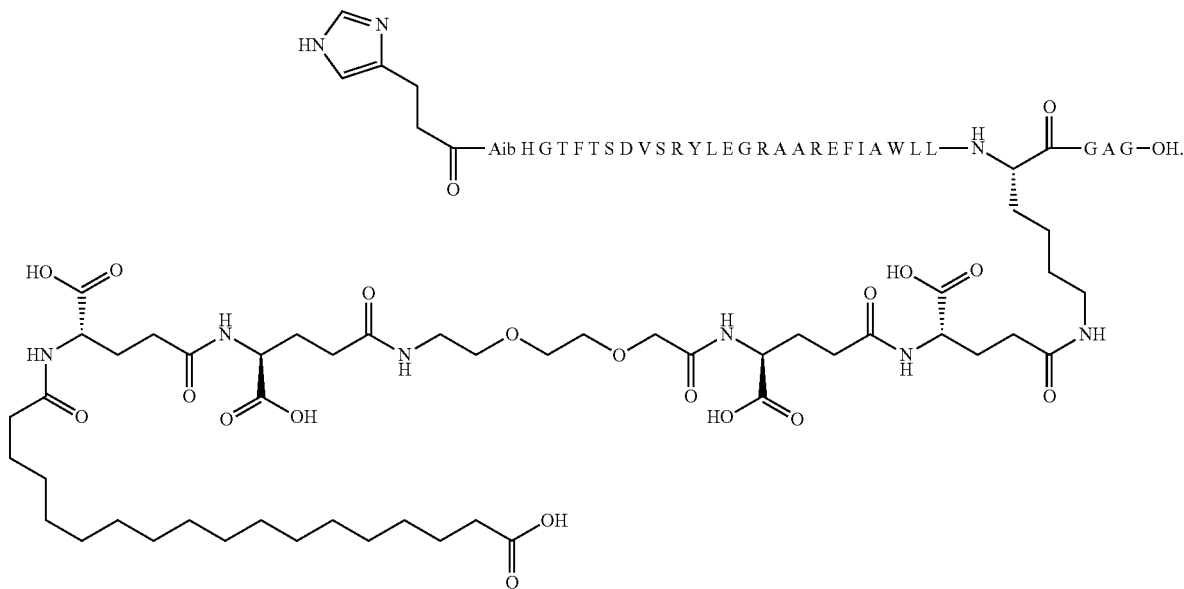

In some embodiments the GLP-1 derivative is $N^{\epsilon 34}$-[(4S)-4-carboxy-4-[[(4S)-4-carboxy-4-[[2-[2-[2-[[(4S)-4-carboxy-4-[[(4S)-4-carboxy-4-(17-carboxyheptadecanoylamino)butanoyl]amino]butanoyl]amino]ethoxy]ethoxy]acetyl]amino]butanoyl]amino]butanoyl]-[Imp7,Aib8,His9,Arg18,Arg23,Arg26,Leu33,Ser36]-GLP-1-(7-37)-peptide (SEQ ID NO: 30)

(Chem. 36)

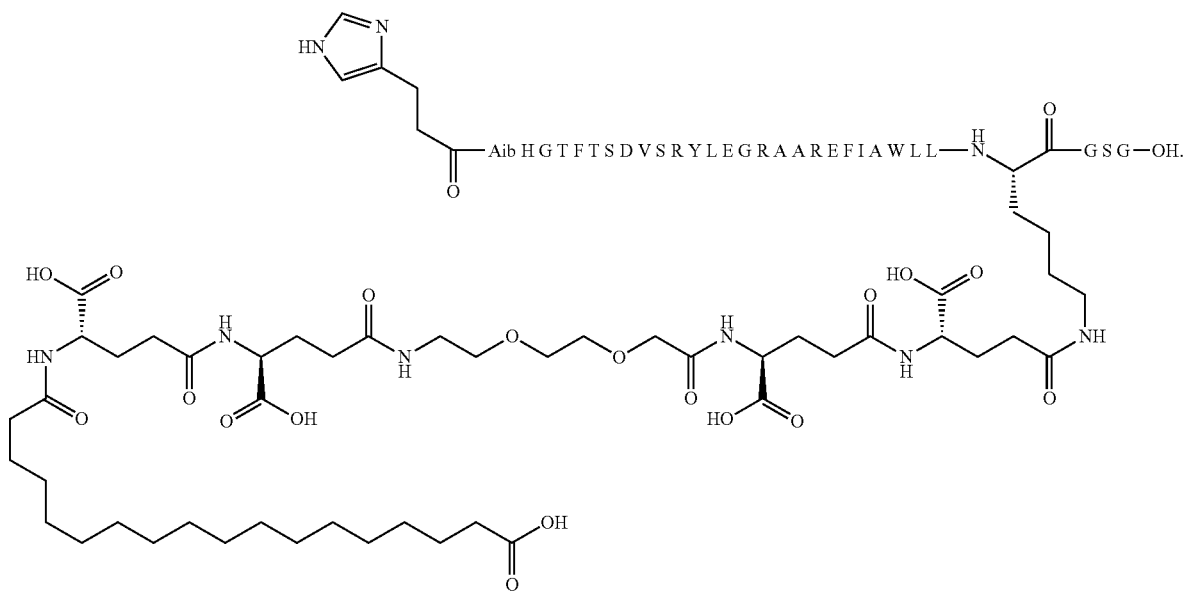

In some embodiments the GLP-1 derivative is $N^{\epsilon 34}$-[2-[[(2S)-2-[[(2S)-4-carboxy-2-[[2-[[(2S)-2-[[(4S)-4-carboxy-4-[[(4S)-4-carboxy-4-(17-carboxyheptadecanoylamino)butanoyl]amino]butanoyl]amino]-3-hydroxypropanoyl]amino]acetyl]amino]butanoyl]amino]-3-hydroxypropanoyl]amino]acetyl]-[Imp7,Gly8,His9,Arg18,Glu22,Arg26,Leu33,Thr35]-GLP-1-(7-35)-peptide amide (SEQ ID NO: 31)

(Chem. 37)

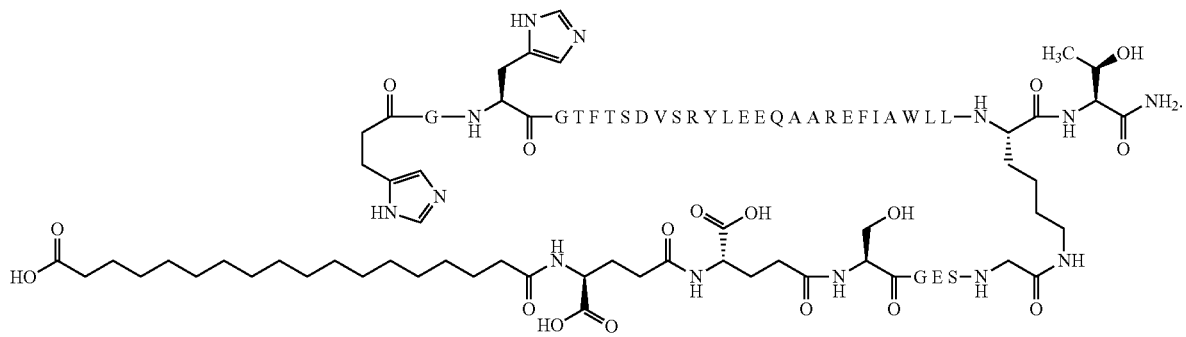

In some embodiments the GLP-1 derivative is N$^{\epsilon 34}$-[2-[2-[2-[[2-[2-[2-[[(4S)-4-carboxy-4-[[(4S)-4-carboxy-4-(17-carboxytridecanoylamino)butanoyl]amino]butanoyl]amino]ethoxy]ethoxy]acetyl]amino]ethoxy]ethoxy]acetyl]-[Imp7,Aib8,His9,Lys18,Glu22,Arg26,Leu33,Thr35]-GLP-1-(7-35)-peptide amide (SEQ ID NO: 5)

(Chem. 38)

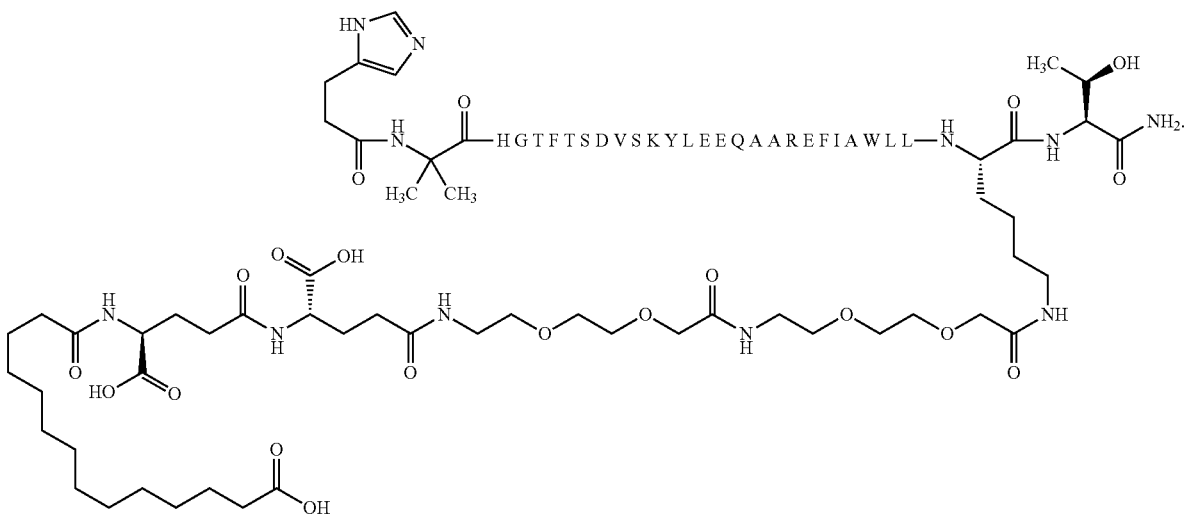

In some embodiments the GLP-1 derivative is N$^{\epsilon 34}$-[2-[2-[2-[[2-[2-[2-[[(4S)-4-carboxy-4-[[(4S)-4-carboxy-4-(15-carboxypentadecanoylamino)butanoyl]amino]butanoyl]amino]ethoxy]ethoxy]acetyl]amino]ethoxy]ethoxy]acetyl]-[Imp7,Aib8,His9,Lys18,Glu22,Arg26,Leu33,Thr35]-GLP-1-(7-35)-peptide amide (SEQ ID NO: 5)

(Chem. 39)

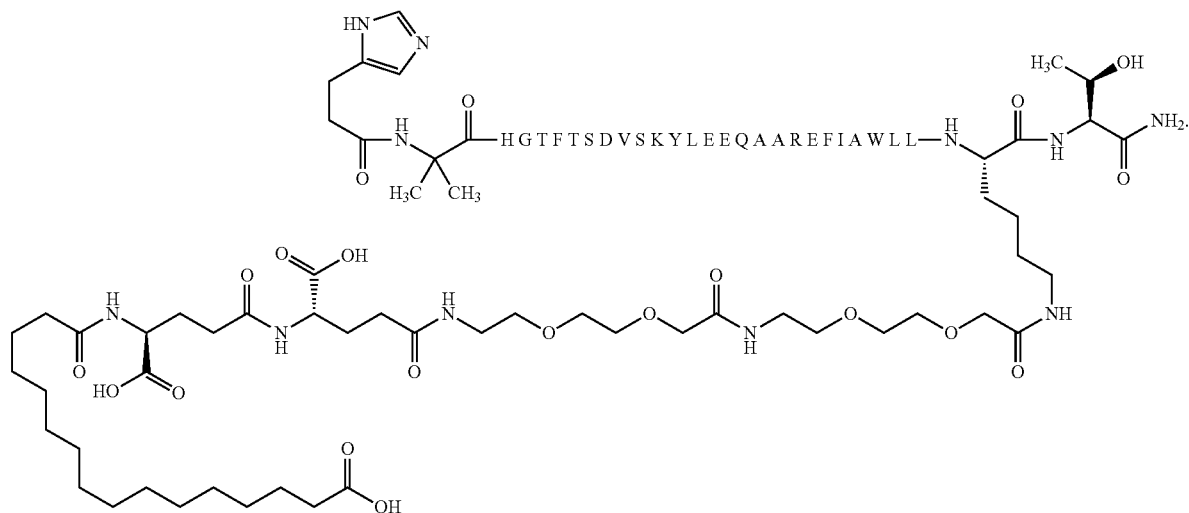

In some embodiments the GLP-1 derivative is $N^{\varepsilon 34}$-[2-[2-[2-[[2-[2-[2-[[(4S)-4-carboxy-4-[[(4S)-4-carboxy-4-(19-carboxynonadecanoylamino)butanoyl]amino]butanoyl]amino]ethoxy]ethoxy]acetyl]amino]ethoxy]ethoxy]acetyl]-[Imp7,Aib8,His9,Lys18,Glu22,Arg26,Leu33,Thr35]-GLP-1-(7-35)-peptide amide (SEQ ID NO: 5)

(Chem. 40)

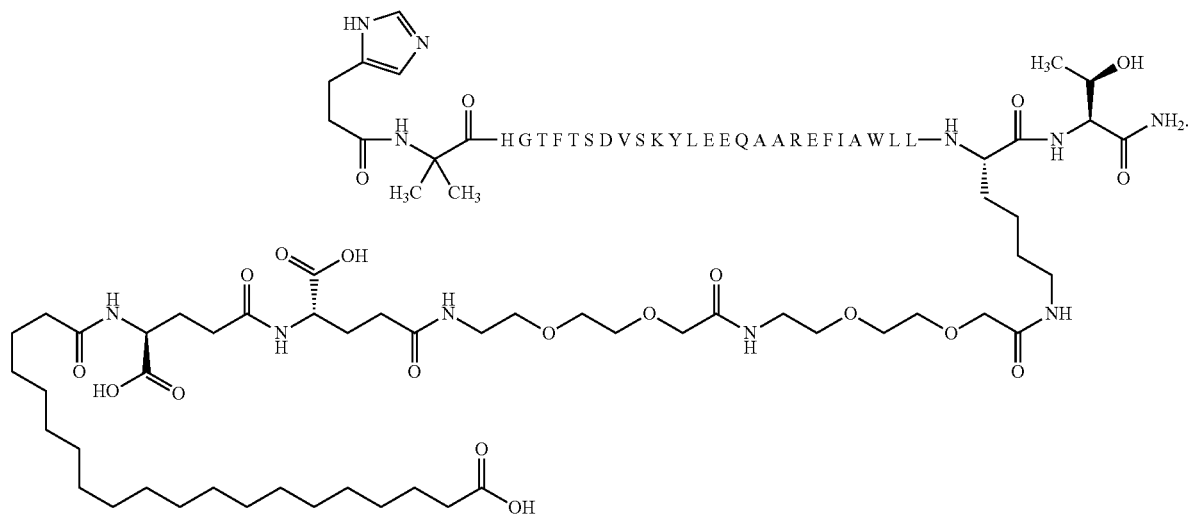

In some embodiments the GLP-1 derivative is $N^{\varepsilon 34}$-[2-[2-[2-[[2-[2-[2-[[(4S)-4-carboxy-4-[[(4S)-4-carboxy-4-(17-carboxyheptadecanoylamino)butanoyl]amino]butanoyl]amino]ethoxy]ethoxy]acetyl]amino]ethoxy]ethoxy]acetyl]-[Imp7,Aib8,His9,Leu16,Lys18,Glu22,Arg26,Leu33,Thr35]-GLP-1-(7-35)-peptide amide (SEQ ID NO: 32)

(Chem. 41)

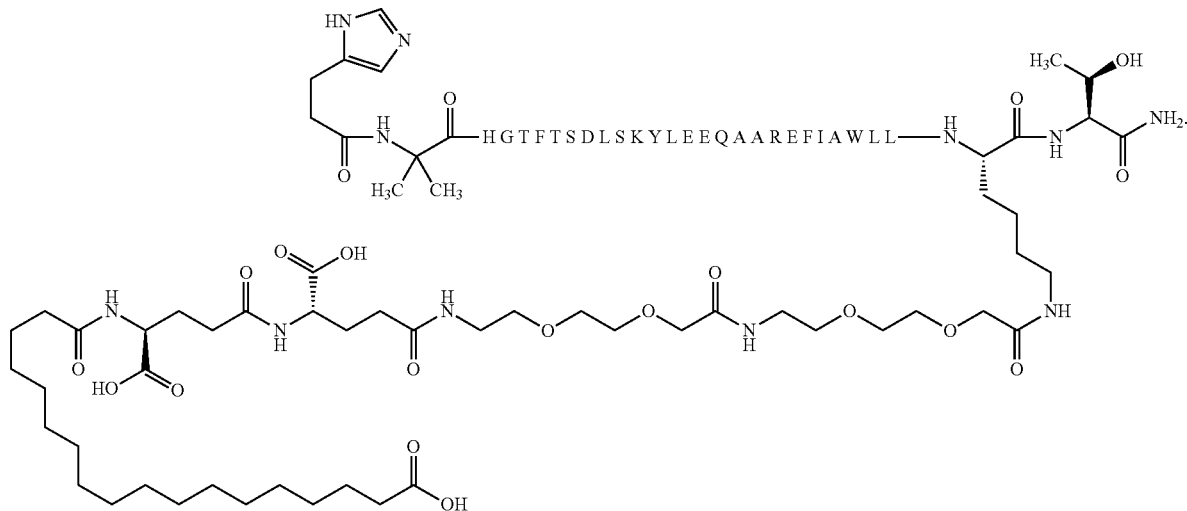

In some embodiments the GLP-1 derivative is N$^{ε34}$-[2-[2-[2-[[2-[2-[2-[[(4S)-4-carboxy-4-[[(4S)-4-carboxy-4-(17-carboxyheptadecanoylamino)butanoyl]amino]butanoyl]amino]ethoxy]ethoxy]acetyl]amino]ethoxy]ethoxy]acetyl]-[Imp7,Aib8,His9,Lys18,Glu22,Arg26,Ile33,Thr35]-GLP-1-(7-35)-peptide amide (SEQ ID NO: 43)

Fmoc-Phe-OH, Fmoc-Pro-OH, Fmoc-Ser(tBu)-OH, Fmoc-Thr(tBu)-OH, Fmoc-Trp(BOC)-OH, Fmoc-Tyr(tBu)-OH, Fmoc-Val-OH, Fmoc-Lys(Mtt)-OH, or Fmoc-Lys(Alloc)-OH supplied from e.g. Anaspec, Bachem, Iris Biotech or NovabioChem. 3-(N-1-Trityl-imidazol-4-yl)-propionic acid is used for incorporating Imp.

(Chem. 42)

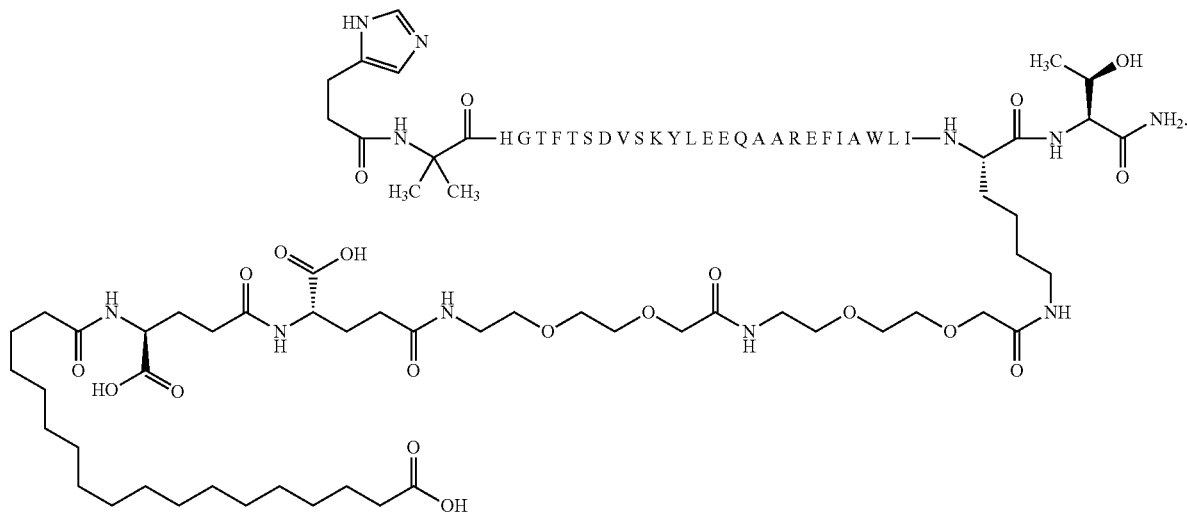

Preparation of Derivatives of GLP-1 Analogues

The derivative of the invention may be prepared by the method described below.

SPPS General Methods

The Fmoc-protected amino acid derivatives to be used may be the standard recommended: Fmoc-Ala-OH, Fmoc-Arg(Pbf)-OH, Fmoc-Asn(Trt)-OH, Fmoc-Asp(OtBu)-OH, Fmoc-Cys(Trt)-OH, Fmoc-Gln(Trt)-OH, Fmoc-Glu(OtBu)-OH, Fmoc-Gly-OH, Fmoc-His(Trt)-OH, Fmoc-Ile-OH, Fmoc-Leu-OH, Fmoc-Lys(BOC)-OH, Fmoc-Met-OH, SPPS may be performed using Fmoc based chemistry on a Prelude Solid Phase Peptide Synthesizer from Protein Technologies (Tucson, Ariz. 85714 U.S.A.). A suitable resin for the preparation of C-terminal carboxylic acids is a Wang resin preloaded with an amino acid such as Fmoc-Thr(tBu)-Wang resin (Low Load, 0.35 mmol/g). In cases where the substituent is attached to the C-terminal lysine, a suitable resin is a pre-loaded Fmoc-Lys(Mtt)-Wang. A suitable resin for the preparation of C-terminal peptide amides is H-Rink Amide-ChemMatrix resin (loading e.g. 0.52 nmol/g) or Rink Amide AM polystyrene resin (Novabiochem, loading e.g. 0.62 mmol/g) or the like. Fmoc-deprotection is achieved with 20% piperidine in NMP. Peptide couplings are performed by using either DIC/HOAt/collidine or DIC/Oxyma Pure with or without collidine with or without preactivation or using DEPBt (3-(diethoxyphosphoryloxy)-1,2,3-benzotriazin-4(3H)-one)/DIPEA for suppression of epimization of eg. His during coupling. Amino acid/HOAt or amino acid/Oxyma Pure solutions (0.3 M/0.3 M in NMP at a molar excess of 3-10 fold) are added to the resin followed by the same molar equivalent of DIC (3 M in NMP) followed by collidine (3 M in NMP). For example, the following amounts of 0.3 M amino acid/HOAt solution can be used per coupling for the following scale reactions: Scale/mL, 0.05 mmol/1.5 mL, 0.10 mmol/3.0 mL, 0.25 mmol/7.5 mL.

If Fmoc-Lys(Mtt)-OH is used, the Mtt group may be removed by washing the resin with HFIP/DCM (75:25) (2×2 min), washing with DCM and suspending the resin in HFIP/DCM (75:25)(2×20 min) and subsequently washed before the substituent can be introduced at the epsilon-position of the lysine moiety.

If Fmoc-Lys(Alloc)-OH is used, the Alloc group may be removed by treating the resin with Pd(PPh$_3$)$_4$ (0.02 equiv) in the presence of one or more scavengers in combination, eg. morpholine (6.0 equiv) and/or dimethyl borane complex (18.0 equiv) (30 min). The resin is then washed with MeOH, NMP or DMF and IPA (isopropyl alcohol), respectively, before the substituent can be introduced at the epsilon-position of the lysine moiety.

Synthesis of Imp (desaminoHis(Trt)-OH)

Imp (desaminoHis) may be synthesized from urocanic acid in a three-step procedure affording the free acid of Imp with a trityl protection (desaminoHis(Trt)-OH) (see Scheme below).

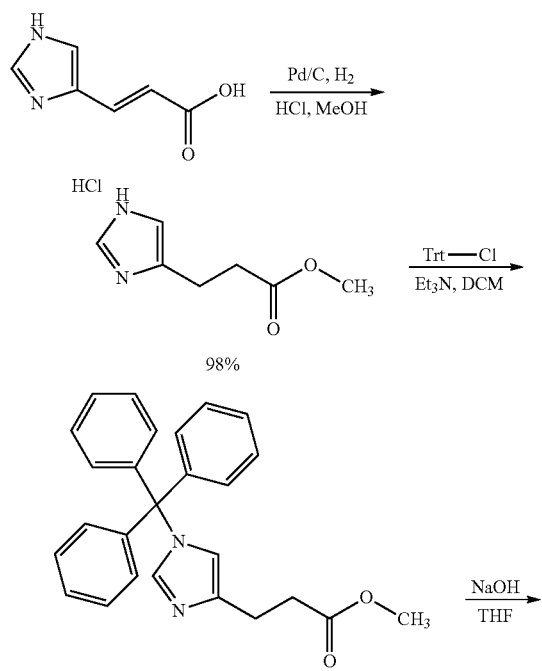

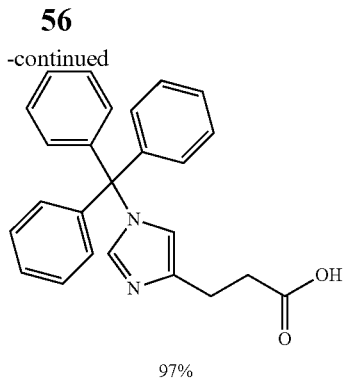

97%

An exemplary Imp synthesized using the three-step procedure is provided:

Step 1: Palladium on carbon (10%, 150 g, 1.41 mol) was added to a solution of urocanic acid (1, 1.01 kg, 7.33 mol) in MeOH (5.50 L), water (5.50 L) and 35% HCl (752 mL, 8.59 mol) and the resulting mixture was hydrogenated at normal pressure for 4 days. Conversion of the reaction was monitored by $^1$H NMR. The catalyst was filtered off after completion and the filtrate was evaporated to dryness. The residue was re-dissolved in MeOH (7.00 L) and 2.2 M solution of HCl in MeOH (500 mL) was added and stirred for 16 hours at 45° C. The solvents were removed by evaporation to dryness. MeOH (10.0 L) and HCl (47.0 g) in MeOH (1.00 L) were added and stirred overnight at 45° C. The mixture was evaporated to dryness to give pure 3-(1H-imidazol-4-yl)-propionic acid methyl ester hydrochloride (2) as off-white solid. Yield: 1.37 kg (98%). $^1$H NMR (300 MHz, MeOD-d$_4$) δ 7.40-7.28 (m, 10H); 7.19-7.07 (m, 6H); 6.55 (s, 1H); 3.63 (s, 3H); 2.94-2.83 (m, 2H); 2.71-2.62 (m, 2H).

Step 2: Trityl chloride (Trt-OH) (2.04 Kg, 7.33 mol) was added to a solution of the above product (2, 1.37 kg, 7.20 mol) in dry DCM (25.2 L) and Et$_3$N (2.62 L, 18.7 mol) was added. The mixture was stirred at 23° C. overnight. The resulting solution was washed with water (15.0 L), aqueous phase was extracted again with DCM (2.50 L). Combined organic phases were washed with 10% aqueous solution of citric acid (10.0 L) and aqueous phase was extracted again with DCM (2.50 L). Combined organic phases were washed with water (10.0 L) and aqueous phase was extracted again with DCM (2.50 L). Combined organic phases were dried over anhydrous magnesium sulfate and evaporated to dryness to give 3-(1-trityl-1H-imidazol-)-propionic acid methyl ester (3) as white solid.

Step 3: A solution of NaOH (570 g, 14.3 mol) in water (5.00 L) was added to a solution of the above ester (3) in THF (20.0 L); the resulting mixture was stirred at 23° C. overnight. Aqueous solution of citric acid (10%, 15.0 L) was added to the residue and the mixture was extracted with DCM (3×5.00 L). Combined organic extracts were washed with water (2×5.00 L), dried over anhydrous magnesium sulfate and evaporated to obtain crystalline material. The residue was suspended in DCM (2.50 L) and cyclohexane (10.0 L) was added. The solid was filtered, washed with cyclohexane (7.00 L). Product contained 0.34% of by-product, so the solid was suspended in MeOH (20.0 L) and filtered. Solid was dried on air and re-dissolved in refluxing DCM (10.0 L) and the solvent was removed by evaporation. Solid was homogenized to give a title product (4) as white powder. Yield: 2679.2 g (97%). $^1$H NMR spectrum (300 MHz, CDCl$_3$) δ 10.49 (bs, 1H); 7.48 (s, 1H); 7.41-7.28 (m, 9H); 7.18-7.05 (m, 6H); 6.60 (s, 1H); 2.93-2.81 (m, 2H); 2.77-2.65 (m, 2H). LC-MS purity: 100% (ELSD). LC-MS R$_t$ (Kinetex C18, 4.6 mm×50 mm, MeCN/water 20:80 to 100:0+0.1% FA): 2.82 min. LC-MS m/z: 383.2 (M+H)$^+$. m.p.: 190-191° C. UPLC purity: 99.74% (214 nm). UPLC R$_t$ (Acquity UPLC BEHC18, 1.7 um, 2.1×150 mm, 40° C., MeCN/water 05:95 to 100:0+0.05% TFA, 6 min.): 2.512 min. Endotoxin level: <0.06 EU/mL (estimated by Limulus Amebocyte Lysate PYROGENT Plus test using a solution of 1 mg of compound in 10% aqueous DMSO).

Attachment of the Substituent

The substituent can be introduced in a stepwise procedure by the Prelude peptide synthesizer as described above using suitably protected building blocks, such as the standard amino acids described above, Fmoc-8-amino-3,6-dioxaoctanoic acid and Fmoc-Glu-OtBu. Introduction of the fatty acid moiety can be achieved using a building block, such as, but not limited to, octadecanedioic acid mono-tert-butyl-ester. After each coupling step, unreacted peptide intermediate can be capped using acetic acid anhydride and collidine in excess (>10 eq.).

After each coupling step, unreacted peptide intermediate can be capped using acetic acid anhydride and collidine in excess (>10 eq.).

The introduction of a substituent on the epsilon-nitrogen of a lysine is achieved using a lysine protected with Mtt (Fmoc-Lys(Mtt)-OH), Alloc (Fmoc-Lys(Alloc)-OH) or an ivDde group (Fmoc-Lys(ivDde)-OH). The incorporation of γGlu moieties in the substituent may be achieved by coupling with the amino acid Fmoc-Glu-OtBu.

Introduction of each moiety in the substituent can be achieved using prolonged coupling time (1×6 hours) followed by capping with acetic anhydride or alternatively acetic acid/DIC/HOAt/collidine.

Cleavage from the Resin

After synthesis the resin is washed with DCM, and the peptide is cleaved from the resin by a 2-3 hour treatment with TFA/TIPS/water (95/2.5/2.5) or TFA/EDT (1,2-ethanedithiol)/water (90/5/5) followed by precipitation with $Et_2O$ (diethyl ether) or IPE (diisopropyl ether). The precipitate is then washed with the solvent used.

Purification and Quantification

The crude peptide is dissolved in a suitable mixture of water and MeCN, such as water/MeCN (4:1) or water/AcOH (1:1) at 60° C. for 1 hour, and purified by reversed-phase preparative HPLC (Waters Deltaprep 4000 or Gilson) on a column comprising C8- or C18-silica gel. Elution is performed with an increasing gradient of MeCN in water comprising 0.1% TFA. Relevant fractions are checked by analytical HPLC or UPLC. Fractions comprising the pure target peptide are mixed and concentrated under reduced pressure. An additional purification step may be introduced using another gradient, eg. containing 0.05M $NH_4HCO_3$. The resulting solution is analyzed (HPLC, LCMS) and the product (i.e. the derivative) is quantified using a chemiluminescent nitrogen specific HPLC detector (Antek 8060 HPLC-CLND) or by measuring UV-absorption at 280 nm. The product is dispensed into glass vials. The vials are capped with Millipore glassfibre prefilters. Freeze-drying affords the peptide trifluoroacetate as a white solid.

In some embodiments, the peptide trifluoroacetate may be changed into the sodium salt by column ion exchange eg. with NaOAc in MeCN. Alternatively, the peptide trifluoroacetate may be changed to the ammonium salt by column chromatography eg. with a gradient containing 0.05M $NH_4HCO_3$, followed by freeze-drying and suspension in water. In some embodiments, the peptide is then changed into the sodium salt by addition of 1M NaOH (equiv according to basic/acidic residues) turning the suspension clear. Finally, the peptide sodium salt may be isolated by freeze-drying.

Intermediate Products

In some embodiments the invention relates to an intermediate product in the form of a GLP-1 analogue selected from the group consisting of:

[Imp7,Acb8,His9,Tyr16,Lys18,Glu22,Arg26,Leu33,Lys35]-GLP-1-(7-35)-peptide amide; (SEQ ID NO: 3)
[Imp7,Acb8,His9,Lys18,Glu22,Arg26,Leu33,Lys35]-GLP-1-(7-35)-peptide amide; (SEQ ID NO: 4)
[Imp7,Aib8,His9,Lys18,Glu22,Arg26,Leu33,Thr35]-GLP-1-(7-35)-peptide amide; (SEQ ID NO: 5)
[Imp7,Aib8,His9,Arg18,Glu22,Arg26,Leu33,Thr35]-GLP-1-(7-35)-peptide amide; (SEQ ID NO: 7)
[Imp7,Aib8,His9,Arg18,Arg26,Leu33,Thr35]-GLP-1-(7-35)-peptide amide; (SEQ ID NO: 8)
[Imp7,Acb8,His9,Lys18,Glu22,Arg26,Leu33,Thr35]-GLP-1-(7-35)-peptide amide; (SEQ ID NO: 9)
[Imp7,His9,Lys18,Arg23,Arg26,Leu33,Thr35]-GLP-1-(7-35)-peptide amide; (SEQ ID NO: 10)
[Imp7,His9,Lys18,Arg23,Arg26,Leu33,Gly36]-GLP-1-(7-37)-peptide; (SEQ ID NO: 38)
[Imp7,Aib8,His9,Lys18,Lys22,Arg26,Leu33,Gly36]-GLP-1-(7-37)-peptide; (SEQ ID NO: 39)
[Imp7,Aib8,His9,Tyr16,Lys18,Glu22,Arg26,Leu33,Lys36]-GLP-1-(7-37)-peptide; (SEQ ID NO: 13)
[Imp7,Aib8,His9,Lys18,Lys23,Arg26,Leu33,Thr35]-GLP-1-(7-35)-peptide amide; (SEQ ID NO: 14)
[Imp7,Aib8,His9,Tyr16,Lys18,Lys23,Arg26,Leu33,Thr35]-GLP-1-(7-35)-peptide amide; (SEQ ID NO: 15)
[Imp7,His9,Arg18,Arg23,Arg26,Leu33]-GLP-1-(7-34)-peptide; (SEQ ID NO: 40)
[Imp7,His9,Arg18,Glu22,Arg26,Lys27,Leu33,Arg34]-GLP-1-(7-34)-peptide; (SEQ ID NO: 17)
[Imp7,Aib8,His9,Arg18,Glu22,Arg26,Lys27,Leu33,Arg34]-GLP-1-(7-34)-peptide; (SEQ ID NO: 41)
[Imp7,Acb8,His9,Lys18,Arg23,Arg26,Leu33,Thr35]-GLP-1-(7-35)-peptide amide; (SEQ ID NO: 19)
[Imp7,Acb8,His9,Tyr16,Lys18,Glu22,Arg26,Leu33,Lys35]-GLP-1-(7-35)-peptide amide; (SEQ ID NO: 3)
[Imp7,Acb8,His9,Tyr16,Arg18,Glu22,Arg26,Leu33,Arg34,Lys35]-GLP-1-(7-35)-peptide amide; (SEQ ID NO: 20)
[Imp7,Acb8,His9,Tyr16,Lys18,Arg22,Arg26,Leu33,Lys35]-GLP-1-(7-35)-peptide amide; (SEQ ID NO: 21)
[Imp7,Acb8,His9,Tyr16,Lys18,Arg22,Arg23,Arg26,Leu33,Lys35]-GLP-1-(7-35)-peptide amide; (SEQ ID NO: 22)
[Imp7,Aib8,His9,Lys18,Glu22,Arg26,Leu33,Thr35]-GLP-1-(7-35)-peptide; (SEQ ID NO: 5)
[Imp7,Acb8,His9,Tyr16,Lys18,Arg23,Arg26,Leu33,Lys35]-GLP-1-(7-35)-peptide amide; (SEQ ID NO: 23)
[Imp7,Acb8,His9,Tyr16,Arg18,Arg23,Arg26,Leu33,Arg34,Lys35]-GLP-1-(7-35)-peptide amide; (SEQ ID NO: 24)
[Imp7,Aib8,His9,Lys18,Glu22,Arg26,Leu33,Thr35]-GLP-1-(7-35)-peptide; (SEQ ID NO: 5)
[Imp7,Aib8,His9,Lys18,Ala22,Arg23,Arg26,Leu33,Gly36]-GLP-1-(7-37)-peptide; (SEQ ID NO: 25)
[Imp7,Acb8,His9,Lys18,Lys22,Arg23,Arg26,Leu33,Thr35]-GLP-1-(7-35)-peptide amide; (SEQ ID NO: 26)
[Imp7,Acb8,His9,Lys18,Lys22,Arg26,Leu33,Thr35]-GLP-1-(7-35)-peptide amide; (SEQ ID NO: 27)
[Imp7,Aib8,His9,Lys18,Ala22,Arg26,Leu33,Thr35]-GLP-1-(7-35)-peptide amide; (SEQ ID NO: 28)
[Imp7,Aib8,His9,Arg18,Arg23,Arg26,Leu33,Ala36]-GLP-1-(7-37)-peptide; (SEQ ID NO: 29)
[Imp7,Aib8,His9,Arg18,Arg23,Arg26,Leu33,Ser36]-GLP-1-(7-37)-peptide; (SEQ ID NO: 30)
[Imp7,Gly8,His9,Arg18,Glu22,Arg26,Leu33,Thr35]-GLP-1-(7-35)-peptide amide; (SEQ ID NO: 31)
[Imp7,Aib8,His9,Leu16,Lys18,Glu22,Arg26,Leu33,Thr35]-GLP-1-(7-35)-peptide amide; (SEQ ID NO: 32) and
[Imp7,Aib8,His9,Lys18,Glu22,Arg26,Ile33,Thr35]-GLP-1-(7-35)-peptide amide; (SEQ ID NO: 43)
or a pharmaceutically acceptable salt thereof.

In some embodiments the invention relates to an intermediate product in the form of a GLP-1 analogue selected from the group consisting of:
[Imp7,Acb8,His9,Tyr16,Lys18,Glu22,Arg26,Leu33,Lys35]-GLP-1-(7-35)-peptide amide; (SEQ ID NO: 3)
[Imp7,Acb8,His9,Lys18,Glu22,Arg26,Leu33,Lys35]-GLP-1-(7-35)-peptide amide; (SEQ ID NO: 4)
[Imp7,Aib8,His9,Lys18,Glu22,Arg26,Leu33,Thr35]-GLP-1-(7-35)-peptide amide; (SEQ ID NO: 5)
[Imp7,Aib8,His9,Arg18,Glu22,Arg26,Leu33,Thr35]-GLP-1-(7-35)-peptide amide; (SEQ ID NO: 7)
[Imp7,Aib8,His9,Arg18,Arg26,Leu33,Thr35]-GLP-1-(7-35)-peptide amide; (SEQ ID NO: 8)
[Imp7,Acb8,His9,Lys18,Glu22,Arg26,Leu33,Thr35]-GLP-1-(7-35)-peptide amide; (SEQ ID NO: 9)
[Imp7,His9,Lys18,Arg23,Arg26,Leu33,Thr35]-GLP-1-(7-35)-peptide amide; (SEQ ID NO: 10)
[Imp7,His9,Lys18,Arg23,Arg26,Leu33,Gly36]-GLP-1-(7-37)-peptide; (SEQ ID NO: 38)
[Imp7,Aib8,His9,Lys18,Lys22,Arg26,Leu33,Gly36]-GLP-1-(7-37)-peptide; (SEQ ID NO: 39)
[Imp7,Aib8,His9,Tyr16,Lys18,Glu22,Arg26,Leu33,Lys36]-GLP-1-(7-37)-peptide; (SEQ ID NO: 13)
[Imp7,Aib8,His9,Lys18,Lys23,Arg26,Leu33,Thr35]-GLP-1-(7-35)-peptide amide; (SEQ ID NO: 14)
[Imp7,Aib8,His9,Tyr16,Lys18,Lys23,Arg26,Leu33,Thr35]-GLP-1-(7-35)-peptide amide; (SEQ ID NO: 15)
[Imp7,His9,Arg18,Arg23,Arg26,Leu33]-GLP-1-(7-34)-peptide; (SEQ ID NO: 40)
[Imp7,His9,Arg18,Glu22,Arg26,Lys27,Leu33,Arg34]-GLP-1-(7-34)-peptide; (SEQ ID NO: 17)
[Imp7,Aib8,His9,Arg18,Glu22,Arg26,Lys27,Leu33,Arg34]-GLP-1-(7-34)-peptide; (SEQ ID NO: 41)
[Imp7,Acb8,His9,Lys18,Arg23,Arg26,Leu33,Thr35]-GLP-1-(7-35)-peptide amide; (SEQ ID NO: 19)
[Imp7,Acb8,His9,Tyr16,Lys18,Glu22,Arg26,Leu33,Lys35]-GLP-1-(7-35)-peptide amide; (SEQ ID NO: 3)
[Imp7,Acb8,His9,Tyr16,Arg18,Glu22,Arg26,Leu33,Arg34,Lys35]-GLP-1-(7-35)-peptide amide; (SEQ ID NO: 20)
[Imp7,Acb8,His9,Tyr16,Lys18,Arg22,Arg26,Leu33,Lys35]-GLP-1-(7-35)-peptide amide; (SEQ ID NO: 21)
[Imp7,Acb8,His9,Tyr16,Lys18,Arg22,Arg23,Arg26,Leu33,Lys35]-GLP-1-(7-35)-peptide amide; (SEQ ID NO: 22)
[Imp7,Aib8,His9,Lys18,Glu22,Arg26,Leu33,Thr35]-GLP-1-(7-35)-peptide; (SEQ ID NO: 5)
[Imp7,Acb8,His9,Tyr16,Lys18,Arg23,Arg26,Leu33,Lys35]-GLP-1-(7-35)-peptide amide; (SEQ ID NO: 23)
[Imp7,Acb8,His9,Tyr16,Arg18,Arg23,Arg26,Leu33,Arg34,Lys35]-GLP-1-(7-35)-peptide amide; (SEQ ID NO: 24)
[Imp7,Aib8,His9,Lys18,Glu22,Arg26,Leu33,Thr35]-GLP-1-(7-35)-peptide amide; (SEQ ID NO: 5)
[Imp7,Aib8,His9,Lys18,Ala22,Arg23,Arg26,Leu33,Gly36]-GLP-1-(7-37)-peptide; (SEQ ID NO: 25)
[Imp7,Acb8,His9,Lys18,Lys22,Arg23,Arg26,Leu33,Thr35]-GLP-1-(7-35)-peptide amide; (SEQ ID NO: 26)
[Imp7,Acb8,His9,Lys18,Lys22,Arg26,Leu33,Thr35]-GLP-1-(7-35)-peptide amide; (SEQ ID NO: 27)
[Imp7,Aib8,His9,Lys18,Ala22,Arg26,Leu33,Thr35]-GLP-1-(7-35)-peptide amide; (SEQ ID NO: 28)
[Imp7,Aib8,His9,Arg18,Arg23,Arg26,Leu33,Ala36]-GLP-1-(7-37)-peptide; (SEQ ID NO: 29)
[Imp7,Aib8,His9,Arg18,Arg23,Arg26,Leu33,Ser36]-GLP-1-(7-37)-peptide; (SEQ ID NO: 30)
[Imp7,Gly8,His9,Arg18,Glu22,Arg26,Leu33,Thr35]-GLP-1-(7-35)-peptide amide; (SEQ ID NO: 31)
[Imp7,Aib8,His9,Leu16,Lys18,Glu22,Arg26,Leu33,Thr35]-GLP-1-(7-35)-peptide amide; (SEQ ID NO: 32) and
[Imp7,Aib8,His9,Lys18,Glu22,Arg26,Ile33,Thr35]-GLP-1-(7-35)-peptide amide; (SEQ ID NO: 43)
or a pharmaceutically acceptable salt thereof.

The GLP-1 derivatives of the invention may be prepared by the following a stepwise synthesis method comprising (i) preparation of the intermediate GLP-1 analogue followed by (ii) attachment of the substituent. Step (i) of this method can be achieved using standard solid phase synthesis as described in the experimental section using protected amino acids; after cleavage from the resin the GLP-1 analogue can be subjected to purification using preparative HPLC as described in the experimental section herein to give the intermediate product. Alternatively, step (i) of this method, preparation of the intermediate product, can be carried out using a semi-recombinant synthesis as described in WO2009/083549. Step (ii) of this method, i.e. the attachment of the substituent to the intermediate product leading to the final product, as well as preparation of the substituent itself can be achieved using methods described in WO2009/083549.

Pharmaceutically Acceptable Salt, Amide or Ester

The derivatives or intermediate products of the invention may be in the form of a pharmaceutically acceptable salt, amide or ester. Salts are e.g. formed by a chemical reaction between a base and an acid, e.g.: $2NH_3+H_2SO_4 \rightarrow (NH_4)_2SO_4$. The salt may be a basic salt, an acid salt or it may be neither nor (i.e. a neutral salt). Basic salts produce hydroxide ions and acid salts hydronium ions in water.

The salts of the derivatives or intermediate products of the invention may be formed with added cations or anions between anionic or cationic groups, respectively. These groups may be situated in the peptide moiety, and/or in the substituent of the derivatives or intermediate products of the invention.

Non-limiting examples of anionic groups of the derivatives or intermediate products of the invention include free carboxylic groups in the substituent, if any, as well as in the peptide moiety. The peptide moiety often includes free carboxylic groups at internal acid amino acid residues such as Asp and Glu.

Non-limiting examples of cationic groups in the peptide moiety include the free amino group at the N-terminus, if present, as well as any free amino group of internal basic amino acid residues such as His, Arg, and Lys.

The ester of the derivatives or intermediate products of the invention may, e.g., be formed by the reaction of a free carboxylic acid group with an alcohol or a phenol, which leads to replacement of at least one hydroxyl group by an alkoxy or aryloxy group. The ester formation may involve the free carboxylic group at the C-terminus of the peptide, and/or any free carboxylic group in the substituent.

The amide of the analogues or derivatives of the invention may, e.g., be formed by the reaction of a free carboxylic acid group with an amine or a substituted amine or by reaction of a free or substituted amino group with a carboxylic acid.

The amide formation may involve the free carboxylic group at the C-terminus of the peptide, any free carboxylic group in the substituent, the free amino group at the N-terminus of the peptide, and/or any free or substituted amino group of the peptide in the peptide and/or the substituent.

In the present context, the term "pharmaceutically acceptable salt" is intended to indicate a salt which is not harmful to the patient. Such salts include pharmaceutically acceptable acid addition salts, pharmaceutically acceptable metal salts, ammonium and alkylated ammonium salts. Acid addition salts include salts of inorganic acids as well as organic acids.

In some embodiments, the peptide is in the form of a pharmaceutically acceptable salt. In some embodiments, the peptide is in the form of a pharmaceutically acceptable amide, preferably with an amide group at the C-terminus of the peptide. In some embodiments, the peptide is in the form a pharmaceutically acceptable ester.

Functional Properties

The GLP-1 derivatives of the invention are capable of binding and activating both the GLP-1 receptor and the glucagon receptor. In other words, the GLP-1 derivative of the invention is both an agonist of the glucagon receptor and an agonist of the GLP-1 receptor, also referred to herein as a "GLP-1/glucagon receptor co-agonist". In some embodiments, the GLP-1 derivatives of the invention are GLP-1 and glucagon receptor agonists, as is reflected by their potency on both receptors.

In some embodiments, the GLP-1 derivative has a lower $EC_{50}$ value on the GLP-1 receptor than on the glucagon receptor.

Also, or alternatively, in some embodiments the GLP-1 derivative is chemically stable, physical stable and soluble, e.g. the chemical stability, physical stability and solubility of the GLP-1 derivative enables sufficient storage stability of the GLP-1 derivative in a liquid pharmaceutical composition.

Also, or alternatively, in some embodiments the GLP-1 derivative has a good receptor binding and potency on the glucagon receptor, e.g. compared to human GLP-1 (SEQ ID NO: 1) or human glucagon.

Also, or alternatively, in some embodiments the GLP-1 derivative has a good receptor binding and potency on the GLP-1 receptor, e.g. compared to human GLP-1 (SEQ ID NO: 1) or human glucagon.

Also, or alternatively, in some embodiments, the GLP-1 derivatives have improved pharmacokinetic properties.

Also, or alternatively, in some embodiments the GLP-1 derivative is a protracted derivative, e.g. compared to human GLP-1 (SEQ ID NO: 1) or human glucagon.

Receptor Binding and Potency

The derivatives of the invention are GLP-1/glucagon receptor co-agonists, i.e. both GLP-1 receptor agonists and glucagon receptor agonists.

A receptor agonist may be defined as a peptide (e.g. a GLP-1 derivative) that binds to a receptor and elicits a response typical of the natural ligand. Thus, for example, a "GLP-1 receptor agonist" may be defined as a compound which is capable of binding to the human GLP-1 receptor and capable of fully or partially activating it. Similarly, the term "glucagon receptor agonist" as used herein may be defined as a compound which is capable of binding to the glucagon receptor and capable of fully or partially activating it. A response typical of the natural ligand may be full or partial activation of intracellular signal transduction pathways, such as activation of adenylate cyclase and increased levels of intracellular cAMP, mediating the physiological effects as is known in the art. For example, the term "GLP-1 receptor activity" refers to the ability to bind to the GLP-1 receptor and initiate a signal transduction pathway resulting in insulinotropic action or other physiological effects as is known in the art.

The derivatives or analogues of the invention may be tested for GLP-1 receptor activity using Assay (I)(a) or Assay (II)(a) described herein or for glucagon receptor activity using Assay (I)(b) or Assay (II)(b) described herein. In some embodiments the term "receptor activity" as used herein refers to the effect of a receptor agonist.

In some embodiments the term "glucagon receptor" as used herein means the human glucagon receptor. In some embodiments the term "GLP-1 receptor" as used herein means the human GLP-1 receptor.

Biological Activity—In Vitro Affinity and Potency

In some embodiments, the terms "affinity" or "receptor binding" as used herein refers to in vitro receptor binding affinity, i.e. performance in a GLP-1 receptor binding affinity assay and in a glucagon receptor binding affinity assay, more in particular to the capability of binding the human GLP-1 receptor and to the human glucagon receptor. The binding affinity of the human GLP-1 receptor may be measured in a binding assay, e.g. on membranes from a BHK cell line that stably expresses the human GLP-1 receptor. Radioactively labelled GLP-1 binds to the receptor and may be displaced competitively by a compound (e.g. GLP-1 derivatives). The remaining bound radioligand may be determined by adding scintillation proximity assay (SPA) beads which binds to cell membranes and when radioactivity is close to the bead it produces light which is measured and is a measure of the in vitro binding affinity of the compound. One non-limiting example of an assay for determination of binding affinity is described in Assay (II) herein. The binding affinity of the human glucagon receptor may be measured in a binding affinity assay, e.g. on membranes from a BHK cell line that stably expresses the human glucagon receptor. Radioactively-labelled glucagon binds to the receptor and may be displaced competitively by a compound (e.g. GLP-1 derivatives). The remaining bound radioligand may be determined by adding scintillation proximity assay (SPA) beads which binds to cell membranes and when radioactivity is close to the bead it produces light which is measured and is a measure of the in vitro binding affinity of the compound.

The term half maximal inhibitory concentration ($IC_{50}$) generally refers to the concentration of competing compound which displaces 50% of the specific binding of the radioligand binding corresponding to halfway between the baseline and maximum, by reference to the dose response curve. $IC_{50}$ is used as a measure of the binding affinity of a compound and is the concentration where 50% of its maximal binding is observed.

The in vitro binding of the GLP-1 derivatives of the invention may be determined as described above, and the $IC_{50}$ of the peptide in question determined. The lower the $IC_{50}$ value, the better the binding affinity.

In some embodiments, the GLP-1 derivative has an in vitro binding affinity on the GLP-1 receptor, determined using the method described in Assay (II)(a) herein, corresponding to an $IC_{50}$ at or below 100 nM, more preferably below 10 nM, even more preferably below 5 nM or most preferably below 1 nM.

The GLP-1 derivative may have an in vitro binding affinity on the glucagon receptor, determined using the method described in Assay (II)(b) herein, corresponding to an $IC_{50}$ at or below 100 nM or below 50 nM or below 10 nM.

In some embodiments, potency and/or activity refers to in vitro potency, i.e. performance in a functional GLP-1 receptor assay and glucagon receptor assay, more in particular to the capability of activating the human GLP-1 receptor and the human glucagon receptor. The response of the human GLP-1 receptor may be measured in a reporter gene assay, e.g. in a BHK cell line that stably expresses the human GLP-1 receptor and comprises the DNA for the cAMP response element (CRE) coupled to a promoter and the gene for firefly luciferase (CRE luciferase). When cAMP is produced as a result of activation of the GLP-1 receptor this in turn results in the luciferase being expressed. Luciferase expression may be determined by adding luciferin, which by the enzyme is converted to oxyluciferin and produces bioluminescence, which is measured and is a measure of the in vitro receptor potency. One non-limiting example of an assay for determination of receptor potency is described in Assay (I) herein. The response of the human glucagon receptor may be measured in a reporter gene assay, e.g. in a BHK cell line that stably expresses the human glucagon receptor and comprises the DNA for the cAMP response element (CRE) coupled to a promoter and the gene for firefly luciferase (CRE luciferase). When cAMP is produced as a result of activation of the glucagon receptor this in turn results in the luciferase being expressed. Luciferase expression may be determined by adding luciferin, which by the enzyme is converted to oxyluciferin and produces bioluminescence, which is measured and is a measure of the in vitro receptor potency.

The term half maximal effective concentration ($EC_{50}$) generally refers to the concentration which induces a response halfway between the baseline and maximum, by reference to the dose response curve. $EC_{50}$ is used as a measure of the potency of a compound (e.g. GLP-1 derivatives) and is the concentration where 50% of its maximal effect is observed.

The in vitro receptor potency of the GLP-1 derivatives of the invention may be determined as described above, and the $EC_{50}$ of the peptide in question determined. The lower the $EC_{50}$ value, the better the potency.

GLP-1/Glucagon Receptor Co-Agonists

A GLP-1/glucagon receptor co-agonist may be defined as a peptide that is able to activate both the GLP-1 receptor and the glucagon receptor. The derivative of the invention has an $EC_{50}$ below 1 nM on the GLP-1 receptor and an $EC_{50}$ below 10 nM on the glucagon receptor. In some embodiments derivative of the invention has an $EC_{50}$ below 100 pM on the GLP-1 receptor and has an $EC_{50}$ below 100 pM on the glucagon receptor; or has an $EC_{50}$ below 50 pM on the GLP-1 receptor and has an $EC_{50}$ below 100 pM on the glucagon receptor; or has an $EC_{50}$ below 10 pM on the GLP-1 receptor and has an $EC_{50}$ below 50 pM on the glucagon receptor. EC50 may be determined as described in Assay (I) herein.

In some embodiments the GLP-1 derivative has a lower $EC_{50}$ value on the GLP-1 receptor than on the glucagon receptor. In some embodiments the GLP-1 derivative has a ratio between its $EC_{50}$ value on the glucagon receptor and $EC_{50}$ on the GLP-1 receptor in the range of 100 to 250, such as in the range of 50 to 100, in the range of 20 to 50, in the range of 10 to 20, or in the range of 1 to 10. In some embodiments the GLP-1 derivative has a ratio between its $EC_{50}$ value on the glucagon receptor and $EC_{50}$ on the GLP-1 receptor in the range of 50 to 100. In some embodiments the GLP-1 derivative has a ratio between its $EC_{50}$ value on the glucagon receptor and $EC_{50}$ on the GLP-1 receptor in the range of 20 to 50. In some embodiments the GLP-1 derivative has a ratio between its $EC_{50}$ value on the glucagon receptor and $EC_{50}$ on the GLP-1 receptor in the range of 10 to 20. In some embodiments the GLP-1 derivative has a ratio between its $EC_{50}$ value on the glucagon receptor and $EC_{50}$ on the GLP-1 receptor in the range of 1 to 10. In some embodiments the $EC_{50}$ on the GLP-1 receptor is determined according to Assay (I)(a) described herein. In some embodiments the $EC_{50}$ on the glucagon receptor is determined according to Assay (I)(b) described herein.

The GLP-1 derivative may have a potency ($EC_{50}$) on the glucagon receptor below 10 nM or below 1 nM or 100 pM or below 10 pM. In some embodiments the GLP-1 derivative has an $EC_{50}<10$ nM on the glucagon receptor. In some embodiments the GLP-1 derivative has an $EC_{50}<1$ nM on the glucagon receptor. In some embodiments the GLP-1 derivative has an $EC_{50}<100$ pM on the glucagon receptor. In some embodiments the GLP-1 derivative has an $EC_{50}<10$ pM on the glucagon receptor.

The GLP-1 derivatives of the present invention may have an $EC_{50}$ on the GLP-1 receptor below 1 nM or below 100 pM or below 50 pM or below 10 pM. In some embodiments the GLP-1 derivative has an $EC_{50}$ below 100 pM on the GLP-1 receptor. In some embodiments the GLP-1 derivative has an $EC_{50}$ below 50 pM on the GLP-1 receptor. In some embodiments the GLP-1 derivative has an $EC_{50}$ below 10 pM on the GLP-1 receptor.

The potency, i.e. $EC_{50}$, on the GLP-1 receptor of a GLP-1 derivative of the invention may be determined according to Assay (I)(a) described herein. The potency, i.e. $EC_{50}$, on the glucagon receptor of a GLP-1 derivative of the invention may be determined according to Assay (I)(b) described herein.

The derivative of the invention has an $IC_{50}$ below 35 nM on the GLP-1 receptor and an $IC_{50}$ below 150 nM on the glucagon receptor. $IC_{50}$ may be determined as described in Assay (II) herein.

In some embodiments the GLP-1 derivative has a lower $IC_{50}$ value on the GLP-1 receptor than on the glucagon receptor. In some embodiments the GLP-1 derivative has a ratio between its $IC_{50}$ value on the glucagon receptor and $IC_{50}$ on the GLP-1 receptor in the range of 1 to 5, such as in the range of 5 to 10, in the range of 10 to 15, in the range of 15 to 25; or such as in the range of 25 to 100, or above 100.

Biological Activity—In Vivo Pharmacology

In some embodiments the GLP-1 derivatives of the invention are potent in vivo, which may be determined as is known in the art in any suitable animal model, as well as in clinical trials.

The diet-induced obese (DIO) mouse is one example of a suitable animal model and the effect on body weight, food intake and glucose tolerance can be assessed during sub-chronic dosing in this model. Effect on body weight and blood glucose may be determined in such mice in vivo. Food intake can be assessed by single housing animals and weighing food consumed per day. This model can also be used to evaluate effects on glucose tolerance by performing an oral or intraperitoneal glucose tolerance test (OGTT or IPGTT). These tests are performed by administration of a glucose load orally or intraperitoneally to semi-fasted animals and subsequent blood glucose measure for up to three hours.

Pharmacokinetics Profile

The GLP-1 derivatives of the invention may have improved pharmacokinetic properties such as increased terminal half-life, e.g. compared to human GLP-1 or human glucagon. Preferably the GLP-1 derivatives of the invention have pharmacokinetic properties suitable for once daily administration or less.

The pharmacokinetic properties of the GLP-1 derivatives of the invention may suitably be determined in-vivo in pharmacokinetic (PK) studies. Such studies are conducted to evaluate how pharmaceutical compounds are absorbed, distributed, and eliminated in the body, and how these processes affect the concentration of the compound in the body, over the course of time.

In the discovery and preclinical phase of pharmaceutical drug development, animal models such as the mouse, rat, monkey, dog or pig, may be used to perform this characterisation. Any of these models can be used to test the pharmacokinetic properties of the GLP-1 derivatives of the invention.

In such studies, animals are typically administered with a single dose of the drug, either intravenously (i.v.), subcutaneously (s.c.) or orally (p.o.) in a relevant pharmaceutical composition. Blood samples are drawn at predefined time points after dosing, and samples are analysed for concentration of drug with a relevant quantitative assay. Based on these measurements, time-plasma concentration profiles for the compound of study are plotted and a so-called non-compartmental pharmacokinetic analysis of the data is performed.

For most compounds, the terminal part of the plasma-concentration profiles will be linear when drawn in a semi-logarithmic plot, reflecting that after the initial absorption and distribution, drug is removed from the body at a constant fractional rate. The rate (lambda Z or $\lambda_z$) is equal to minus the slope of the terminal part of the plot. From this rate, also a terminal half-life may be calculated, as $t½=\ln(2)/\lambda_z$ (see, e.g., Johan Gabrielsson and Daniel Weiner: Pharmacokinetics and Pharmacodynamic Data Analysis. Concepts & Applications, 3rd Ed., Swedish Pharmaceutical Press, Stockholm (2000)).

Clearance can be determined after i.v. administration and is defined as the dose (D) divided by area under the curve (AUC) on the plasma concentration versus time profile (Rowland, M and Tozer T N: Clinical Pharmacokinetics: Concepts and Applications, 3$^{rd}$ edition, 1995 Williams Wilkins).

The estimate of terminal half-life and/or clearance is relevant for evaluation of dosing regimens and an important parameter in drug development, in the evaluation of new drug compounds.

Pharmacokinetics Profile—Half Life In Vivo in Rats

The pharmacokinetic properties of the GLP-1 derivatives may be determined as terminal half-life ($T_{1/2}$) in vivo in rats after i.v. and s.c. administration. In some embodiments, the terminal half-life of the GLP-1 derivatives is at least 1 hour, preferably at least 3 hours, preferably at least 4 hours, even more preferably at least 5 hours or most preferably at least 6 hours.

Pharmacokinetics Profile—Half Life In Vivo in Mice

The GLP-1 derivatives of the invention may have improved pharmacokinetic properties compared to human GLP-1 or human glucagon. Preferably the GLP-1 derivatives of the invention have pharmacokinetic properties suitable for once daily administration or less.

In some embodiments, the pharmacokinetic properties of the GLP-1 derivatives may be determined as terminal half-life ($T_{1/2}$) in vivo in mice after i.v. and s.c. administration. In some embodiments, the terminal half-life of the GLP-1 derivatives is at least 1 hour, preferably at least 3 hours, preferably at least 4 hours, even more preferably at least 5 hours or most preferably at least 6 hours. A suitable assay for determining terminal half-life of the GLP-1 derivatives in mice after s.c. administration is described in Assay (IV) herein.

Pharmacokinetics Profile—Half Life In Vivo in Minipigs

The GLP-1 derivatives of the invention may have improved pharmacokinetic properties compared to hGLP-1 and preferably suitable for once daily or once weekly administration. In some embodiments, the pharmacokinetic properties of the GLP-1 derivatives may be determined as terminal half-life ($T_{1/2}$) in vivo in minipigs after i.v. administration, e.g. as described below.

In some embodiments, the terminal half-life of the GLP-1 derivatives in minipigs is at least 5 hours, preferably at least 10 hours, even more preferably at least 15 hours or most preferably at least 20 hours.

The purpose of this study is to determine the pharmacokinetic properties in vivo of the GLP-1 derivatives after i.v. administration to minipigs. This is done in a pharmacokinetic (PK) study, where among other parameters the terminal half-life and the clearance of the derivative in question is determined. Increasing the terminal half-life and decreasing the clearance means that the compound of study is eliminated slower from the body. For GLP-1 derivatives this entails an extended duration of pharmacological effect.

Female Göttingen minipigs are obtained from Ellegaard Göttingen Minipigs (Dalmose, Denmark) approximately 7-14 months of age and weighing from approximately 16-35 kg are used in the studies. The minipigs are housed either individually (pigs with permanent catheters) or in a group, and are fed restrictedly once or twice daily with SDS minipig diet (Special Diets Services, Essex, UK).

In some studies two permanent central venous catheters are implanted in vena cava caudalis or cranialis in each animal after at least 2 weeks of acclimatiation. The animals are allowed 1 week recovery after the surgery, and are then used for repeated pharmacokinetic studies with a suitable wash-out period between successive GLP-1 derivative dosings. In other studies the animals are acclimatized for 1 week, after which they are used for repeated pharmacokinetic studies with a suitable wash-out period between successive GLP-1 derivative dosings. On each dosing occasion these pigs are instrumented with a venflon in one ear vein through which the derivatives were dosed. Blood sampling are performed by venipuncture in v. jugularis or v. cava cranialis.

The animals are either unfasted or fasted for approximately 18 h before dosing and from 0 to 4 h after dosing, but have ad libitum access to water during the whole period.

The GLP-1 derivatives are usually dissolved in 50 mM sodium phosphate, 145 mM sodium chloride, 0.05% tween 80, pH 7.4 to a concentration of usually from 20-60 nmol/ml. Intravenous injections (the volume corresponding to usually 2-3 nmol/kg, for example 0.1 ml/kg) of the compounds are given through one catheter or through the venflon, and blood are sampled at predefined time points for up till 13 days post dosing (preferably through the other catheter or by venipuncture). Blood samples (for example 0.8 ml) are collected in tubes with EDTA buffer (8 mM) (sometimes aprotinin 500 KIU/ml blood was added) and then centrifuged at 4° C. and 1942 G for 10 minutes. Plasma is pipetted into Micronic tubes on dry ice, and kept at −20° C. until analyzed for plasma concentration of the respective GLP-1 derivative using an appropriate quantitative assay like ELISA or LC-MS.

Based on these measurements, time-plasma concentration profiles for the compound of study are plotted and a so-called non-compartmental pharmacokinetic analysis of the data is performed in WinNonlin v. 5.0 or Phoenix v. 6.2 (Pharsight Inc., Mountain View, Calif., USA) or other relevant software for PK analysis. For most compounds, the terminal part of the plasma-concentration profiles will be linear when drawn in a semi-logarithmic plot, reflecting that after the initial distribution, drug is removed from the body at a constant fractional rate. The rate (lambda Z or $\lambda z$) is equal to minus the slope of the terminal part of the plot. From this rate, also the terminal half-life may be calculated, as $t\frac{1}{2}=\ln(2)/\lambda z$ (see, e.g., Johan Gabrielsson and Daniel Weiner: Pharmacokinetics and Pharmacodynamic Data Analysis. Concepts & Applications, 3rd Ed., Swedish Pharmaceutical Press, Stockholm (2000)). Clearance is defined as the dose (D) divided by area under the curve (AUC) on the plasma concentration versus time profile (Rowland, M and Tozer T N: Clinical Pharmacokinetics: Concepts and Applications, 3rd edition, 1995 Williams Wilkins).

When compounds according to the present invention were tested in mini-pigs as described above, a significantly prolonged in vivo half-life was observed.

Physical Stability

Peptides may undergo various changes of physical state. Peptides may precipitate due to lack of solubility at a certain set of conditions, e.g. due to neutralization of repulsing charges on amino acid side chains due to a change of pH. Another physical change is the formation of amyloid fibrils, which involves a conformational change into beta-sheet rich macromolecular fibre structures. Other macromolecular structures may be formed by less systematic structural repeats due to aggregation. In the two latter instances peptide substance may eventually be observed as a precipitate. In fact these physical changes may to some extent be interrelated, e.g. solubility versus pH and fibril formation is related [Schmittschmitt and Scholtz, Protein Science, 12, 10, 2374-2378, 2003]. Furthermore, it is very difficult to distinguish these phenomena by visual inspection only, therefore the result of these changes are often described by the general term "precipitate".

Other changes of physical state include adsorption to surfaces observed as a loss of content of peptide from solution, and the change from a liquid solution to a gel. Nevertheless, the observation of a precipitate regardless its nature or formation of a gel is a problem when in a pharmaceutical injectable during its storage and in-use time.

The term "physical stability" of the derivative or composition as used herein refers to the tendency of the peptide and/or protein (i.e. herein the GLP-1 derivative) to form biologically inactive and/or insoluble aggregates of the peptide and/or protein as a result of exposure of the peptide and/or protein to thermo-mechanical stresses and/or interaction with interfaces and surfaces that are destabilizing, such as hydrophobic surfaces and interfaces. Physical stability of an aqueous peptide and/or protein compositions is evaluated by means of visual inspection and/or turbidity measurements after exposing the composition filled in suitable containers (e.g. cartridges or vials) to mechanical/physical stress (e.g. agitation) at different temperatures for various time periods. Visual inspection of the compositions is performed in a sharp focused light with a dark background. The turbidity of the composition is characterized by a visual score ranking the degree of turbidity for instance on a scale from 0 to 3 (a composition showing no turbidity corresponds to a visual score 0, and a composition showing visual turbidity in daylight corresponds to visual score 3). A composition may be classified physical unstable with respect to protein aggregation, when it shows visual turbidity in daylight. Alternatively, the turbidity of the composition can be evaluated by simple turbidity measurements well-known to the skilled person. Physical stability of the aqueous peptide and/or protein compositions can also be evaluated by using a spectroscopic agent or probe of the conformational status of the peptide and/or protein. The probe is preferably a small molecule that preferentially binds to a non-native conformer of the peptide and/or protein. One example of a small molecular spectroscopic probe of peptide and/or protein structure is Thioflavin T. Thioflavin T is a fluorescent dye that has been widely used for the detection of amyloid fibrils. In the presence of fibrils, and perhaps other peptide and/or protein configurations as well, Thioflavin T gives rise to a new excitation maximum at about 450 nm and enhanced emission at about 482 nm when bound to a fibril peptide and/or protein form. Unbound Thioflavin T is essentially non-fluorescent at these wavelengths.

Other small molecules can be used as probes of the changes in peptide and/or protein structure from native to non-native states. For instance the "hydrophobic patch" probes that bind preferentially to exposed hydrophobic patches of a peptide and/or protein. The hydrophobic patches are generally buried within the tertiary structure of a peptide and/or protein in its native state, but become exposed as a peptide and/or protein begins to unfold or denature. Examples of these small molecular, spectroscopic probes are aromatic, hydrophobic dyes, such as antrhacene, acridine, phenanthroline or the like.

Physical stability of the derivative may be determined by the recovery and/or lag time in Assay (III) described herein, i.e. the ThT fibrillation assay. In some embodiments the physically stable derivative has more than 70% recovery and/or more than 7 hours lag time in Assay (III) described herein.

In some embodiments the derivative has more than 70% recovery in a ThT fibrillation assay, such as Assay (III) described herein. In some embodiments the derivative has more than 90%, such as more than 95% or more than 98%, recovery in a ThT fibrillation assay, such as Assay (III) described herein. In some embodiments the derivative has about 100% recovery in a ThT fibrillation assay, such as Assay (III) described herein.

In some embodiments the derivative has more than 7 hours, such as more than 20 hours or more than 45 hours, lag time in a ThT fibrillation assay, such as Assay (III) described herein.

In some embodiments the GLP-1 derivative has more than 70% recovery in the ThT fibrillation assay. In some embodiments the GLP-1 derivative has more than 90% recovery in the ThT fibrillation assay. In some embodiments the GLP-1 derivative has about 100% recovery in the ThT fibrillation assay. In some embodiments the GLP-1 derivative has more than 7 hours lag time in the ThT fibrillation assay. In some embodiments the GLP-1 derivative has more than 20 hours lag time in the ThT fibrillation assay. In some embodiments the GLP-1 derivative has 45 hours lag time or more in the ThT fibrillation assay. In some embodiments the ThT fibrillation assay is Assay (III) described herein.

Chemical Stability

The terms "chemical stability" and "chemically stable" when used in connection with the derivative or composition herein refers to chemical covalent changes in the peptide structure leading to formation of chemical degradation products with potential less biological potency and/or potential increased immunogenic properties. Various chemical degradation products can be formed depending on the type and nature of the native peptide and the environment to which the peptide is exposed. Elimination of chemical degradation can most likely not be completely avoided and increasing amounts of chemical degradation products is often seen during prolonged storage. Most peptides are prone to deamidation, a process in which the side chain amide group in glutaminyl or asparaginyl residues is hydrolysed to form a free carboxylic acid. Other degradations pathways involves formation of high molecular weight transformation products where two or more peptide molecules are covalently bound to each other through transamidation and/or disulfide interactions leading to formation of covalently bound dimer, oligomer and polymer degradation products (Stability of Protein Pharmaceuticals, Ahern. T. J. & Manning M. C., Plenum Press, New York 1992). Oxidation (of for instance methionine residues) can be mentioned as another variant of chemical degradation. Peptides comprising asparagine or aspartic acid may be prone to isomerization via the formation of an intermediate aspartimide giving rise to the corresponding iso-aspartic acid isomer in where both the D- and L-isomer can be formed. The aspartimide intermediate may also lead to the formation of the D-aspartic acid isomer. (Formulation Consideration for Proteins Susceptible to Asparagine Deamidation and Aspartate Isomerization, Wakankar and Borchardt, Journal of Pharmaceutical Sciences, 2006, Vol. 95, no. 11, p 2321). Finally, peptides may also undergo hydrolytic cleavage in which peptide fragments or single amino acids are cleaved by hydrolysis of the peptide bond.

The chemical stability of the composition can be evaluated by measuring the amount of the chemical degradation products at various time-points after exposure to different environmental conditions (the formation of degradation products can often be accelerated by for instance increasing temperature). The amount of each individual degradation product is often determined by separation of the degradation products depending on molecule size and/or charge using various chromatography techniques (e.g. SE-HPLC and/or RP-UPLC).

Hence, as outlined above, a "stabilized composition" refers to a composition with increased physical stability, increased chemical stability or increased physical and chemical stability. In general, a composition must be stable during use and storage (in compliance with recommended use and storage conditions) until the expiration date is reached.

Chemical stability of the derivative may be measured by determination of the chemical degradation in Assay (V) described herein. In some embodiments the derivative has less than 14% degradation in the chemical stability assay. In some embodiments the GLP-1 derivative has less than 13% degradation in the chemical stability assay. In some embodiments the GLP-1 derivative has less than 12% degradation in the chemical stability assay. In some embodiments the GLP-1 derivative has less than 10% degradation in the chemical stability assay. In some embodiments the GLP-1 derivative has less than 9% degradation in the chemical stability assay. In some embodiments the GLP-1 derivative has less than 7% degradation in the chemical stability assay. In some embodiments the GLP-1 derivative has less than 5% degradation in the chemical stability assay. In some embodiments the GLP-1 derivative has less than 3% degradation in the chemical stability assay. In some embodiments the GLP-1 derivative has less than 2% degradation in the chemical stability assay. In some embodiments the GLP-1 derivative has less than 1% degradation in the chemical stability assay. In some embodiments the chemically stable derivative has a chemical degradation of less than 5%, such as less than 4%, less than 3% or less than 2%, wherein said chemical degradation may be determined by Assay (V) described herein.

Solubility

The GLP-1 derivatives of the invention may be soluble and, for example, have a solubility of at least 0.1 mmol/l, such as at least 0.2 mmol/l, at least 0.5 mmol/l, or at least 2 mmol/l. The GLP-1 derivatives of the invention may be soluble, and for example, have a solubility of at least 4 mmol/l, such as at least 8 mmol/l, at least 10 mmol/l, or at least 15 mmol/l, e.g. in an aqueous 10 mM phosphate solution.

The GLP-1 derivatives of the invention may soluble in the pH range of pH 7.0-8.2, such as pH 7.0-7.7 or pH 7.2-7.5, or soluble at pH 7.4, e.g. in an aqueous 10 mM phosphate solution. Specifically, the GLP-1 derivatives of the invention may soluble in the pH range of pH 7.0-8.2 and have a solubility of with a solubility of at least 0.1 mmol/l, e.g. in an aqueous 10 mM phosphate solution.

In some embodiments solubility of the GLP-1 derivative is at room temperature, e.g. 20-25° C. In some embodiments solubility of the GLP-1 derivative is at low temperature, e.g. 4-10° C., 4-8° C. or 4-5° C.

In the present context, if not stated otherwise, the terms "soluble", "solubility", "soluble in aqueous solution", "aqueous solubility", "water soluble", "water-soluble", "water solubility" and "water-solubility", refer to the solubility of a compound in water or in an aqueous salt or aqueous buffer solution, for example a 10 mM phosphate solution or in an aqueous solution comprising other compounds, and e.g. at room temperature. Solubility may be assessed using the following assay:

pH Dependent Solubility Assay

The solubility of peptides and proteins depends on the pH of the solution. Often a protein or peptide precipitates at or close to its isoelectric point (pI), at which its net charge is zero. At low pH (i.e. lower than the pI) proteins and peptides are typically positively charged, at pH higher than the pI they are negatively charged.

It is advantageous for a therapeutic peptide if it is soluble in a sufficient concentration at a given pH, which is suitable for both formulating a stable drug product and for administrating the drug product to the patient e.g. by subcutaneous injection.

Solubility versus pH curves are measured as described: a formulation or a peptide solution in water is prepared and aliquots are adjusted to pH values in the desired range by adding HCl and NaOH. These samples are left equilibrating at room temperature for 2-4 days. Then the samples are centrifuged. A small aliquot of each sample is withdrawn for reverse HPLC analysis for determination of the concentration of the proteins in solution. The pH of each sample is measured after the centrifugation, and the concentration of each protein is depicted versus the measured pH.

DPP-IV Stability

In some embodiments the GLP-1 derivative is a DPPIV protected compound. In some embodiments the GLP-1 derivative is a DPPIV stabilised compound.

DPP-IV stability may be determined using the following assay: 10 μM of peptide is incubated with DPP-IV (2 μg/ml) in duplicate at 37° C. in a HEPES buffer to which 0.005% Tween20 is added. In the experiment human GLP-1 is used as a positive control. Aliquots of sample are taken at 3, 15, 30, 60, 120 and 240 min and three volumes of ethanol are added to stop the reaction. The samples are analysed by LC-MS for parent peptide. Data are plotted according to $1^{st}$ order kinetics, and the stability is reported as half-lives.

Combinations

In some embodiments the invention relates to the GLP-1 derivative of the invention in combination with one or more additional therapeutically active compounds, such as a GLP-1 compound or with an insulin compound. In some embodiments the GLP-1 derivative of the invention is in combination with a GLP-1 compound. In some embodiments the GLP-1 derivative of the invention is in combination with an insulin compound.

As used herein, a "GLP-1 compound" is a compound which is able to active the GLP-1 receptor and not e.g. the glucagon receptor.

As used herein, an "insulin compound" is a compound which is able to active the insulin receptor.

In some embodiments the GLP-1 compound of the combination is selected from the group consisting of:

N-epsilon26-((S)-4-Carboxy-4-hexadecanoylamino-butyryl)[Arg34]GLP-1-(7-37):

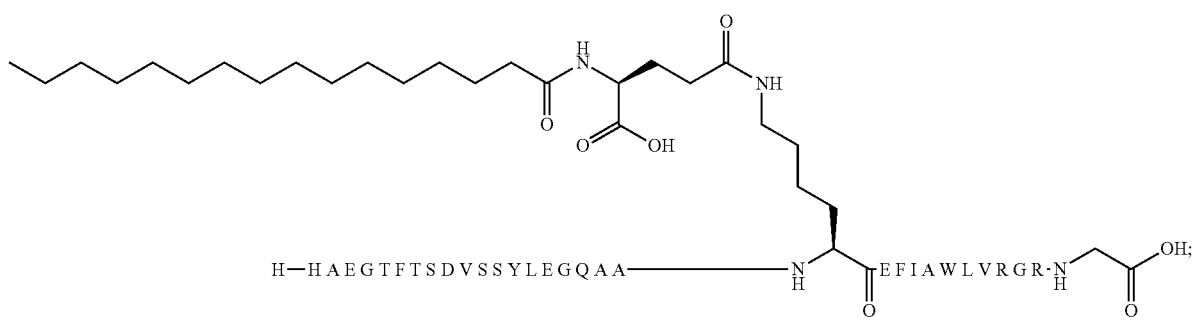

(compound G1)

N-epsilon37-[2-(2-{2-[2-(2-{2-[(S)-Carboxy-4-({trans-4-[(19-carboxynonadecanoylamino)methyl]cyclohexanecarbonyl}amino)butyrylamino]ethoxy}ethoxy)acetylamino]ethoxy}ethoxy)acetyl][DesaminoHis7,Glu22,Arg26,Arg34,Lys37]GLP-1-(7-37) (SEQ ID NO: 34):

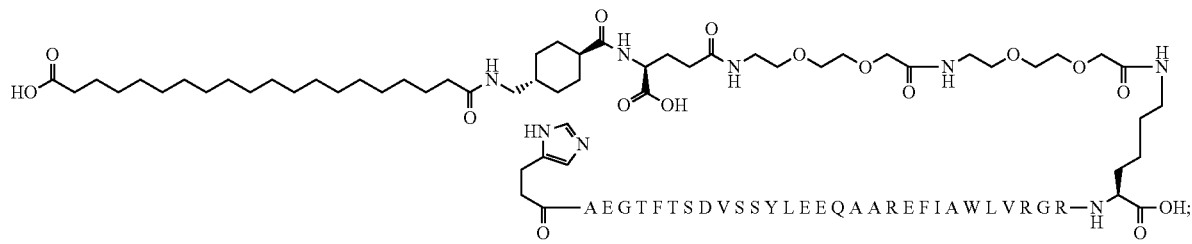

(compound G2)

N-epsilon26-[2-(2-{2-[2-(2-{2-[(S)-Carboxy-4-(17-carboxyheptadecanoylamino)butyrylamino]ethoxy}ethoxy)acetylamino]ethoxy}ethoxy)acetyl][Aib8,Arg34]GLP-1-(7-37) (SEQ ID NO: 35):

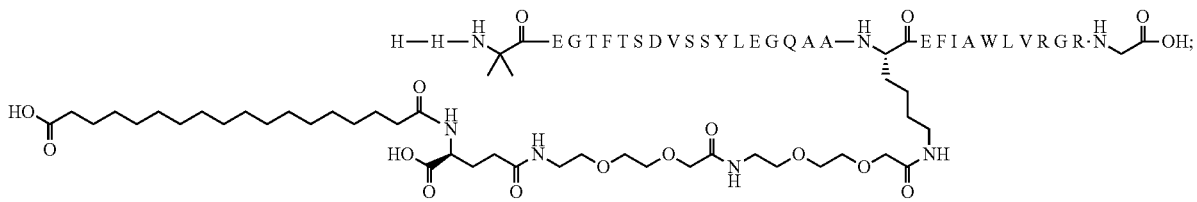

(compound G3)

N-epsilon37-[2-(2-{2-[2-(2-{2-[(S)-carboxy-4-(15-carboxy-pentadecanoylamino)-butyrylamino]-ethoxy}-ethoxy)-acetylamino]-ethoxy}-ethoxy)-acetyl][Aib8,22,35,Lys37]GLP-1-(7-37) (SEQ ID NO: 36):

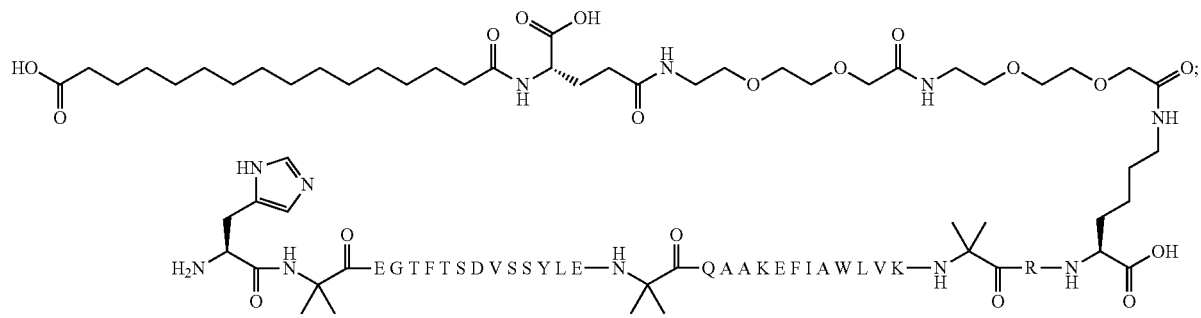

(compound G4)

and their pharmaceutically acceptable salts, amides, alkyls or esters.

In some embodiments the insulin compound of the combination is: N-epsilon-B29-[(S)-4-Carboxy-4-(15-carboxypentadecanoylamino)butyryl]desB30 human insulin:

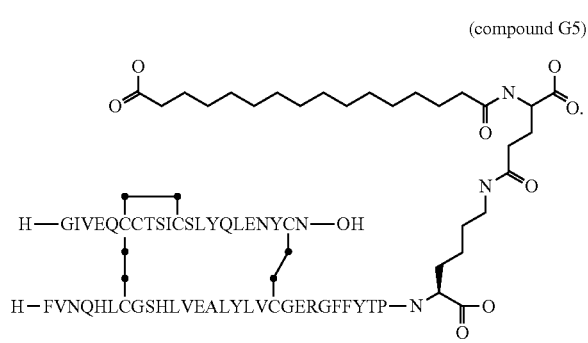

(compound G5)

Pharmaceutical Compositions

In some embodiments the invention relates to a pharmaceutical composition comprising the derivative of the invention and one or more pharmaceutically acceptable excipients. In some embodiments the composition is suited for parenteral administration, such as SC, IM or IV administration. The term "pharmaceutical composition" as used herein means a product comprising an active compound or a salt thereof together with pharmaceutical excipients such as buffer, preservative, and optionally a tonicity modifier and/or a stabilizer. Thus a pharmaceutical composition is also known in the art as a pharmaceutical formulation. The terms "pharmaceutical composition", "composition", and "formulation" are used interchangeably herein.

Pharmaceutical compositions comprising a derivative of the invention may be prepared by conventional techniques, e.g. as described in Remington's Pharmaceutical Sciences, 1985 or in Remington: The Science and Practice of Pharmacy, 19th edition, 1995.

In some embodiments the invention relates to a pharmaceutical composition comprising a derivative of the invention, wherein said GLP-1 derivative is present in a concentration from about 0.01 mg/mL to about 25 mg/mL, such as from about 0.05 mg/mL to about 5 mg/mL and from about 0.1 mg/mL to about 2 mg/mL, and wherein said composition has a pH from 2.0 to 10.0. The pharmaceutical composition may comprise a derivative of the invention, wherein said GLP-1 derivative is present in a concentration from about 0.01 mg/mL to about 50 mg/mL, and wherein said composition has a pH from 2.0 to 10.0.

In some embodiments the pharmaceutical composition comprises an aqueous solution of a derivative of the invention, and a buffer, wherein said GLP-1 derivative is present in a concentration from 0.01 mg/mL or above, and wherein said composition has a pH from about 2.0 to about 10.0. In some embodiments the pharmaceutical composition comprises an aqueous solution of a derivative of the invention, and a buffer, wherein said GLP-1 derivative is present in a concentration from 0.01 mg/mL or above, and wherein said composition has a pH from about 6.5 to about 8.5.

In some embodiments the composition of the invention has a pH from about 2.0 to about 10.0. In some embodiments the composition has a pH from about 6.5 to about 8.5. In some embodiments the composition has a pH from about 7.0 to about 8.5, such as from about 7.2 to about 8.2.

The composition may further comprise a buffer system, preservative(s), isotonicity agent(s), chelating agent(s), stabilizers and surfactants. In some embodiments the pharmaceutical composition is an aqueous composition, i.e. a composition comprising water. Such composition is typically a solution or a suspension. In some embodiments of the invention the pharmaceutical composition is an aqueous solution. The term "aqueous composition" is defined as a composition comprising at least 50% w/w water. Likewise, the term "aqueous solution" is defined as a solution comprising at least 50% w/w water. In some embodiments the composition comprises a non-aqueous organic solvent.

In some embodiments the pharmaceutical composition is a freeze-dried composition to which solvents and/or diluents are added prior to use, e.g. by the physician or the patient.

In some embodiments the pharmaceutical composition is a dried composition (e.g. freeze-dried or spray-dried) ready for use without any prior dissolution.

In some embodiments the invention relates to a composition comprising the derivative of the invention and one or more other active ingredients, such as GLP-1, insulin or analogues and/or derivatives thereof. In some embodiments the invention relates to a composition comprising the derivative of the invention and GLP-1 or analogues and/or derivatives thereof. In some embodiments the invention relates to a composition comprising the derivative of the invention and insulin or analogues and/or derivatives thereof. A composition comprising a combination of the derivative of the invention and one or more other active ingredients may be referred to as a "co-formulation". In some embodiments such co-formulations are physically stable and/or chemically stable compositions.

The fact that the derivatives of the invention may be soluble at neutral pH, may allow a co-formulation with insulin and allow for more stable blood glucose levels and a reduced number of hypoglycaemic episodes, as well as a reduced risk of diabetes related complications.

The term "excipient" as used herein means the chemical compounds which are normally added to pharmaceutical compositions, e.g. buffers, tonicity agents, preservatives and the like.

In some embodiments the pharmaceutical composition further comprises one or more additional therapeutically active compounds or substances. In some embodiments the additional therapeutically active compound is a GLP-1 compound or an insulin compound. In some embodiments the additional therapeutically active compound is a GLP-1 compound. In some embodiments the additional therapeutically active compound is an insulin compound. In some embodiments the GLP-1 compound is selected from the group consisting of:

N-epsilon26-((S)-4-Carboxy-4-hexadecanoylamino-bu-
tyryl)[Arg34]GLP-1-(7-37)
(Compound G1) (SEQ ID NO: 37):
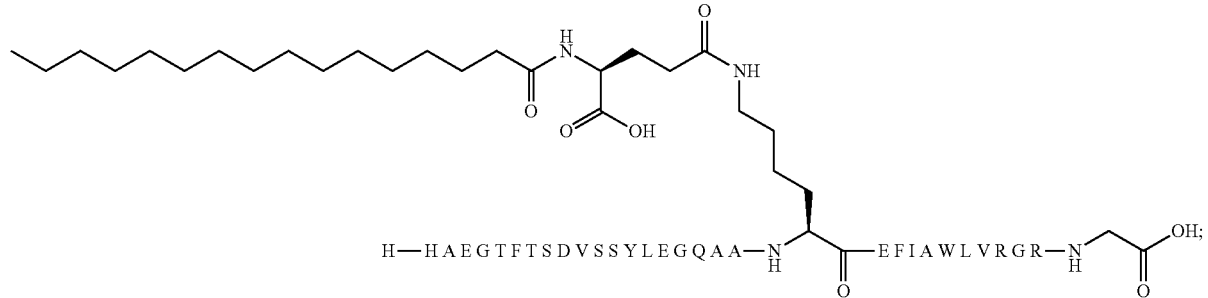
N-epsilon37-[2-(2-{2-[2-(2-{2-[(S)-Carboxy-4-({trans-4-
[(19-carboxynonadecanoylamino)methyl]
cyclohexanecarbonyl}amino)butyrylamino]
ethoxy}ethoxy)acetylamino]ethoxy}ethoxy)acetyl]
[DesaminoHis7,Glu22,Arg26,Arg34,Lys37]GLP-1-(7-
37)
(Compound G2) (SEQ ID NO: 34):

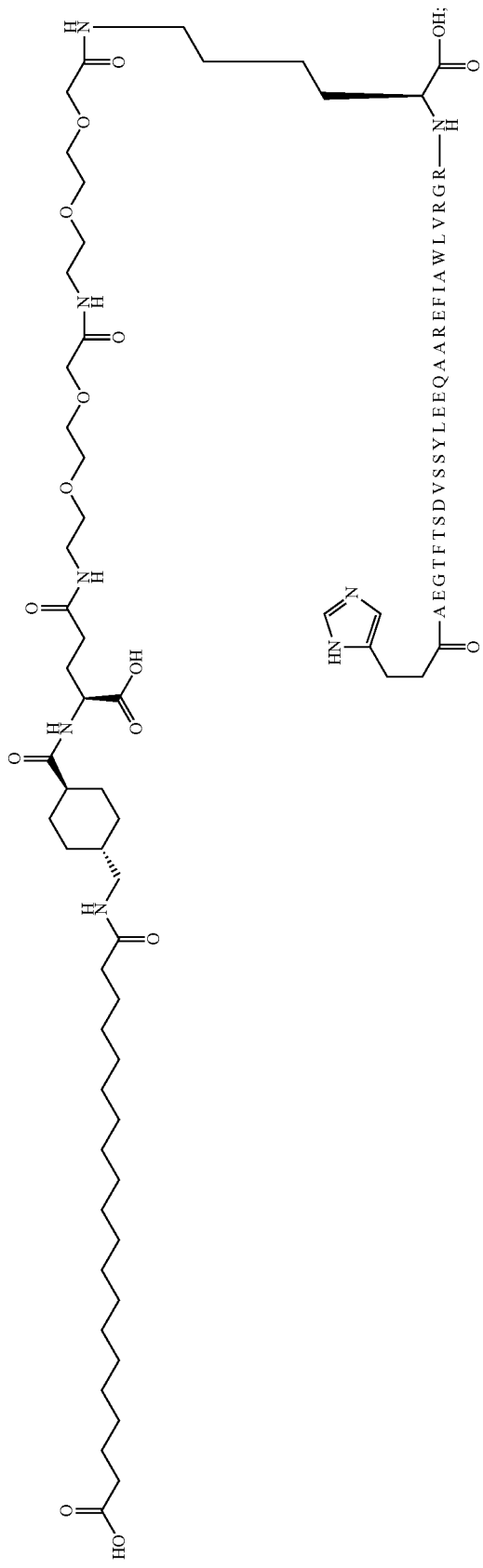

N-epsilon26-[2-(2-{2-[2-(2-{2-[(S)-Carboxy-4-(17-carboxyheptadecanoylamino)butyrylamino]ethoxy}ethoxy)acetylamino]ethoxy}ethoxy)acetyl][Aib8,Arg34]GLP-1-(7-37)
(Compound G3) (SEQ ID NO: 35):

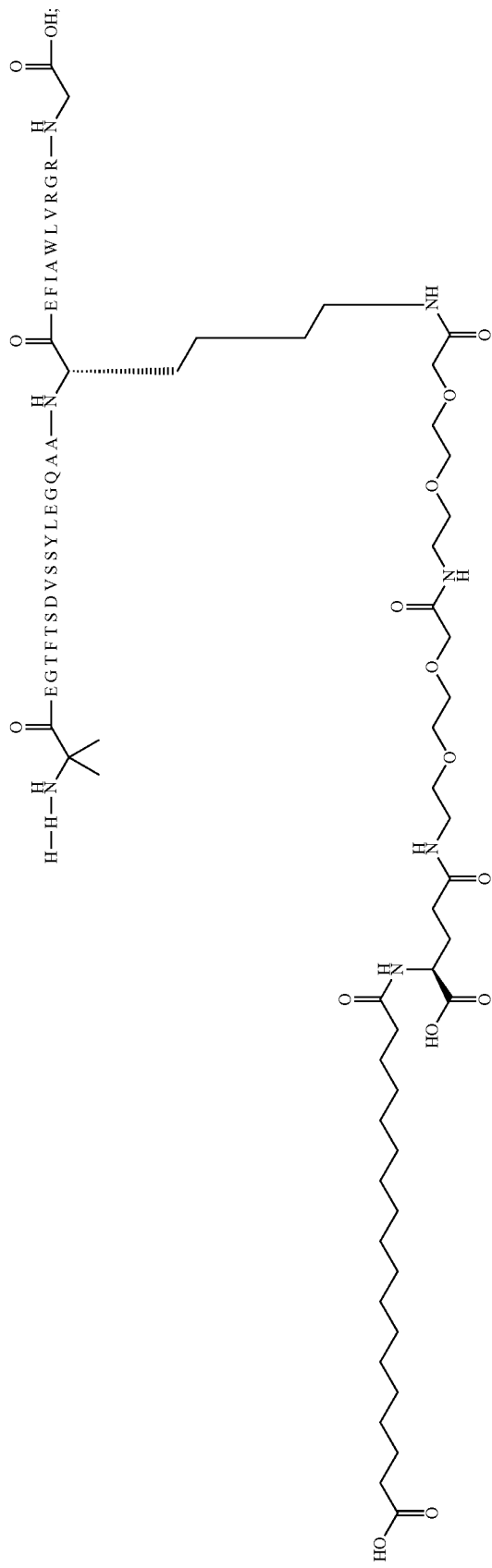

and
N-epsilon37-[2-(2-{2-[2-(2-{2-[(S)-carboxy-4-(15-car-
   boxy-pentadecanoylamino)-butyrylamino]ethoxy}-
   ethoxy)-acetylamino]-ethoxy}-acetyl][Aib8,22,
   35,Lys37]GLP-1-(7-37)
(Compound G4) (SEQ ID NO: 36):

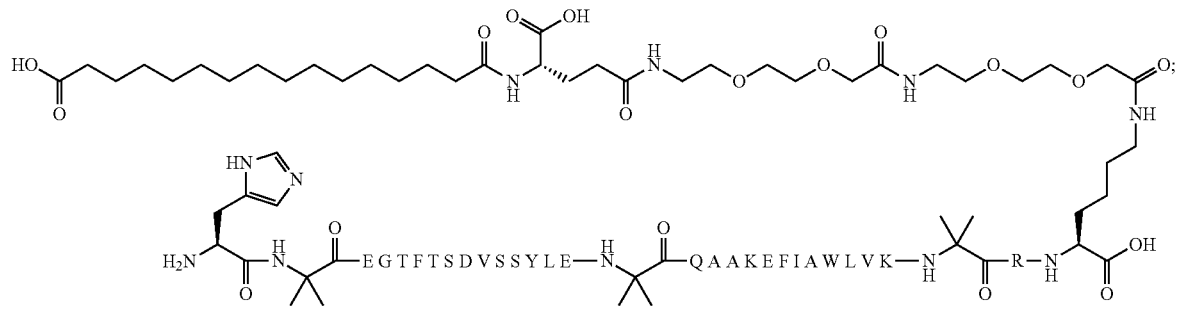

and their pharmaceutically acceptable salts, amides, alkyls or esters.

In some embodiments the insulin compound is N-epsilon-B29-[(S)-4-Carboxy-4-(15-carboxypentadecanoylamino) butyryl]desB30 human insulin
(Compound G5):

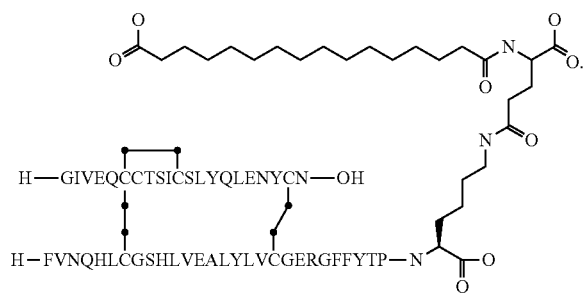

In some embodiments the pharmaceutical composition is in a unit dosage form comprising from about 0.01 mg to about 1000 mg, such as from about 0.1 mg to about 500 mg, from about 0.5 mg to about 5 mg, e.g. from about 0.5 mg to about 200 mg, of a GLP-1 derivative as defined in any one of the preceding embodiments.

In some embodiments the pharmaceutical composition is suited for parenteral administration.

Pharmaceutical Administration

The derivative of the invention may be administered parenterally to a patient. The route of administration of the derivative may be intramuscular (IM), subcutaneous (SC) or intravenous (IV). It is recommended that the dosage of the compositions comprising the derivative of this invention which is to be administered to the patient be selected by a physician.

Parenteral administration may be performed by subcutaneous, intramuscular, intraperitoneal or intravenous injection by means of a syringe, optionally a pen-like syringe. In some embodiments the compositions comprising the derivative of the invention can be used in ready to use pen devices for glucagon administration. Alternatively, parenteral administration can be performed by means of an infusion pump. In some embodiments the compositions comprising the derivative of the invention can be used in pumps for glucagon administration. Parenteral administration may be nasal administration. As a further option, the glucagon preparations comprising the derivative of the invention can also be adapted to transdermal administration, e.g. by needle-free injection or from a patch, optionally an iontophoretic patch or transmucosal, e.g. buccal, administration.

A typical dosage of a derivative or composition of the invention when employed in a method according to the invention is in the range of from about 0.0001 to about 1 mg/kg body weight per day, preferably from about 0.001 to about 1 mg/kg body weight, more preferably from about 0.005 to about 0.02 mg/kg body. As described above, derivatives of the invention may be administered or applied in combination with one or more additional therapeutically active compounds or substances, and suitable additional compounds or substances may be selected, for example, from antidiabetic agents, antihyperlipidemic agents, anti-obesity agents, antihypertensive agents and agents for the treatment of complications resulting from or associated with, diabetes.

Suitable antidiabetic agents include insulin, insulin derivatives or analogues, GLP-1 (glucagon like peptide-1) derivatives or analogues [such as those disclosed in WO 98/08871 (Novo Nordisk A/S) or other GLP-1 analogues such as exenatide (Byetta, Eli Lilly/Amylin; AVE0010, Sanofi-Aventis), taspoglutide (Roche), albiglutide (Syncria, GlaxoSmithKline), dulaglutide (Trulicity, Eli Lilly)], amylin, amylin analogues (e.g. Symlin/Pramlintide) as well as orally active hypoglycaemic agents.

In the case of administration of a GLP-1 derivative of the invention, optionally in combination with one or more additional therapeutically active compounds or substances as disclosed above, for a purpose related to treatment or prevention of obesity or overweight, i.e. related to reduction or prevention of excess adiposity, it may be of relevance to employ such administration in combination with surgical intervention for the purpose of achieving weight loss or preventing weight gain, e.g. in combination with bariatric surgical intervention. Examples of frequently used bariatric surgical techniques include, but are not limited to, the following: vertical banded gastroplasty (also known as "stomach stapling"), wherein a part of the stomach is stapled to create a smaller pre-stomach pouch which serves as a new stomach; gastric banding, e.g. using an adjustable gastric band system (such as the Swedish Adjustable Gastric Band (SAGB), the LAP-BAND™ or the MIDband™), wherein a small pre-stomach pouch which is to serve as a new stomach is created using an elastomeric (e.g. silicone) band which can be adjusted in size by the patient; and gastric bypass surgery, e.g. "Roux-en-Y" bypass wherein a small stomach pouch is created using a stapler device and is connected to the distal small intestine, the upper part of the small intestine being reattached in a Y-shaped configuration.

The administration of a GLP-1 derivative of the invention (optionally in combination with one or more additional therapeutically active compounds as disclosed above) may take place for a period prior to carrying out the bariatric surgical intervention in question and/or for a period of time subsequent thereto. In many cases it may be preferable to begin administration of a compound of the invention after bariatric surgical intervention has taken place.

The GLP-1 derivative s of the present invention and anti-obesity or anti-diabetic agents as defined herein, may be administered simultaneously or sequentially. The factors may be supplied in single-dosage form wherein the single-dosage form comprises both compounds or in the form of a kit-of-parts comprising a preparation of a GLP-1 derivative s of the present invention as a first unit dosage form and a preparation of an anti-obesity or anti-diabetic agents as a second unit dosage form. Whenever a first or second or third, etc., unit dose is mentioned throughout this specification this does not indicate the preferred order of administration, but is merely done for convenience purposes.

By "simultaneous" dosing of a preparation of a GLP-1 derivative s of the present invention and a preparation of anti-obesity or anti-diabetic agents is meant administration of the compounds in single-dosage form or administration of a first agent followed by administration of a second agent with a time separation of no more than 15 minutes, preferably 10, more preferred 5, more preferred 2 minutes. Either factor may be administered first.

By "sequential" dosing is meant administration of a first agent followed by administration of a second agent with a time separation of more than 15 minutes. Either of the two unit dosage form may be administered first. Preferably, both products are injected through the same intravenous access.

As already indicated, in all of the therapeutic methods or indications disclosed above, a GLP-1 derivative of the present invention may be administered alone. However, it may also be administered in combination with one or more additional therapeutically active compounds, either sequentially or concomitantly.

A typical dosage of a compound of the invention, e.g. a GLP-1 derivative, when employed in a method according to the present invention is in the range of from about 0.0001 to about 100 mg/kg body weight per day, preferably from about 0.001 to about 10 mg/kg body weight, more preferably from about 0.001 to about 5 mg/kg body weight per day, e.g. from about 0.001 to about 10 mg/kg body weight per day or from about 0.001 to about 5 mg/kg body weight per day administered in one or more doses, such as from 1 to 3 doses. The exact dosage will depend upon the frequency and mode of administration, the sex, age, weight and general condition of the subject treated, the nature and severity of the condition treated, any concomitant diseases to be treated and other factors evident to those skilled in the art.

Compounds of the invention comprise compounds that are believed to be well-suited to administration with longer intervals than, for example, once daily, thus, appropriately formulated compounds of the invention may be suitable for, e.g., twice-weekly or once-weekly administration by a suitable route of administration, such as one of the routes disclosed herein.

As described above, compounds of the present invention may be administered or applied in combination with one or more additional therapeutically active compounds or substances, and suitable additional compounds or substances may be selected, for example, from antidiabetic agents, antihyperlipidemic agents, antiobesity agents, antihypertensive agents and agents for the treatment of complications resulting from or associated with, diabetes.

Pharmaceutical Indications

In some embodiments the invention relates to the GLP-1 derivative as defined herein for use in medicine, optionally in combination with one or more additional therapeutically active compounds.

As use herein, the term "therapeutically effective amount" of a compound, e.g. a GLP-1 derivative, refers to an amount sufficient to cure, alleviate or partially arrest the clinical manifestations of a given disease and/or its complications. An amount adequate to accomplish this is defined as a "therapeutically effective amount". Effective amounts for each purpose will depend on the severity of the disease or injury, as well as on the weight and general state of the subject. It will be understood that determination of an appropriate dosage may be achieved using routine experimentation, by constructing a matrix of values and testing different points in the matrix, all of which is within the level of ordinary skill of a trained physician or veterinarian.

The terms "treatment", "treating" and other variants thereof as used herein refer to the management and care of a patient for the purpose of combating a condition, such as a disease or a disorder. The terms are intended to include the full spectrum of treatments for a given condition from which the patient is suffering, such as administration of the active compound(s) in question to alleviate symptoms or complications thereof, to delay the progression of the disease, disorder or condition, to cure or eliminate the disease, disorder or condition, and/or to prevent the condition, in that prevention is to be understood as the management and care of a patient for the purpose of combating the disease, condition or disorder, and includes the administration of the active compound(s) in question to prevent the onset of symptoms or complications. The patient to be treated is preferably a mammal, in particular a human being, but treatment of other animals, such as dogs, cats, cows, horses, sheep, goats or pigs, is within the scope of the invention.

The term "diabetes" or "diabetes mellitus" includes type 1 diabetes, type 2 diabetes, gestational diabetes (during pregnancy) and other states that cause hyperglycaemia. The term is used for a metabolic disorder in which the pancreas produces insufficient amounts of insulin or in which the cells of the body fail to respond appropriately to insulin thus preventing cells from absorbing glucose. As a result, glucose builds up in the blood.

Type 1 diabetes, also called insulin-dependent diabetes mellitus (IDDM) and juvenile-onset diabetes, is caused by beta-cell destruction, usually leading to absolute insulin deficiency.

Type 2 diabetes, also known as non-insulin-dependent diabetes mellitus (NIDDM) and adult-onset diabetes, is associated with predominant insulin resistance and thus relative insulin deficiency and/or a predominantly insulin secretory defect with insulin resistance.

The term "euglycaemia" as used herein means normal concentration of glucose in the blood. Also called normoglycaemia.

The term "obesity" implies an excess of adipose tissue. When energy intake exceeds energy expenditure, the excess calories are stored in adipose tissue, and if this net positive balance is prolonged, obesity results, i.e. there are two components to weight balance, and an abnormality on either side (intake or expenditure) can lead to obesity. In this context, obesity is best viewed as any degree of excess adipose tissue that imparts a health risk. The distinction between normal and obese individuals can only be approximated, but the health risk imparted by obesity is probably a continuum with increasing adipose tissue. However, in the context of the present invention, individuals with a body mass index (BMI=body weight in kilograms divided by the square of the height in meters) above 25 are to be regarded as obese.

In some embodiments the invention relates to a GLP-1 derivative as defined herein for use treating obesity or preventing overweight. In some embodiments the invention relates to a GLP-1 derivative as defined herein for use in for decreasing food intake. In some embodiments the invention relates to a GLP-1 derivative as defined herein for use in increasing energy expenditure. In some embodiments the invention relates to a GLP-1 derivative as defined herein for use in reducing body weight. In some embodiments the invention relates to a GLP-1 derivative as defined herein for use regulating appetite. In some embodiments the invention relates to a GLP-1 derivative as defined herein for use inducing satiety. In some embodiments the invention relates to a GLP-1 derivative as defined herein for use in preventing weight regain after successful weight loss. In some embodiments the invention relates to a GLP-1 derivative as defined herein for use in treating a disease or state related to overweight or obesity. In some embodiments the invention relates to a GLP-1 derivative as defined herein for use in treating bulimia. In some embodiments the invention relates to a GLP-1 derivative as defined herein for use in treating binge-eating.

In some embodiments the invention relates to a GLP-1 derivative as defined herein for use in treating atherosclerosis. In some embodiments the invention relates to a GLP-1 derivative as defined herein for use in treating hypertension. In some embodiments the invention relates to a GLP-1 derivative as defined herein for use in treating dyslipidaemia. In some embodiments the invention relates to a GLP-1 derivative as defined herein for use in treating coronary heart disease. In some embodiments the invention relates to a GLP-1 derivative as defined herein for use in treating hepatic steatosis.

In some embodiments the invention relates to a GLP-1 derivative as defined herein for use in treating type 2 diabetes. In some embodiments the invention relates to a GLP-1 derivative as defined herein for use in treating impaired glucose tolerance. In some embodiments the invention relates to a GLP-1 derivative as defined herein for use in delaying or preventing disease progression in type 2 diabetes. In some embodiments the invention relates to a GLP-1 derivative as defined herein for use in delaying the progression from impaired glucose tolerance (IGT) to type 2 diabetes. In some embodiments the invention relates to a GLP-1 derivative as defined herein for use in delaying the progression from type 2 diabetes to insulin-requiring diabetes.

In some embodiments the invention relates to a method for treating obesity, preventing overweight, decreasing food intake, increasing energy expenditure, reducing body weight, regulating appetite, inducing satiety, preventing weight regain after successful weight loss, treating a disease or state related to overweight or obesity, treating bulimia, or treating binge-eating comprising administering to a patient in need thereof, an effective amount of a GLP-1 derivative as defined herein, optionally in combination with one or more additional therapeutically active compounds.

In some embodiments the invention relates to a method for treating atherosclerosis, hypertension, dyslipidaemia, coronary heart disease, or hepatic steatosis comprising administering to a patient in need thereof, an effective amount of a GLP-1 derivative as defined herein, optionally in combination with one or more additional therapeutically active compounds.

In some embodiments the invention relates to a method for treating type 2 diabetes, treating impaired glucose tolerance, delaying the progression from impaired glucose tolerance (IGT) to type 2 diabetes, delaying the progression from type 2 diabetes to insulin-requiring diabetes comprising administering to a patient in need thereof, an effective amount of a GLP-1 derivative as defined herein, optionally in combination with one or more additional therapeutically active compounds.

In some embodiments the invention relates to a use of a GLP-1 derivative as defined herein for the preparation of a medicament. In some embodiments the invention relates to use of a GLP-1 derivative as defined in any one of the preceding embodiments, for the preparation of a medicament for the treatment or prevention of obesity, hyperglycaemia, type 2 diabetes, impaired glucose tolerance, and type 1 diabetes.

EMBODIMENTS OF THE INVENTION

The invention may be further described by the following non-limiting embodiments:
1. A GLP-1 derivative comprising a polypeptide consisting of the amino acid sequence of Formula I (SEQ ID NO: 2):

```
Imp-X8-His-Gly-Thr-Phe-Thr-Ser-Asp-X16-Ser-X18-
Tyr-Leu-Glu-X22-X23-Ala-Ala-X26-X27-Phe-Ile-
Ala-Trp-Leu-X33-X34-X35-X36-X37 [I],
``` wherein
  X8 is Ala, Aib, Acb, or Gly;
  X16 is Val, Leu, Ile, or Tyr (alternatively, X16 is Val, Leu, or Tyr);
  X18 is Lys or Arg;
  X22 is Gly, Ala, Glu, Lys, Arg, Ser, or Aib (alternatively, X22 is Gly, Ala, Glu, Lys, Arg, or Ser);
  X23 is Gln, Arg, or Lys;
  X26 is Lys or Arg (alternatively, X26 is Arg);
  X27 is Glu or Lys;
  X33 is Val, Leu, or Ile (alternatively, X33 is Leu, or Ile);
  X34 is Lys or Arg;
  X35 is Gly, Thr, Lys, or is absent;
  X36 is Ala, Gly, Lys, Ser, or is absent (alternatively, X36 is Arg);
  X37 is Gly or is absent;
wherein said GLP-1 derivative further comprises a substituent comprising a lipophilic moiety and at least two negatively charged moieties, wherein one of said negatively charged moieties is distal of a lipophilic moiety;
wherein said polypeptide optionally comprises a C-terminal amide;
or a pharmaceutically acceptable salt and/or ester thereof.
2. The GLP-1 derivative according to embodiment 1, wherein said substituent is covalently attached via an amino acid residue in said polypeptide at one of the amino acid positions selected from the group consisting of position 22, 23, 27, 34, 35, and 36.
3. The GLP-1 derivative according to embodiment 1, wherein said substituent is attached at the epsilon position of a lysine residue in said polypeptide at one of the amino acid positions selected from the group consisting of position 22, 23, 27, 34, 35, and 36.
4. The GLP-1 derivative according to any one of the preceding embodiments, wherein said polypeptide comprises a C-terminal acid group, such as a carboxylic acid group.
5. The GLP-1 derivative according to any one of the preceding embodiments, wherein said polypeptide comprises a C-terminal amide.
6. The GLP-1 derivative according to any one of the preceding embodiments, wherein said polypeptide has 3-15 amino acid residue modifications, such as substitutions, additions or deletions, as compared to human GLP-1 (SEQ ID NO: 1).

7. The GLP-1 derivative according to any one of the preceding embodiments, wherein said polypeptide has up to 14, such as up to 13 or up to 12, amino acid residue modifications, such as substitutions, additions or deletions, as compared to human GLP-1 (SEQ ID NO: 1).

8. The GLP-1 derivative according to any one of the preceding embodiments, wherein said polypeptide has up to 11, such as up to 10 or up to 9, amino acid residue modifications, such as substitutions, additions or deletions, as compared to human GLP-1 (SEQ ID NO: 1).

9. The GLP-1 derivative according to any one of the preceding embodiments, wherein said polypeptide has up to 8, such as up to 7 or up to 6, amino acid residue modifications, such as substitutions, additions or deletions, as compared to human GLP-1 (SEQ ID NO: 1).

10. The GLP-1 derivative according to any one of the preceding embodiments, wherein said GLP-1 derivative comprises up to 5 amino acid residue modifications, such as substitutions, additions or deletions, in said polypeptide as compared to human GLP-1 (SEQ ID NO: 1).

11. The GLP-1 derivative according to any one of the preceding embodiments, wherein
X8 is Ala, Aib, Acb;
X22 is Ala or Glu;
X35 is Gly or Thr; and/or
X36 is Gly or is absent.

12. The GLP-1 derivative according to any one of the preceding embodiments, wherein X8 is Ala, Aib, Acb, or Gly.

13. The GLP-1 derivative according to any one of the preceding embodiments, wherein X8 is Ala, Aib or Acb.

14. The GLP-1 derivative according to any one of the preceding embodiments, wherein X16 is Val, Leu, Ile, or Tyr.

15. The GLP-1 derivative according to any one of the preceding embodiments, wherein X18 is Lys or Arg.

16. The GLP-1 derivative according to any one of the preceding embodiments, wherein X22 is Gly, Ala, Glu, Lys, Arg, Ser, or Aib.

17. The GLP-1 derivative according to any one of the preceding embodiments, wherein X22 is Gly, Ala, or Glu.

18. The GLP-1 derivative according to any one of the preceding embodiments, wherein X22 is Lys, Arg, Ser, or Aib.

19. The GLP-1 derivative according to any one of the preceding embodiments, wherein X22 is Ala or Glu.

20. The GLP-1 derivative according to any one of the preceding embodiments, wherein X23 is Gln, Arg, or Lys.

21. The GLP-1 derivative according to any one of the preceding embodiments, wherein X26 is Lys or Arg.

22. The GLP-1 derivative according to any one of the preceding embodiments, wherein X27 is Glu or Lys.

23. The GLP-1 derivative according to any one of the preceding embodiments, wherein X33 is Val, Leu, or Ile.

24. The GLP-1 derivative according to any one of the preceding embodiments, wherein X34 is Lys or Arg.

25. The GLP-1 derivative according to any one of the preceding embodiments, wherein X35 is Gly, Thr, Lys, or is absent.

26. The GLP-1 derivative according to any one of the preceding embodiments, wherein X35 is Gly or Thr.

27. The GLP-1 derivative according to any one of the preceding embodiments, wherein X36 is Ala, Gly, Lys, Ser, or is absent.

28. The GLP-1 derivative according to any one of the preceding embodiments, wherein X36 is Ala, Gly, or Lys.

29. The GLP-1 derivative according to any one of the preceding embodiments, wherein X36 is Gly or is absent.

30. The GLP-1 derivative according to any one of the preceding embodiments, wherein if X35 is absent, then X36 and X37 are also absent.

31. The GLP-1 derivative according to any one of the preceding embodiments, wherein if X36 is absent, then X37 is also absent.

32. The GLP-1 derivative according to any one of the preceding embodiments, wherein if X35 is absent, then X36 and X37 are also absent, and said GLP-1 derivative comprises a C-terminal carboxylic acid group.

33. The GLP-1 derivative according to any one of the preceding embodiments, wherein if X36 is absent, then X37 is also absent.

34. The GLP-1 derivative according to any one of the preceding embodiments, wherein if X36 is absent, then X37 is also absent, and said GLP-1 derivative comprises a C-terminal carboxylic amide.

35. The GLP-1 derivative according to any one of the preceding embodiments, wherein said substituent comprises at least three negatively charged moieties.

36. The GLP-1 derivative according to any one of the preceding embodiments, wherein said lipophilic moiety comprises an alkyl group of at least 12 carbon atoms, such as 12-20 carbon atoms or 14-18 carbon atoms, or such as 16 carbon atoms.

37. The GLP-1 derivative according to any one of the preceding embodiments, wherein said substituent is covalently attached to the side chain of an amino acid, such as the nitrogen atom of the side chain of a lysine.

38. The GLP-1 derivative according to any one of the preceding embodiments, wherein said substituent is attached to the amino acid residue at a position selected from the group consisting of position 22, 23, 27, 34, 35, and 36 in said polypeptide.

39. The GLP-1 derivative according to any one of the preceding embodiments, wherein said substituent is attached at the epsilon position of a lysine residue at an amino acid position selected from the group consisting of position 34 and 35 in said polypeptide.

40. The GLP-1 derivative according to any one of the preceding embodiments, wherein said substituent comprises Formula II:

$$Z_1-Z_2-Z_3-Z_4-Z_5-Z_6-Z_7-Z_8-Z_9-Z_{10}- \quad \text{[II]},$$

wherein $Z_1$ comprises Formula IIa:

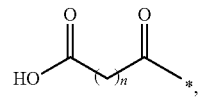

[IIa]

wherein in Formula IIa n is 6-20 and the symbol * represents the attachment point to the nitrogen of the neighbouring group;
wherein Z2, Z3, Z4, Z5, Z6, Z7, Z8, Z9, and Z10 individually are absent or are amino acids selected from the group consisting of Glu, γGlu, Gly, Ser, Ala, Thr, Ado; and
wherein $Z_1-Z_2-Z_3-Z_4-Z_5-Z_6-Z_7-Z_8-Z_9-Z_{10}$ together comprises at least two negatively charged moieties.

41. The GLP-1 derivative according to any one of the preceding embodiments, wherein said substituent comprises Formula II:

$$Z_1—Z_2—Z_3—Z_4—Z_5—Z_6—Z_7—Z_8—Z_9—Z_{10}—\quad\quad [II],$$

wherein Z1 comprises Formula IIa:

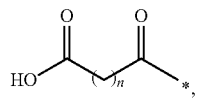

[IIa]

wherein in Formula IIa n is 6-20 and the symbol * represents the attachment point to the nitrogen of the neighbouring group;
wherein Z2, Z3, Z4, Z5, Z6, Z7, Z8, Z9, and Z10 individually are absent or are amino acids selected from the group consisting of Glu, γGlu, Gly, Ser, Ala, Thr, Ado; and
wherein said substituent is attached at the epsilon position of a lysine residue of said polypeptide; and
wherein $Z_1—Z_2—Z_3—Z_4—Z_5—Z_6—Z_7—Z_8—Z_9—Z_{10}—$ together comprises at least two negatively charged moieties.

42. The GLP-1 derivative according to any one of the preceding embodiments, wherein said substituent comprises three, four or five negatively charged moieties.

43. The GLP-1 derivative according to any one of the preceding embodiments, wherein said substituent comprises three or four negatively charged moieties.

44. The GLP-1 derivative according to any one of the preceding embodiments, wherein said substituent comprises three negatively charged moieties.

45. The GLP-1 derivative according to any one of the preceding embodiments, wherein said substituent binds non-covalently to albumin.

46. The GLP-1 derivative according to any one of the preceding embodiments, wherein said substituent is negatively charged at physiological pH.

47. The GLP-1 derivative according to any one of the preceding embodiments, wherein $Z_1$ consists of Formula IIa;

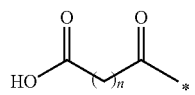

[IIa]

wherein n is an integer in the range of from 12 to 18.

48. The GLP-1 derivative according to any one of the preceding embodiments, wherein n in Formula IIa is 12, 14, 16 or 18.

49. The GLP-1 derivative according to any one of the preceding embodiments, wherein n in Formula IIa is 16 (i.e. $Z_1$ is 17-carboxyheptadecanoyl).

50. The GLP-1 derivative according to any one of the preceding embodiments, wherein in Formula II $Z_2—Z_3—Z_4—Z_5—Z_6—Z_7—Z_8—Z_9—Z_{10}—$ is a linker, wherein each of $Z_2, Z_3, Z_4, Z_5, Z_6, Z_7, Z_8, Z_9,$ or $Z_{10}$ individually are any one of the following amino acid residues: Glu, γGlu, Gly, Ser, Ala, Thr and/or Ado; or one or more of residues $Z_2, Z_3, Z_4, Z_5, Z_6, Z_7, Z_8, Z_9,$ or $Z_{10}$ are absent; provided, however, that at least two of residues $Z_2, Z_3, Z_4, Z_5, Z_6, Z_7, Z_8, Z_9,$ or $Z_{10}$ are present; and wherein $Z_1—Z_2—Z_3—Z_4—Z_5—Z_6—Z_7—Z_8—Z_9—Z_{10}—$ together comprises at least three negatively charged moieties.

51. The GLP-1 derivative according to any one of the preceding embodiments, wherein $Z_2, Z_3, Z_4, Z_5, Z_6, Z_7, Z_8, Z_9,$ and $Z_{10}$ individually are any one of the following amino acid residues: Glu, γGlu, Gly, Ser, and/or Ado; or one or more of residues $Z^2$ to $Z^{10}$ are absent; provided, however, that at least two of residues $Z^2$ to $Z^{10}$ are present.

52. The GLP-1 derivative according to any one of the preceding embodiments, wherein $Z_2, Z_3, Z_4, Z_5, Z_6, Z_7, Z_8, Z_9,$ and $Z_{10}$ individually are any one of the following amino acid residues: γGlu and/or Ado; or one or more of residues $Z_2, Z_3, Z_4, Z_5, Z_6, Z_7, Z_8, Z_9,$ or $Z_{10}$ are absent; provided, however, that at least two of $Z_2, Z_3, Z_4, Z_5, Z_6, Z_7, Z_8, Z_9,$ or $Z_{10}$ are present.

53. The GLP-1 derivative according to any one of the preceding embodiments, wherein at least three of residues $Z_2, Z_3, Z_4, Z_5, Z_6, Z_7, Z_8, Z_9,$ or $Z_{10}$ are present.

54. The GLP-1 derivative according to any one of the preceding embodiments, wherein at least four of residues $Z_2, Z_3, Z_4, Z_5, Z_6, Z_7, Z_8, Z_9,$ or $Z_{10}$ are present.

55. The GLP-1 derivative according to any one of the preceding embodiments, wherein at least five of residues $Z_2, Z_3, Z_4, Z_5, Z_6, Z_7, Z_8, Z_9,$ or $Z_{10}$ are present.

56. The GLP-1 derivative according to any one of the preceding embodiments, wherein at least six of residues $Z_2, Z_3, Z_4, Z_5, Z_6, Z_7, Z_8, Z_9,$ or $Z_{10}$ are present.

57. The GLP-1 derivative according to any one of the preceding embodiments, wherein in Formula II $Z_2—Z_3—Z_4—Z_5—Z_6—Z_7—Z_8—Z_9—Z_{10}—$ is a linker which comprises a structure selected from the group consisting of:
γGlu-γGlu-Ado-Ado-;
γGlu-γGlu-Ado-Ado-γGlu-;
γGlu-γGlu-Ado-γGlu-γGlu-;
γGlu-γGlu-Ado-γGlu-Ado-γGlu-Ado-γGlu-;
γGlu-γGlu-Ser-Gly-;
γGlu-γGlu-Ser-Gly-Glu-Ser-Gly-;
γGlu-γGlu-γGlu-Ado-Ado-;
γGlu-γGlu-γGlu-γGlu-;
γGlu-Ado-Ado-;
γGlu-Ado-Ado-γGlu-γGlu-;
Gly-Ser-Glu-Gly-Ser-γGlu-γGlu-.

58. The GLP-1 derivative according to any one of the preceding embodiments, wherein said substituent is selected from the group consisting of:

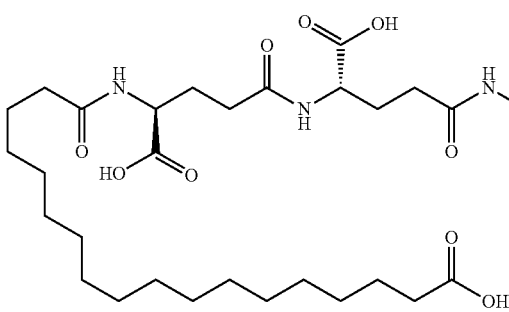
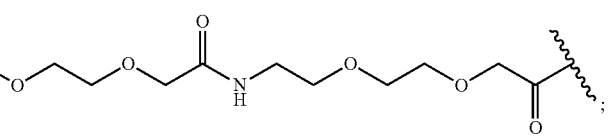

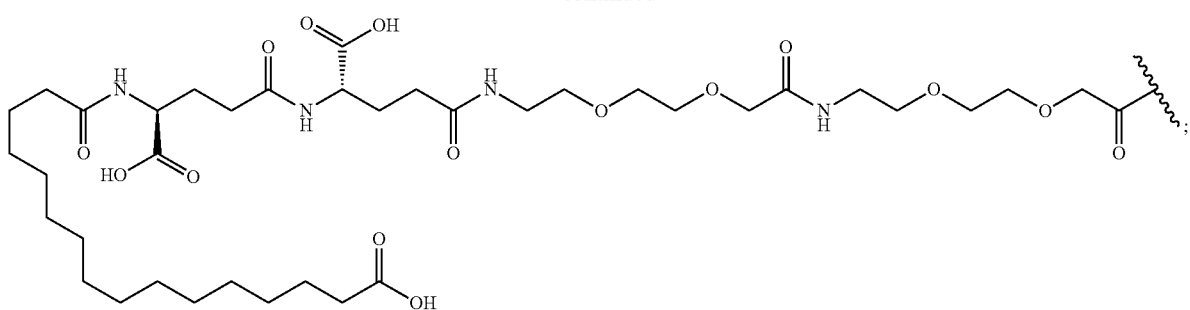
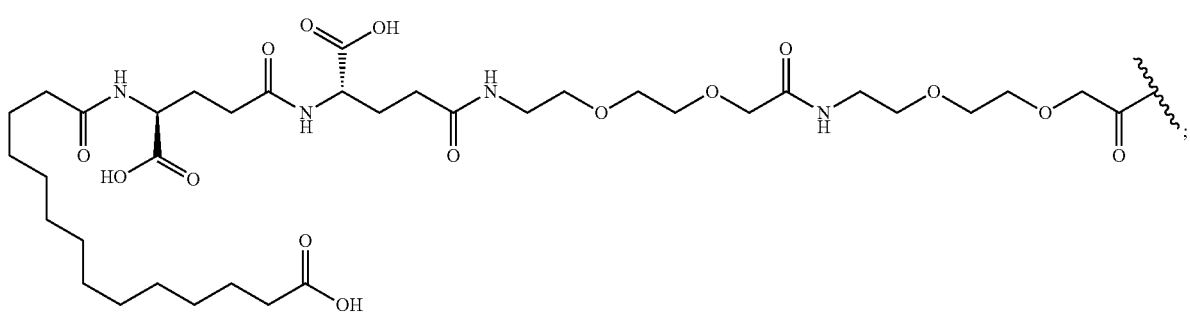
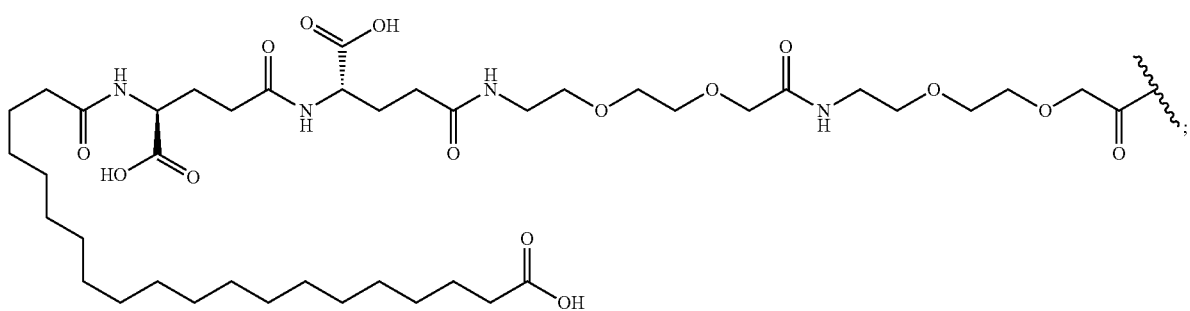
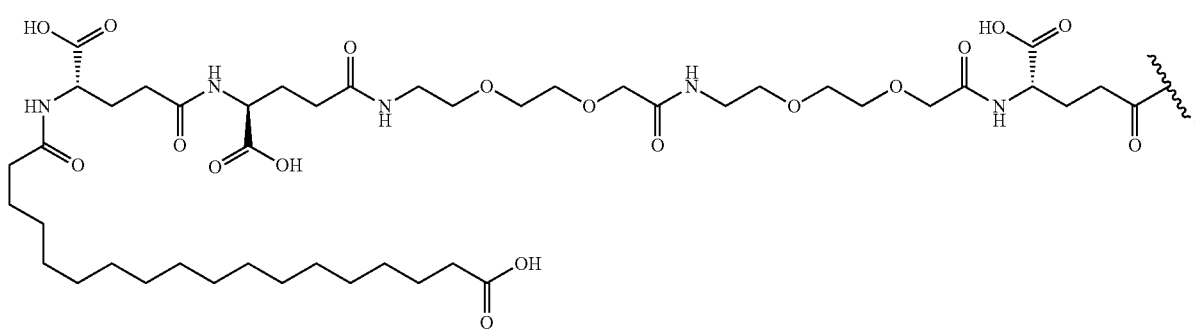
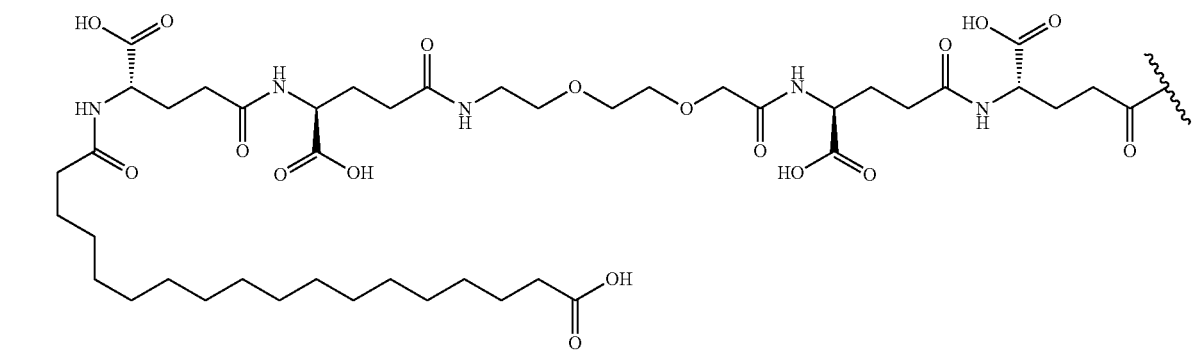

-continued
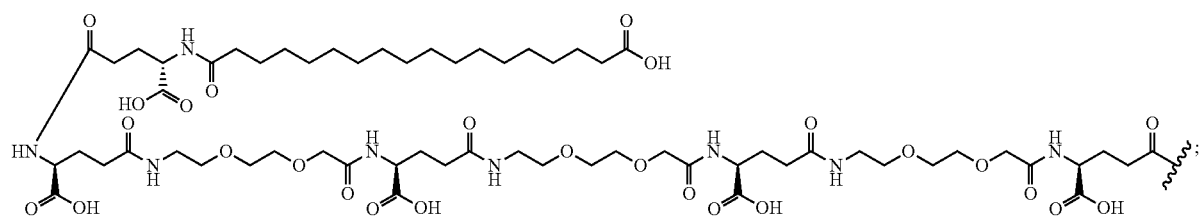
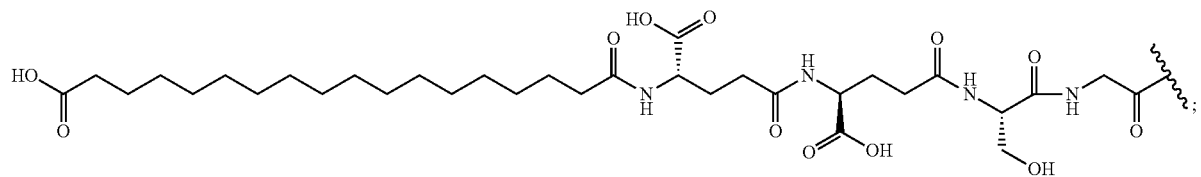
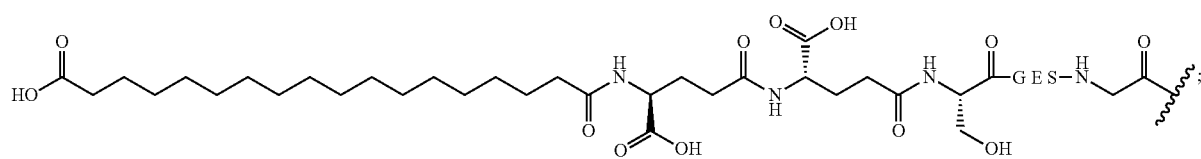
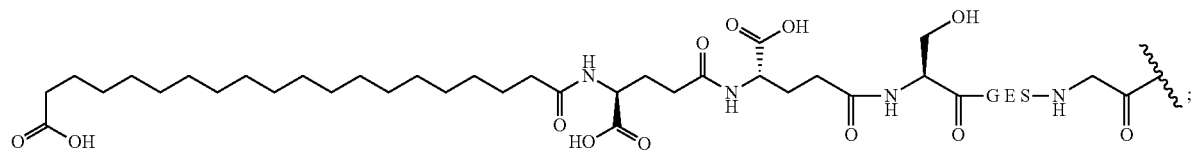
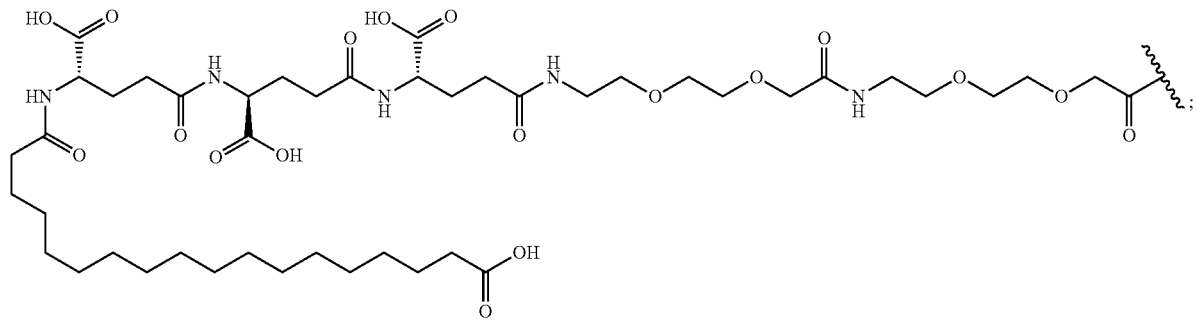
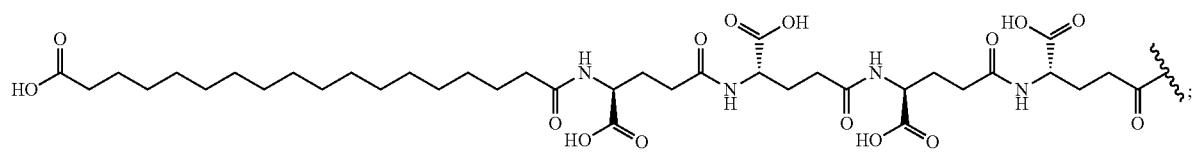
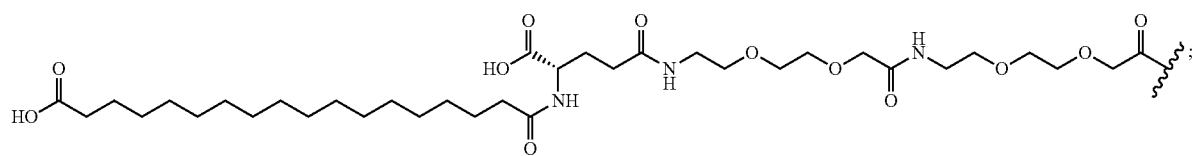

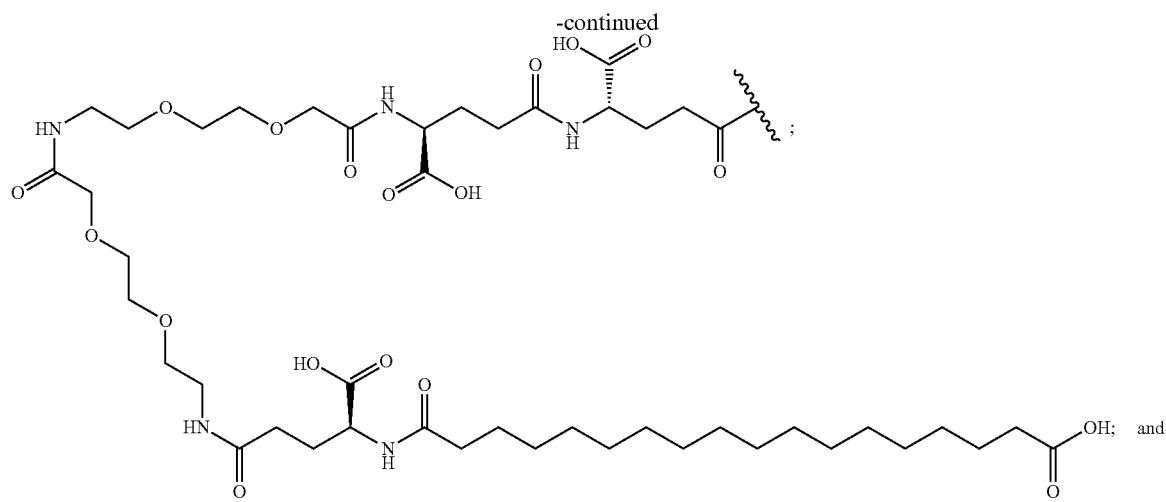

and wherein said substituent may be covalently attached to said polypeptide via the carbonyl group marked with a waved line in the structural formula of said substituent.

59. The GLP-1 derivative according to any one of the preceding embodiments, wherein said GLP-1 derivative is selected from the group consisting of: N^ε35-[2-[[(2S)-2-[[(2S)-4-carboxy-2-[[2-[[(2S)-2-[[(4S)-4-carboxy-4-[[(4S)-4-carboxy-4-(17-carboxyheptadecanoylamino)butanoyl]amino]butanoyl]amino]-3-hydroxypropanoyl]amino]acetyl]amino]butanoyl]amino]-3-hydroxypropanoyl]amino]acetyl]-[Imp7,Acb8,His9,Tyr16,Lys18,Glu22,Arg26,Leu33,Lys35]-GLP-1-(7-35)-peptide amide (SEQ ID NO: 3)

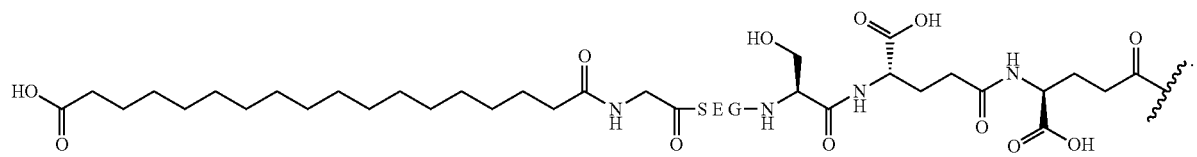

(Chem. 1)

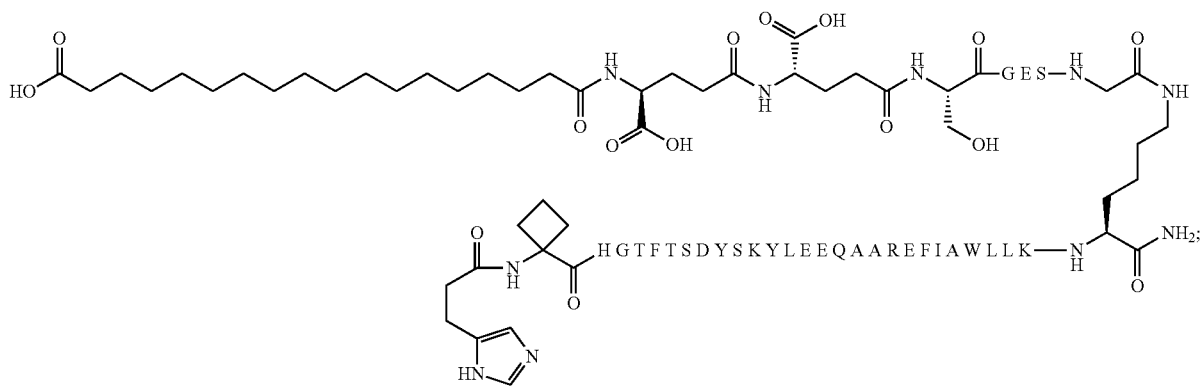

N^ε35-[2-[[(2S)-2-[[(2S)-4-carboxy-2-[[2-[[(2S)-2-[[(4S)-4-carboxy-4-[[(4S)-4-carboxy-4-(17-carboxyheptadecanoylamino)butanoyl]amino]butanoyl]amino]-3-hydroxypropanoyl]amino]acetyl]amino]butanoyl]amino]-3-hydroxypropanoyl]amino]acetyl]-[Imp7,Acb8,His9,Lys18,Glu22,Arg26,Leu33,Lys35]-GLP-1-(7-35)-peptide amide (SEQ ID NO: 4)

(Chem. 2)

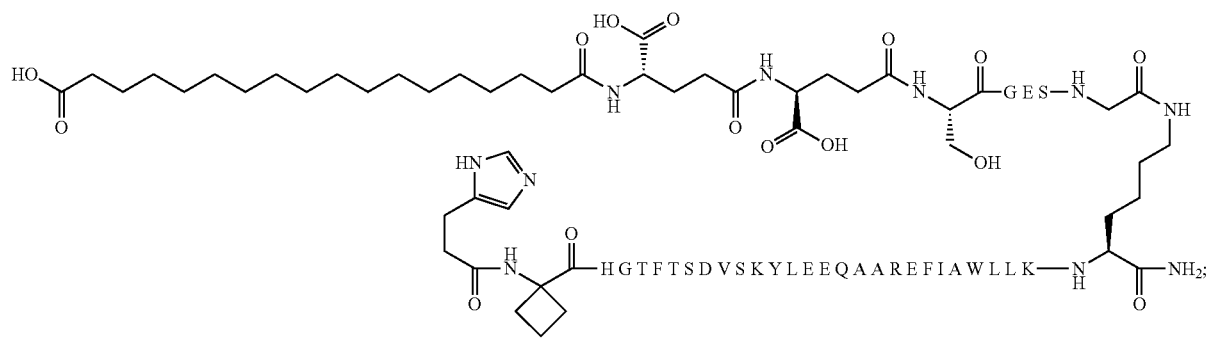

N^ε34-[2-[[(2S)-2-[[(2S)-4-carboxy-2-[[2-[[(2S)-2-[[(4S)-4-carboxy-4-[[(4S)-4-carboxy-4-(17-carboxyheptadecanoylamino)butanoyl]amino]butanoyl]amino]-3-hydroxypropanoyl]amino]acetyl]amino]butanoyl]amino]-3-hydroxypropanoyl]amino]acetyl]-[Imp7,Aib8,His9,Lys18,Glu22,Arg26,Leu33,Thr35]-GLP-1-(7-35)-peptide amide (SEQ ID NO: 5)

(Chem. 3)

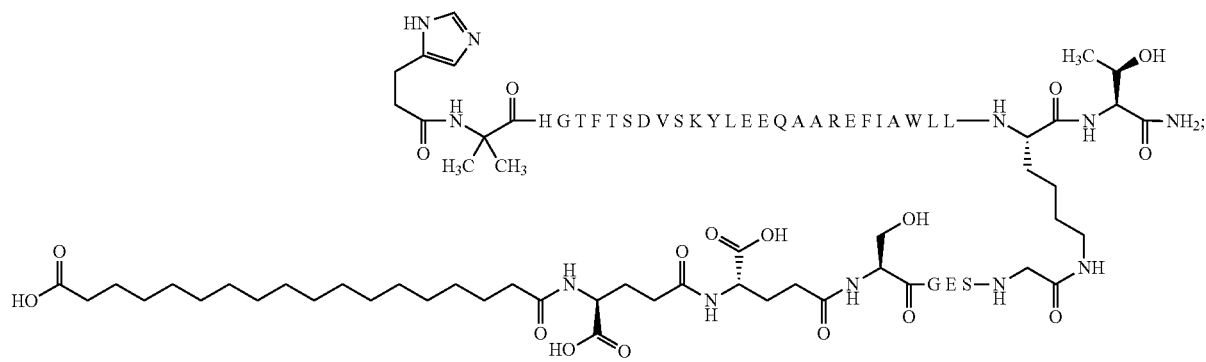

N^ε34-[2-[[(2S)-2-[[(4S)-4-carboxy-4-[[(4S)-4-carboxy-4-(17-carboxyheptadecanoylamino)butanoyl]amino]butanoyl]amino]-3-hydroxypropanoyl]amino]acetyl]-[Imp7,Aib8,His9,Lys18,Glu22,Arg26,Leu33,Thr35]-GLP-1-(7-35)-peptide amide (SEQ ID NO: 5)

(Chem. 4)

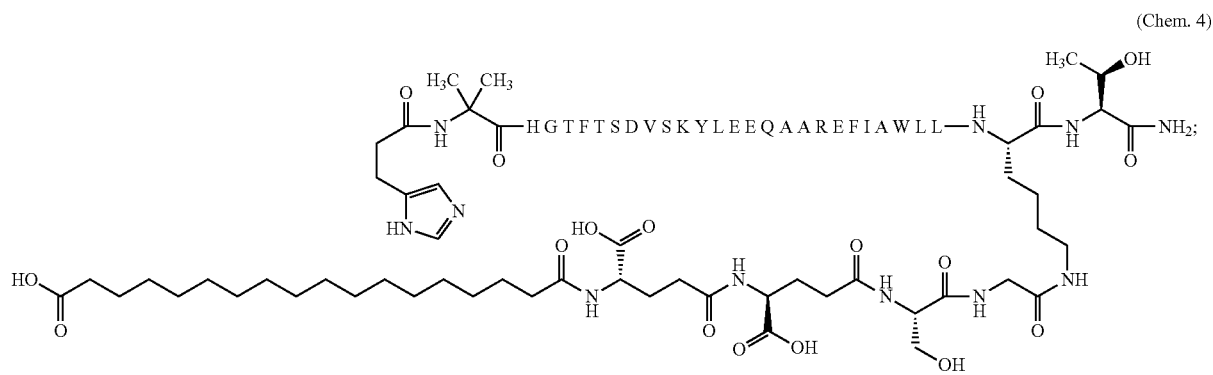

$N^{\varepsilon 34}$-[2-[2-[2-[[2-[2-[2-[[(4S)-4-carboxy-4-[[(4S)-4-carboxy-4-(17-carboxyheptadecanoylamino)butanoyl]amino]butanoyl]amino]ethoxy]ethoxy]acetyl]amino]ethoxy]ethoxy]acetyl]-[Imp7,Aib8,His9,Lys18,Glu22,Arg26,Leu33,Thr35]-GLP-1-(7-35)-peptide amide (SEQ ID NO: 5)

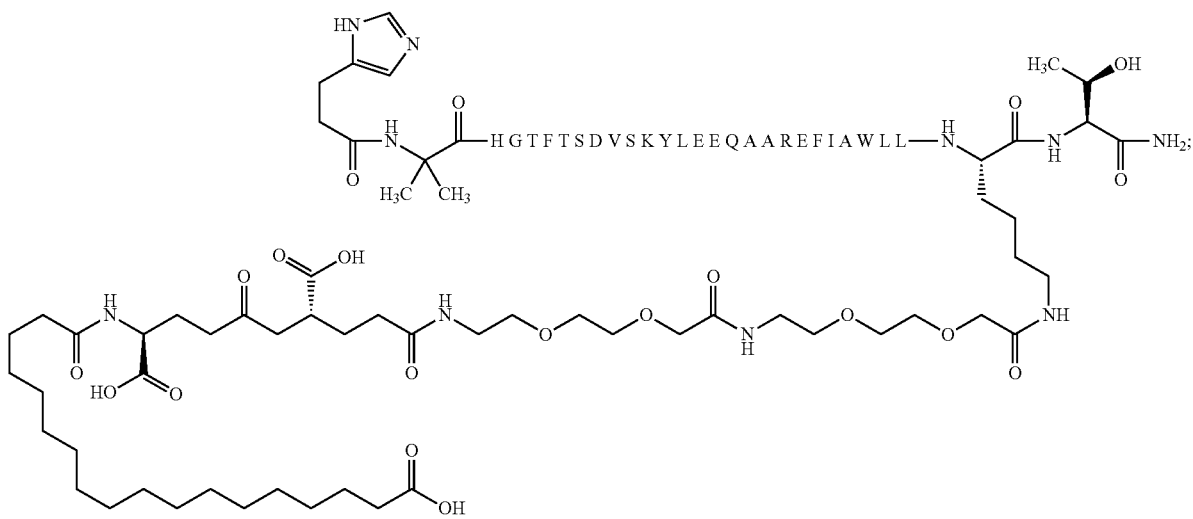

(Chem. 5)

$N^{\varepsilon 34}$-[(4S)-4-carboxy-4-[[(4S)-4-carboxy-4-[[(4S)-4-carboxy-4-[[(4S)-4-carboxy-4-(17-carboxyheptadecanoylamino)butanoyl]amino]butanoyl]amino]butanoyl]amino]butanoyl]-[Imp7,Aib8,His9,Lys18,Glu22,Arg26,Leu33,Thr35]-GLP-1-(7-35)-peptide amide (SEQ ID NO: 5)

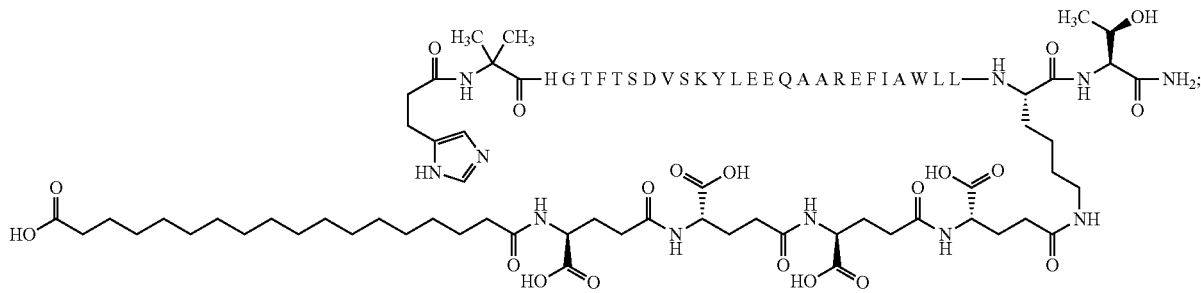

(Chem. 6)

$N^{\varepsilon 34}$-[2-[[(2S)-2-[[(2S)-4-carboxy-2-[[2-[[(2S)-2-[[(4S)-4-carboxy-4-[[(4S)-4-carboxy-4-(17-carboxyheptadecanoylamino)butanoyl]amino]butanoyl]amino]-3-hydroxypropanoyl]amino]acetyl]amino]butanoyl]amino]-3-hydroxypropanoyl]amino]acetyl]-[Imp7,Aib8,His9,Arg18,Glu22,Arg26,Leu33,Thr35]-GLP-1-(7-35)-peptide amide (SEQ ID NO: 7)

(Chem. 7)

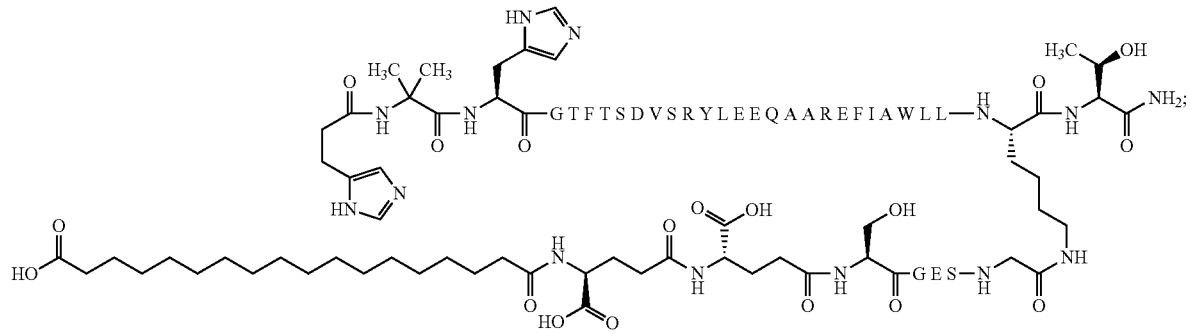

N^ε34-[2-[[(2S)-2-[[(2S)-4-carboxy-2-[[2-[[(2S)-2-[[(4S)-4-carboxy-4-[[(4S)-4-carboxy-4-(17-carboxyheptadecanoylamino)butanoyl]amino]butanoyl]amino]-3-hydroxypropanoyl]amino]acetyl]amino]butanoyl]amino]-3-hydroxypropanoyl]amino]acetyl]-[Imp7,Aib8,His9,Arg18,Arg26,Leu33,Thr35]-GLP-1-(7-35)-peptide amide (SEQ ID NO: 8)

(Chem. 8)

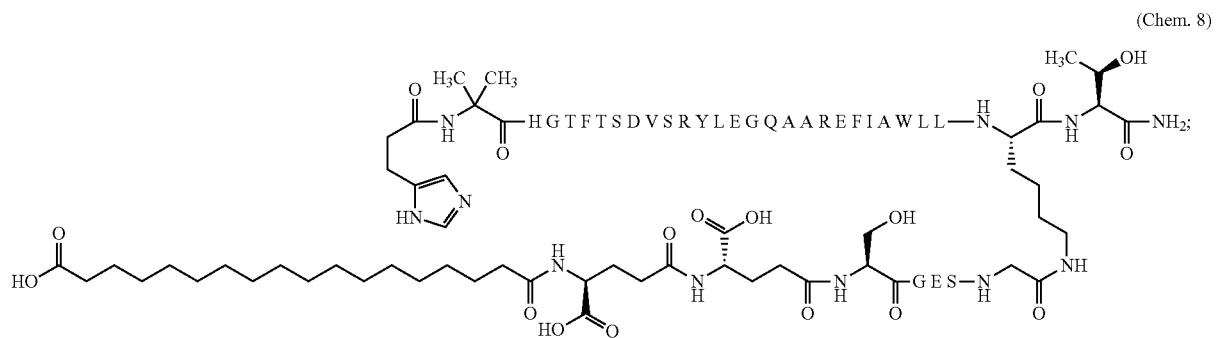

N^ε34-[2-[[(2S)-2-[[(2S)-4-carboxy-2-[[2-[[(2S)-2-[[(4S)-4-carboxy-4-[[(4S)-4-carboxy-4-(17-carboxyheptadecanoylamino)butanoyl]amino]butanoyl]amino]-3-hydroxypropanoyl]amino]acetyl]amino]butanoyl]amino]-3-hydroxypropanoyl]amino]acetyl]-[Imp7,Acb8,His9,Lys18,Glu22,Arg26,Leu33,Thr35]-GLP-1-(7-35)-peptide amide (SEQ ID NO: 9)

(Chem.9)

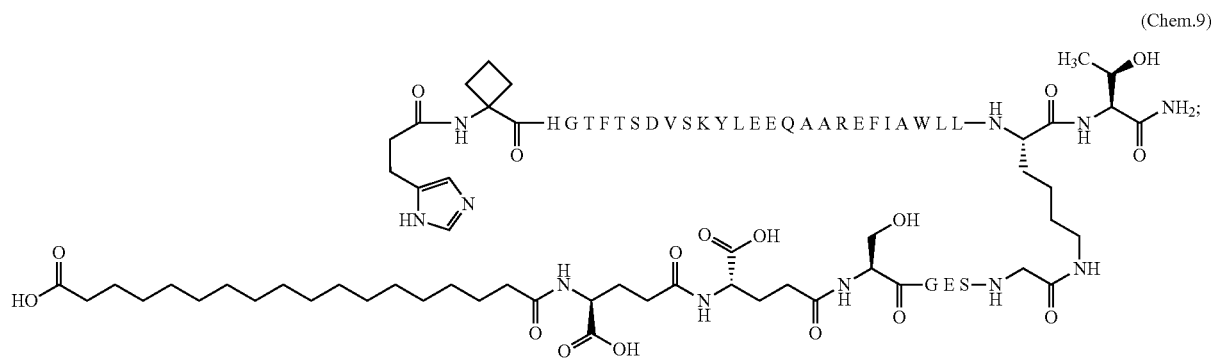

N^{ε34}-[2-[2-[2-[[2-[2-[2-[[(4S)-4-carboxy-4-[[(4S)-4-carboxy-4-[[(4S)-4-carboxy-4-(17-carboxyheptadecanoylamino)butanoyl]amino]butanoyl]amino]butanoyl]amino]ethoxy]ethoxy]acetyl]amino]ethoxy]ethoxy]acetyl]-[Imp7,His9,Lys18,Arg23,Arg26,Leu33,Thr35]-GLP-1-(7-35)-peptide amide (SEQ ID NO: 10)

(Chem. 10)

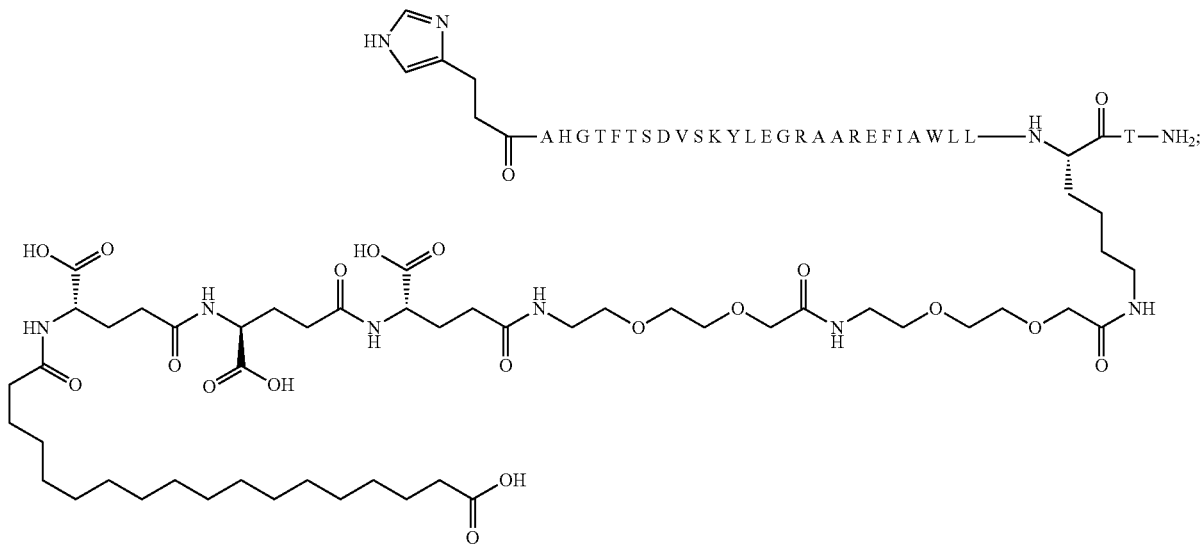

N^{ε34}-[2-[2-[2-[[2-[2-[2-[[(4S)-4-carboxy-4-[[(4S)-4-carboxy-4-[[(4S)-4-carboxy-4-(17-carboxyheptadecanoylamino)butanoyl]amino]butanoyl]amino]butanoyl]amino]ethoxy]ethoxy]acetyl]amino]ethoxy]ethoxy]acetyl]-[Imp7,His9,Lys18,Arg23,Arg26,Leu33,Gly36]-GLP-1-(7-37)-peptide (SEQ ID NO: 38)

(Chem. 11)

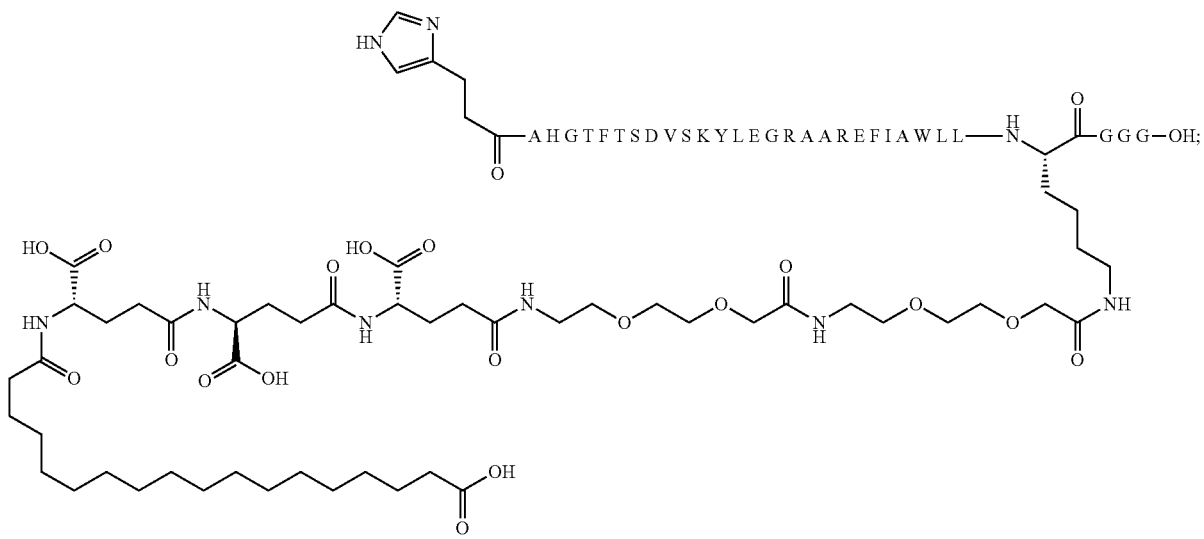

N^{ε34}-[2-[2-[2-[[2-[2-[2-[[(4S)-4-carboxy-4-(17-carboxyheptadecanoylamino)butanoyl]amino]ethoxy]ethoxy]acetyl]amino]ethoxy]ethoxy]acetyl]-[Imp7,Aib8,His9,Lys18,Glu22,Arg26,Leu33,Thr35]-GLP-1-(7-35)-peptide amide (SEQ ID NO: 5)

(Chem. 12)

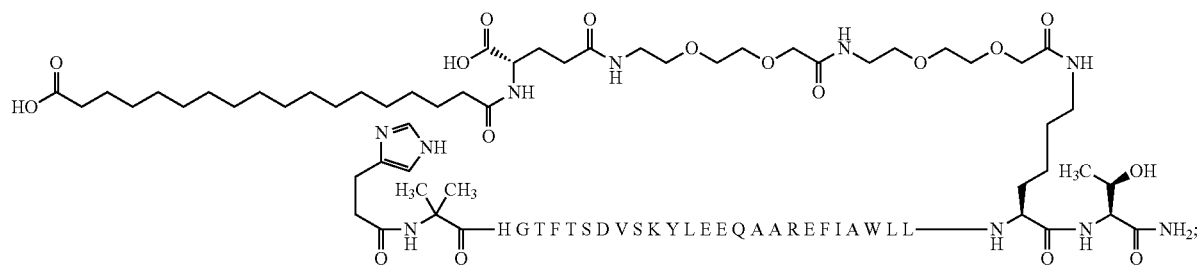

N$^{\epsilon 22}$-[(4S)-4-carboxy-4-[[(4S)-4-carboxy-4-[[2-[2-[2-[[2-[2-[2-[[(4S)-4-carboxy-4-(17-carboxyheptadecanoylamino)butanoyl]amino]ethoxy]ethoxy]acetyl]amino]ethoxy]ethoxy]acetyl]amino]butanoyl]amino]butanoyl]-[Imp7,Aib8,His9,Lys18,Lys22,Arg26,Leu33,Gly36]-GLP-1-(7-37)-peptide (SEQ ID NO: 39)

(Chem. 13)

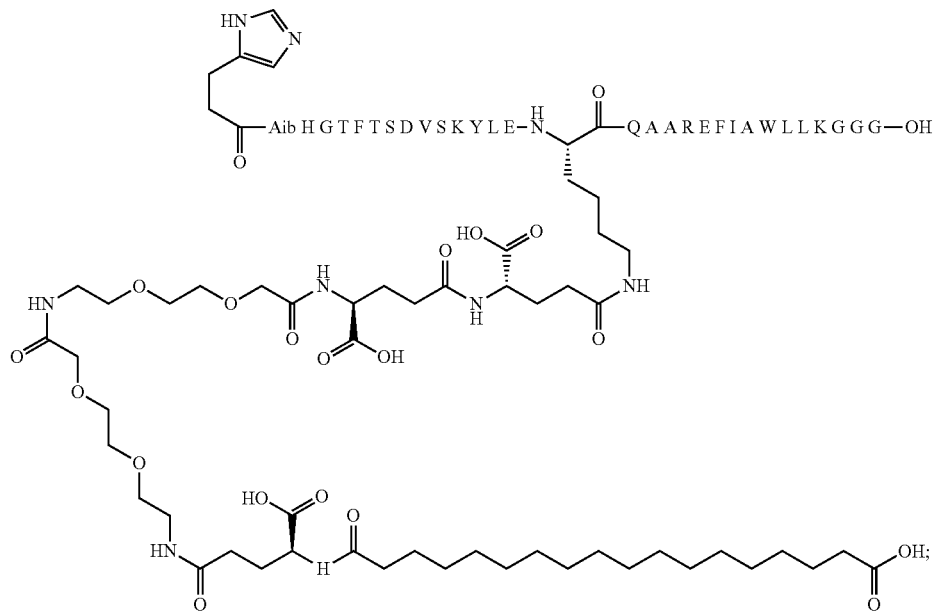

N$^{\epsilon 36}$-[2-[[(2S)-2-[[(2S)-4-carboxy-2-[[2-[[(2S)-2-[[(4S)-4-carboxy-4-[[(4S)-4-carboxy-4-(17-carboxyheptadecanoylamino)butanoyl]amino]butanoyl]amino]-3-hydroxypropanoyl]amino]acetyl]amino]butanoyl]amino]-3-hydroxypropanoyl]amino]acetyl]-[Imp7,Aib8,His9,Tyr16,Lys18,Glu22,Arg26,Leu33,Lys36]-GLP-1-(7-37)-peptide (SEQ ID NO: 13)

(Chem. 14)

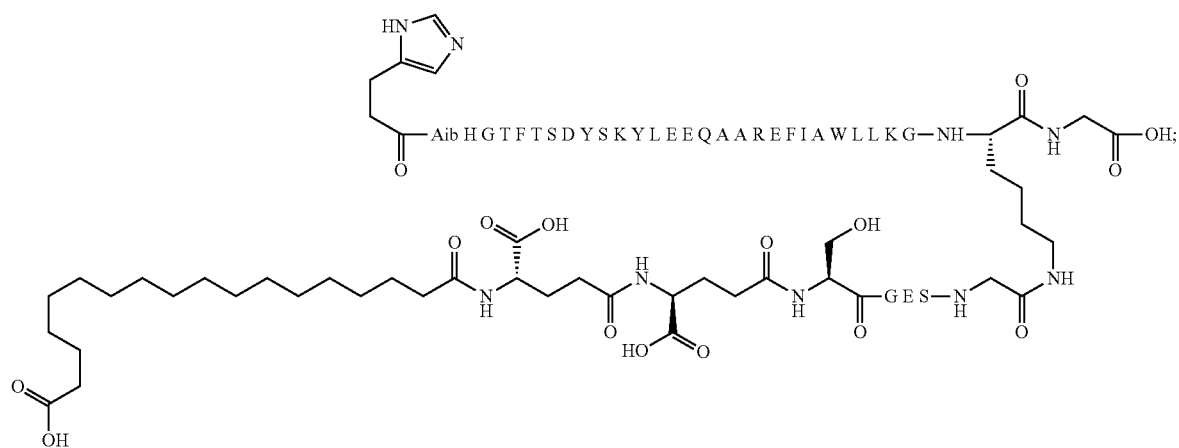

$N^{\epsilon 23}$-[2-[2-[2-[[2-[2-[2-[[(4S)-4-carboxy-4-(17-carboxy-heptadecanoylamino)butanoyl]amino]ethoxy]ethoxy]acetyl]amino]ethoxy]ethoxy]acetyl]-[Imp7,Aib8,His9,Lys18,Lys23,Arg26,Leu33,Thr35]-GLP-1-(7-35)-peptide amide (SEQ ID NO: 14)

(Chem. 15)

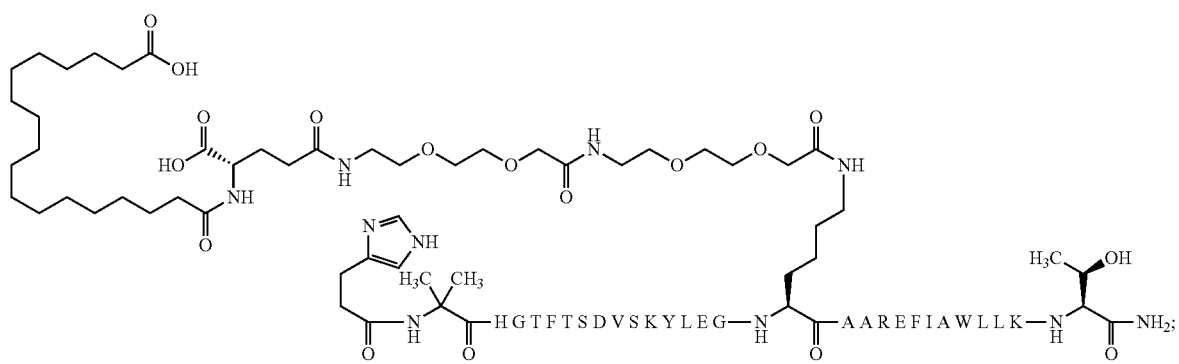

$N^{\epsilon 23}$-[2-[2-[2-[[2-[2-[2-[[(4S)-4-carboxy-4-(17-carboxy-heptadecanoylamino)butanoyl]amino]ethoxy]ethoxy]acetyl]amino]ethoxy]ethoxy]acetyl]-[Imp7,Aib8,His9,Tyr16,Lys18,Lys23,Arg26,Leu33,Thr35]-GLP-1-(7-35)-peptide amide (SEQ ID NO: 15)

(Chem. 16)

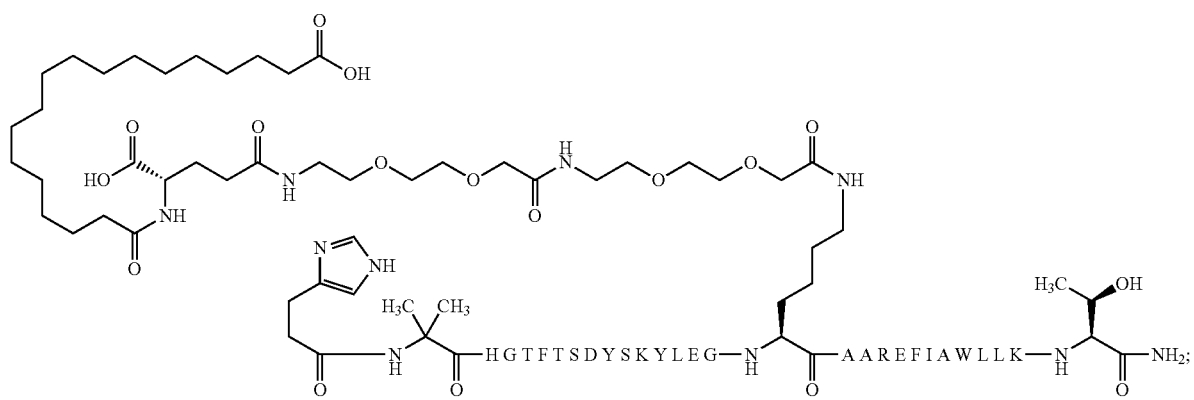

N^{ε34}-[2-[2-[2-[[2-[2-[2-[[(4S)-4-carboxy-4-[[(4S)-4-carboxy-4-[[(4S)-4-carboxy-4-(17-carboxyheptadecanoylamino)butanoyl]amino]butanoyl]amino]butanoyl]amino]ethoxy]ethoxy]acetyl]amino]ethoxy]ethoxy]acetyl]-[Imp7,His9,Arg18,Arg23,Arg26,Leu33]-GLP-1-(7-34)-peptide (SEQ ID NO: 40)

(Chem. 17)

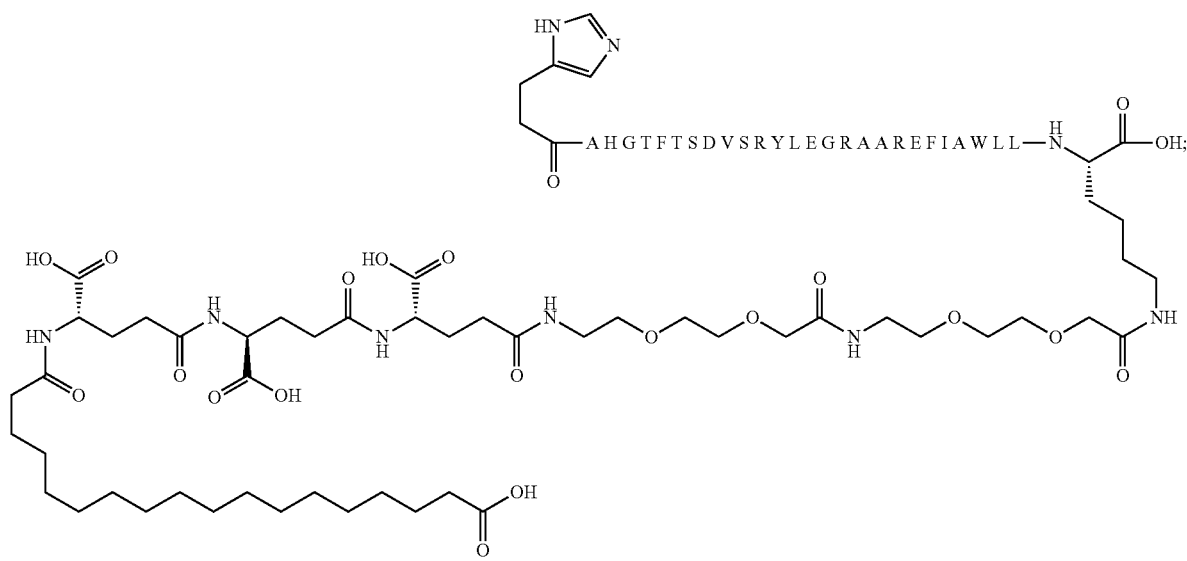

N^{ε27}-[2-[2-[2-[[2-[2-[2-[[(4S)-4-carboxy-4-[[(4S)-4-carboxy-4-[[(4S)-4-carboxy-4-(17-carboxyheptadecanoylamino)butanoyl]amino]butanoyl]amino]butanoyl]amino]ethoxy]ethoxy]acetyl]amino]ethoxy]ethoxy]acetyl]-[Imp7,His9,Arg18,Glu22,Arg26,Lys27,Leu33,Arg34]-GLP-1-(7-34)-peptide (SEQ ID NO: 17)

(Chem. 18)

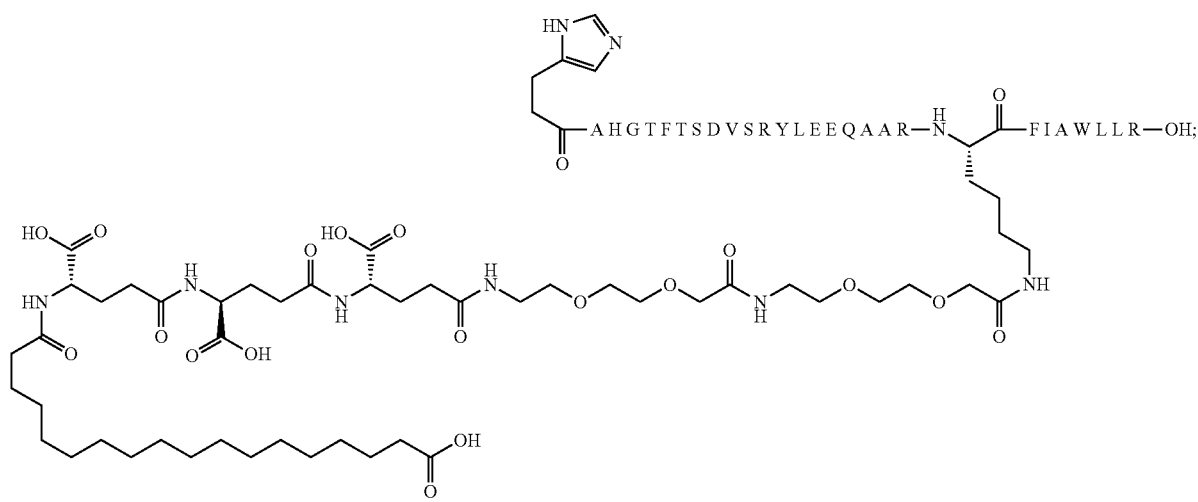

N^{ε27}-[2-[2-[2-[[2-[2-[2-[[(4S)-4-carboxy-4-[[(4S)-4-carboxy-4-[[(4S)-4-carboxy-4-(17-carboxyheptadecanoylamino)butanoyl]amino]butanoyl]amino]butanoyl]amino]ethoxy]ethoxy]acetyl]amino]ethoxy]ethoxy]acetyl]-[Imp7,Aib8,His9,Arg18,Glu22,Arg26,Lys27,Leu33,Arg34]-GLP-1-(7-34)-peptide (SEQ ID NO: 41)

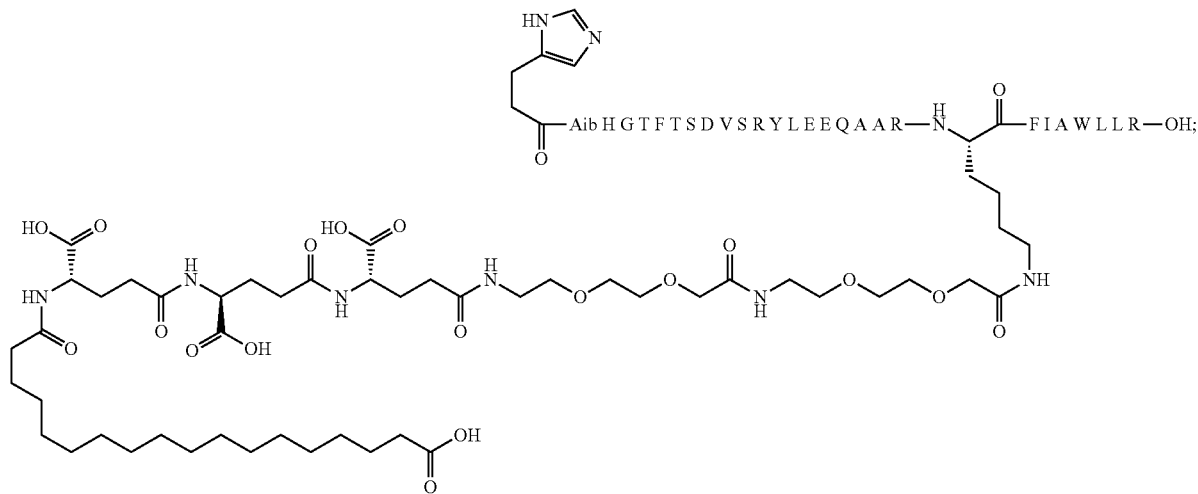

(Chem. 19)

$N^{\epsilon 34}$-[2-[[(2S)-2-[[(2S)-4-carboxy-2-[[2-[[(2S)-2-[[(4S)-4-carboxy-4-[[(4S)-4-carboxy-4-(17-carboxyheptadecanoylamino)butanoyl]amino]butanoyl]amino]-3-hydroxypropanoyl]amino]acetyl]amino]butanoyl]amino]-3-hydroxypropanoyl]amino]acetyl]-[Imp7,Acb8,His9,Lys18,Arg23,Arg26,Leu33,Thr35]-GLP-1-(7-35)-peptide amide (SEQ ID NO: 19)

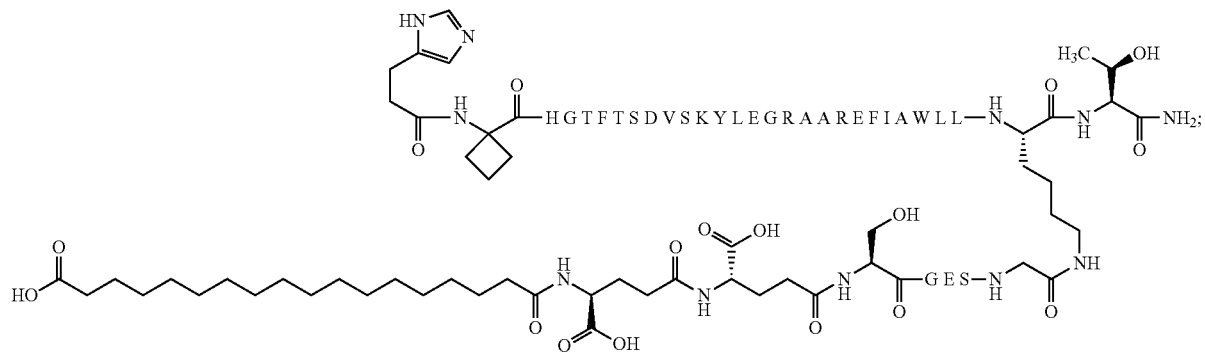

(Chem.20)

$N^{\epsilon 35}$-[(4S)-4-carboxy-4-[[2-[2-[2-[[(4S)-4-carboxy-4-[[2-[2-[2-[[(4S)-4-carboxy-4-[[2-[2-[2-[[(4S)-4-carboxy-4-[[(4S)-4-carboxy-4-(17-carboxyheptadecanoylamino)butanoyl]amino]butanoyl]amino]ethoxy]ethoxy]acetyl]amino]butanoyl]amino]ethoxy]ethoxy]acetyl]amino]butanoyl]amino]ethoxy]ethoxy]acetyl]amino]butanoyl]-[Imp7,Acb8,His9,Tyr16,Lys18,Glu22,Arg26,Leu33,Lys35]-GLP-1-(7-35)-peptide amide (SEQ ID NO: 3)

(Chem. 21)

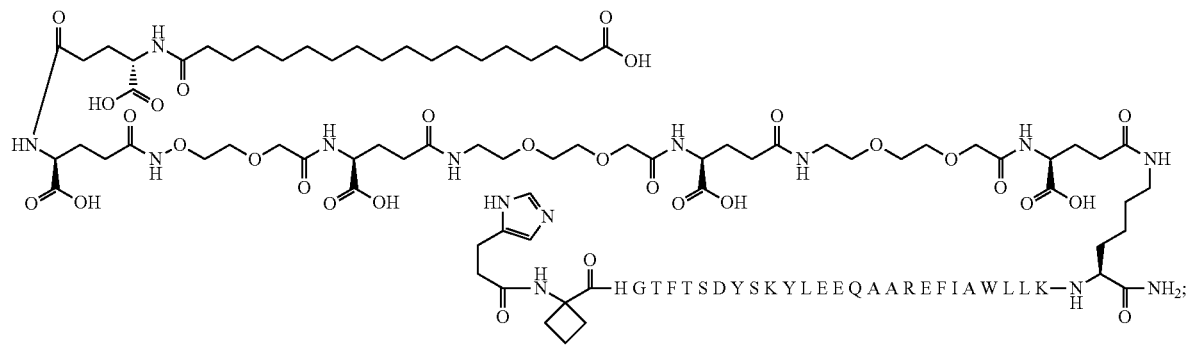

N^ε35-[(4S)-4-carboxy-4-[[2-[2-[2-[[(4S)-4-carboxy-4-[[2-[2-[2-[[(4S)-4-carboxy-4-[[2-[2-[2-[[(4S)-4-carboxy-4-[[(4S)-4-carboxy-4-(17-carboxyheptadecanoylamino)butanoyl]amino]butanoyl]amino]ethoxy]ethoxy]acetyl]amino]butanoyl]amino]ethoxy]ethoxy]acetyl]amino]butanoyl]amino]ethoxy]ethoxy]acetyl]amino]butanoyl]-[Imp7,Acb8,His9,Tyr16,Arg18,Glu22,Arg26,Leu33,Arg34,Lys35]-GLP-1-(7-35)-peptide amide (SEQ ID NO: 20)

(Chem. 22)

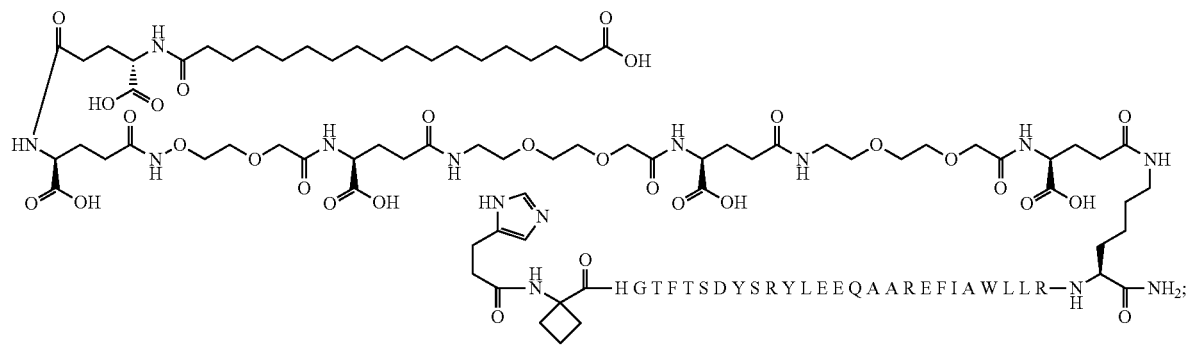

N^ε35-[(4S)-4-carboxy-4-[[2-[2-[2-[[(4S)-4-carboxy-4-[[2-[2-[2-[[(4S)-4-carboxy-4-[[2-[2-[2-[[(4S)-4-carboxy-4-[[(4S)-4-carboxy-4-(17-carboxyheptadecanoylamino)butanoyl]amino]butanoyl]amino]ethoxy]ethoxy]acetyl]amino]butanoyl]amino]ethoxy]ethoxy]acetyl]amino]butanoyl]amino]ethoxy]ethoxy]acetyl]amino]butanoyl]-[Imp7,Acb8,His9,Tyr16,Lys18,Arg22,Arg26,Leu33,Lys35]-GLP-1-(7-35)-peptide amide (SEQ ID NO: 21)

(Chem. 23)

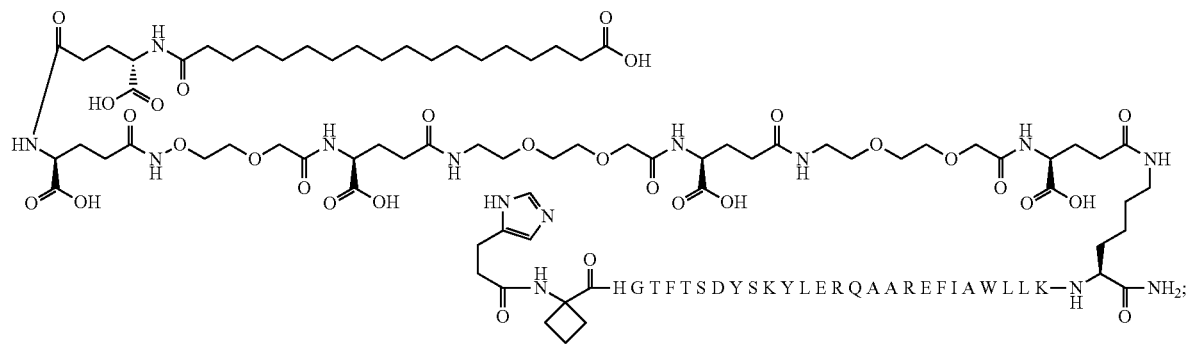

N^ε35-[(4S)-4-carboxy-4-[[2-[2-[2-[[(4S)-4-carboxy-4-[[2-[2-[2-[[(4S)-4-carboxy-4-[[2-[2-[2-[[(4S)-4-carboxy-4-[[(4S)-4-carboxy-4-(17-carboxyheptadecanoylamino)butanoyl]amino]butanoyl]amino]ethoxy]ethoxy]acetyl]amino]butanoyl]amino]ethoxy]ethoxy]acetyl]amino]butanoyl]amino]ethoxy]ethoxy]acetyl]amino]butanoyl]-[Imp7,Acb8,His9,Tyr16,Lys18,Arg22,Arg23,Arg26, Leu33, Lys35]-GLP-1-(7-35)-peptide amide (SEQ ID NO: 22)

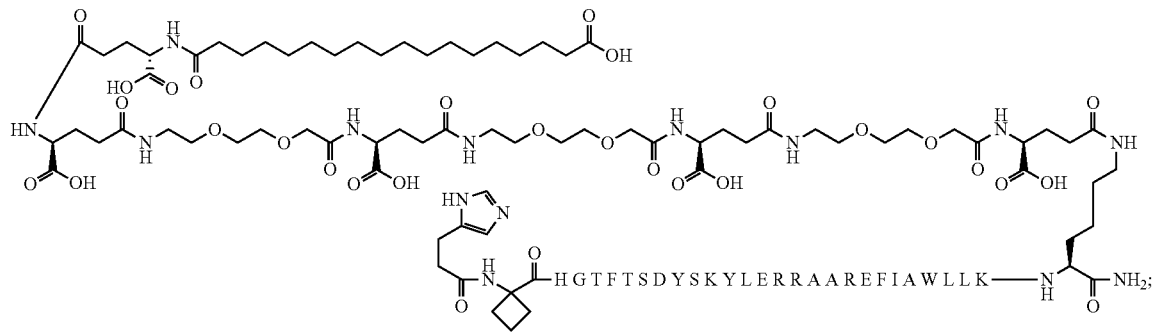

(Chem. 24)

N^ε34-[2-[[(2S)-2-[[(2S)-4-carboxy-2-[[2-[[(2S)-2-[[(4S)-4-carboxy-4-[[(4S)-4-carboxy-4-(17-carboxyheptadecanoylamino)butanoyl]amino]butanoyl]amino]-3-hydroxypropanoyl]amino]acetyl]amino]butanoyl]amino]-3-hydroxypropanoyl]amino]acetyl]-[Imp7,Aib8,His9,Lys18,Glu22,Arg26,Leu33,Thr35]-GLP-1-(7-35)-peptide (SEQ ID NO: 5)

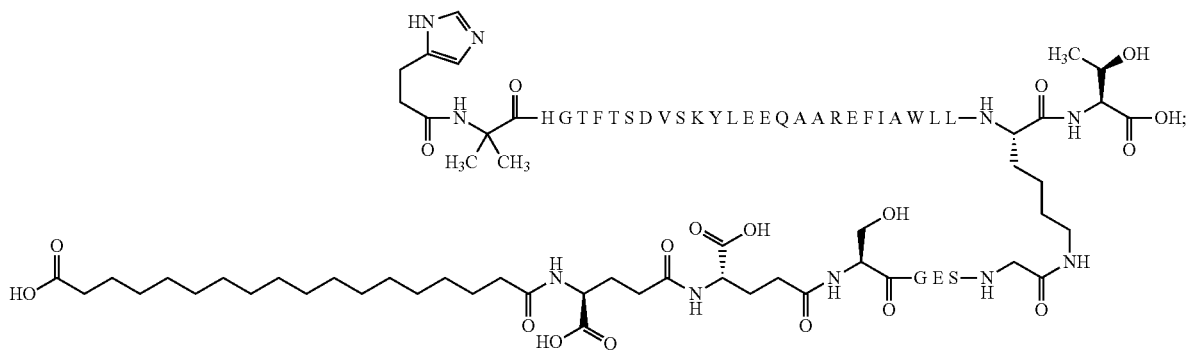

(Chem. 25)

N^ε35-[(4S)-4-carboxy-4-[[2-[2-[2-[[(4S)-4-carboxy-4-[[2-[2-[2-[[(4S)-4-carboxy-4-[[2-[2-[2-[[(4S)-4-carboxy-4-[[(4S)-4-carboxy-4-(17-carboxyheptadecanoylamino)butanoyl]amino]butanoyl]amino]ethoxy]ethoxy]acetyl]amino]butanoyl]amino]ethoxy]ethoxy]acetyl]amino]butanoyl]amino]ethoxy]ethoxy]acetyl]amino]butanoyl]-[Imp7,Acb8,His9,Tyr16,Lys18,Arg23,Arg26,Leu33, Lys35]-GLP-1-(7-35)-peptide amide (SEQ ID NO: 42)

(Chem. 26)

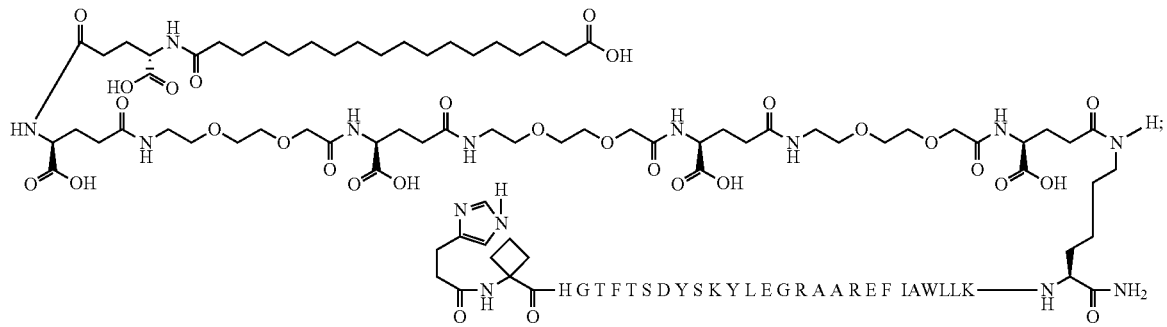

$N^{\varepsilon 34}$-[(4S)-4-carboxy-4-[[(4S)-4-carboxy-4-[[(2S)-2-[[2-[[(2S)-4-carboxy-2-[[(2S)-2-[[2-(17-carboxyheptade-canoylamino)acetyl]amino]-3-hydroxypropanoyl]amino]butanoyl]amino]acetyl]amino]-3-hydroxypropanoyl]amino]butanoyl]amino]butanoyl]-[Imp7,Aib8,His9,Lys18,Glu22,Arg26,Leu33,Thr35]-GLP-1-(7-35)-peptide (SEQ ID NO: 5)

(Chem. 27)

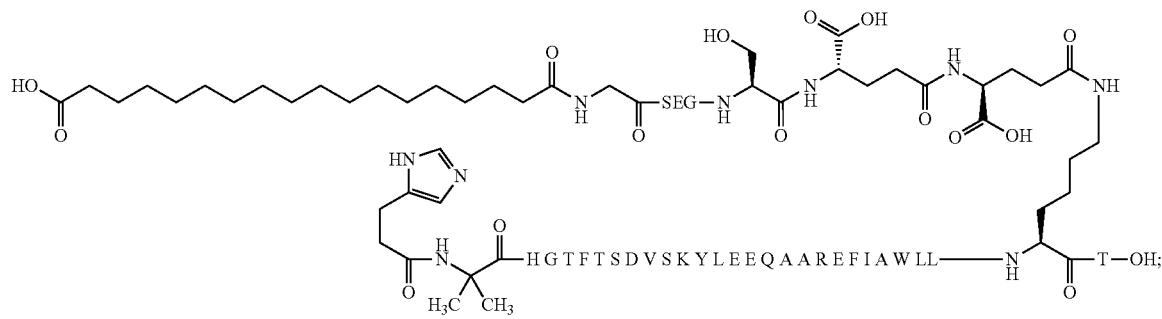

$N^{\varepsilon 35}$-[(4S)-4-carboxy-4-[[2-[2-[2-[[(4S)-4-carboxy-4-[[2-[2-[2-[[(4S)-4-carboxy-4-[[2-[2-[2-[[(4S)-4-carboxy-4-[[(4S)-4-carboxy-4-(17-carboxyheptadecanoylamino)bu-tanoyl]amino]butanoyl]amino]ethoxy]ethoxy]acetyl]amino]butanoyl]amino]ethoxy]ethoxy]acetyl]amino]butanoyl]amino]ethoxy]ethoxy]acetyl]amino]butanoyl]-[Imp7,Acb8,His9,Tyr16,Arg18,Arg23,Arg26,Leu33,Arg34,Lys35]-GLP-1-(7-35)-peptide amide (SEQ ID NO: 24)

(Chem. 28)

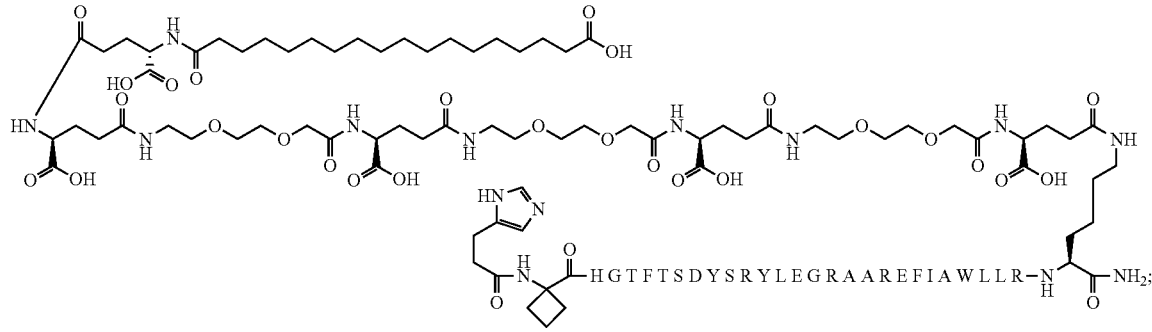

N^ε34-[2-[2-[2-[[2-[2-[2-[[(4S)-4-carboxy-4-[[(4S)-4-carboxy-4-[[(4S)-4-carboxy-4-(17-carboxyheptadecanoylamino)butanoyl]amino]butanoyl]amino]butanoyl]amino]ethoxy]ethoxy]acetyl]amino]ethoxy]ethoxy]acetyl]-[Imp7,Aib8,His9,Lys18,Glu22,Arg26,Leu33,Thr35]-GLP-1-(7-35)-peptide (SEQ ID NO: 5)

(Chem. 29)

N^ε34-[2-[[(2S)-2-[[(2S)-4-carboxy-2-[[2-[[(2S)-2-[[(4S)-4-carboxy-4-[[(4S)-4-carboxy-4-(19-carboxynonadecanoylamino)butanoyl]amino]butanoyl]amino]-3-hydroxypropanoyl]amino]acetyl]amino]butanoyl]amino]-3-hydroxypropanoyl]amino]acetyl]-[Imp7,Aib8,His9,Lys18,Glu22,Arg26,Leu33,Thr35]-GLP-1-(7-35)-peptide amide (SEQ ID NO: 5)

(Chem. 30)

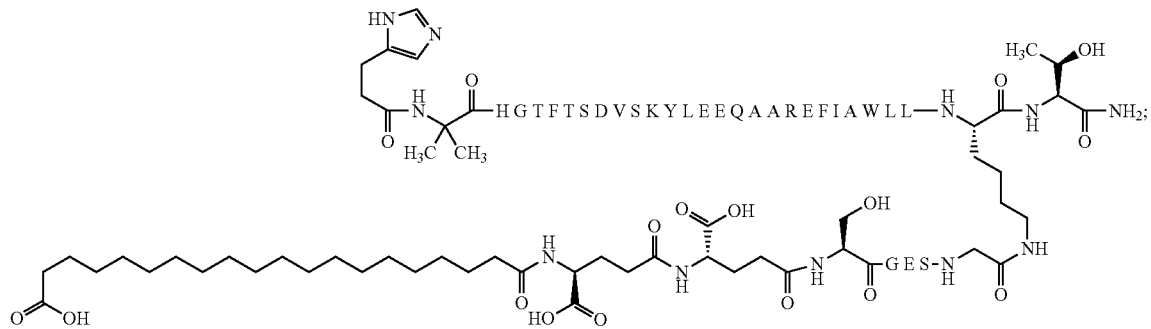

N^ε34-[(4S)-4-carboxy-4-[[2-[2-[2-[[2-[2-[2-[[(4S)-4-carboxy-4-[[(4S)-4-carboxy-4-(17-carboxyheptadecanoylamino)butanoyl]amino]butanoyl]amino]ethoxy]ethoxy]acetyl]amino]ethoxy]ethoxy]acetyl]amino]butanoyl]-[Imp7,Aib8,His9,Lys18,Ala22,Arg23,Arg26,Leu33,Gly36]-GLP-1-(7-37)-peptide (SEQ ID NO: 25)

(Chem. 31)

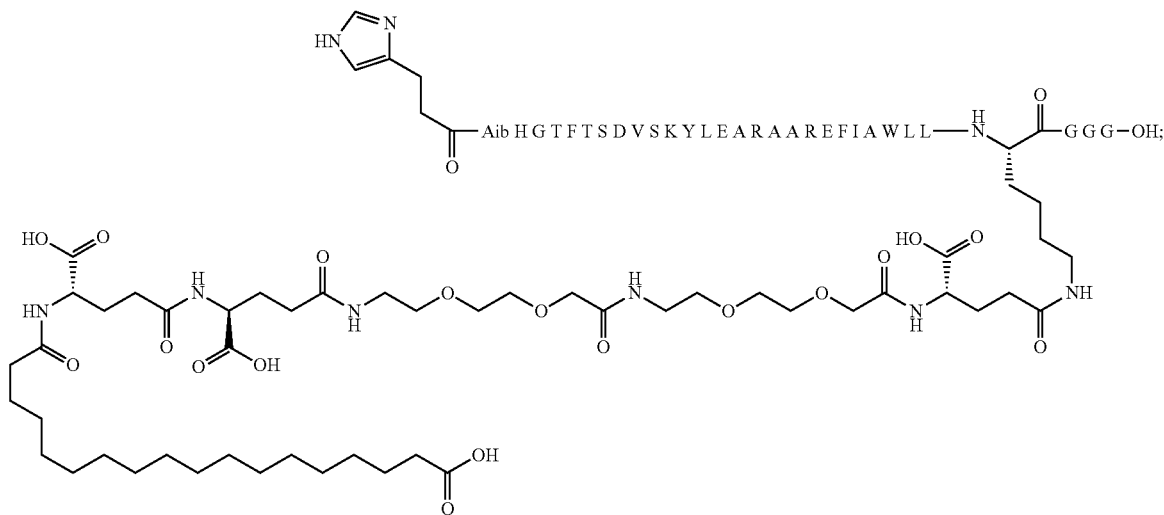

$N^{\varepsilon 22}$-[(4S)-4-carboxy-4-[[(4S)-4-carboxy-4-[[2-[2-[2-[[2-[2-[2-[[(4S)-4-carboxy-4-(17-carboxyheptadecanoylamino)butanoyl]amino]ethoxy]ethoxy]acetyl]amino]ethoxy]ethoxy]acetyl]amino]butanoyl]amino]butanoyl]-[Imp7,Acb8,His9,Lys18,Lys22,Arg23,Arg26,Leu33,Thr35]-GLP-1-(7-35)-peptide amide (SEQ ID NO: 26)

(Chem. 32)

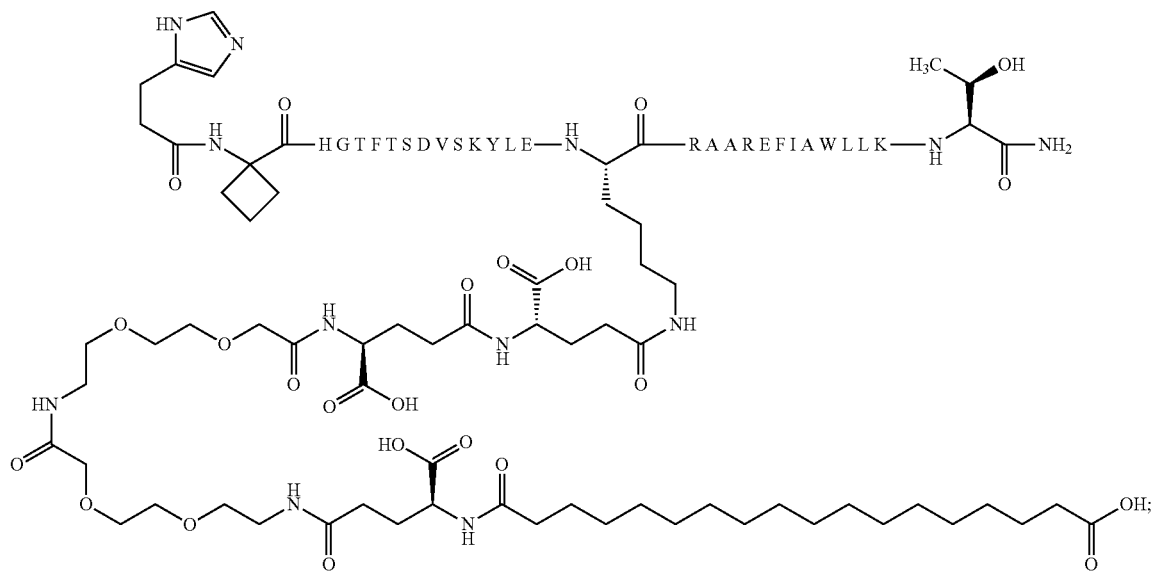

$N^{\varepsilon 22}$-[(4S)-4-carboxy-4-[[(4S)-4-carboxy-4-[[2-[2-[2-[[2-[2-[2-[[(4S)-4-carboxy-4-(17-carboxyheptadecanoylamino)butanoyl]amino]ethoxy]ethoxy]acetyl]amino]ethoxy]ethoxy]acetyl]amino]butanoyl]amino]butanoyl]-[Imp7,Acb8,His9,Lys18,Lys22,Arg26,Leu33,Thr35]-GLP-1-(7-35)-peptide amide (SEQ ID NO: 27)

(Chem. 33)

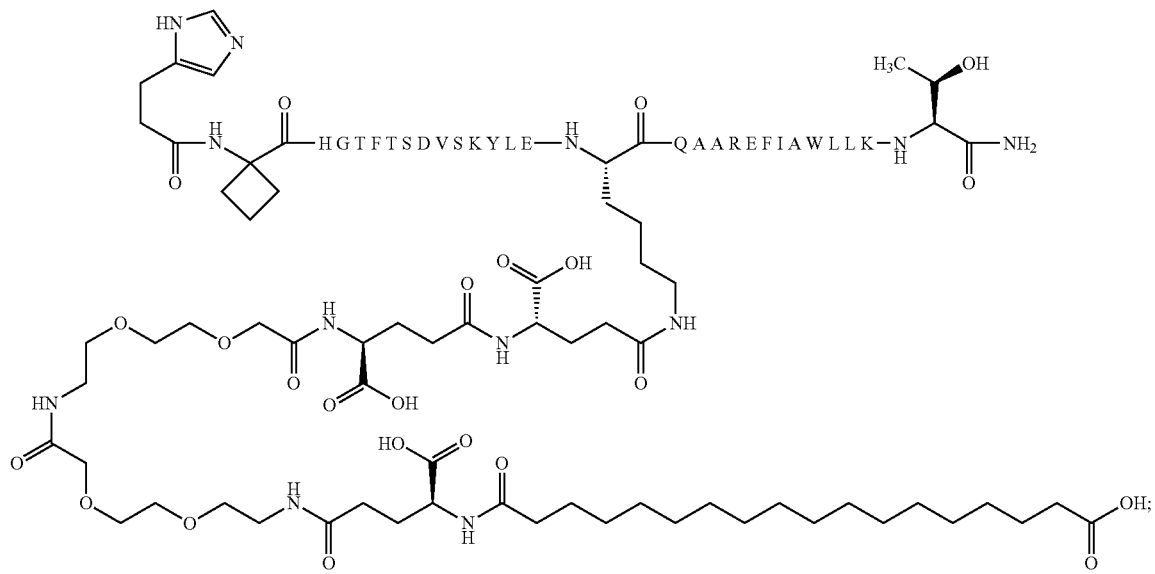

$N^{\varepsilon34}$-[(4S)-4-carboxy-4-[[(4S)-4-carboxy-4-[[2-[2-[2-[[(4S)-4-carboxy-4-[[(4S)-4-carboxy-4-(17-carboxyheptadecanoylamino)butanoyl]amino]butanoyl]amino]ethoxy]ethoxy]acetyl]amino]butanoyl]amino]butanoyl]-[Imp7,Aib8,His9,Lys18,Ala22,Arg26,Leu33,Thr35]-GLP-1-(7-35)-peptide amide (SEQ ID NO: 28)

(Chem. 34)

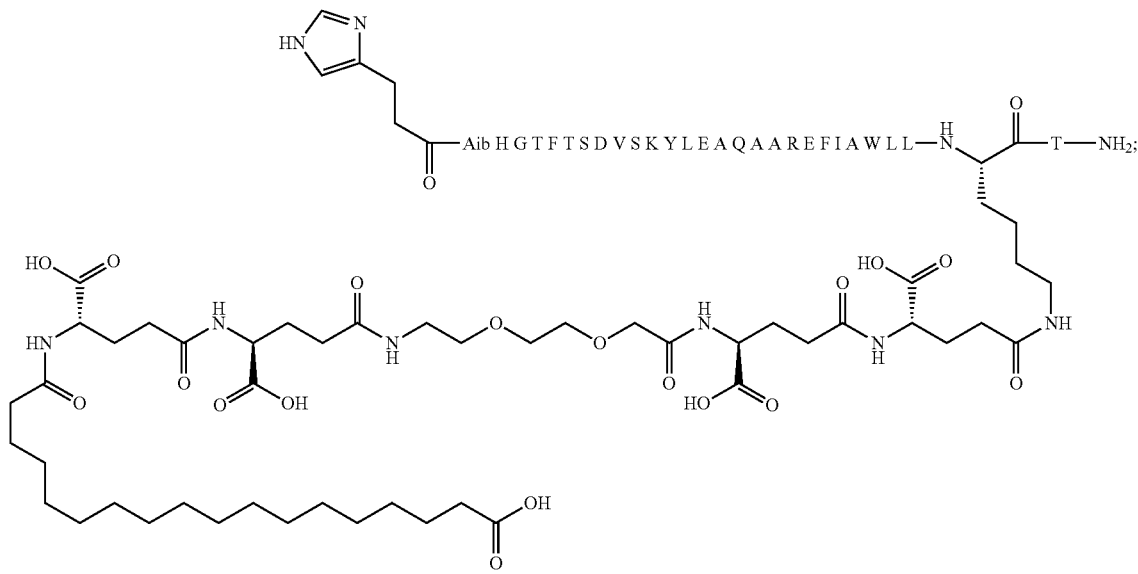

$N^{\varepsilon34}$-[(4S)-4-carboxy-4-[[(4S)-4-carboxy-4-[[2-[2-[2-[[(4S)-4-carboxy-4-[[(4S)-4-carboxy-4-(17-carboxyheptadecanoylamino)butanoyl]amino]butanoyl]amino]ethoxy]ethoxy]acetyl]amino]butanoyl]amino]butanoyl]-[Imp7,Aib8,His9,Arg18,Arg23,Arg26,Leu33,Ala36]-GLP-1-(7-37)-peptide (SEQ ID NO: 29)

(Chem. 35)

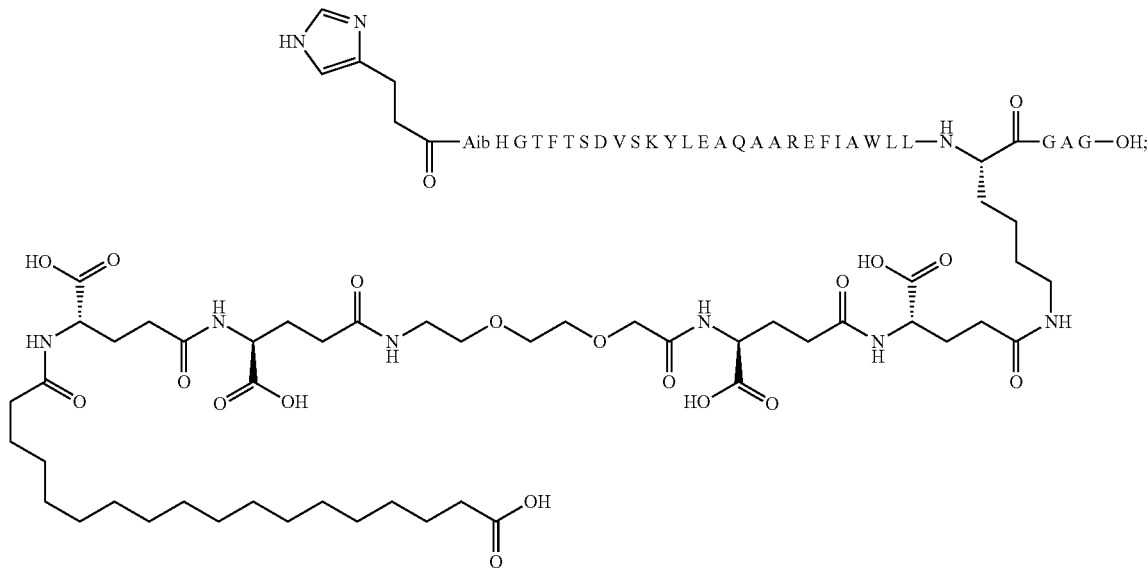

N^ε34-[(4S)-4-carboxy-4-[[(4S)-4-carboxy-4-[[2-[2-[2-[[(4S)-4-carboxy-4-[[(4S)-4-carboxy-4-(17-carboxyheptadecanoylamino)butanoyl]amino]butanoyl]amino]ethoxy]ethoxy]acetyl]amino]butanoyl]amino]butanoyl]-[Imp7,Aib8,His9,Arg18,Arg23,Arg26,Leu33,Ser36]-GLP-1-(7-37)-peptide (SEQ ID NO: 30)

(Chem. 36)

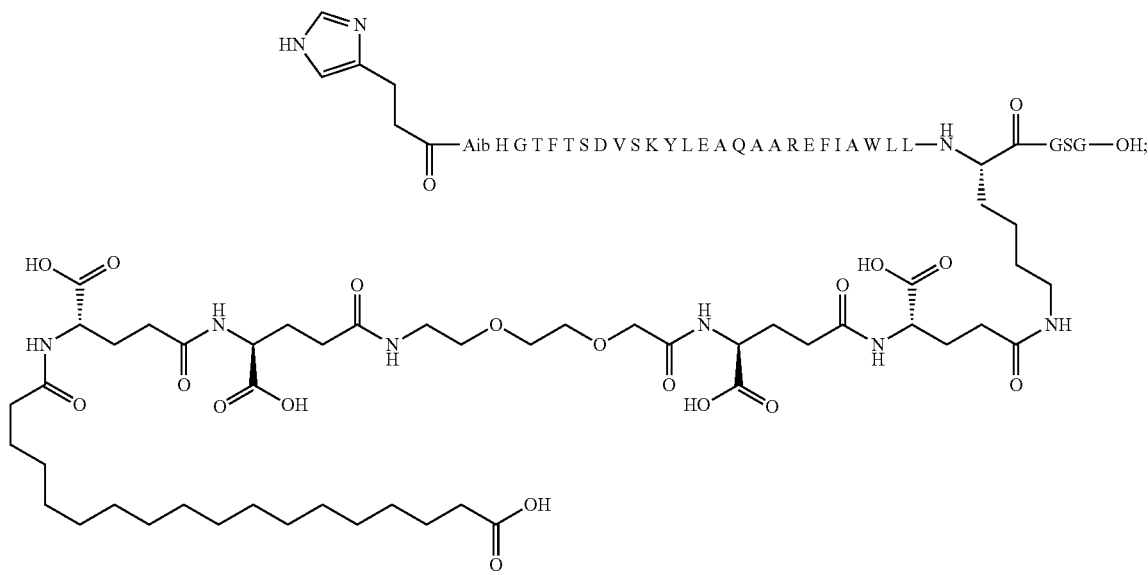

N^ε34-[2-[[(2S)-2-[[(2S)-4-carboxy-2-[[2-[[(2S)-2-[[(4S)-4-carboxy-4-[[(4S)-4-carboxy-4-(17-carboxyheptadecanoylamino)butanoyl]amino]butanoyl]amino]-3-hydroxypropanoyl]amino]acetyl]amino]butanoyl]amino]-3-hydroxypropanoyl]amino]acetyl]-[Imp7,Gly8,His9,Arg18,Glu22,Arg26,Leu33,Thr35]-GLP-1-(7-35)-peptide amide (SEQ ID NO: 31)

(Chem. 37)

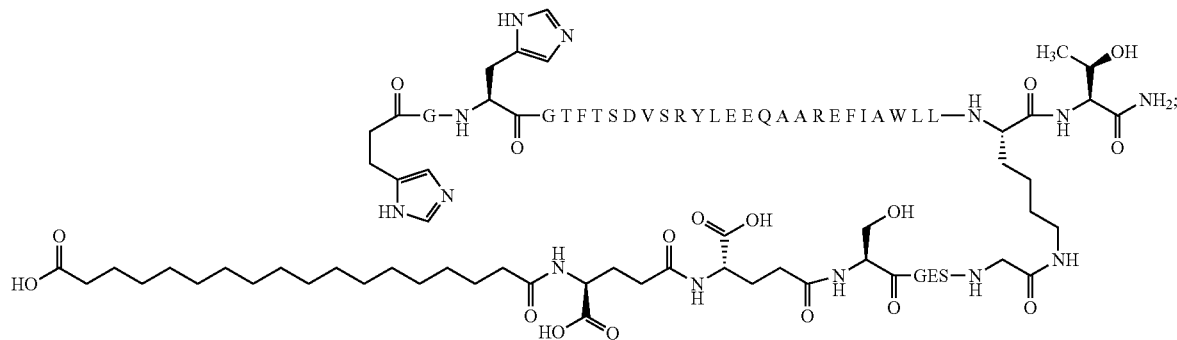

N$^{\varepsilon 34}$-[2-[2-[2-[[2-[2-[2-[[(4S)-4-carboxy-4-[[(4S)-4-carboxy-4-(13-carboxytridecanoylamino)butanoyl]amino]butanoyl]amino]ethoxy]ethoxy]acetyl]amino]ethoxy]ethoxy]acetyl]-[Imp7,Aib8,His9,Lys18,Glu22,Arg26,Leu33,Thr35]-GLP-1-(7-35)-peptide amide (SEQ ID NO: 5)

(Chem. 38)

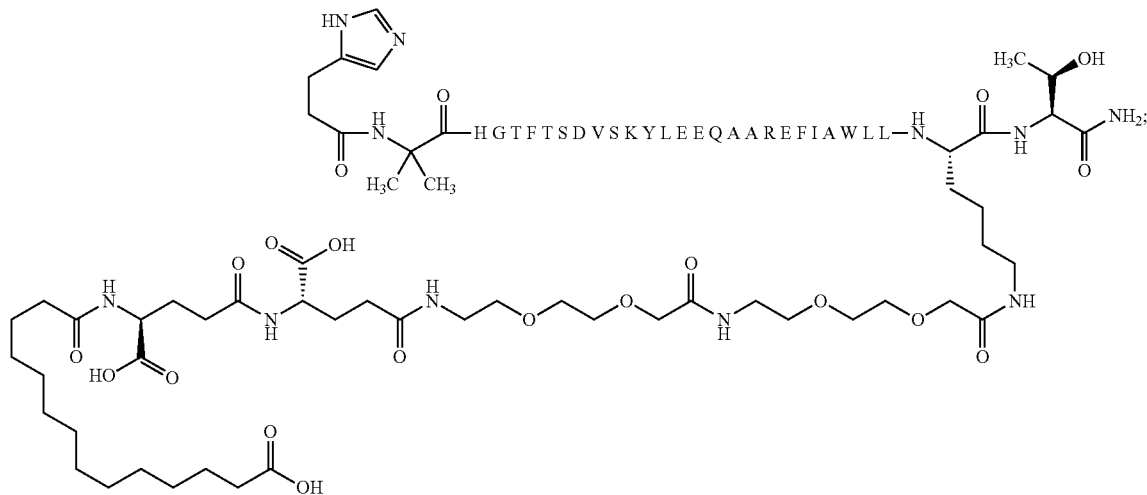

N$^{\varepsilon 34}$-[2-[2-[2-[[2-[2-[2-[[(4S)-4-carboxy-4-[[(4S)-4-carboxy-4-(15-carboxypentadecanoylamino)butanoyl]amino]butanoyl]amino]ethoxy]ethoxy]acetyl]amino]ethoxy]ethoxy]acetyl]-[Imp7,Aib8,His9,Lys18,Glu22,Arg26,Leu33,Thr35]-GLP-1-(7-35)-peptide amide (SEQ ID NO: 5)

(Chem. 39)

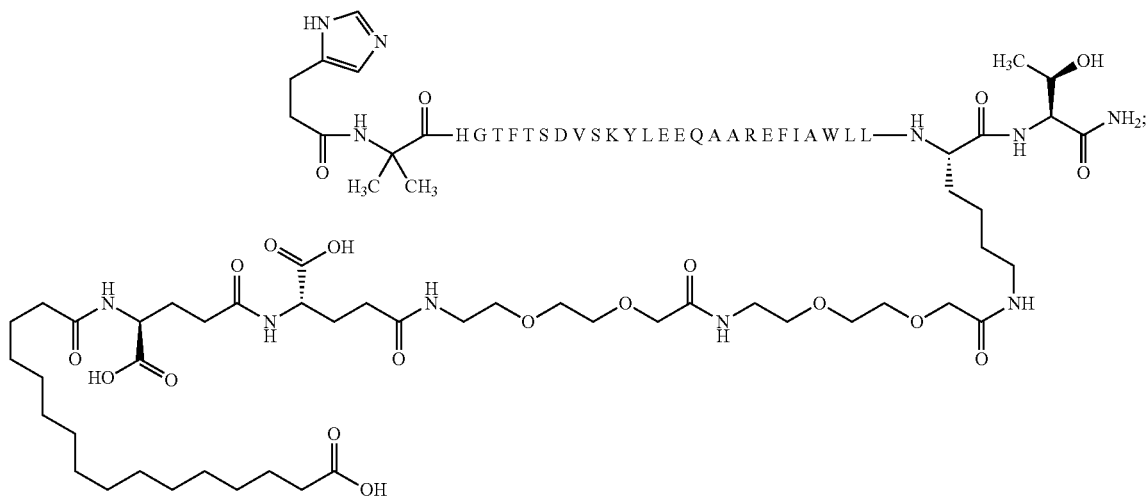

$N^{\varepsilon 34}$-[2-[2-[2-[[2-[2-[2-[[(4S)-4-carboxy-4-[[(4S)-4-carboxy-4-(19-carboxynonadecanoylamino)butanoyl]amino]butanoyl]amino]ethoxy]ethoxy]acetyl]amino]ethoxy]ethoxy]acetyl]-[Imp7,Aib8,His9,Lys18,Glu22,Arg26,Leu33,Thr35]-GLP-1-(7-35)-peptide amide (SEQ ID NO: 5)

(Chem. 40)

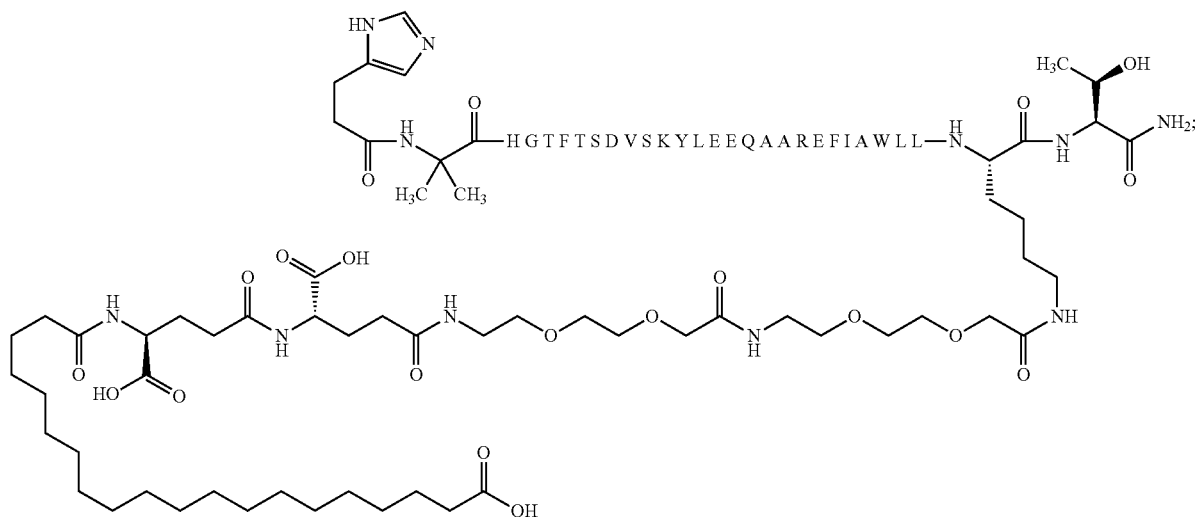

$N^{\varepsilon 34}$-[2-[2-[2-[[2-[2-[2-[[(4S)-4-carboxy-4-[[(4S)-4-carboxy-4-(17-carboxyheptadecanoylamino)butanoyl]amino]butanoyl]amino]ethoxy]ethoxy]acetyl]amino]ethoxy]ethoxy]acetyl]-[Imp7,Aib8,His9,Leu16,Lys18,Glu22,Arg26,Leu33,Thr35]-GLP-1-(7-35)-peptide amide (SEQ ID NO: 32)

(Chem. 41)

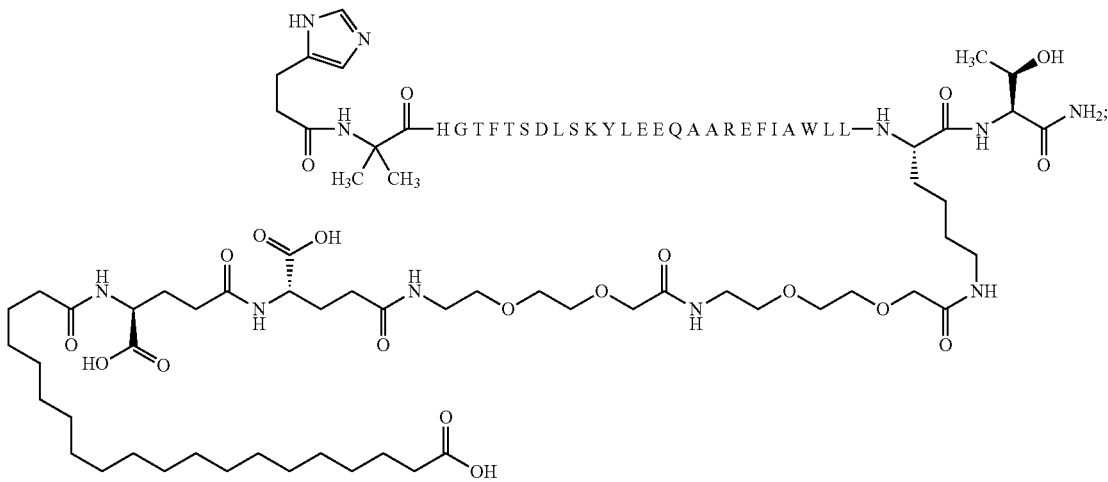

$N^{\varepsilon 34}$-[2-[2-[2-[[2-[2-[2-[[(4S)-4-carboxy-4-[[(4S)-4-carboxy-4-(17-carboxyheptadecanoylamino)butanoyl]amino]butanoyl]amino]ethoxy]ethoxy]acetyl]amino]ethoxy]ethoxy]acetyl]-[Imp7,Aib8,His9,Lys18,Glu22,Arg26,Ile33,Thr35]-GLP-1-(7-35)-peptide amide (SEQ ID NO: 43)

60. The GLP-1 derivative according to any one of the preceding embodiments, wherein said GLP-1 derivative is in the form of a pharmaceutically acceptable salt, amide and/or ester of said GLP-1 derivative.

61. The GLP-1 derivative according to any one of the preceding embodiments, wherein said polypeptide comprises a C-terminal amide.

62. The GLP-1 derivative according to any one of the preceding embodiments, wherein said GLP-1 derivative is in the form of a pharmaceutically acceptable salt of said GLP-1 derivative.

63. The GLP-1 derivative according to any one of the preceding embodiments, wherein said GLP-1 derivative is in the form of an ester of said GLP-1 derivative.

64. The GLP-1 derivative according to any one of the preceding embodiments, wherein said GLP-1 derivative is an agonist of the glucagon receptor and an agonist of the GLP-1 receptor.

65. The GLP-1 derivative according to any one of the preceding embodiments, wherein said GLP-1 derivative has (Chem. 42)

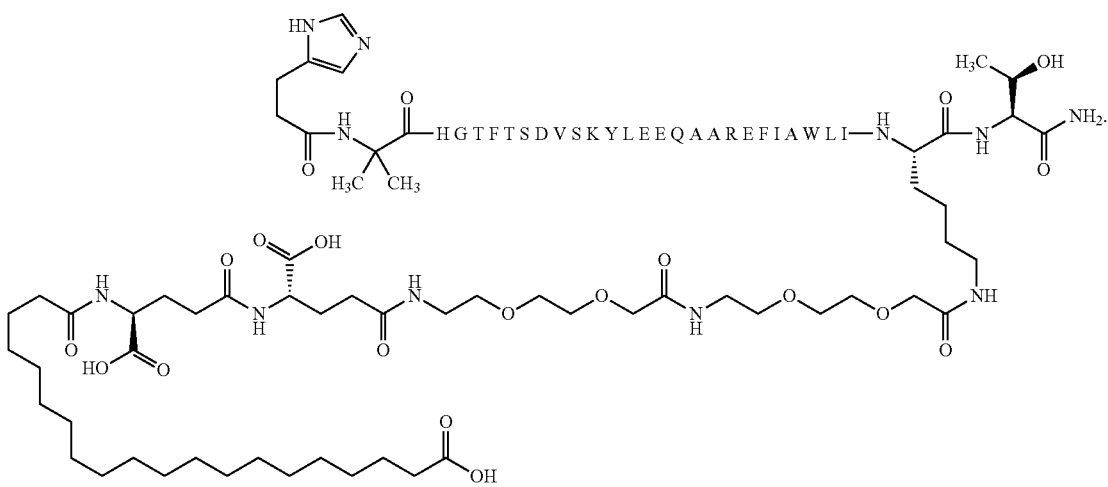

a ratio between its $EC_{50}$ value on the glucagon receptor and $EC_{50}$ on the GLP-1 receptor in the range of 100 to 250, such as in the range of 50 to 100, in the range of 20 to 50, in the range of 10 to 20, or in the range of 1 to 10.

66. The GLP-1 derivative according to any one of the preceding embodiments, wherein said GLP-1 derivative has a ratio between its $EC_{50}$ value on the glucagon receptor and $EC_{50}$ on the GLP-1 receptor in the range of 50 to 100.

67. The GLP-1 derivative according to any one of the preceding embodiments, wherein said GLP-1 derivative has a ratio between its $EC_{50}$ value on the glucagon receptor and $EC_{50}$ on the GLP-1 receptor in the range of 20 to 50.

68. The GLP-1 derivative according to any one of the preceding embodiments, wherein said GLP-1 derivative has a ratio between its $EC_{50}$ value on the glucagon receptor and $EC_{50}$ on the GLP-1 receptor in the range of 10 to 20.
69. The GLP-1 derivative according to any one of the preceding embodiments, wherein said GLP-1 derivative has a ratio between its $EC_{50}$ value on the glucagon receptor and $EC_{50}$ on the GLP-1 receptor in the range of 1 to 10.
70. The GLP-1 derivative according to any one of the preceding embodiments, wherein said GLP-1 derivative has a ratio between its $EC_{50}$ value on the glucagon receptor and $EC_{50}$ on the GLP-1 receptor in the range of 1 to 10.
71. The GLP-1 derivative according to any one of the preceding embodiments, wherein said GLP-1 derivative has an $EC_{50}<10$ nM on the glucagon receptor.
72. The GLP-1 derivative according to any one of the preceding embodiments, wherein said GLP-1 derivative has an $EC_{50}<1$ nM on the glucagon receptor.
73. The GLP-1 derivative according to any one of the preceding embodiments, wherein said GLP-1 derivative has an $EC_{50}<100$ pM on the glucagon receptor.
74. The GLP-1 derivative according to any one of the preceding embodiments, wherein said GLP-1 derivative has an $EC_{50}<10$ pM on the glucagon receptor.
75. The GLP-1 derivative according to any one of the preceding embodiments, wherein said GLP-1 derivative has an $EC_{50}<100$ pM on the GLP-1 receptor.
76. The GLP-1 derivative according to any one of the preceding embodiments, wherein said GLP-1 derivative has an $EC_{50}<50$ pM on the GLP-1 receptor.
77. The GLP-1 derivative according to any one of the preceding embodiments, wherein said GLP-1 derivative has an $EC_{50}<10$ pM on the GLP-1 receptor.
78. The GLP-1 derivative according to any one of the preceding embodiments, wherein said GLP-1 derivative has a lower $EC_{50}$ value on the GLP-1 receptor than on the glucagon receptor.
79. The GLP-1 derivative according to any one of the preceding embodiments, wherein said $EC_{50}$ on the GLP-1 receptor is determined according to Assay (I)(a) described herein.
80. The GLP-1 derivative according to any one of the preceding embodiments, wherein said $EC_{50}$ on the glucagon receptor is determined according to Assay (I)(b) described herein.
81. The GLP-1 derivative according to any one of the preceding embodiments, wherein said GLP-1 derivative has a ratio between its $IC_{50}$ value on the glucagon receptor and $IC_{50}$ on the GLP-1 receptor in the range of 1 to 5, such as in the range of 5 to 10, in the range of 10 to 15, in the range of 15 to 25, or in the range of 25 to 100, or such as of above 100.
82. The GLP-1 derivative according to any one of the preceding embodiments, wherein said GLP-1 derivative has a ratio between its $IC_{50}$ value on the glucagon receptor and $IC_{50}$ on the GLP-1 receptor in the range of 5 to 10.
83. The GLP-1 derivative according to any one of the preceding embodiments, wherein said GLP-1 derivative has a ratio between its $IC_{50}$ value on the glucagon receptor and $IC_{50}$ on the GLP-1 receptor in the range of 10 to 15.
84. The GLP-1 derivative according to any one of the preceding embodiments, wherein said GLP-1 derivative has a ratio between its $IC_{50}$ value on the glucagon receptor and $IC_{50}$ on the GLP-1 receptor in the range of 15 to 25.
85. The GLP-1 derivative according to any one of the preceding embodiments, wherein said GLP-1 derivative has a ratio between its $IC_{50}$ value on the glucagon receptor and $IC_{50}$ on the GLP-1 receptor in the range of 25 to 100.
86. The GLP-1 derivative according to any one of the preceding embodiments, wherein said GLP-1 derivative has a ratio between its $IC_{50}$ value on the glucagon receptor and $IC_{50}$ on the GLP-1 receptor of above 100.
87. The GLP-1 derivative according to any one of the preceding embodiments, wherein said $IC_{50}$ on the GLP-1 receptor is determined according to Assay (II)(a) described herein.
88. The GLP-1 derivative according to any one of the preceding embodiments, wherein said $IC_{50}$ on the glucagon receptor is determined according to Assay (II)(b) described herein.
89. The GLP-1 derivative according to any one of the preceding embodiments, wherein said GLP-1 derivative has more than 70% recovery in the ThT fibrillation assay.
90. The GLP-1 derivative according to any one of the preceding embodiments, wherein said GLP-1 derivative has more than 90% recovery in the ThT fibrillation assay.
91. The GLP-1 derivative according to any one of the preceding embodiments, wherein said GLP-1 derivative has about 100% recovery in the ThT fibrillation assay.
92. The GLP-1 derivative according to any one of the preceding embodiments, wherein said GLP-1 derivative has more than 7 hours lag time in the ThT fibrillation assay.
93. The GLP-1 derivative according to any one of the preceding embodiments, wherein said GLP-1 derivative has more than 20 hours lag time in the ThT fibrillation assay.
94. The GLP-1 derivative according to any one of the preceding embodiments, wherein said GLP-1 derivative has 45 hours lag time or more in the ThT fibrillation assay.
95. The GLP-1 derivative according to any one of the preceding embodiments, wherein said ThT fibrillation assay is Assay (III) described herein.
96. The GLP-1 derivative according to any one of the preceding embodiments, wherein said GLP-1 derivative has less than 14% degradation in the chemical stability assay.
97. The GLP-1 derivative according to any one of the preceding embodiments, wherein said GLP-1 derivative has less than 13% degradation in the chemical stability assay.
98. The GLP-1 derivative according to any one of the preceding embodiments, wherein said GLP-1 derivative has less than 12% degradation in the chemical stability assay.
99. The GLP-1 derivative according to any one of the preceding embodiments, wherein said GLP-1 derivative has less than 10% degradation in the chemical stability assay.
100. The GLP-1 derivative according to any one of the preceding embodiments, wherein said GLP-1 derivative has less than 9% degradation in the chemical stability assay.
101. The GLP-1 derivative according to any one of the preceding embodiments, wherein said GLP-1 derivative has less than 7% degradation in the chemical stability assay.
102. The GLP-1 derivative according to any one of the preceding embodiments, wherein said GLP-1 derivative has less than 5% degradation in the chemical stability assay.
103. The GLP-1 derivative according to any one of the preceding embodiments, wherein said GLP-1 derivative has less than 3% degradation in the chemical stability assay.

104. The GLP-1 derivative according to any one of the preceding embodiments, wherein said GLP-1 derivative has less than 2% degradation in the chemical stability assay.
105. The GLP-1 derivative according to any one of the preceding embodiments, wherein said GLP-1 derivative has less than 1% degradation in the chemical stability assay.
106. The GLP-1 derivative according to any one of the preceding embodiments, wherein said chemical stability assay is Assay (V) described herein.
107. The GLP-1 derivative according to any one of the preceding embodiments, wherein said GLP-1 derivative is a DPPIV protected compound.
108. The GLP-1 derivative according to any one of the preceding embodiments, wherein said GLP-1 derivative is a DPPIV stabilised compound.
109. The GLP-1 derivative according to any one of the preceding embodiments, wherein said GLP-1 derivative is in the form of a pharmaceutically acceptable salt and/or ester of said GLP-1 derivative.
110. A pharmaceutical composition comprising the GLP-1 derivative as defined in any one of the preceding embodiments and one or more pharmaceutically acceptable excipients.
111. The pharmaceutical composition as defined in any one of the preceding embodiments, further comprising one or more additional therapeutically active compounds or substances.
112. The pharmaceutical composition as defined in any one of the preceding embodiments, wherein said additional therapeutically active compound is a GLP-1 compound or an insulin compound.
113. The pharmaceutical composition as defined in any one of the preceding embodiments, wherein said additional therapeutically active compound is a GLP-1 compound.
114. The pharmaceutical composition as defined in any one of the preceding embodiments, wherein said additional therapeutically active compound is an insulin compound.
115. The pharmaceutical composition as defined in any one of the preceding embodiments, wherein the GLP-1 compound is selected from the group consisting of:

N-epsilon26-((S)-4-Carboxy-4-hexadecanoylamino-butyryl)[Arg34]GLP-1-(7-37)

(Compound G1)

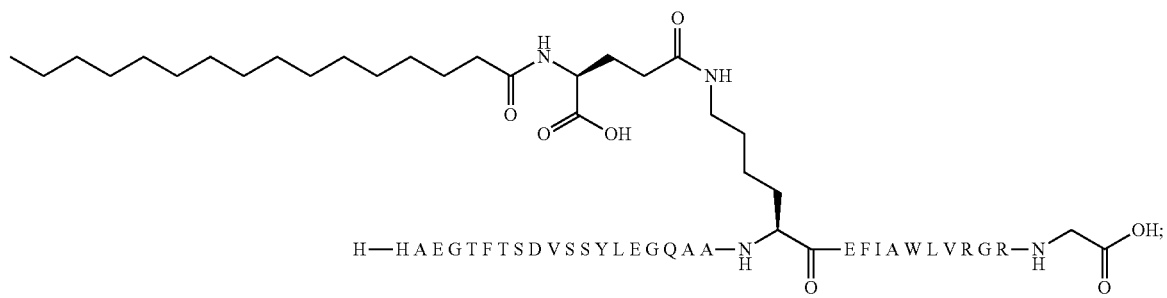

N-epsilon37-[2-(2-{2-[2-(2-{2-[(S)-Carboxy-4-({trans-4-[(19-carboxynonadecanoylamino)methyl]cyclohexanecarbonyl}amino)butyrylamino]ethoxy}ethoxy)acetylamino]ethoxy}ethoxy)acetyl][DesaminoHis7,Glu22,Arg26,Arg34,Lys37]GLP-1-(7-37) (SEQ ID NO: 34)

(Compound G2)

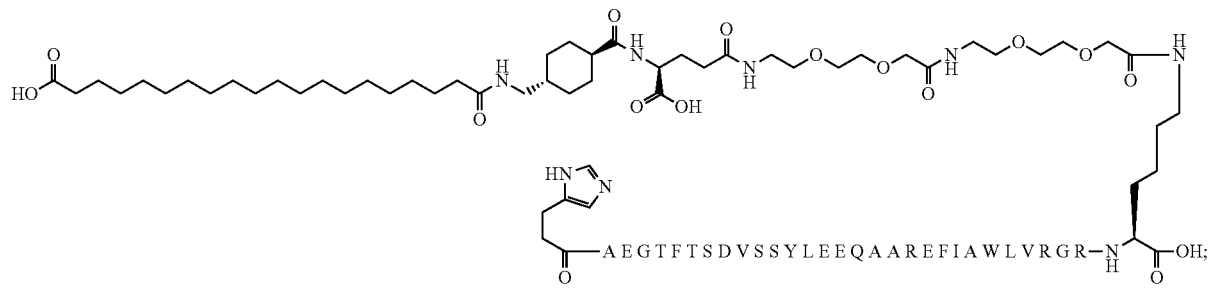

N-epsilon26-[2-(2-{2-[2-(2-{2-[(S)-Carboxy-4-(17-carboxyheptadecanoylamino)butyrylamino]ethoxy}ethoxy)acetylamino]ethoxy}ethoxy)acetyl][Aib8,Arg34]GLP-1-(7-37) (SEQ ID NO: 35)

(Compound G3)

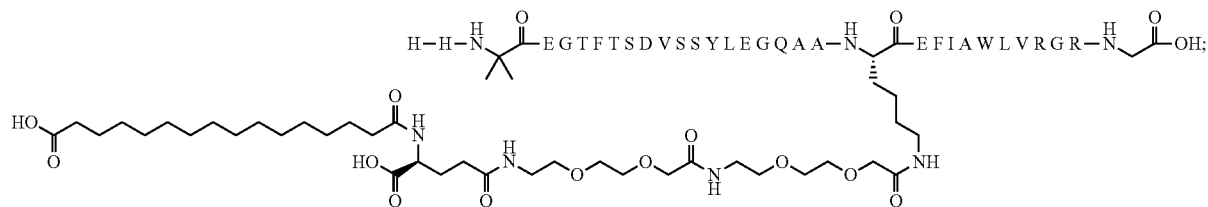

and
N-epsilon37-[2-(2-{2-[2-(2-{2-[(S)-carboxy-4-(15-car-boxy-pentadecanoylamino)-butyrylamino]-ethoxy}-ethoxy)-acetylamino]ethoxy}-ethoxy)-acetyl][Aib8,22,35,Lys37]GLP-1-(7-37) (SEQ ID NO: 36)

(Compound G4)

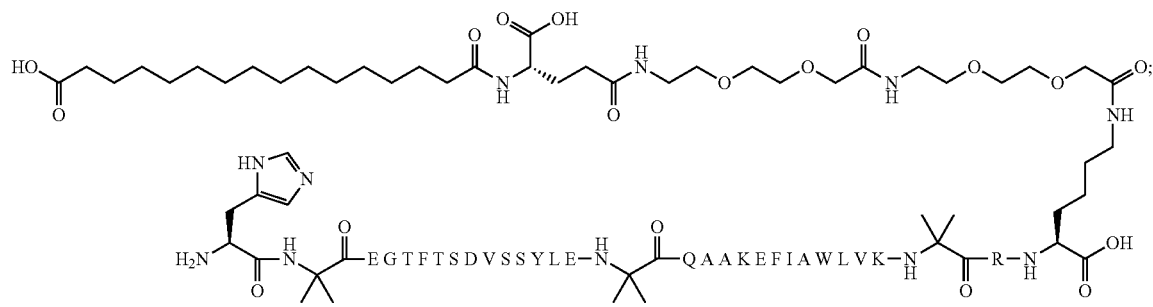

and their pharmaceutically acceptable salts, amides, alkyls or esters.

116. The pharmaceutical composition as defined in any one of the preceding embodiments, wherein the insulin compound is N-epsilon-B29-[(S)-4-Carboxy-4-(15-carboxypentadecanoylamino)butyryl]desB30 human insulin (Compound G5)

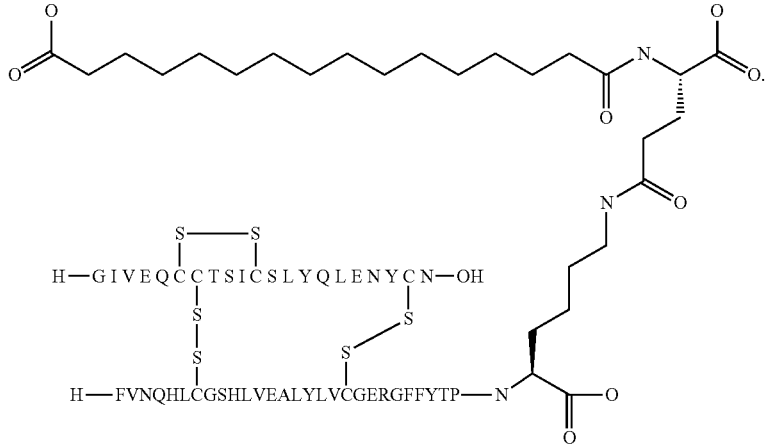

117. The pharmaceutical composition as defined in any one of the preceding embodiments, in unit dosage form comprising from about 0.01 mg to about 1000 mg, such as from about 0.1 mg to about 500 mg, from about 0.5 mg to about 5 mg, e.g. from about 0.5 mg to about 200 mg, of a GLP-1 derivative as defined in any one of the preceding embodiments.

118. The pharmaceutical composition as defined in any one of the preceding embodiments, which is suited for parenteral administration.

119. A GLP-1 derivative as defined in any one of the preceding embodiments for use in medicine.

120. The GLP-1 derivative as defined in any one of the preceding embodiments for use in the prevention and/or treatment of type 2 diabetes and/or obesity.

121. The GLP-1 derivative as defined in any one of the preceding embodiments for use in the treatment or prevention of obesity, hyperglycaemia, type 2 diabetes, impaired glucose tolerance, and/or type 1 diabetes.

122. The GLP-1 derivative as defined in any one of the preceding embodiments for use in the treatment or prevention of obesity.

123. The GLP-1 derivative as defined in any one of the preceding embodiments for use in the treatment or prevention of hyperglycaemia, type 2 diabetes, impaired glucose tolerance, and/or type 1 diabetes.

124. The GLP-1 derivative as defined in any one of the preceding embodiments for use in the treatment or prevention of obesity or preventing overweight, decreasing food intake, increasing energy expenditure, regulating appetite, inducing satiety, preventing weight regain after successful weight loss, treating a disease or state related to overweight or obesity, treating bulimia, and/or treating binge-eating.

125. The GLP-1 derivative as defined in any one of the preceding embodiments for use in the treatment or prevention of type 2 diabetes, treating impaired glucose tolerance, delaying or preventing disease progression in type 2 diabetes, delaying the progression from impaired glucose tolerance (IGT) to type 2 diabetes, and/or delaying the progression from type 2 diabetes to insulin-requiring diabetes.

126. The GLP-1 derivative as defined in any one of the preceding embodiments for use in the treatment or prevention of atherosclerosis, hypertension, dyslipidaemia, coronary heart disease and/or hepatic steatosis.

127. The GLP-1 derivative for use according to any one of the preceding embodiments, wherein said GLP-1 derivative is administered in combination with one or more additional therapeutically active compounds.

128. A method of prevention and/or treatment of type 2 diabetes and/or obesity comprising administering a therapeutically effective amount of the GLP-1 derivative as defined in any one of the preceding embodiments to a patient in need thereof.

129. A method for treating obesity or preventing overweight comprising administering to a patient in need thereof, an effective amount of a GLP-1 derivative as defined in any one of the preceding embodiments, optionally in combination with one or more additional therapeutically active compounds.

130. A method for treating obesity or preventing overweight, decreasing food intake, increasing energy expenditure, reducing body weight, regulating appetite, inducing satiety, preventing weight regain after successful weight loss, treating a disease or state related to overweight or obesity, treating bulimia, and/or treating binge-eating, comprising administering to a patient in need thereof, an effective amount of a GLP-1 derivative as defined in any one of the preceding embodiments, optionally in combination with one or more additional therapeutically active compounds.

131. A method for the treatment or prevention of type 2 diabetes, impaired glucose tolerance, delaying or preventing disease progression in type 2 diabetes, delaying the progression from impaired glucose tolerance (IGT) to type 2 diabetes, and/or delaying the progression from type 2 diabetes to insulin-requiring diabetes, comprising administering to a patient in need thereof, an effective amount of a GLP-1 derivative as defined in any one of the preceding embodiments, optionally in combination with one or more additional therapeutically active compounds.

132. A method for the treatment or prevention of atherosclerosis, treating hypertension, treating dyslipidaemia, treating coronary heart disease, and/or treating hepatic steatosis, comprising administering to a patient in need thereof, an effective amount of a GLP-1 derivative as defined in any one of the preceding embodiments, optionally in combination with one or more additional therapeutically active compounds.

133. The method of treatment according to any one of the preceding embodiments, wherein said GLP-1 derivative is administered in combination with one or more additional therapeutically active compounds.

134. Use of a GLP-1 derivative as defined in any one of the preceding embodiments for the preparation of a medicament.

135. Use of a GLP-1 derivative as defined in any one of the preceding embodiments, for the preparation of a medicament for the treatment or prevention of obesity, hyperglycaemia, type 2 diabetes, impaired glucose tolerance, and type 1 diabetes.

136. A GLP-1 analogue selected from the group consisting of:
[Imp7,Acb8,His9,Tyr16,Lys18,Glu22,Arg26,Leu33, Lys35]-GLP-1-(7-35)-peptide amide; (SEQ ID NO: 3)
[Imp7,Acb8,His9,Lys18,Glu22,Arg26,Leu33,Lys35]-GLP-1-(7-35)-peptide amide; (SEQ ID NO: 4)
[Imp7,Aib8,His9,Lys18,Glu22,Arg26,Leu33,Thr35]-GLP-1-(7-35)-peptide amide; (SEQ ID NO: 5)
[Imp7,Aib8,His9,Arg18,Glu22,Arg26,Leu33,Thr35]-GLP-1-(7-35)-peptide amide; (SEQ ID NO: 7)
[Imp7,Aib8,His9,Arg18,Arg26,Leu33,Thr35]-GLP-1-(7-35)-peptide amide; (SEQ ID NO: 8)
[Imp7,Acb8,His9,Lys18,Glu22,Arg26,Leu33,Thr35]-GLP-1-(7-35)-peptide amide; (SEQ ID NO: 9)
[Imp7,His9,Lys18,Arg23,Arg26,Leu33,Thr35]-GLP-1-(7-35)-peptide amide; (SEQ ID NO: 10)
[Imp7,His9,Lys18,Arg23,Arg26,Leu33,Gly36]-GLP-1-(7-37)-peptide; (SEQ ID NO: 38)
[Imp7,Aib8,His9,Lys18,Lys22,Arg26,Leu33,Gly36]-GLP-1-(7-37)-peptide; (SEQ ID NO: 39)
[Imp7,Aib8,His9,Tyr16,Lys18,Glu22,Arg26,Leu33,Lys36]-GLP-1-(7-37)-peptide; (SEQ ID NO: 13)
[Imp7,Aib8,His9,Lys18,Lys23,Arg26,Leu33,Thr35]-GLP-1-(7-35)-peptide amide; (SEQ ID NO: 14)
[Imp7,Aib8,His9,Tyr16,Lys18,Lys23,Arg26,Leu33,Thr35]-GLP-1-(7-35)-peptide amide; (SEQ ID NO: 15)
[Imp7,His9,Arg18,Arg23,Arg26,Leu33]-GLP-1-(7-34)-peptide; (SEQ ID NO: 40)
[Imp7,His9,Arg18,Glu22,Arg26,Lys27,Leu33,Arg34]-GLP-1-(7-34)-peptide; (SEQ ID NO: 17)
[Imp7,Aib8,His9,Arg18,Glu22,Arg26,Lys27,Leu33, Arg34]-GLP-1-(7-34)-peptide; (SEQ ID NO: 41)
[Imp7,Acb8,His9,Lys18,Arg23,Arg26,Leu33,Thr35]-GLP-1-(7-35)-peptide amide; (SEQ ID NO: 19)
[Imp7,Acb8,His9,Tyr16,Lys18,Glu22,Arg26,Leu33, Lys35]-GLP-1-(7-35)-peptide amide; (SEQ ID NO: 3)
[Imp7,Acb8,His9,Tyr16,Arg18,Glu22,Arg26,Leu33,Arg34, Lys35]-GLP-1-(7-35)-peptide amide (SEQ ID NO: 20);
[Imp7,Acb8,His9,Tyr16,Lys18,Arg22,Arg26,Leu33, Lys35]-GLP-1-(7-35)-peptide amide; (SEQ ID NO: 21)
[Imp7,Acb8,His9,Tyr16,Lys18,Arg22,Arg23,Arg26,Leu33, Lys35]-GLP-1-(7-35)-peptide amide; (SEQ ID NO: 22)
[Imp7,Aib8,His9,Lys18,Glu22,Arg26,Leu33,Thr35]-GLP-1-(7-35)-peptide; (SEQ ID NO: 5)
[Imp7,Acb8,His9,Tyr16,Lys18,Arg23,Arg26,Leu33, Lys35]-GLP-1-(7-35)-peptide amide; (SEQ ID NO: 23)
[Imp7,Acb8,His9,Tyr16,Arg18,Arg23,Arg26,Leu33,Arg34, Lys35]-GLP-1-(7-35)-peptide amide; (SEQ ID NO: 34)
[Imp7,Aib8,His9,Lys18,Glu22,Arg26,Leu33,Thr35]-GLP-1-(7-35)-peptide amide; (SEQ ID NO: 5)
[Imp7,Aib8,His9,Lys18,Ala22,Arg23,Arg26,Leu33, Gly36]-GLP-1-(7-37)-peptide; (SEQ ID NO: 25)
[Imp7,Acb8,His9,Lys18,Lys22,Arg23,Arg26,Leu33, Thr35]-GLP-1-(7-35)-peptide amide; (SEQ ID NO: 26)
[Imp7,Acb8,His9,Lys18,Lys22,Arg26,Leu33,Thr35]-GLP-1-(7-35)-peptide amide; (SEQ ID NO: 27)

[Imp7,Aib8,His9,Lys18,Ala22,Arg26,Leu33,Thr35]-GLP-1-(7-35)-peptide amide; (SEQ ID NO: 28)
[Imp7,Aib8,His9,Arg18,Arg23,Arg26,Leu33,Ala36]-GLP-1-(7-37)-peptide; (SEQ ID NO: 29)
[Imp7,Aib8,His9,Arg18,Arg23,Arg26,Leu33,Ser36]-GLP-1-(7-37)-peptide; (SEQ ID NO: 30)
[Imp7,Gly8,His9,Arg18,Glu22,Arg26,Leu33,Thr35]-GLP-1-(7-35)-peptide amide; (SEQ ID NO: 31)
[Imp7,Aib8,His9,Leu16,Lys18,Glu22,Arg26,Leu33, Thr35]-GLP-1-(7-35)-peptide amide; (SEQ ID NO: 32) and [Imp7,Aib8,His9,Lys18,Glu22,Arg26,Ile33,Thr35]-GLP-1-(7-35)-peptide amide; or a pharmaceutically acceptable salt thereof. (SEQ ID NO: 43)

EXAMPLES

The invention is further illustrated with reference to the following examples, which are not intended to be in any way limiting to the scope of the invention as claimed.

LIST OF ABBREVIATIONS

BOC: tert-Butyl oxycarbonyl
DCM: Dichloromethane
DIC: Diisopropylcarbodiimide
Fmoc: 9-fluorenylmethyloxycarbonyl
HFIP 1,1,1,3,3,3-Hexafluoro-2-isopropanol
HOAt: 1-hydroxy-7-azabenzotriazole
HPLC: High Performance Liquid Chromatography
LCMS: Liquid Chromatography Mass Spectroscopy
MeCN: Acetonitrile
Mtt: 4-Methyltrityl
NMP: N-methyl pyrrolidone
Oxyma Pure: Cyano-hydroxyimino-acetic acid ethyl ester
Pbf 2,2,4,6,7-pentamethyldihydrobenzofuran-5-sulfonyl
RP: Reverse Phase
RP-HPLC: Reverse Phase High Performance Liquid Chromatography
RT: Room Temperature
Rt: Retention time
SPPS: Solid Phase Peptide Synthesis
TFA: Trifluoroacetic acid
TIPS: Triisopropylsilane
Trt Trityl
UPLC: Ultra Performance Liquid Chromatography
10EE: 10 to the power (e.g. "10EE(X)" refers to the number 10 to the power (X), or simply the number $10^{(x)}$, i.e. 5×10EE3 is 5×10$^3$)

General Methods

This section relates to methods for synthesising resin bound peptide (SPPS methods, including methods for de-protection of amino acids, methods for cleaving the peptide from the resin, and for its purification), as well as methods for detecting and characterising the resulting peptide (LCMS and UPLC methods).

The compounds in Examples 1-42 herein were prepared, purified and analysed essentially according to the general procedures described below.

SPPS General Methods

The Fmoc-protected amino acid derivatives used were the standard recommended: Fmoc-Ala-OH, Fmoc-Arg(Pbf)-OH, Fmoc-Asn(Trt)-OH, Fmoc-Asp(OtBu)-OH, Fmoc-Cys(Trt)-OH, Fmoc-Gln(Trt)-OH, Fmoc-Glu(OtBu)-OH, Fmoc-Gly-OH, Fmoc-His(Trt)-OH, Fmoc-Ile-OH, Fmoc-Leu-OH, Fmoc-Lys(Boc)-OH, Fmoc-Met-OH, Fmoc-Phe-OH, Fmoc-Pro-OH, Fmoc-Ser(tBu)-OH, Fmoc-Thr(tBu)-OH, Fmoc-Trp(BOC)-OH, Fmoc-Tyr(tBu)-OH, Fmoc-Val-OH and Fmoc-Lys(Mtt)-OH or Fmoc-Lys(Alloc)-OH supplied from e.g. Anaspec, Bachem, Iris Biotech, or Novabioche. The N-terminal Imp was incorporated using 3-(N-1-Trityl-imidazol-4-yl)-propionic acid.

The introduction of the substituent on the epsilon-nitrogen of a lysine was achieved using a Lysine protected with Mtt (Fmoc-Lys(Mtt)-OH) or Alloc (Fmoc-Lys(Alloc)-OH). Suitably protected building blocks such as Fmoc-8-amino-3,6-dioxaoctanoic acid, Fmoc-Glu-OtBu as well as the protected standard amino acids described above were used for the introduction of the substituent. Introduction of the fatty acid moiety was achieved using a mono tert-butylated di-acid such as 18-tert-butoxy-18-oxo-octadecanoic acid.

SPPS was performed on a Prelude Solid Phase Peptide Synthesizer from Protein Technologies (Tucson, Ariz. 85714 U.S.A.) at 100 or 250-µmol scale. Rink Amide AM polystyrene resin (Novabiochem, loading e.g. 0.62 mmol/g) or a preloaded Wang resin (e.g. Novabiochem) was used as the solid support. Fmoc-deprotection was performed using 20% piperidine in NMP. Coupling was performed using an excess, compared to resin of a mixture of amino acid/Oxyma Pure®)/DIC/collidine (100 µmol scale: 10:9:9:9; 250 µmol scale: 7:6:6:6) in NMP. Alternatively, DEPBt (3-(diethoxyphosphoryloxy)-1,2,3-benzotriazin-4(3H)-one)/DIPEA may be used for suppression of epimerization of eg. His during coupling. NMP and DCM top washes (5-7 ml, 0.5 min, 2×2 each) were performed between deprotection and coupling steps. Coupling times were typically 60 minutes. Some amino acids including, but not limited to Fmoc-Arg(Pbf)-OH, Fmoc-Aib-OH or Boc-His(Trt)-OH as well as the building blocks comprising the substituent were "double coupled", meaning that after the first coupling (e.g. 60 min), the resin was drained and more reagents are added (amino acid, (HOAt or Oxyma Pure®), DIC, and collidine), and the mixture allowed to react again (e.g. 60 min).

If Fmoc-Lys(Mtt)-OH is used, the Mtt group was removed by washing the resin with HFIP/DCM (75:25) (2×2 min), washed with DCM and suspending the resin in HFIP/DCM (75:25)(2×20 min) and subsequently washed in sequence with piperidine/NMP (20:80), DCM(1×), NMP (1×), DCM(1×), NMP(1×).

If Fmoc-Lys(Alloc)-OH is used, the Alloc group may be removed by treating the resin with Pd(PPh$_3$)$_4$ (0.02 equiv) in the presence of one or more scavengers in combination, eg. morpholine (6.0 equiv) and/or dimethyl borane complex (18.0 equiv) (30 min). The resin is then washed with MeOH, NMP or DMF and IPA (isopropyl alcohol), respectively, before the substituent can be introduced at the epsilon-position of the lysine moiety.

Cleavage from the Resin

After synthesis the resin was washed with DCM, and the peptide was cleaved from the resin by a 2-3 hour treatment with TFA/TIPS/water (95/2.5/2.5)) or TFA/EDT (1,2-ethanedithiol)/water (90/5/5) followed by precipitation with Et$_2$O (diethyl ether) or IPE (diisopropyl ether). The precipitate was washed with used solvent.

Purification and Quantification

The crude peptide was dissolved in a suitable mixture of water and MeCN such as water/MeCN (4:1) or water/AcOH (1:1) at 60° C. for 1 hour and purified by reversed-phase preparative HPLC (Waters Deltaprep 4000 or Gilson) on a column comprising C8- or C18-silica gel. Elution was performed with an increasing gradient of MeCN in water comprising 0.1% TFA. Relevant fractions are checked by analytical HPLC or UPLC. Fractions comprising the pure target peptide were pooled and concentrated under reduced pressure. An additional purification step may be introduced using another gradient, eg. containing 0.05M NH$_4$HCO$_3$. The resulting solution was analyzed (HPLC, LCMS) and the product is quantified using a chemiluminescent nitrogen specific HPLC detector (Antek 8060 HPLC-CLND) or by measuring UV-absorption at 280 nm. The product is dispensed into glass vials. The vials were capped with Millipore glassfibre prefilters. Freeze-drying affords the peptide trifluoroacetate as a white solid.

The peptide trifluoroacetate may be changed into the sodium salt by column ion exchange eg. with NaOAc in MeCN. Alternatively, the peptide trifluoroacetate may be changed to the ammonium salt by column chromatography eg. with a gradient containing 0.05M $NH_4HCO_3$, followed by freeze-drying and suspension in water. The peptide was changed into the sodium salt by addition of 1M NaOH (equiv according to basic/acidic residues) turning the suspension clear. Finally, the peptide sodium salt may be isolated by freeze-drying.

Methods for Detection and Characterization
LCMS Methods
Method: LCMS01

| System | LC-system: Waters Acquity UPLC |
| --- | --- |
| | Column:: Waters Acquity UPLC BEH, C-18, 1.7 μm, 2.1 mm × 50 mm |
| | Detector:: Waters (Micromass) LCT Premier XE |
| Detector setup | Ionisation method: ES |
| | Scanning range: 500-2000 amu |
| | Operating mode: W mode |
| | positive/negative: positive mode |
| | Cone Voltage: 50 V |
| | Scantime 1.0 s |
| Conditions | Linear gradient: 5% to 95% B |
| | Gradient run-time: 4.0 minutes |
| | Total run-time: 7.0 minutes |
| | Flow rate: 0.4 ml/min |
| | Column temperature: 40° C. |
| Eluents | Solvent A: 99.90% MQ-water, 0.1% formic acid |
| | Solvent B: 99.90% acetonitrile, 0.1% formic acid |
| | Solvent C: NA |
| Results specification and validation | Mass found is the mass found of the compound |
| | M/z found is the molecular ion found ((M + z)/z) of the compound |
| | Calculated mass is the molecular weight of the desired compound |

Method: LCMS13

| System | System: Waters Acquity UPLC SQD 2000 |
| --- | --- |
| | Column: Acquity UPLC BEH 1.7μ C18 100 Å 2.1 × 100 mm |
| | Detector: UV: PDA, SQD 2000 |
| Detector setup | Ionisation method: ES+ |
| | Scanning range: 500-2000 |
| | Cone Voltage: 60 V |
| | Scantime 0.5 s |
| Conditions | Linear gradient: 10% to 90% B |
| | Gradient run-time: 3 min |
| | Total run-time: 4 min |
| | low rate: 0.3 ml/min |
| | Column temperature: 40° C. |
| | PDA: 210-400 nm |
| Eluents | Solvent A: 99.90% H2O, 0.1% TFA |
| | Solvent B: 99.90% CH3CN, 0.1% TFA |
| | Solvent C: NA |
| Results specification and validation | Mass found is the mass found of the compound |
| | M/z found is the molecular ion found ((M + z)/z) of the compound |
| | Calculated mass is the molecular weight of the desired compound |

UPLC Methods
Method: UPLC02

| System | System: Waters Acquity UPLC system |
| --- | --- |
| | Column: ACQUITY UPLC BEH C18, 1.7 um, 2.1 mm × 150 mm column |
| | Detectors: Waters Acquity TUV Detector |
| Detector setup | 214 nm and 254 nm |
| Conditions | Linear gradient: 5% to 95% B |
| | Gradient run-time: 16 minutes |
| | Flow rate: 0.40 ml/min fixed |
| | Column temperature: 40° C. |
| Eluents | Solvent A: 99.95% Water, 0.05% Trifluoroacetic acid |
| | Solvent B: 99.95% Acetonitrile, 0.05% Trifluoroacetic acid |

Example 1

$N^{ε35}$-[2-[[(2S)-2-[[(2S)-4-carboxy-2-[[2-[[(2S)-2-[[(4S)-4-carboxy-4-[[(4S)-4-carboxy-4-(17-carboxy-heptadecanoylamino)butanoyl]amino]butanoyl]amino]-3-hydroxypropanoyl]amino]acetyl]amino]butanoyl]amino]-3-hydroxypropanoyl]amino]acetyl]-[Imp7,Acb8,His9,Tyr16,Lys18,Glu22,Arg26,Leu33,Lys35]-GLP-1-(7-35)-peptide amide (SEQ ID NO: 3)

(Chem. 1)

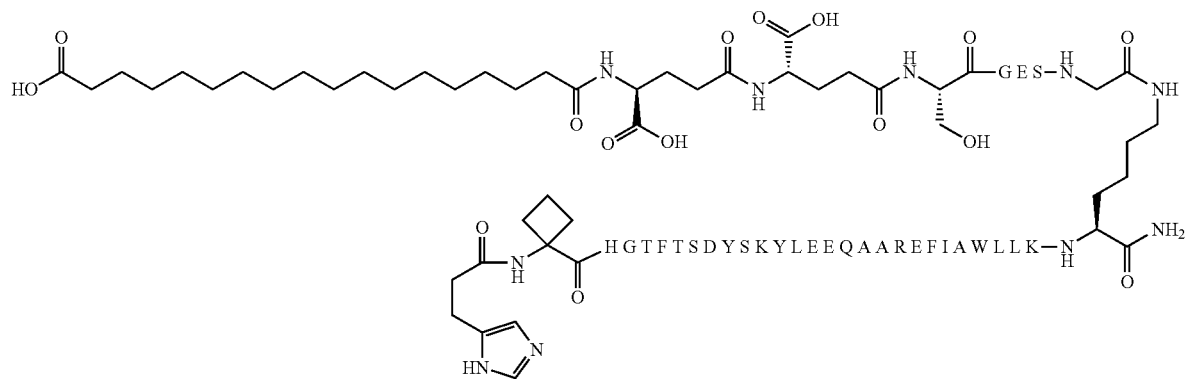

UPLC02: Rt=8.7 min
LCMS01: Calc m/1=4423. Found m/3=1475. Found m/4=1107. Found m/5=886.

Example 2

N^{ε35}-[2-[[(2S)-2-[[(2S)-4-carboxy-2-[[2-[[(2S)-2-[[(4S)-4-carboxy-4-[[(4S)-4-carboxy-4-(17-carboxy-heptadecanoylamino)butanoyl]amino]butanoyl]amino]-3-hydroxypropanoyl]amino]acetyl]amino]butanoyl]amino]-3-hydroxypropanoyl]amino]acetyl]-[Imp7,Acb8,His9,Lys18,Glu22,Arg26,Leu33,Lys35]-GLP-1-(7-35)-peptide amide (SEQ ID NO: 4)

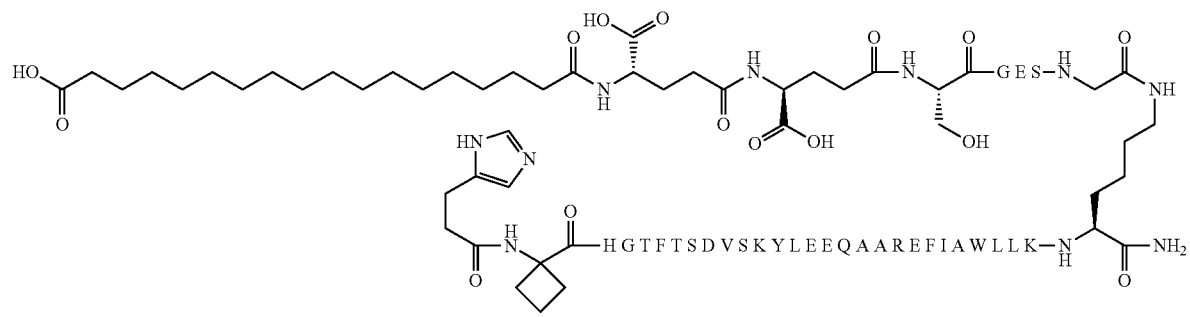
(Chem. 2)

UPLC02: Rt=8.3
LCMS01: Rt=2.2 min; Calc m/1=4359. Found m/1=4359. Found m/3=1453. Found m/4=1091. Found m/5=873.

Example 3

N^{ε34}-[2-[[(2S)-2-[[(2S)-4-carboxy-2-[[2-[[(2S)-2-[[(4S)-4-carboxy-4-[[(4S)-4-carboxy-4-(17-carboxy-heptadecanoylamino)butanoyl]amino]butanoyl]amino]-3-hydroxypropanoyl]amino]acetyl]amino]butanoyl]amino]-3-hydroxypropanoyl]amino]acetyl]-[Imp7,Aib8,His9,Lys18,Glu22,Arg26,Leu33,Thr35]-GLP-1-(7-35)-peptide amide (SEQ ID NO: 5)

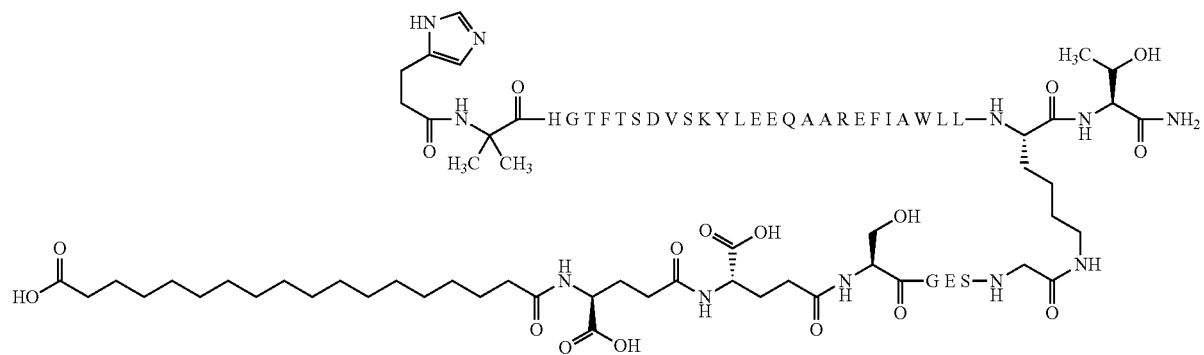
(Chem. 3)

UPLC02: Rt=8.8 min
LCMS01: Rt=2.3 minutes; Calc m/1=4320. Found m/1=4320. Found m/3=1441. Found m/4=1081. Found m/5=865.

Example 4

$N^{\varepsilon 34}$-[2-[[(2S)-2-[[(4S)-4-carboxy-4-[[(4S)-4-carboxy-4-(17-carboxyheptadecanoylamino)butanoyl]amino]butanoyl]amino]-3-hydroxypropanoyl]amino]acetyl]-[Imp7,Aib8,His9,Lys18,Glu22,Arg26,Leu33,Thr35]-GLP-1-(7-35)-peptide amide (SEQ ID NO: 5)

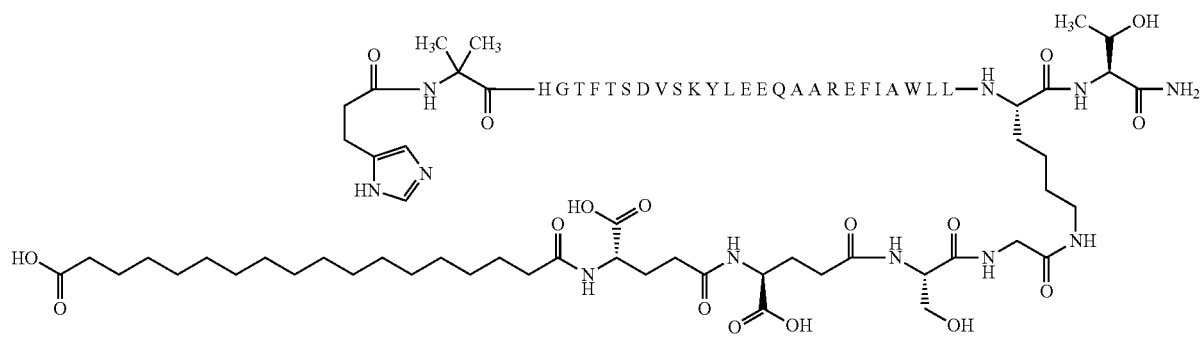

(Chem. 4)

UPLC02: Rt=9.1 min
LCMS01: Rt=2.3 min; Calc m/1=4046. Found m/3=1350. Found m/4=1012. Found m/5=810. Found m/z=4047.

Example 5

$N^{\varepsilon 34}$-[2-[2-[2-[[2-[2-[2-[[(4S)-4-carboxy-4-[[(4S)-4-carboxy-4-(17-carboxyheptadecanoylamino)butanoyl]amino]butanoyl]amino]ethoxy]ethoxy]acetyl]amino]ethoxy]ethoxy]acetyl]-[Imp7,Aib8,His9,Lys18,Glu22,Arg26,Leu33,Thr35]-GLP-1-(7-35)-peptide amide (SEQ ID NO: 5)

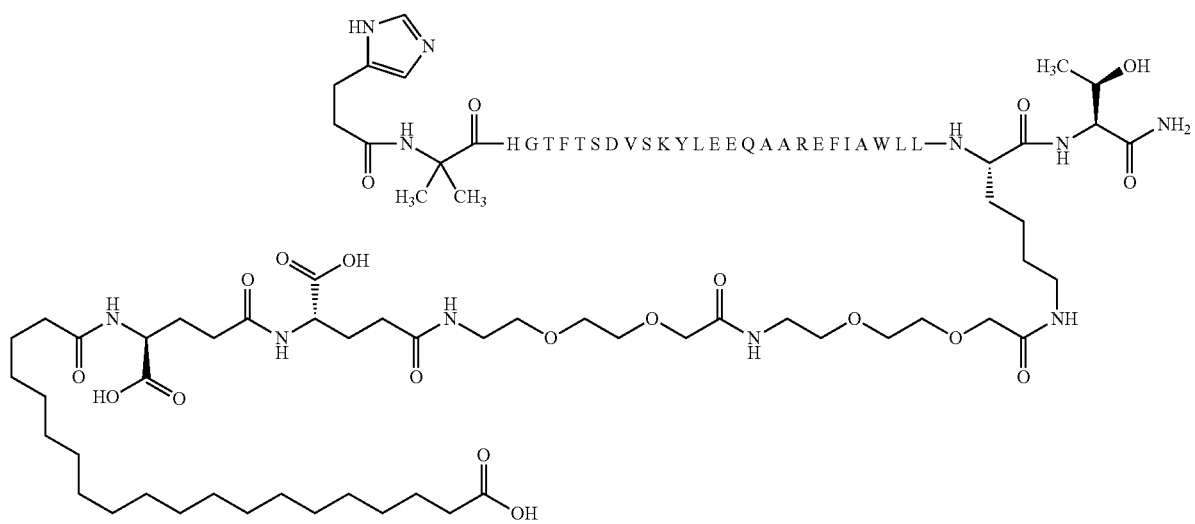

(Chem. 5)

UPLC02: Rt=9.0 min
LCMS01: RT=2.3 min; Calc m/1=4193. Found m/3=1398. Found m/4=1049. Found m/5=839. Found m/z=4193.

Example 6

$N^{\varepsilon 34}$-[(4S)-4-carboxy-4-[[(4S)-4-carboxy-4-[[(4S)-4-carboxy-4-[[(4S)-4-carboxy-4-(17-carboxyheptadecanoylamino)butanoyl]amino]butanoyl]amino]butanoyl]amino]butanoyl]-[Imp7,Aib8,His9,Lys18,Glu22,Arg26,Leu33,Thr35]-GLP-1-(7-35)-peptide amide (SEQ ID NO: 5)

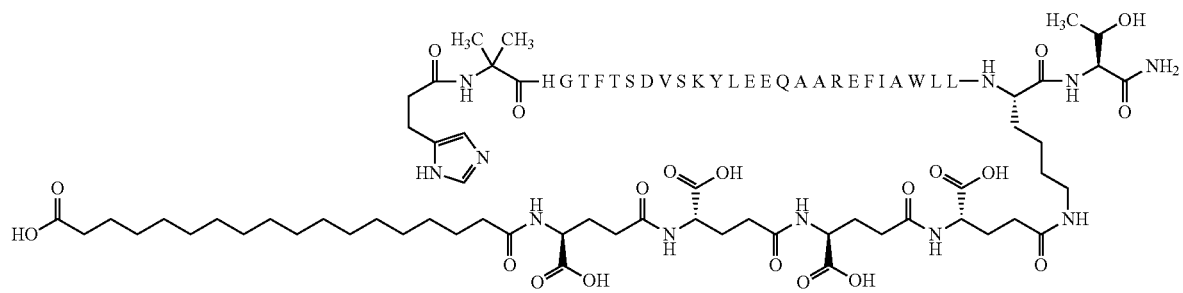

(Chem. 6)

UPLC02: Rt=9.0 min
LCMS01: RT=2.3 min; Calc m/1=4161. Found m/3=1388. Found m/4=1041. Found m/5=833. Found m/z=4162.

Example 7

$N^{\varepsilon 34}$-[2-[[(2S)-2-[[(2S)-4-carboxy-2-[[2-[[(2S)-2-[[(4S)-4-carboxy-4-[[(4S)-4-carboxy-4-(17-carboxyheptadecanoylamino)butanoyl]amino]butanoyl]amino]-3-hydroxypropanoyl]amino]acetyl]amino]butanoyl]amino]-3-hydroxypropanoyl]amino]acetyl]-[Imp7,Aib8,His9,Arg18,Glu22,Arg26,Leu33,Thr35]-GLP-1-(7-35)-peptide amide (SEQ ID NO: 7)

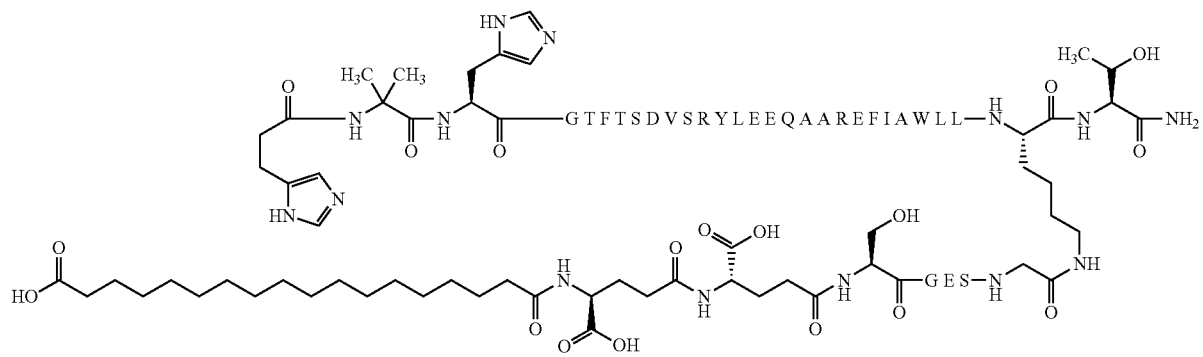

(Chem. 7)

UPLC02: Rt=8.9 min
LCMS01: Rt=2.3 min; Calc m/1=4348. Found m/1=4348. Found m/3=1449. Found m/4=1087. Found m/5=870.

Example 8

N$^{\epsilon 34}$-[2-[[(2S)-2-[[(2S)-4-carboxy-2-[[2-[[(2S)-2-[[(4S)-4-carboxy-4-[[(4S)-4-carboxy-4-(17-carboxy-heptadecanoylamino)butanoyl]amino]butanoyl]amino]-3-hydroxypropanoyl]amino]acetyl]amino]butanoyl]amino]-3-hydroxypropanoyl]amino]acetyl]-[Imp7,Aib8,His9,Arg18,Arg26,Leu33,Thr35]-GLP-1-(7-35)-peptide amide (SEQ ID NO: 8)

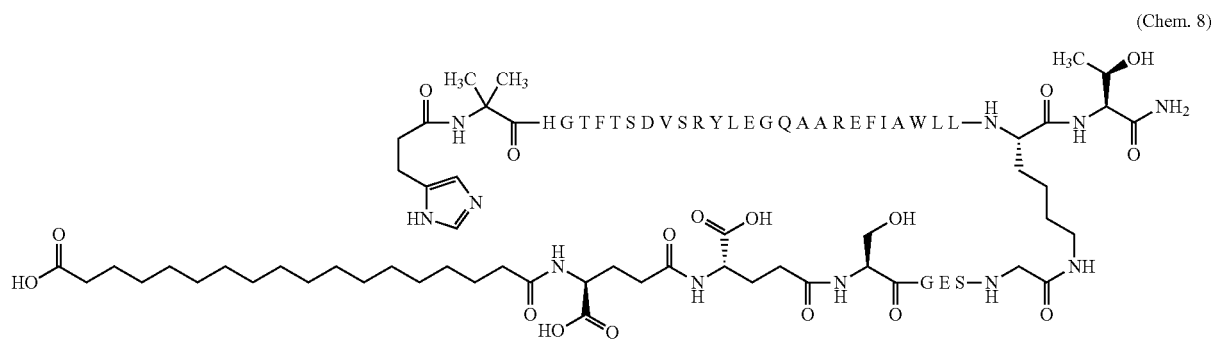

(Chem. 8)

UPLC02: Rt=9.0 min
LCMS01: Rt=2.3 min; Calc m/1=4276. Found m/1=4276. Found m/3=1426. Found m/4=1070. Found m/5=856.

Example 9

N$^{\epsilon 34}$-[2-[[(2S)-2-[[(2S)-4-carboxy-2-[[2-[[(2S)-2-[[(4S)-4-carboxy-4-[[(4S)-4-carboxy-4-(17-carboxy-heptadecanoylamino)butanoyl]amino]butanoyl]amino]-3-hydroxypropanoyl]amino]acetyl]amino]butanoyl]amino]-3-hydroxypropanoyl]amino]acetyl]-[Imp7,Acb8,His9,Lys18,Glu22,Arg26,Leu33,Thr35]-GLP-1-(7-35)-peptide amide (SEQ ID NO: 9)

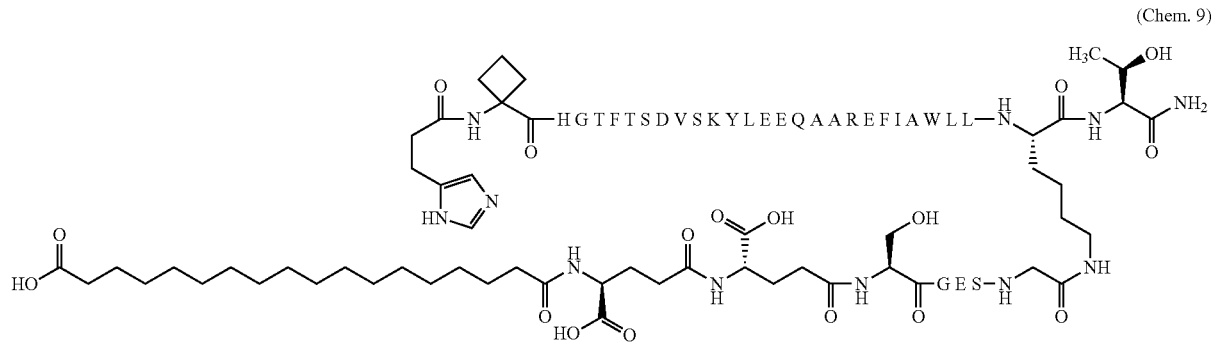

(Chem. 9)

UPLC02: Rt=8.9 min
LCMS01: Rt=2.3 min; Calc m/1=4332. Found m/1=4332. Found m/3=1445. Found m/4=1084. Found m/5=867.

Example 10

$N^{\epsilon 34}$-[2-[2-[2-[[2-[2-[2-[[(4S)-4-carboxy-4-[[(4S)-4-carboxy-4-[[(4S)-4-carboxy-4-(17-carboxyheptade-canoylamino)butanoyl]amino]butanoyl]amino]butanoyl]amino]ethoxy]ethoxy]acetyl]amino]ethoxy]ethoxy]acetyl]-[Imp7,His9,Lys18,Arg23,Arg26,Leu33,Thr35]-GLP-1-(7-35)-peptide amide (SEQ ID NO: 10)

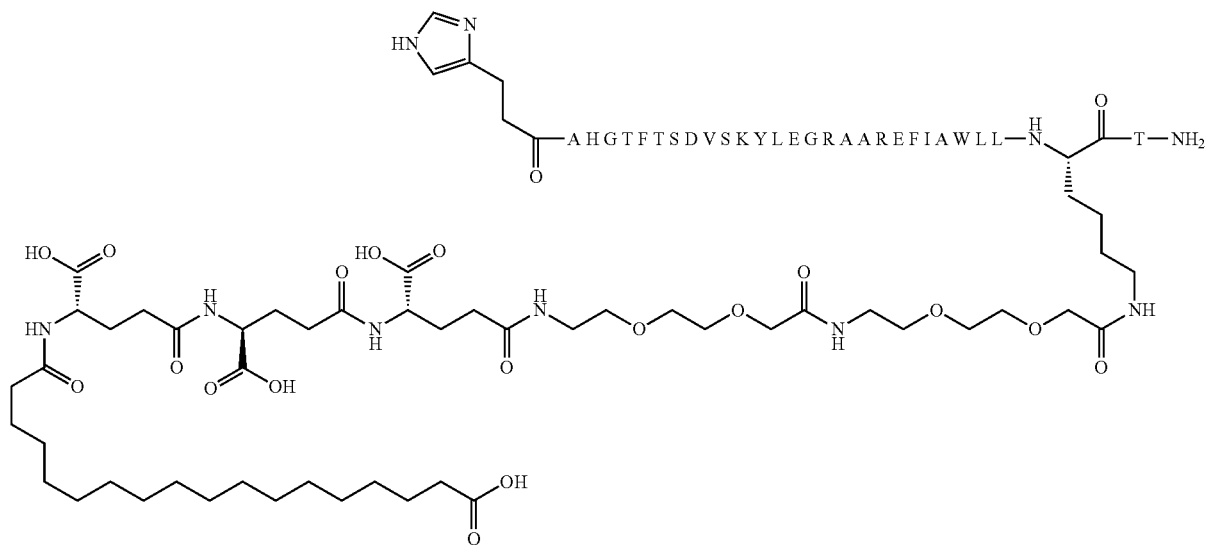

(Chem. 10)

UPLC02: Rt=8.6 min
LCMS13: Rt=2.3 min; Calc m/1=4264. Found m/3=1422. Found m/4=1067.

Example 11

$N^{\epsilon 34}$-[2-[2-[2-[[2-[2-[2-[[(4S)-4-carboxy-4-[[(4S)-4-carboxy-4-[[(4S)-4-carboxy-4-(17-carboxyheptade-canoylamino)butanoyl]amino]butanoyl]amino]butanoyl]amino]ethoxy]ethoxy]acetyl]amino]ethoxy]ethoxy]acetyl]-[Imp7,His9,Lys18,Arg23,Arg26,Leu33,Gly36]-GLP-1-(7-37)-peptide (SEQ ID NO: 38)

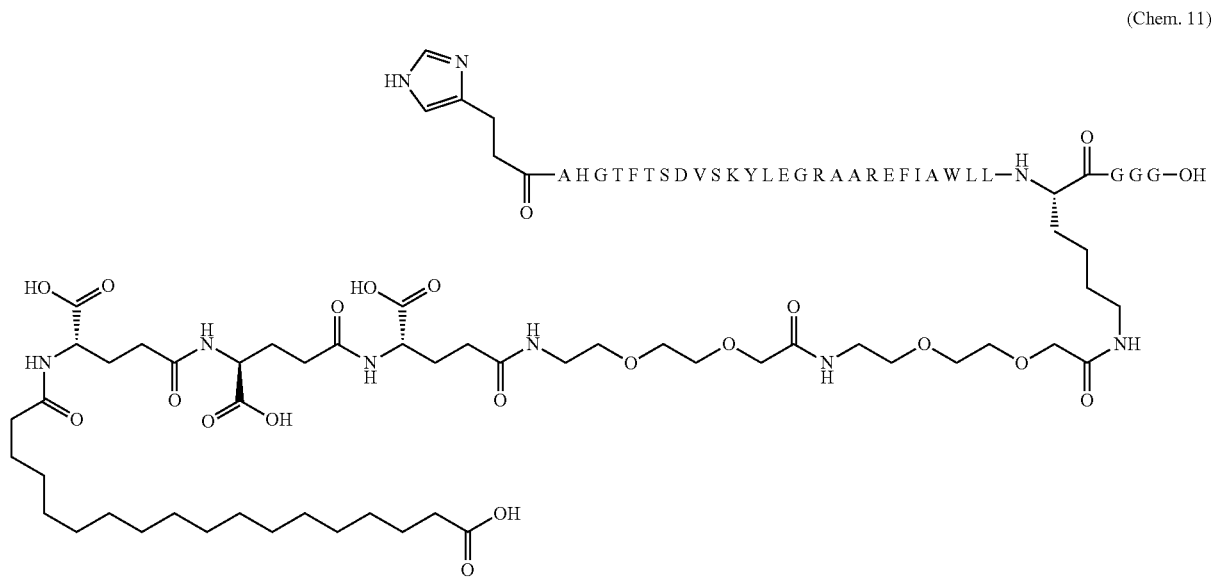

(Chem. 11)

UPLC02: Rt=8.7 min
LCMS13: Rt=2.3 min; Calc m/1=4335. Found m/3=1445. Found m/4=1084.

Example 12

N$^{\epsilon 34}$-[2-[2-[2-[[2-[2-[2-[[(4S)-4-carboxy-4-(17-carboxyheptadecanoylamino)butanoyl]amino]ethoxy]ethoxy]acetyl]amino]ethoxy]ethoxy]acetyl]-[Imp7,Aib8,His9,Lys18,Glu22,Arg26,Leu33,Thr35]-GLP-1-(7-35)-peptide amide (SEQ ID NO: 5)

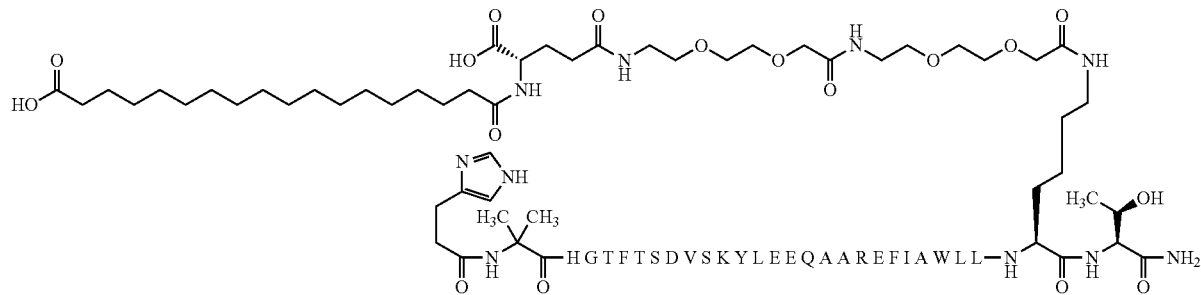

(Chem. 12)

UPLC02: Rt=9.3 min
LCMS01: Rt=2.3 min; Calc m/1=4064. Found m/1=4064. Found m/3=1356. Found m/4=1017.
m

Example 13

N$^{\epsilon 22}$-[(4S)-4-carboxy-4-[[(4S)-4-carboxy-4-[[2-[2-[2-[[2-[2-[2-[[(4S)-4-carboxy-4-(17-carboxyheptadecanoylamino)butanoyl]amino]ethoxy]ethoxy]acetyl]amino]ethoxy]ethoxy]acetyl]amino]butanoyl]amino]butanoyl]-[Imp7,Aib8,His9,Lys18,Lys22,Arg26,Leu33,Gly36]-GLP-1-(7-37)-peptide (SEQ ID NO: 39)

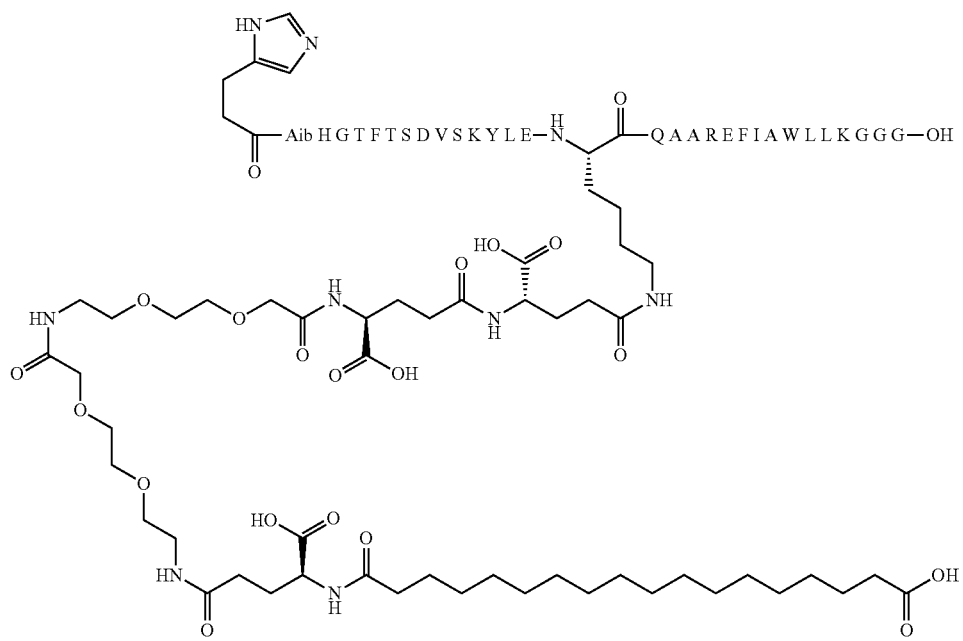

(Chem. 13)

UPLC02: Rt=8.4 min
LCMS01: Rt=2.2 min; Calc m/1=4392. Found m/1=4392. Found m/3=1465. Found m/4=1099.

Example 14

$N^{\varepsilon 36}$-[2-[[(2S)-2-[[(2S)-4-carboxy-2-[[2-[[(2S)-2-[[(4S)-4-carboxy-4-[[(4S)-4-carboxy-4-(17-carboxy-heptadecanoylamino)butanoyl]amino]butanoyl]amino]-3-hydroxypropanoyl]amino]acetyl]amino]butanoyl]amino]-3-hydroxypropanoyl]amino]acetyl]-[Imp7,Aib8,His9,Tyr16,Lys18,Glu22,Arg26,Leu33,Lys36]-GLP-1-(7-37)-peptide (SEQ ID NO: 13)

(Chem. 14)

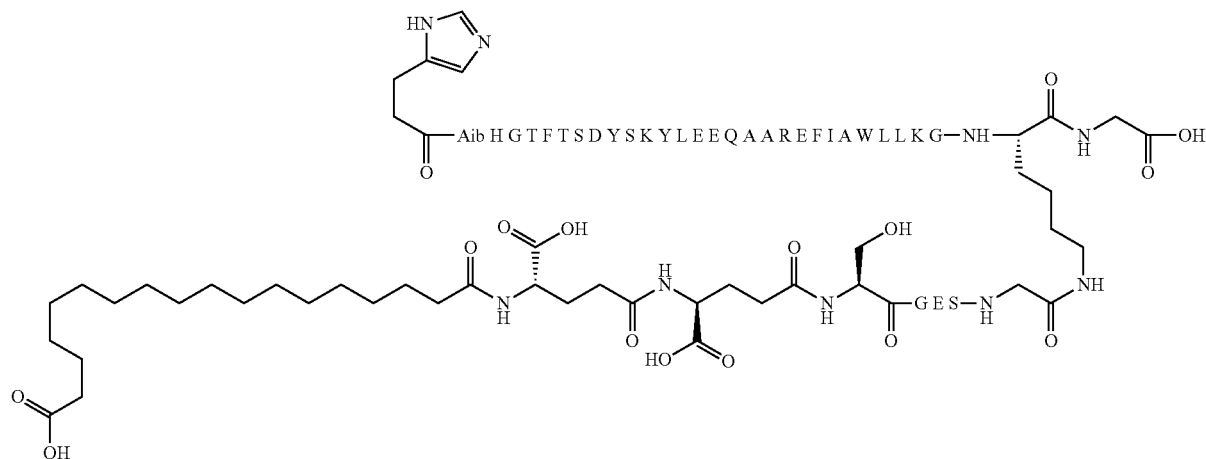

UPLC02: Rt=8.2 min
LCMS01: Rt=2.1 min; Calc m/1=4526. Found m/1=4526. Found m/3=1510. Found m/4=1133.

Example 15

$N^{\varepsilon 23}$-[2-[2-[2-[[2-[2-[2-[[(4S)-4-carboxy-4-(17-carboxyheptadecanoylamino)butanoyl]amino]ethoxy]ethoxy]acetyl]amino]ethoxy]ethoxy]acetyl]-[Imp7,Aib8,His9,Lys18,Lys23,Arg26,Leu33,Thr35]-GLP-1-(7-35)-peptide amide (SEQ ID NO: 14)

(Chem. 15)

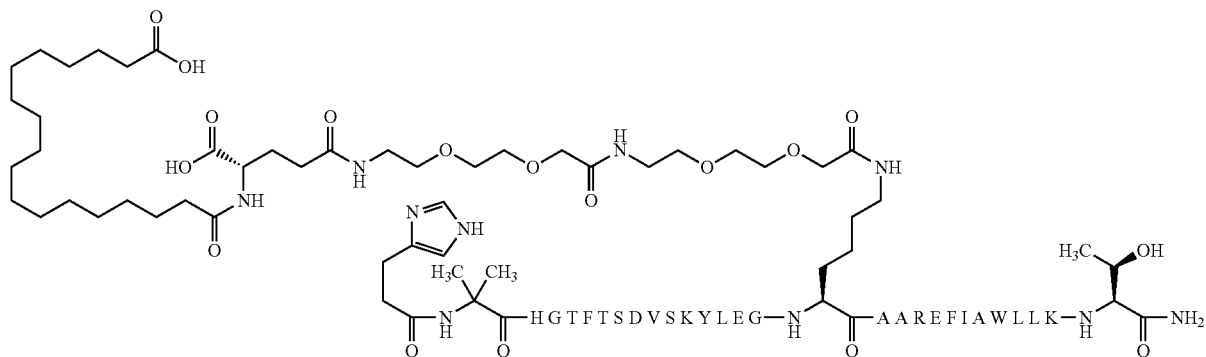

UPLC02: Rt=8.8 min
LCMS01: Rt=2.3 min; Calc m/1=3992. Found m/1=3992. Found m/3=1332. Found m/4=999.

Example 16

$N^{\varepsilon 23}$-[2-[2-[2-[[2-[2-[2-[[(4S)-4-carboxy-4-(17-carboxyheptadecanoylamino)butanoyl]amino]ethoxy]ethoxy]acetyl]amino]ethoxy]ethoxy]acetyl]-[Imp7, Aib8,His9,Tyr16,Lys18,Lys23,Arg26,Leu33,Thr35]-GLP-1-(7-35)-peptide amide (SEQ ID NO: 15)

(Chem. 16)

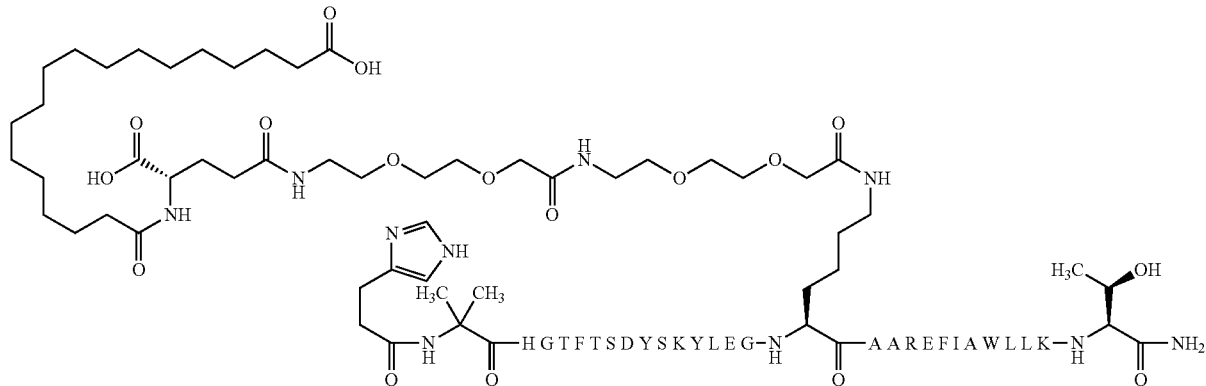

UPLC02: Rt=8.6 min
LCMS01: Rt=2.3 min; Calc m/1=4056. Found m/1=4055. Found m/3=1353. Found m/4=1015.

Example 17

$N^{\varepsilon 34}$-[2-[2-[2-[[2-[2-[2-[[(4S)-4-carboxy-4-[[(4S)-4-carboxy-4-[[(4S)-4-carboxy-4-(17-carboxyheptadecanoylamino)butanoyl]amino]butanoyl]amino]butanoyl]amino]ethoxy]ethoxy]acetyl]amino]ethoxy]ethoxy]acetyl]-[Imp7,His9,Arg18,Arg23,Arg26, Leu33]-GLP-1-(7-34)-peptide (SEQ ID NO: 40)

(Chem. 17)

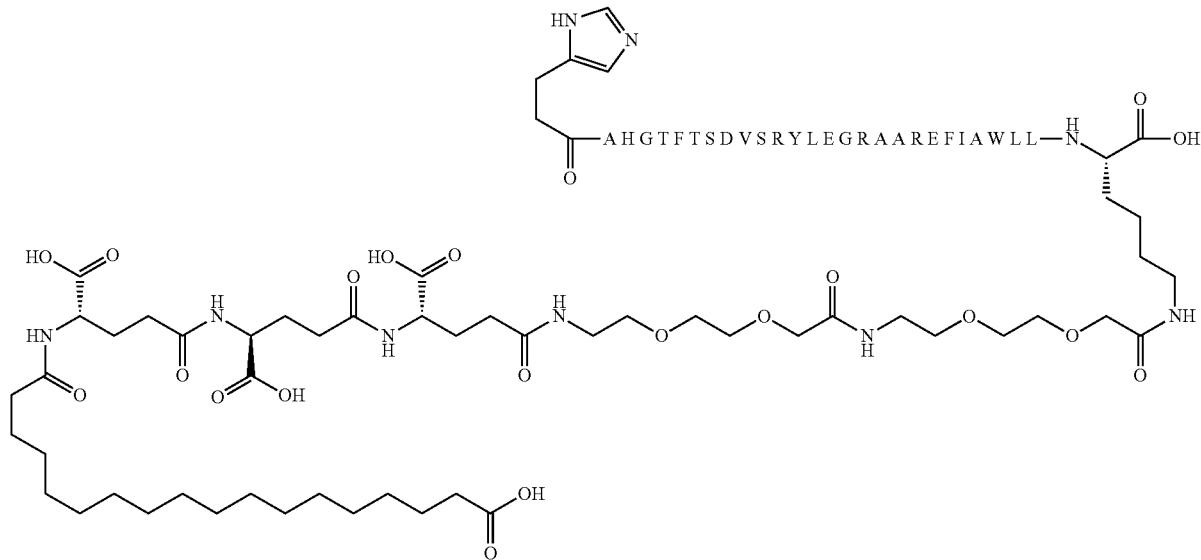

UPLC02: Rt=9.5 min
LCMS01: Rt=2.9 min; Calc m/1=4192. Found m/1=4192. Found m/3=1398. Found m/4=1049.

Example 18

N^ε27-[2-[2-[2-[[2-[2-[2-[[(4S)-4-carboxy-4-[[(4S)-4-carboxy-4-[[(4S)-4-carboxy-4-(17-carboxyheptadecanoylamino)butanoyl]amino]butanoyl]amino]butanoyl]amino]ethoxy]ethoxy]acetyl]amino]ethoxy]ethoxy]acetyl]-[Imp7,His9,Arg18,Glu22,Arg26,Lys27,Leu33,Arg34]-GLP-1-(7-34)-peptide (SEQ ID NO: 17)

(Chem. 18)

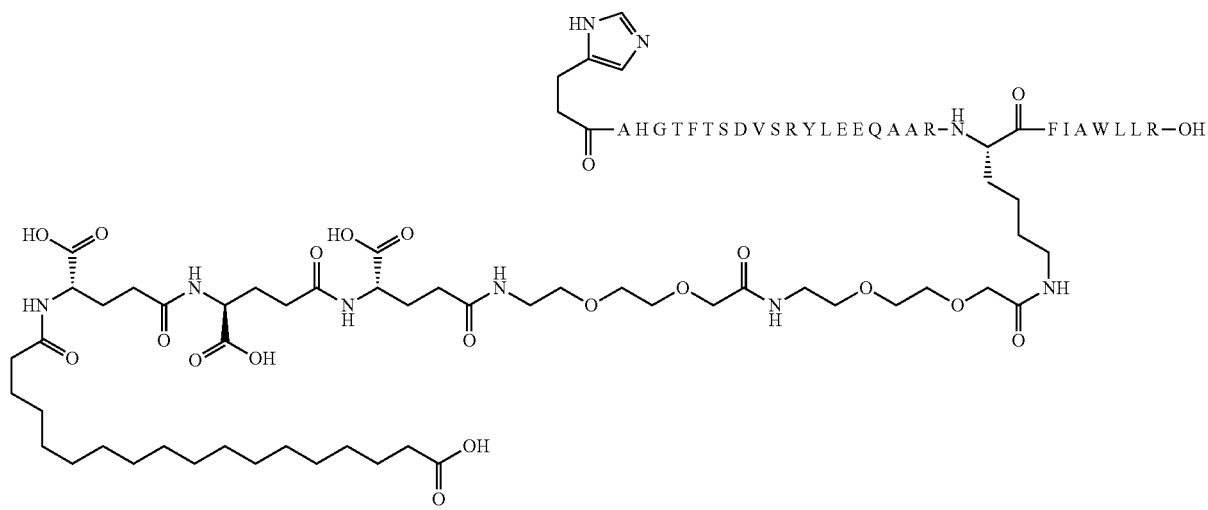

UPLC02: Rt=8.7 min
LCMS01: Rt=2.1 min; Calc m/1=4263. Found m/3=1422. Found m/4=1067. Found m/5=853.

Example 19

N^ε27-[2-[2-[2-[[2-[2-[2-[[(4S)-4-carboxy-4-[[(4S)-4-carboxy-4-[[(4S)-4-carboxy-4-(17-carboxyheptadecanoylamino)butanoyl]amino]butanoyl]amino]butanoyl]amino]ethoxy]ethoxy]acetyl]amino]ethoxy]ethoxy]acetyl]-[Imp7,Aib8,His9,Arg18,Glu22,Arg26,Lys27,Leu33,Arg34]-GLP-1-(7-34)-peptide (SEQ ID NO: 41)

(Chem. 19)

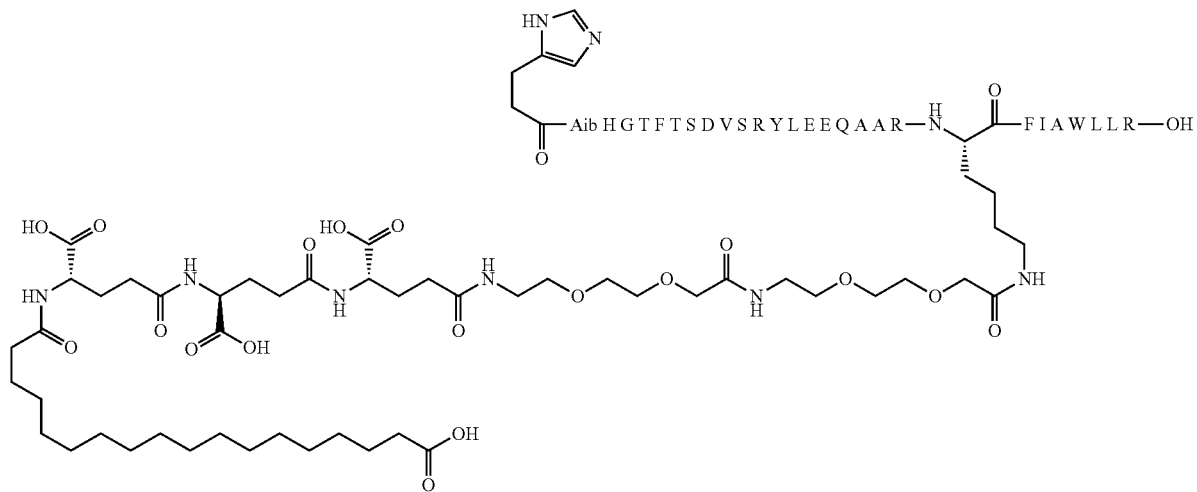

UPLC02: Rt=8.7 min
LCMS01: Rt=2.2 min; Calc m/1=4277. Found m/3=1426. Found m/4=1070. Found m/5=856.

Example 20

N$^{\varepsilon34}$-[2-[[(2S)-2-[[(2S)-4-carboxy-2-[[2-[[(2S)-2-[[(4S)-4-carboxy-4-[[(4S)-4-carboxy-4-(17-carboxy-heptadecanoylamino)butanoyl]amino]butanoyl]amino]-3-hydroxypropanoyl]amino]acetyl]amino]butanoyl]amino]-3-hydroxypropanoyl]amino]acetyl]-[Imp7,Acb8,His9,Lys18,Arg23,Arg26,Leu33,Thr35]-GLP-1-(7-35)-peptide amide (SEQ ID NO: 19)

(Chem. 20)

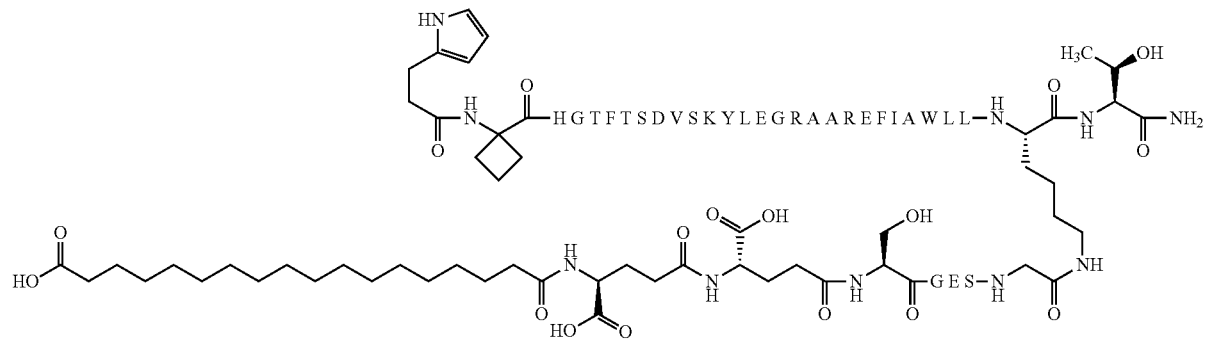

UPLC02: Rt=8.6 min
LCMS01: Rt=2.2 min; Calc m/1=4287.88. Found m/1=4290. Found m/3=1430. Found m/4=1073. Found m/5=858.

Example 21

N$^{\varepsilon35}$-[(4S)-4-carboxy-4-[[2-[2-[2-[[(4S)-4-carboxy-4-[[2-[2-[2-[[(4S)-4-carboxy-4-[[2-[2-[2-[[(4S)-4-carboxy-4-[[(4S)-4-carboxy-4-(17-carboxyheptadecanoylamino)butanoyl]amino]butanoyl]amino]ethoxy]ethoxy]acetyl]amino]butanoyl]amino]ethoxy]ethoxy]acetyl]amino]butanoyl]amino]ethoxy]ethoxy]acetyl]amino]butanoyl]-[Imp7,Acb8,His9,Tyr16,Lys18,Glu22,Arg26,Leu33,Lys35]-GLP-1-(7-35)-peptide amide (SEQ ID NO: 3)

(Chem. 21)

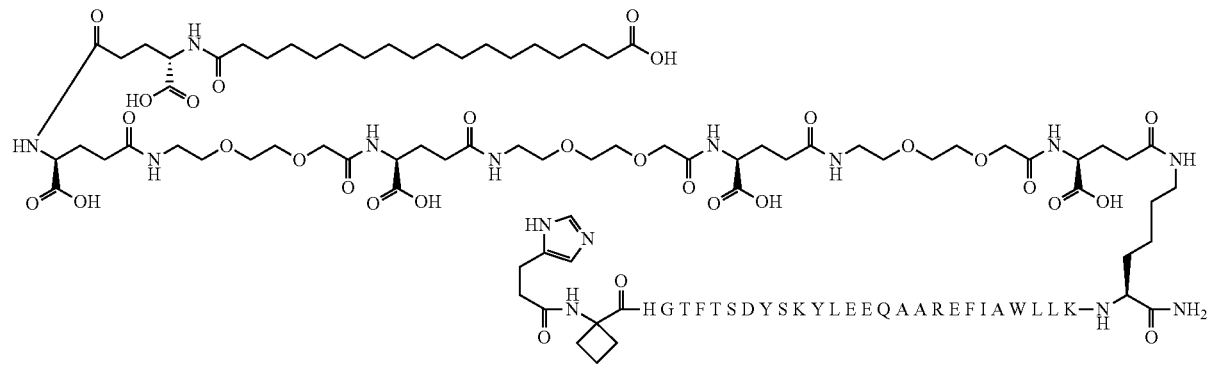

UPLC02: Rt=8.5 min
LCMS01: Rt=2.2 min; Calc m/1=4829. Found m/3=1610. Found m/4=1208. Found m/5=966.

Example 22

N^ε35-[(4S)-4-carboxy-4-[[2-[2-[2-[[(4S)-4-carboxy-4-[[2-[2-[2-[[(4S)-4-carboxy-4-[[2-[2-[2-[[(4S)-4-carboxy-4-[[(4S)-4-carboxy-4-(17-carboxyheptadecanoylamino)butanoyl]amino]butanoyl]amino]ethoxy]ethoxy]acetyl]amino]butanoyl]amino]ethoxy]ethoxy]acetyl]amino]butanoyl]amino]ethoxy]ethoxy]acetyl]amino]butanoyl]-[Imp7,Acb8,His9,Tyr16,Arg18,Glu22,Arg26,Leu33,Arg34,Lys35]-GLP-1-(7-35)-peptide amide (SEQ ID NO: 20)

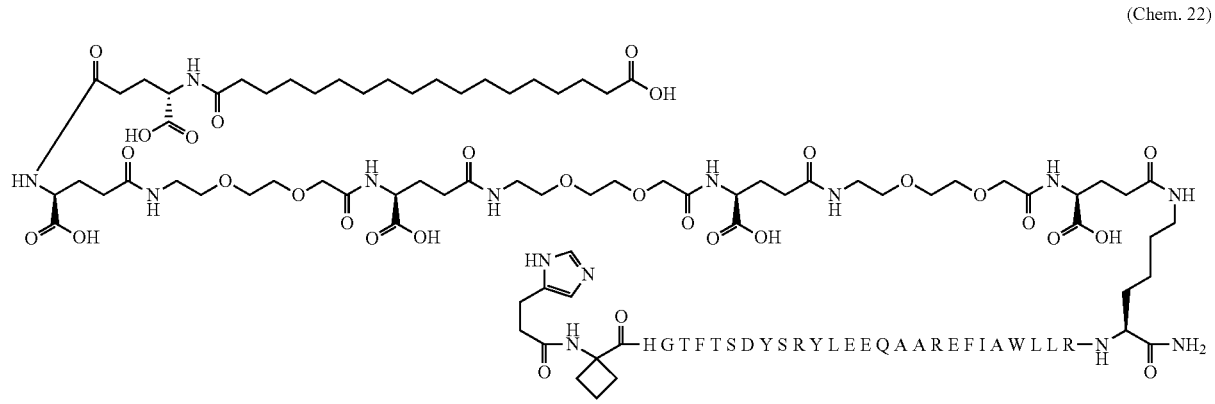

(Chem. 22)

UPLC02: Rt=8.5 min
LCMS01: Rt=2.3 min; Calc m/1=4884. Found m/4=1222. Found m/5=978. Found m/z=4885.

Example 23

N^ε35-[(4S)-4-carboxy-4-[[2-[2-[2-[[(4S)-4-carboxy-4-[[2-[2-[2-[[(4S)-4-carboxy-4-[[2-[2-[2-[[(4S)-4-carboxy-4-[[(4S)-4-carboxy-4-(17-carboxyheptadecanoylamino)butanoyl]amino]butanoyl]amino]ethoxy]ethoxy]acetyl]amino]butanoyl]amino]ethoxy]ethoxy]acetyl]amino]butanoyl]amino]ethoxy]ethoxy]acetyl]amino]butanoyl]-[Imp7,Acb8,His9,Tyr16,Lys18,Arg22,Arg26,Leu33,Lys35]-GLP-1-(7-35)-peptide amide (SEQ ID NO: 21)

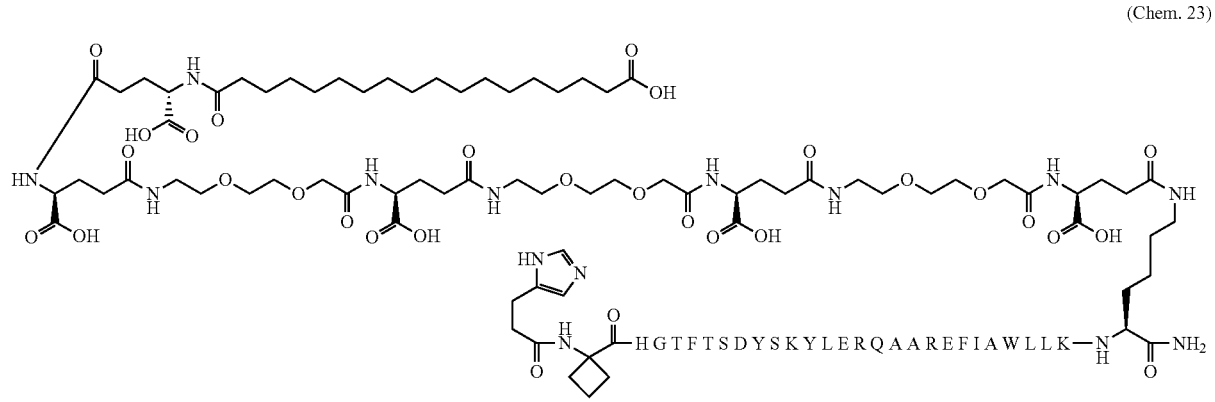

(Chem. 23)

LCMS01: Rt=2.1 min; Calc m/1=4855. Found m/4=1215. Found m/5=972. Found m/z=4856.

Example 24

N^ε35-[(4S)-4-carboxy-4-[[2-[2-[2-[[(4S)-4-carboxy-4-[[2-[2-[2-[[(4S)-4-carboxy-4-[[2-[2-[2-[[(4S)-4-carboxy-4-[[(4S)-4-carboxy-4-(17-carboxyheptadecanoylamino)butanoyl]amino]butanoyl]amino]ethoxy]ethoxy]acetyl]amino]butanoyl]amino]ethoxy]ethoxy]acetyl]amino]butanoyl]amino]ethoxy]ethoxy]acetyl]amino]butanoyl]-[Imp7,Acb8,His9,Tyr16,Lys18,Arg22,Arg23,Arg26, Leu33, Lys35]-GLP-1-(7-35)-peptide amide (SEQ ID NO: 22)

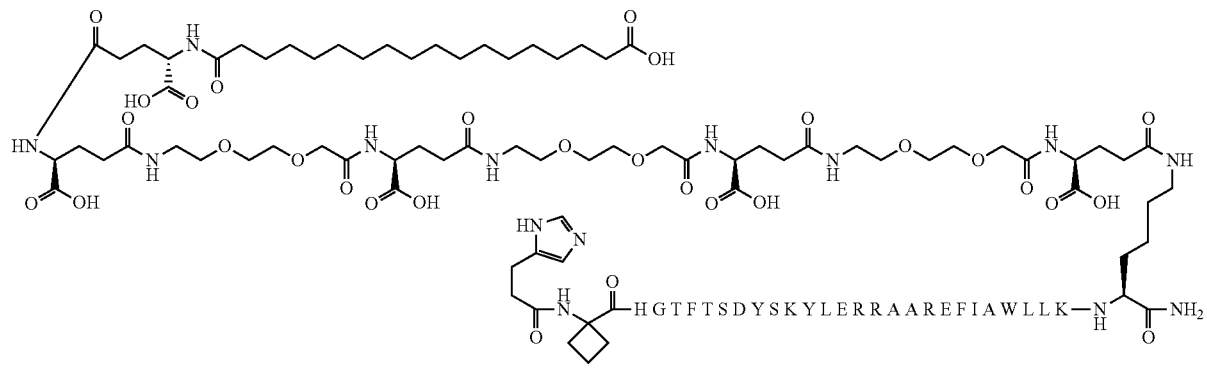

(Chem. 24)

UPLC02: Rt=8.0 min
LCMS01: Rt=2.1 min; Calc m/1=4884. Found m/3=1629. Found m/4=1222. Found m/5=978.

Example 25

N^ε34-[2-[[(2S)-2-[[(2S)-4-carboxy-2-[[2-[[(2S)-2-[[(4S)-4-carboxy-4-[[(4S)-4-carboxy-4-(17-carboxyheptadecanoylamino)butanoyl]amino]butanoyl]amino]-3-hydroxypropanoyl]amino]acetyl]amino]butanoyl]amino]-3-hydroxypropanoyl]amino]acetyl]-[Imp7,Aib8,His9,Lys18,Glu22,Arg26,Leu33,Thr35]-GLP-1-(7-35)-peptide (SEQ ID NO: 5)

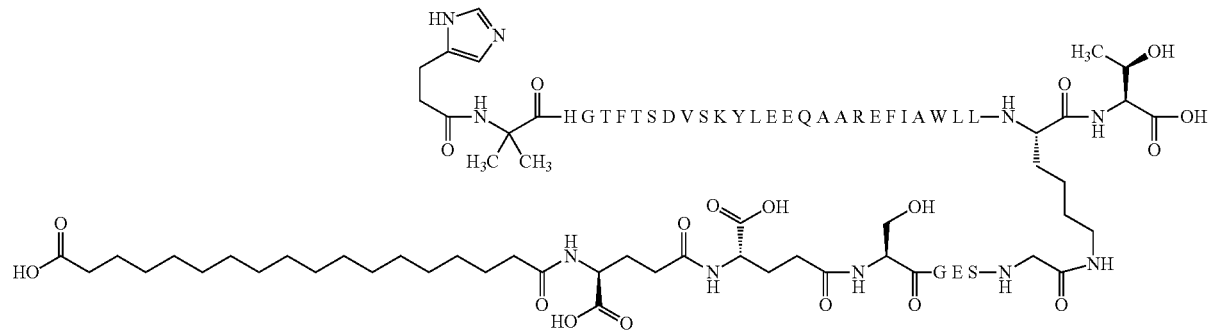

(Chem. 25)

UPLC02: Rt=9.0 min
LCMS01: Rt=2.2 min; Calc m/1=4321. Found m/3=1441. Found m/4=1081. Found m/5=865.

Example 26

N^ε35-[(4S)-4-carboxy-4-[[2-[2-[2-[[(4S)-4-carboxy-4-[[2-[2-[2-[[(4S)-4-carboxy-4-[[2-[2-[2-[[(4S)-4-carboxy-4-[[(4S)-4-carboxy-4-(17-carboxyheptade-canoylamino)butanoyl]amino]butanoyl]amino]ethoxy]ethoxy]acetyl]amino]butanoyl]amino]ethoxy]ethoxy]acetyl]amino]butanoyl]amino]ethoxy]ethoxy]acetyl]amino]butanoyl]-[Imp7,Acb8,His9,Tyr16,Lys18,Arg23,Arg26,Leu33,Lys35]-GLP-1-(7-35)-peptide amide (SEQ ID NO: 42)

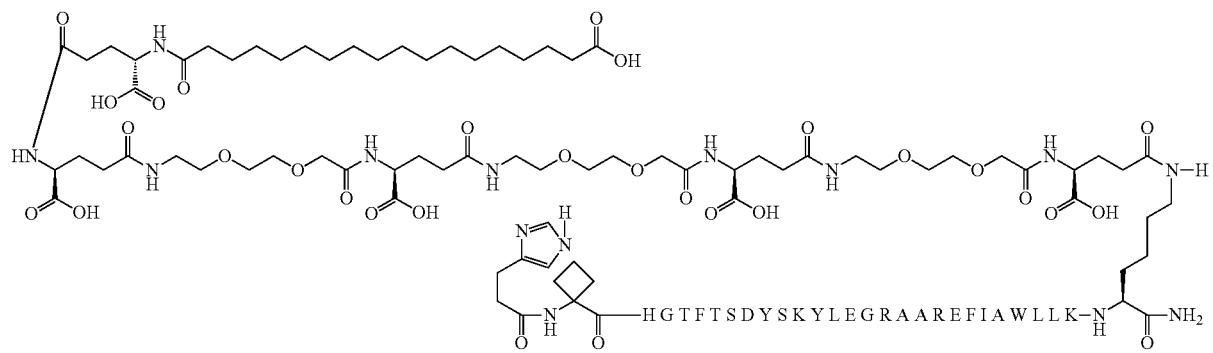

(Chem. 26)

UPLC02: Rt=8.1 min
LCMS01: Rt=2.2 min; Calc m/1=4784. Found m/3=1596. Found m/4=1197. Found m/5=958. Found m/z=4785.

Example 27

N^ε34-[(4S)-4-carboxy-4-[[(4S)-4-carboxy-4-[[(2S)-2-[[2-[[(2S)-4-carboxy-2-[[(2S)-2-[[2-(17-carboxyhep-tadecanoylamino)acetyl]amino]-3-hydroxypro-panoyl]amino]butanoyl]amino]acetyl]amino]-3-hydroxypropanoyl]amino]butanoyl]amino]butanoyl]-[Imp7,Aib8,His9,Lys18,Glu22,Arg26,Leu33,Thr35]-GLP-1-(7-35)-peptide (SEQ ID NO: 5)

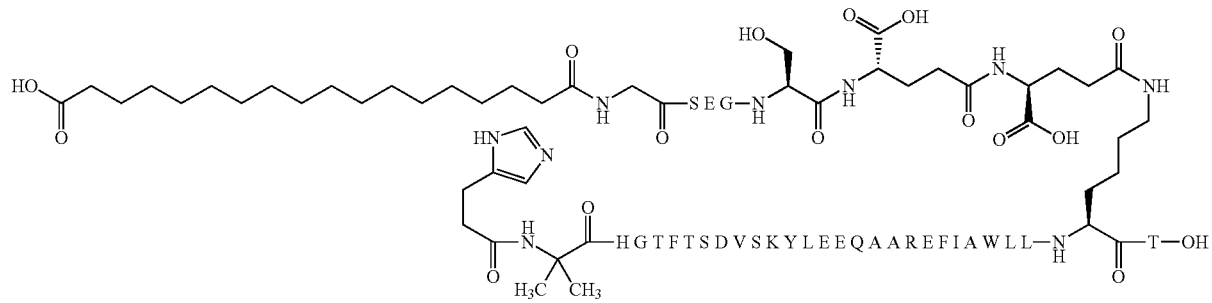

(Chem. 27)

UPLC02: Rt=9.06 min
LCMS01: Rt=2.3 min; Calc m/1=4321. Found m/3=1441. Found m/4=1081. Found m/5=865.

Example 28

N^ε35-[(4S)-4-carboxy-4-[[2-[2-[2-[[(4S)-4-carboxy-4-[[2-[2-[2-[[(4S)-4-carboxy-4-[[2-[2-[2-[[(4S)-4-carboxy-4-[[(4S)-4-carboxy-4-(17-carboxyheptadecanoylamino)butanoyl]amino]butanoyl]amino]ethoxy]ethoxy]acetyl]amino]butanoyl]amino]ethoxy]ethoxy]acetyl]amino]butanoyl]amino]ethoxy]ethoxy]acetyl]amino]butanoyl]-[Imp7,Acb8,His9,Tyr16,Arg18,Arg23,Arg26,Leu33,Arg34,Lys35]-GLP-1-(7-35)-peptide amide (SEQ ID NO: 24)

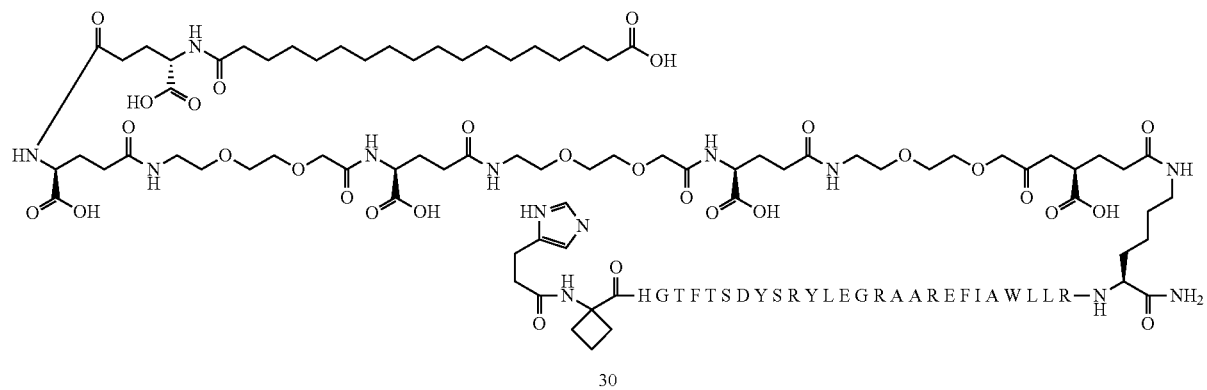

(Chem. 28)

UPLC02: Rt=8.3 min
LCMS01: Rt=2.3 min; Calc m/1=4840. Found m/4=1211. Found m/5=969.

Example 29

N^ε34-[2-[2-[2-[[2-[2-[2-[[(4S)-4-carboxy-4-[[(4S)-4-carboxy-4-[[(4S)-4-carboxy-4-(17-carboxyheptadecanoylamino)butanoyl]amino]butanoyl]amino]butanoyl]amino]ethoxy]ethoxy]acetyl]amino]ethoxy]ethoxy]acetyl]-[Imp7,Aib8,His9,Lys18,Glu22,Arg26,Leu33,Thr35]-GLP-1-(7-35)-peptide (SEQ ID NO: 5)

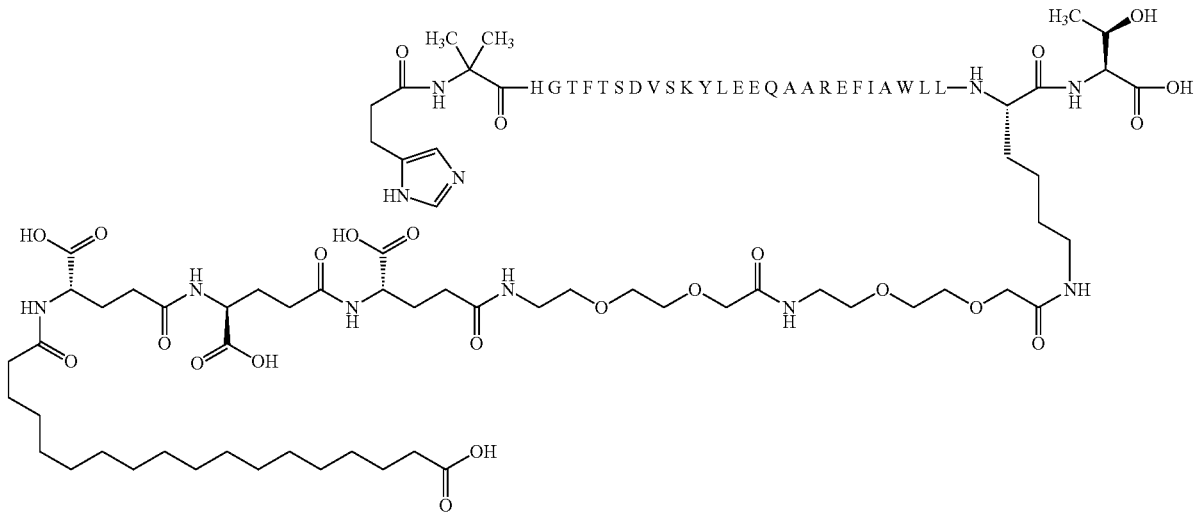

(Chem. 29)

UPLC02: Rt=9.05 min
LCMS01: Rt=2.2 min; Calc m/1=4323. Found m/3=1442. Found m/4=1082. Found m/5=866.

Example 30

N^(ε34)-[2-[[(2S)-2-[[(2S)-4-carboxy-2-[[2-[[(2S)-2-[[(4S)-4-carboxy-4-[[(4S)-4-carboxy-4-(19-carboxynonadecanoylamino)butanoyl]amino]butanoyl]amino]-3-hydroxypropanoyl]amino]acetyl]amino]butanoyl]amino]-3-hydroxypropanoyl]amino]acetyl]-[Imp7,Aib8,His9,Lys18,Glu22,Arg26,Leu33,Thr35]-GLP-1-(7-35)-peptide amide (SEQ ID NO: 5)

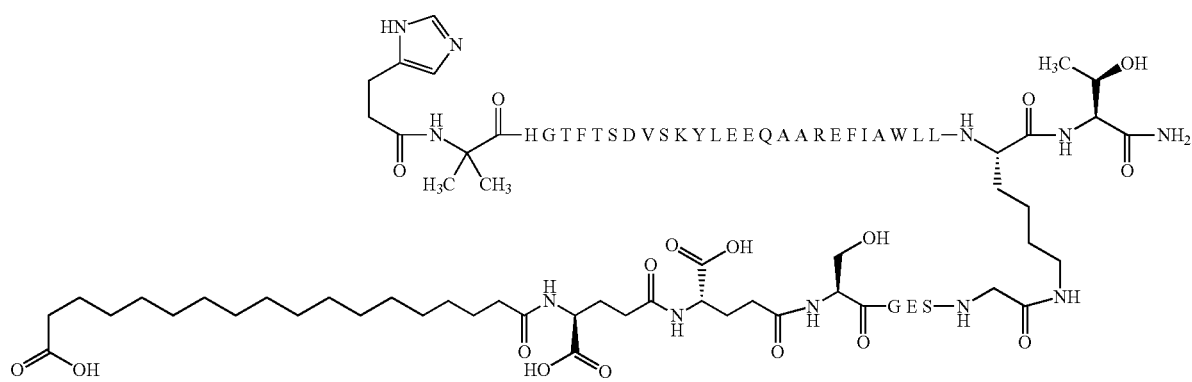

(Chem. 30)

UPLC02: Rt=9.3 min
LCMS01: Rt=3.0 min; Calc m/1=4348. Found m/1=4348. Found m/3=1450. Found m/4=1088.

Example 31

N^(ε34)-[(4S)-4-carboxy-4-[[2-[2-[2-[[2-[2-[2-[[(4S)-4-carboxy-4-[[(4S)-4-carboxy-4-(17-carboxyheptadecanoylamino)butanoyl]amino]butanoyl]amino]ethoxy]ethoxy]acetyl]amino]ethoxy]ethoxy]acetyl]amino]butanoyl]-[Imp7,Aib8,His9,Lys18,Ala22,Arg23,Arg26,Leu33,Gly36]-GLP-1-(7-37)-peptide (SEQ ID NO: 25)

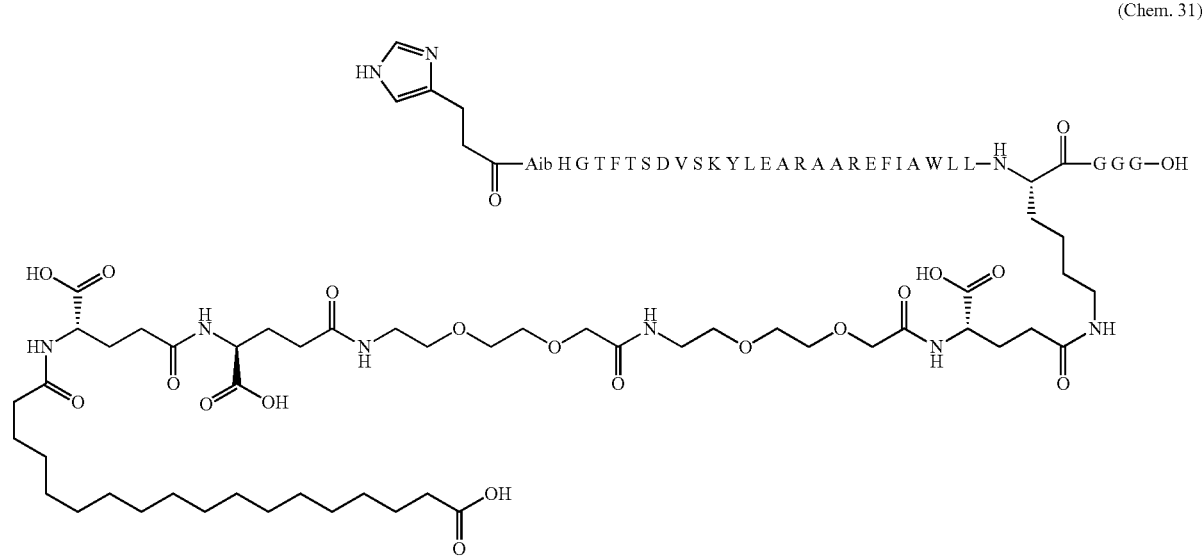

(Chem. 31)

UPLC02: Rt=8.4 min
LCMS13: Rt=2.3 min; Calc m/1=4363. Found m/3=1455. Found m/4=1091.
Example 32
N$^{\varepsilon 22}$-[(4S)-4-carboxy-4-[[(4S)-4-carboxy-4-[[2-[2-[2-[[2-[2-[2-[[(4S)-4-carboxy-4-(17-carboxyheptadecanoylamino)butanoyl]amino]ethoxy]ethoxy]acetyl]amino]ethoxy]ethoxy]acetyl]amino]butanoyl]amino]butanoyl]-[Imp7,Acb8,His9,Lys18,Lys22,Arg23,Arg26,Leu33,Thr35]-GLP-1-(7-35)-peptide amide (SEQ ID NO: 26)
(Chem. 32)
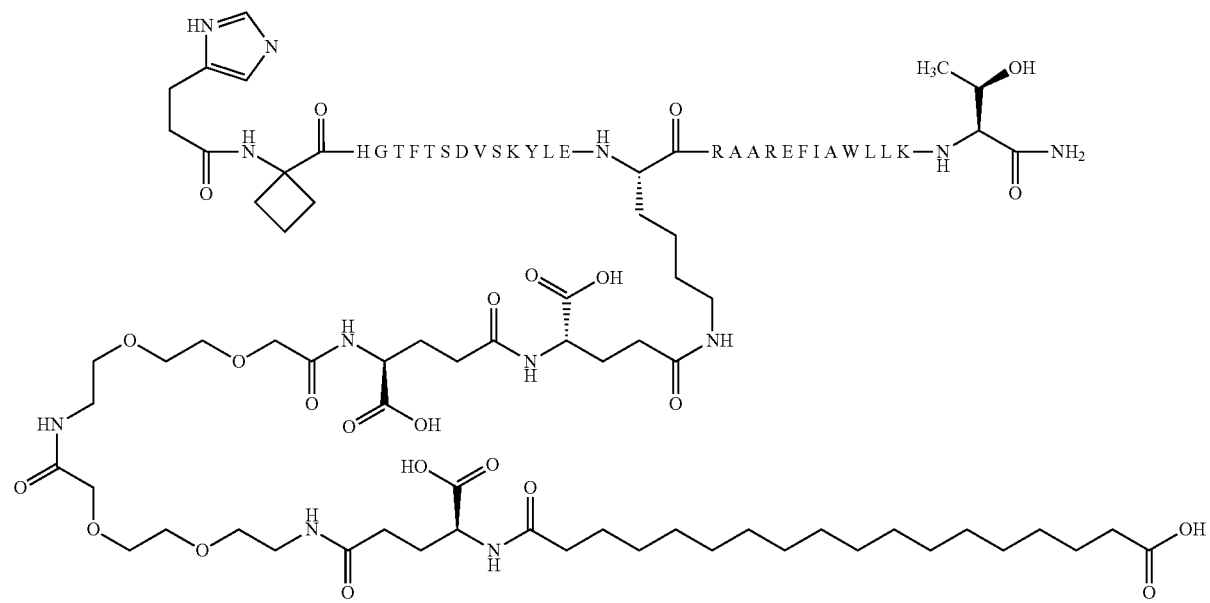
UPLC02: Rt=8.6 min
LCMS13: Rt=2.1 min; Calc m/1=4361. Found m/4=1091. Found m/5=873.

Example 33

$N^{\varepsilon 22}$-[(4S)-4-carboxy-4-[[(4S)-4-carboxy-4-[[2-[2-[2-[[2-[2-[2-[[(4S)-4-carboxy-4-(17-carboxyheptade-canoylamino)butanoyl]amino]ethoxy]ethoxy]acetyl]amino]ethoxy]ethoxy]acetyl]amino]butanoyl]amino]butanoyl]-[Imp7,Acb8,His9,Lys18,Lys22,Arg26,Leu33,Thr35]-GLP-1-(7-35)-peptide amide (SEQ ID NO: 27)

(Chem. 33)

UPLC02: Rt=8.3 min

LCMS13: Rt=2.2 min; Calc m/1=4333. Found m/3=1445. Found m/4=1084. Found m/5=867.

Example 34
N$^{\varepsilon 34}$-[(4S)-4-carboxy-4-[[(4S)-4-carboxy-4-[[2-[2-[2-[[(4S)-4-carboxy-4-[[(4S)-4-carboxy-4-(17-carboxyheptadecanoylamino)butanoyl]amino]butanoyl]amino]ethoxy]ethoxy]acetyl]amino]butanoyl]amino]butanoyl]-[Imp7,Aib8,His9,Lys18,Ala22,Arg26,Leu33,Thr35]-GLP-1-(7-35)-peptide amide (SEQ ID NO: 28)
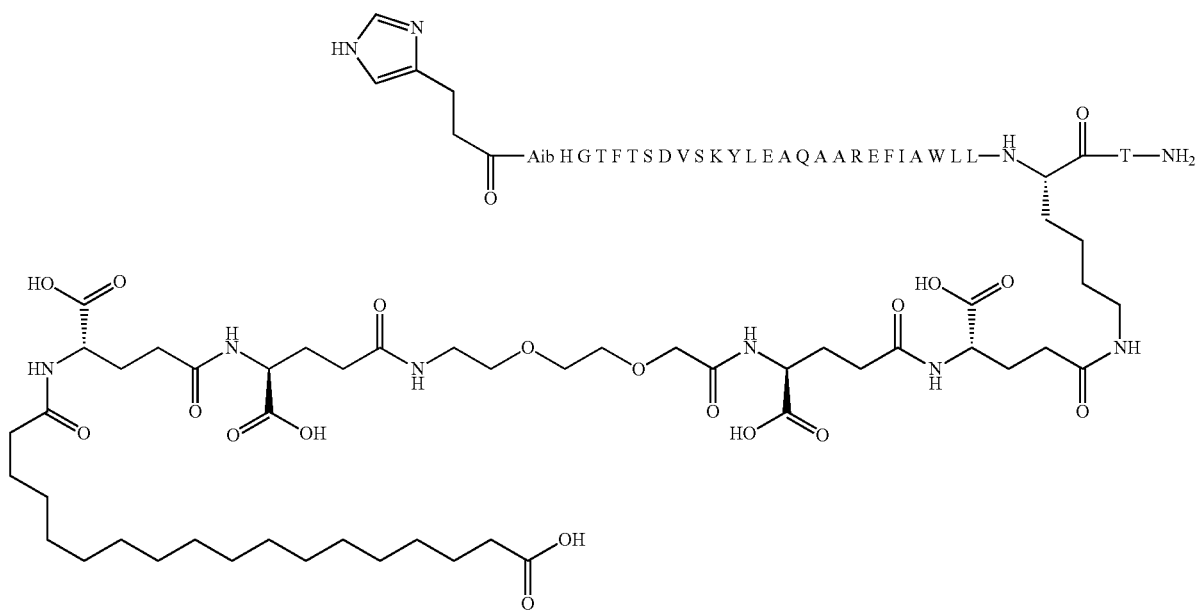
(Chem. 34)
UPLC02: Rt=8.9 min
LCMS13: Rt: =2.4 min; Calc m/1=4248. Found m/3=1417.

Example 35
$N^{\epsilon 34}$-[(4S)-4-carboxy-4-[[(4S)-4-carboxy-4-[[2-[2-[2-[[(4S)-4-carboxy-4-[[(4S)-4-carboxy-4-(17-carboxyheptadecanoylamino)butanoyl]amino]butanoyl]amino]ethoxy]ethoxy]acetyl]amino]butanoyl]amino]butanoyl]-[Imp7,Aib8,His9,Arg18,Arg23,Arg26,Leu33,Ala36]-GLP-1-(7-37)-peptide (SEQ ID NO: 29)
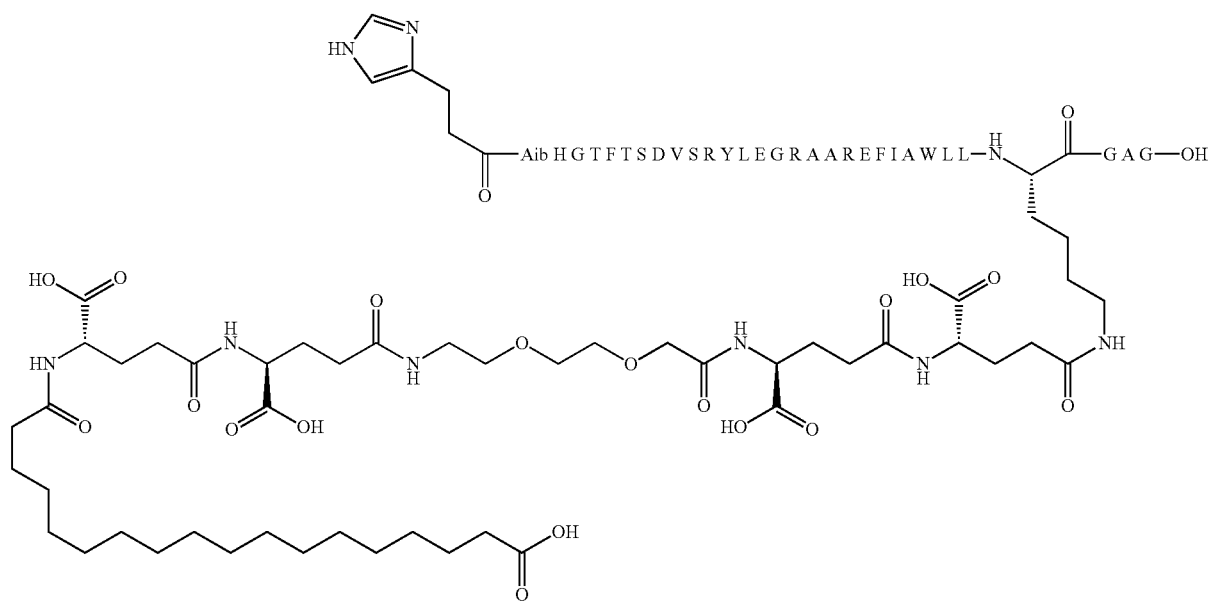
(Chem. 35)
UPLC02: Rt=9.8 min
LCMS13: Rt=2.3 min; Calc m/1=4375. Found m/3=1459. Found m/4=1095.

Example 36

N^ε34-[(4S)-4-carboxy-4-[[(4S)-4-carboxy-4-[[2-[2-[2-[[(4S)-4-carboxy-4-[[(4S)-4-carboxy-4-(17-carboxyheptadecanoylamino)butanoyl]amino]butanoyl]amino]ethoxy]ethoxy]acetyl]amino]butanoyl]amino]butanoyl]-[Imp7,Aib8,His9,Arg18,Arg23,Arg26,Leu33,Ser36]-GLP-1-(7-37)-peptide (SEQ ID NO: 30)

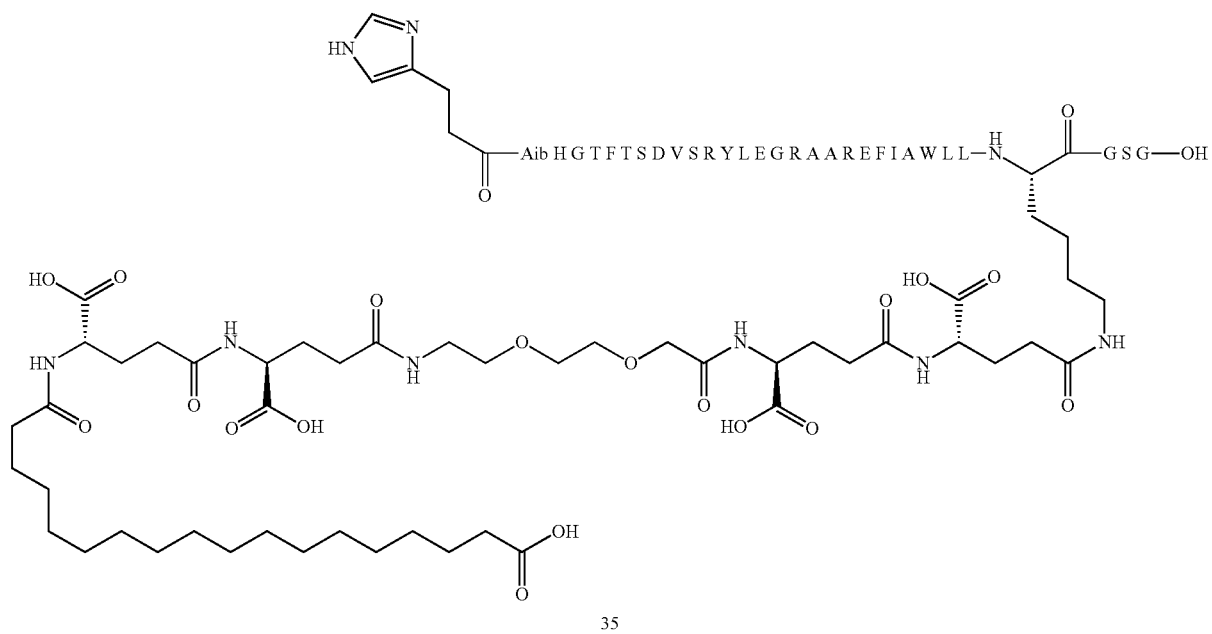

(Chem. 36)

UPLC02: Rt=9.7 min
LCMS13: Rt=2.3 min; Calc m/1=4391. Found m/3=1465. Found m/4=1099.

Example 37

N^ε34-[2-[[(2S)-2-[[(2S)-4-carboxy-2-[[2-[[(2S)-2-[[(4S)-4-carboxy-4-[[(4S)-4-carboxy-4-(17-carboxyheptadecanoylamino)butanoyl]amino]butanoyl]amino]-3-hydroxypropanoyl]amino]acetyl]amino]butanoyl]amino]-3-hydroxypropanoyl]amino]acetyl]-[Imp7,Gly8,His9,Arg18,Glu22,Arg26,Leu33,Thr35]-GLP-1-(7-35)-peptide amide (SEQ ID NO: 31)

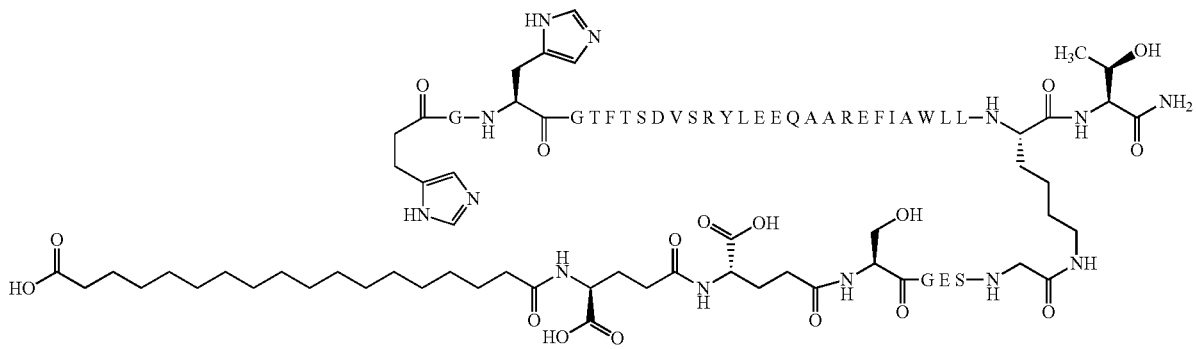

(Chem. 37)

UPLC02: Rt=9.0 min
LCMS01: Rt=2.2 min; Calc m/1=4320. Found m/3=1441. Found m/4=1081. Found m/5=865.

Example 38

N$^{\varepsilon 34}$-[2-[2-[2-[[2-[2-[2-[[(4S)-4-carboxy-4-[[(4S)-4-carboxy-4-(13-carboxytridecanoylamino)butanoyl]amino]butanoyl]amino]ethoxy]ethoxy]acetyl]amino]ethoxy]ethoxy]acetyl]-[Imp7,Aib8,His9,Lys18,Glu22,Arg26,Leu33,Thr35]-GLP-1-(7-35)-peptide amide (SEQ ID NO: 5)

(Chem. 38)

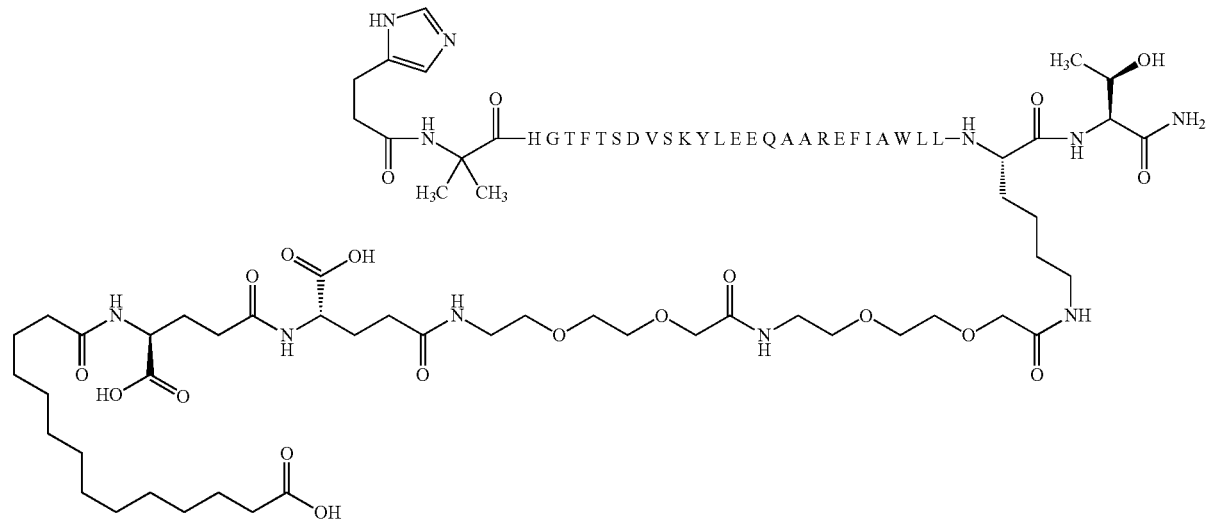

UPLC02: Rt=8.7 min
LCMS01: Rt=2.1 min; Calc m/1=4137. Found m/3=1380. Found m/4=1035. Found m/5=828.

Example 39

N$^{\varepsilon 34}$-[2-[2-[2-[[2-[2-[2-[[(4S)-4-carboxy-4-[[(4S)-4-carboxy-4-(15-carboxypentadecanoylamino)butanoyl]amino]butanoyl]amino]ethoxy]ethoxy]acetyl]amino]ethoxy]ethoxy]acetyl]-[Imp7,Aib8,His9,Lys18,Glu22,Arg26,Leu33,Thr35]-GLP-1-(7-35)-peptide amide (SEQ ID NO: 5)

(Chem. 39)

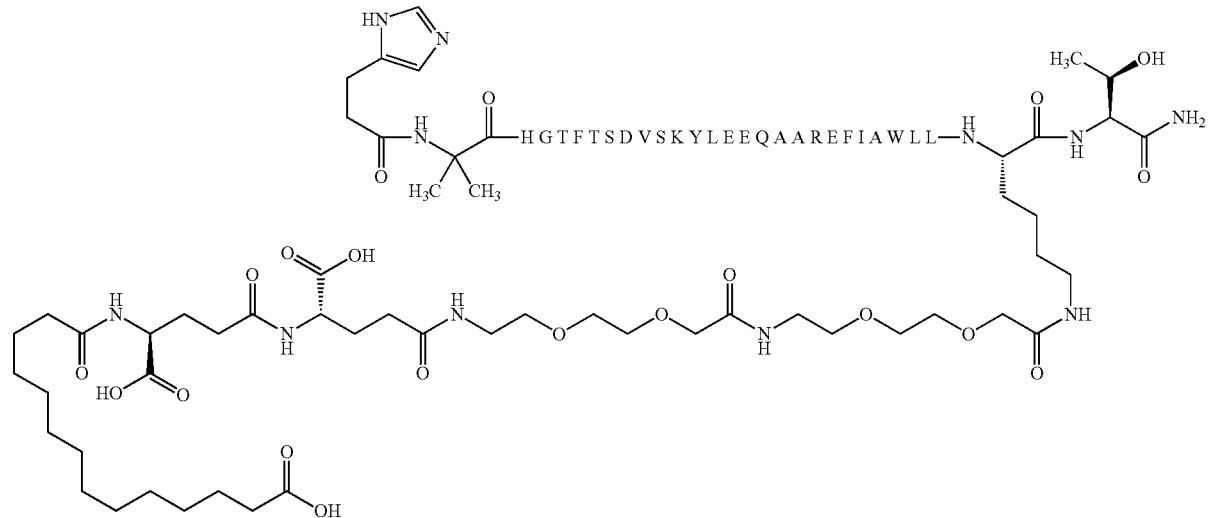

UPLC02: Rt=9.8 min
LCMS01: Rt=2.2 min; Calc m/1=4165. Found m/3=1389. Found m/4=1042. Found m/5 834.

Example 40

N$^{\epsilon34}$-[2-[2-[2-[[2-[2-[2-[[(4S)-4-carboxy-4-[[(4S)-4-carboxy-4-(19-carboxynonadecanoylamino)butanoyl]amino]butanoyl]amino]ethoxy]ethoxy]acetyl]amino]ethoxy]ethoxy]acetyl]-[Imp7,Aib8,His9,Lys18,Glu22,Arg26,Leu33,Thr35]-GLP-1-(7-35)-peptide amide (SEQ ID NO: 5)

(Chem. 40)

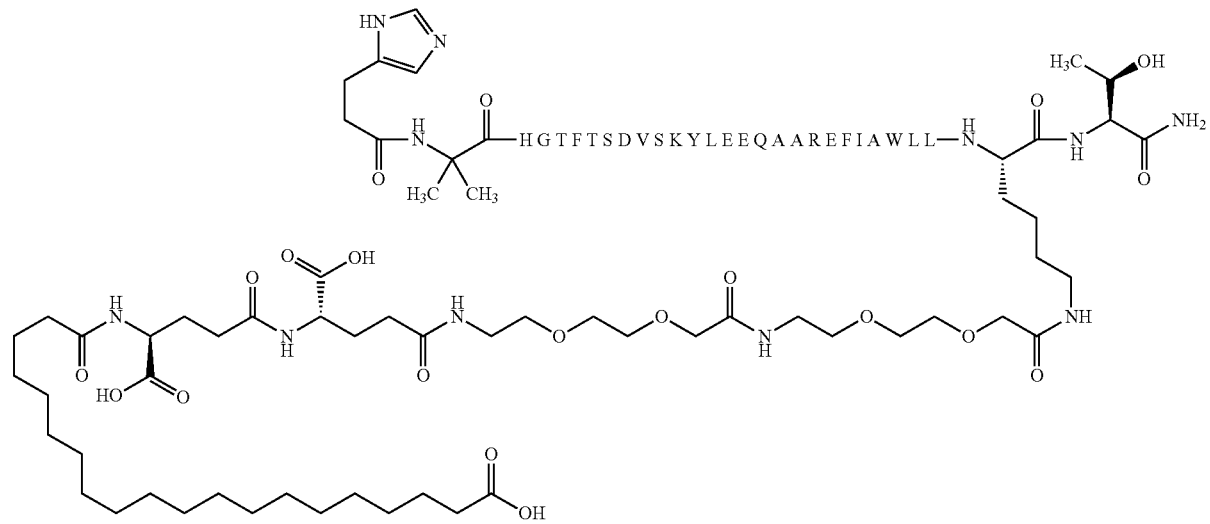

UPLC02: Rt=9.0 min
LCMS01: Rt=2.4 min; Calc m/1=4221. Found m/3=1408. Found m/4=1056. Found m/5=845.

Example 41

N$^{\epsilon34}$-[2-[2-[2-[[2-[2-[2-[[(4S)-4-carboxy-4-[[(4S)-4-carboxy-4-(17-carboxyheptadecanoylamino)butanoyl]amino]butanoyl]amino]ethoxy]ethoxy]acetyl]amino]ethoxy]ethoxy]acetyl]-[Imp7,Aib8,His9,Leu16,Lys18,Glu22,Arg26,Leu33,Thr35]-GLP-1-(7-35)-peptide amide (SEQ ID NO: 32)

(Chem. 41)

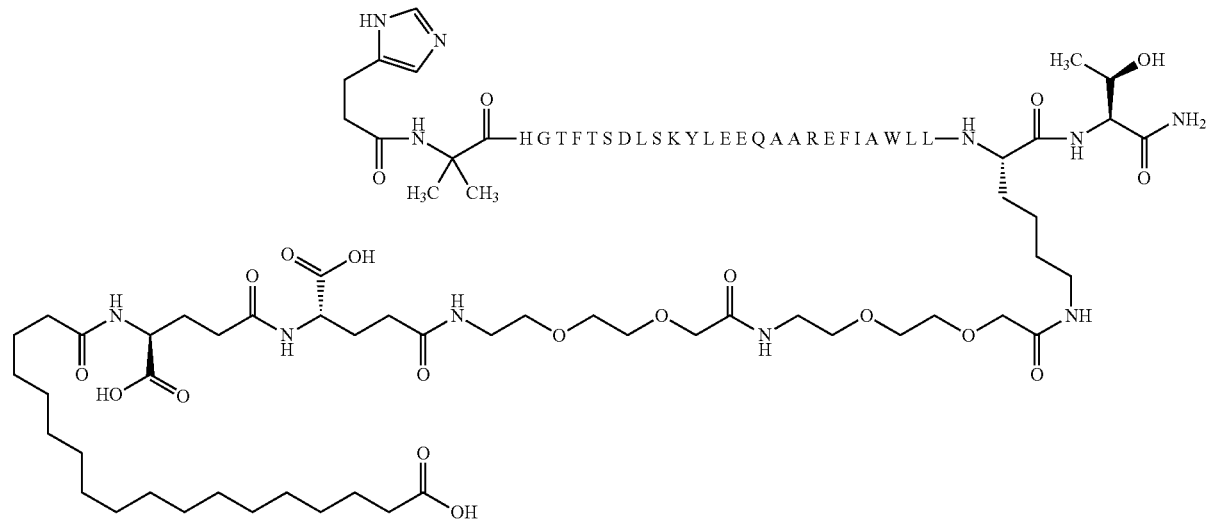

UPLC02: Rt=10.1 min
LCMS01: Rt=2.5 min; Calc m/1=4207. Found m/3=1403. Found m/4=1053. Found m/5=842.

Example 42

N$^{\epsilon 34}$-[2-[2-[2-[[2-[2-[2-[[(4S)-4-carboxy-4-[[(4S)-4-carboxy-4-(17-carboxyheptadecanoylamino)butanoyl]amino]butanoyl]amino]ethoxy]ethoxy]acetyl]amino]ethoxy]ethoxy]acetyl]-[Imp7,Aib8, His9, Lys18,Glu22,Arg26,Ile33,Thr35]-GLP-1-(7-35)-peptide amide (SEQ ID NO: 43)

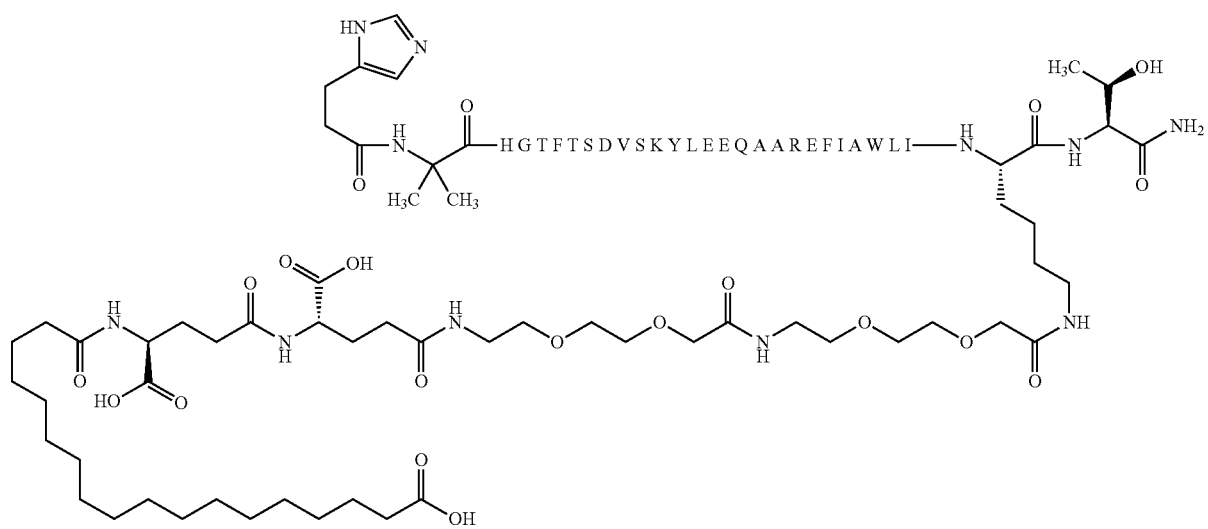

(Chem. 42)

UPLC02: Rt=9.9 min
LCMS01: Rt=2.5 min; Calc m/1=4193. Found m/3=1398. Found m/4=1049. Found m/5=839.

Assay (I): GLP-1 and Glucagon Receptor Potency

The purpose of this example was to test the activity or potency, of the GLP-1 derivatives of the invention, in vitro. The in vitro potency is the measure of human GLP-1 receptor (GLP-1R) or glucagon receptor (glucagonR) activation, respectively, in a whole cell assay.

Principle

In vitro potency was determined by measuring the cellular response of human GLP-1 or glucagon receptor activation, respectively, in a reporter gene assay. The assay was performed in a BHK cell line that stably expresses either the human GLP-1 receptor or the human glucagon receptor and comprises the DNA for the cAMP response element (CRE) coupled to a promoter and the gene for firefly luciferase (CRE luciferase). When the human GLP-1 or glucagon receptor, respectively, was activated it resulted in the production of cAMP, which in turn resulted in the luciferase protein being expressed. When assay incubation was completed, the luciferase substrate (luciferin) was added and the enzyme converted luciferin to oxyluciferin and produces bioluminescence. The luminescence was measured as the readout for the assay.

(a) GLP-1 Receptor Activation

Cell Culture and Preparation

The cells used in this assay (clone FCW467-12A/KZ10-1) were BHK cells with BHKTS13 as a parent cell line. The cells were derived from a clone (FCW467-12A) that expresses the human GLP-1 receptor and were established by further transfection with CRE luciferase to obtain the current clone.

The cells were cultured at 5% CO2 in DMEM medium with 10% FBS, 1×GlutaMAX, 1 mg/ml G418, 240 nM MTX (methotrexate) and 1% pen/strep (penicillin/streptomycin). They were aliquoted and stored in liquid nitrogen. Before each assay, an aliquot was taken up and washed three times in PBS before being suspended at the desired concentration in assay medium. For 96-well plates the suspension was made to give a final concentration of 5×10EE3 cells/well.

Materials

The following chemicals were used in the assay: Pluronic F-68 (10%) (Gibco 2404), Ovalbumin (Sigma A5503), DMEM w/o phenol red (Gibco 11880-028), 1 M Hepes (Gibco 15630), Glutamax 100× (Gibco 35050) and steady-lite plus (PerkinElmer 6016757). Assay Medium consisted of DMEM w/o phenol red, 10 mM Hepes, 1×GlutaMAX, 2% Ovalbumin and 0.2% Pluronic F-68.

Procedure

Cell stocks were thawed in a 37° C. water bath. Cells were washed three times in PBS. The cells were counted and adjusted to 5×10EE3 cells/50 μl (1×10EE5 cells/ml) in Assay Medium. A 50 μl aliquot of cells was transferred to each well in the assay plate. Stocks of the test compounds and reference compounds were diluted to a concentration of 0.2 μM in Assay Medium. Compounds were diluted 10-fold to give the following concentrations: 2×10EE-6 M, 2×10EE-7 M, 2×10EE-8 M; 2×10EE-9 M, 2×10EE-10 M, 2×10EE-11 M, 2×10EE-12 M and 2×10EE-13 M. For each compound a blank assay medium control was also included.

A 50 µl aliquot of compound or blank was transferred from the dilution plate to the assay plate. Compounds were tested at the following final concentrations: 1×10EE-6 M, 1×10EE-7 M, 1×10EE-8 M; 1×10EE-9 M, 1×10EE-10 M, 1×10EE-11 M and 1×10EE-12 M and 1×10EE-13 M.

The assay plate was incubated for 3 h in a 5% CO2 incubator at 37° C. The assay plate was removed from the incubator and allowed to stand at room temperature for 15 min. A 100 µl aliquot of steadylite plus reagent was added to each well of the assay plate (reagent is light sensitive). Each assay plate was covered with aluminum foil to protect it from light and shaken for 30 min at room temperature. Each assay plate was read in a Perkin Elmer TopCount NXT instrument.

Calculations

The data from the TopCount instrument was transferred to GraphPad Prism software. The software performed a non-linear regression (log(agonist) vs response-Variable slope (four parameter)). EC50 values were calculated by the software and reported in pM.

(b) Glucagon Receptor Activation

Cell Culture and Preparation

The cells used in this assay (clone pLJ6'-4-25) were BHK cells with BHK570 as a parent cell line expressing the CRE luciferase gene (clone BHK/KZ10-20-48) and were established by further transfection with the human glucagon receptor (clone pLJ6' in pHZ-1 vector).

The cells were cultured at 5% CO2 in DMEM medium with 10% FBS, 1×GlutaMAX, 1 mg/ml G418, 240 nM MTX (methotrexate) and 1% pen/strep (penicillin/streptomycin). They were aliquoted and stored in liquid nitrogen. Before each assay, an aliquot was taken up and washed three times in PBS before being suspended at the desired concentration in assay medium. For 96-well plates the suspension was made to give a final concentration of 5×10EE3 cells/well.

Materials

The following chemicals were used in the assay: Pluronic F-68 (10%) (Gibco 2404), Ovalbumin (Sigma A5503), DMEM w/o phenol red (Gibco 11880-028), 1 M Hepes (Gibco 15630), Glutamax 100× (Gibco 35050) and steadylite plus (PerkinElmer 6016757). Assay Medium consisted of DMEM w/o phenol red, 10 mM Hepes, 1×GlutaMAX, 2% Ovalbumin and 0.2% Pluronic F-68.

Procedure

Cell stocks were thawed in a 37° C. water bath. Cells were washed three times in PBS. The cells were counted and adjusted to 5×10EE3 cells/50 µl (1×10EE5 cells/ml) in Assay Medium. A 50 µl aliquot of cells was transferred to each well in the assay plate.

Stocks of the test compounds and reference compounds were diluted to a concentration of 0.2 µM in Assay Medium. Compounds were diluted 10-fold to give the following concentrations: 2×10EE-6 M, 2×10EE-7 M, 2×10EE-8 M; 2×10EE-9 M, 2×10EE-10 M, 2×10EE-11 M, 2×10EE-12 M and 2×10EE-13 M. For each compound a blank assay medium control was also included.

A 50 µl aliquot of compound or blank was transferred from the dilution plate to the assay plate. Compounds were tested at the following final concentrations: 1×10EE-6 M, 1×10EE-7 M, 1×10EE-8 M; 1×10EE-9 M, 1×10EE-10 M, 1×10EE-11 M and 1×10EE-12 M and 1×10EE-13 M.

The assay plate was incubated for 3 h in a 5% CO2 incubator at 37° C. The assay plate was removed from the incubator and allowed to stand at room temperature for 15 min. A 100 µl aliquot of steadylite plus reagent was added to each well of the assay plate (reagent is light sensitive). Each assay plate was covered with aluminum foil to protect it from light and shaken for 30 min at room temperature. Each assay plate was read in a Perkin Elmer TopCount NXT instrument.

Calculations

The data from the TopCount instrument was transferred to GraphPad Prism software. The software performed a non-linear regression (log(agonist) vs response-Variable slope (four parameter)). EC50 values were calculated by the software and reported in pM.

Assay (II): GLP-1 and Glucagon Receptor Binding

The purpose of this assay is to test the in vitro receptor binding activity of the GLP-1 derivatives of the invention.

(a) GLP-1 Receptor Binding

The GLP-1 receptor (GLP-1R) binding is a measure of the affinity of a derivative for the human GLP-1 receptor.

Principle

The GLP-1 receptor binding of each derivatives were determined with competitive binding, displacing [$^{125}$I] GLP-1 bound to GLP-1 receptors expressed in cell membranes associated with wheat germ agglutinin (WGA) scintillation proximity assay (SPA) beads. Each derivative was added in a series of concentrations to isolated membranes comprising the human GLP-1 receptor and displacement of the labelled radioligand was monitored. The receptor binding was reported as the concentration at which half of the labelled ligand is displaced from the receptor, the $IC^{50}$ value.

Materials

The following chemicals were used in the assay: MEM w/o phenol red (Gibco 11880-028), Pen/strep (Invitrogen 15140-122), G418 (Invitrogen 10131-027), 1 M Hepes (Gibco 15630), EDTA (Invitrogen 15575-038), PBS (Invitrogen 14190-094), fetal calf serum (Invitrogen 16140-071), EGTA, MgCl2 (Merck 1.05832.1000), Tween 20 (Amresco 0850C335), SPA particles (wheat germ agglutinin (WGA) SPA beads, Perkin Elmer RPNQ0001), [125I]-GLP-1]-(7-36)NH2 (produced in-house), OptiPlate™-96 (Perkin Elmer).

Buffer 1 consisted of 20 mM Na-HEPES plus 10 mM EDTA and pH was adjusted to 7.4. Buffer 2 consisted of 20 mM Na-HEPES plus 0.1 mM EDTA and pH was adjusted to 7.4. Assay buffer consisted of 50 mM HEPES supplemented with 5 mM EGTA, 5 mM MgCl2, 0.005% Tween 20 and pH was adjusted to 7.4. A 0.02% albumin stock consisted of HSA dissolved at 0.02% (w/v) in assay buffer.

Cell Culture and Membrane Preparation

The cells used in this assay (clone FCW467-12A) were BHK cells with BHKTS13 as a parent cell line. The cells express the human GLP-1 receptor.

The cells were grown at 5% CO2 in DMEM, 10% fetal calf serum, 1% Pen/Strep (Penicillin/Streptomycin) and 1.0 mg/ml of the selection marker G418. To make a membrane preparation the cells were grown to approximately 80% confluence. The cells were washed twice in phosphate-buffered saline and harvested. The cells were pelleted using a brief centrifugation and the cell pellet was kept on ice. The cell pellet was homogenised with ULTRA-THURRAX dispersing instrument for 20-30 seconds in a suitable amount of buffer 1 (e.g., 10 ml). The homogenate was centrifuged for 15 minutes. The pellet was re-suspended (homogenised) in 10 ml buffer 2 and centrifuged. This step was repeated once more. The resulting pellet was re-suspended in buffer 2 and the protein concentration was determined. The membranes were aliquoted and stored at minus 80° C.

Procedure

1. For the receptor binding assay 50 µl of the assay buffer was added to each well of an assay plate.
2. Test compounds were serially diluted to give the following concentrations: 8×10EE-7 M, 8×10EE-8 M, 8×10EE-9 M, 8×10EE-10 M, 8×10EE-11 M, 8×10EE-12 M and 8×10EE-13 M. Twenty-five µl were added to appropriate wells in the assay plate.
3. Cell membrane aliquots were thawed and diluted to their working concentration. Fifty µl were added to each well in the assay plate.
4. WGA SPA beads were suspended in assay buffer at 20 mg/ml. The suspension was diluted to 10 mg/ml in assay buffer just prior to addition to the assay plate. Fifty µl were added to each well in the assay plate.
5. The incubation was started by adding 25 µl of 480 pM solution of [125I]-GLP-1]-(7-36)NH2 to each well of the assay plate. A 25 µl aliquot was reserved for measuring total counts/well.
6. The assay plate was incubated for 2 h at 30° C.
7. The assay plate was centrifuged for 10 min.
8. The assay plate was read in a Perkin Elmer TopCount NXT instrument.

Calculations

The data from the TopCount instrument were transferred to GraphPad Prism software. The software averaged the values for the replicates and performed a non-linear regression. IC50 values were calculated by the software and reported in nM.

(b) Glucagon Receptor Binding

The glucagon receptor (glucagonR) binding activity is a measure of affinity of a derivative for the human glucagon receptor.

Principle

The glucagon receptor binding of each derivative were determined with competitive binding, displacing [$^{125}$I]-glucagon bound to glucagon receptors expressed in cell membranes associated with wheat germ agglutinin (WGA) scintillation proximity assay (SPA) beads. Each derivative was added in a series of concentrations to isolated membranes comprising the human glucagon receptor and displacement of the labelled ligand was monitored. The receptor binding was reported as the concentration at which half of the labelled ligand is displaced from the receptor, the $IC^{50}$ value.

Materials

The following chemicals were used in the assay: DMEM w Glutamax (Gibco 61965-026), Pen/strep (Invitrogen 15140-122), G418 (Invitrogen 10131-027), Versene (Gibco 15040), 1 M Hepes (Gibco 15630), PBS (Invitrogen 14190-094), fetal calf serum (Invitrogen 16140-071), MgCl2 (Merck 1.05832.1000), EDTA (Invitrogen 15575-038), CaCl2 (Sigma, C5080), Tween 20 (Amresco 0850C335), ovalbumin (Sigma A5503), SPA particles (wheat germ agglutinin (WGA) SPA beads, Perkin Elmer RPNQ0001), [125I]-glucagon (produced in-house), OptiPlate™-96 (Packard 6005290).

HME buffer consisted of 25 mM HEPES, 2 mM MgCl2 and 1 mM EDTA, and pH was adjusted to 7.4. Assay buffer consisted of 50 mM HEPES supplemented with 5 mM MgCl2, 1 mM CaCl2, 0.02% Tween 20 and 0.1% Ovalbumin, and pH was adjusted to 7.4.

Cell Culture and Membrane Preparation

The cells used in this assay (clone BHK hGCGR A3*25) were BHK cells stable transfected with an expression plasmid comprising the cDNA encoding the human glucagon receptor.

The cells were grown at 5% CO2 in DMEM, 10% fetal calf serum, 1% Pen/Strep (Penicillin/Streptomycin) and 1.0 mg/ml of the selection marker G418. To make a membrane preparation the cells were grown to approximately 80% confluence. The cells were washed twice in phosphate-buffered saline and harvested. The cells were pelleted using a brief centrifugation and the cell pellet was kept on ice. Lyse the cells by adding approx. 5 ml HME buffer, mix by pipetting and snap freeze in liquid nitrogen. Thaw quickly and add HME buffer to 10 ml. The cell pellet was homogenised with an ULTRA-THURRAX dispersing instrument for 20-30 seconds. The homogenate was centrifuged at 20.000× G, 4° C. for 10 minutes. The pellet was resuspended (homogenised) in 1-2 ml HME buffer. The protein concentration was determined. The membranes were aliquoted and snapfrozen in liquid nitrogen and stored at minus 80° C.

Procedure

1. For the receptor binding assay 50 µl of the assay buffer was added to each well of an assay plate.
2. Test compounds were serially diluted to give the following concentrations: 8×10EE-7 M, 8×10EE-8 M, 8×10EE-9 M, 8×10EE-10 M, 8×10EE-11 M, 8×10EE-12 M and 8×10EE-13 M. Twenty-five µl were added to appropriate wells in the assay plate.
3. Cell membrane aliquots were thawed and diluted to their working concentration. Fifty µl were added to each well in the assay plate.
4. WGA SPA beads were suspended in assay buffer at 20 mg/ml. The suspension was diluted to 10 mg/ml in assay buffer just prior to addition to the assay plate. Fifty µl were added to each well in the assay plate.
5. The incubation was started by adding 25 µl of 480 pM solution of [125I]-glucagon to each well of the assay plate. A 25 µl aliquot was reserved for measuring total counts/well.
6. The assay plate was incubated for 2 h at 25° C.
7. The assay plate was centrifuged for 10 min at 1500 rpm.
8. The assay plate was read in a Perkin Elmer TopCount NXT instrument.

Calculations

The data from the TopCount instrument were transferred to GraphPad Prism software. The software averaged the values for the replicates and performed a non-linear regression. $IC^{50}$ values were calculated by the software and reported in nM.

Assay (III): ThT Fibrillation Assay for the Assessment of Physical Stability of Peptide Compositions The purpose of this assay is to assess the physical stability of the GLP-1 derivatives of the invention in aqueous solutions.

Low physical stability of a peptide may lead to amyloid fibril formation, which is observed as well-ordered, thread-like macromolecular structures in the sample, which eventually may lead to gel formation. This has traditionally been measured by visual inspection of the sample. However, that kind of measurement is very subjective and depending on the observer. Therefore, the application of a small molecule indicator probe is much more advantageous. Thioflavin T (ThT) is such a probe and has a distinct fluorescence signature when binding to fibrils [Naiki et al. (1989) Anal. Biochem. 177, 244-249; LeVine (1999) Methods. Enzymol. 309, 274-284].

The time course for fibril formation can be described by a sigmoidal curve with the following expression [Nielsen et al. (2001) Biochemistry 40, 6036-6046]:

$$F = f_i + m_i t + \frac{f_f + m_f t}{1 + e^{-[(t-t_0)/\tau]}} \quad \text{Eq. (1)}$$

Here, as depicted in FIG. 1, F is the ThT fluorescence at the time t. The constant t0 is the time needed to reach 50% of maximum fluorescence. The two important parameters describing fibril formation are the lag-time calculated by t0−2τ and the apparent rate constant kapp 1/τ.

Formation of a partially folded intermediate of the peptide is suggested as a general initiating mechanism for fibrillation. Few of those intermediates nucleate to form a template onto which further intermediates may assembly and the fibrillation proceeds. The lag-time corresponds to the interval in which the critical mass of nucleus is built up and the apparent rate constant is the rate with which the fibril itself is formed.

Samples were prepared freshly before each assay. Each sample composition is described in the legends. The pH of the sample was adjusted to the desired value using appropriate amounts of concentrated NaOH and HCl. Thioflavin T was added to the samples from a stock solution in $H_2O$ to a final concentration of 1 μM.

Sample aliquots of 200 μl (250 pM of the GLP-1 derivative in 10 mM HEPES buffer, pH 7.5) were placed in a 96 well microtiter plate (Packard OptiPlate™-96, white polystyrene). Usually, four or eight replica of each sample (corresponding to one test condition) were placed in one column of wells. The plate was sealed with Scotch Pad (Qiagen).

Incubation at given temperature, shaking and measurement of the ThT fluorescence emission were done in a Fluoroskan Ascent FL fluorescence platereader (Thermo Labsystems). The temperature was adjusted to 37° C. The plate was incubated with orbital shaking adjusted to 960 rpm with an amplitude of 1 mm. Fluorescence measurement was done using excitation through a 444 nm filter and measurement of emission through a 485 nm filter.

Each run was initiated by incubating the plate at the assay temperature for 10 min. The plate was measured every 20 minutes for a desired period of time. Between each measurement, the plate was shaken and heated as described.

After completion of the ThT assay the four or eight replica of each sample was pooled and centrifuged at 20000 rpm for 30 minutes at 18° C. The supernatant was filtered through a 0.22 μm filter and an aliquot was transferred to a HPLC vial.

The concentration of peptide in the initial sample and in the filtered supernatant was determined by reverse phase HPLC using an appropriate standard as reference. The percentage fraction the concentration of the filtered sample constituted of the initial sample concentration was reported as the recovery.

The measurement points were saved in Microsoft Excel format for further processing and curve drawing and fitting was performed using GraphPad Prism. The background emission from ThT in the absence of fibrils was negligible. The data points are typically a mean of four or eight samples and shown with standard deviation error bars. Only data obtained in the same experiment (i.e. samples on the same plate) are presented in the same graph ensuring a relative measure of fibrillation between experiments.

The data set may be fitted to Eq. (1). However, the lag time before fibrillation may be assessed by visual inspection of the curve identifying the time point at which ThT fluorescence increases significantly above the background level.

Assay (IV): Pharmacokinetic Profile in Mice

The purpose of this assay is to assess the pharmocokinetic profiles of the GLP-1 derivatives of the invention in mice.

The pharmacokinetic profile of GLP-1 derivatives may be tested in normal male c57/BL6 mice (approximately body weight: 30 grams), n=12 with for example 3 mice represented at each time point (for example: t=0.25, 0.5, 1, 3, 6, 10, 24, 30 and 48 hours). The test compound may be dosed as a single subcutaneous dose of 10 nmol/kg.

The plasma levels of the GLP-1 derivatives may be determined using an ELISA/LOCI assay or LCMS. Pharmacokinetic calculations such as half-life ($T_{1/2}$) maximum concentration ($C_{max}$) and time for maximum concentration ($T_{max}$) of the compounds may be determined using the PC based software, Phoenix (WinNonLin version 6.3 from Pharsight, Certara).

Assay (V): Chemical Stability Assessment

The purpose of this assay is to assess the chemical stability of the GLP-1 derivatives of the present invention in aqueous solutions.

Chemical stability of GLP-1 derivatives may be investigated by RP-UPLC separation and UV detection. Lyophilized samples are dissolved in a 8 mM Phosphate buffer pH 8.6, followed by adjustment to pH 7.3 using HCl to a final concentration of 333 μM. Samples are incubated for 14 days at 5° C. and 37° C. followed by RP-UPLC analysis. Purity is defined as the area percentage of the main peak in relation to the total area of all integrated peaks in each chromatogram. Purity loss, also referred to herein as chemical degradation, after 14 days at 37° C. is determined as the difference in purity between the samples incubated at 5° C. and 37° C., divided by the purity of the sample after incubation for 14 days at 5° C.

RP-UPLC analysis is performed using a Waters BEH130 2.1 mm×150 mm, 1.7 μm column operated at 50° C. and a flow rate of 0.4 mL/min using a mobile phase system consisting of A: 0.05% TFA in MQ-water, and B: 0.05%

TFA in Acetonitrile. UV-detection is performed at 215 nm. The typical gradient profile used for most of the samples is shown below.

TABLE 4

Typical gradient profile used for RP-UPLC analysis

| Time (min) | % B |
|---|---|
| Injection | 20 |
| 30 | 60 |
| 31 | 99 |
| 37 | 99 |
| 39 | 20 |
| 40 | 20 |
| 45 | 20 |

For some individual derivatives eluting at substantially different retention times compared with the majority of derivatives, some adjustments to the gradient profile are made to better enable purity assessment comparison across samples.

Example 44 and Table 2 present information produced using Assay (V).

Example 43: Receptor Potency, Receptor Binding and Physical Stability of GLP-1 Derivatives GLP-1 and glucagon receptor potency (EC50) and affinity (IC50) as well as physical stability were determined for selected GLP-1 derivatives of the invention according to the methods described in Assay (I), (II) and (III) herein. Assay (III) was carried out at pH 7.5. The results are shown in Table 1.

TABLE 1

EC50 and IC50 values on the human GLP-1 and glucagon receptors and physical stability of GLP-1 derivatives assessed in the ThT assay.

| Compound of Example no. | EC50 GLP-1R [pM] | IC50 GLP-1R [nM] | EC50 GlucagonR [pM] | IC50 GlucagonR [nM] | ThT assay pH 7.5: Lag time [h] | ThT assay pH 7.5: Recovery [%] |
|---|---|---|---|---|---|---|
| Example 1 | 5.7 | 0.7 | 117.0 | 16.0 | 45.0 | 100.0 |
| Example 2 | 2.0 | 0.1 | 163.0 | 43.9 | 45.0 | 100.0 |
| Example 3 | 5.0 | 0.4 | 40.7 | 3.2 | 45.0 | 94.0 |
| Example 4 | 7.0 | 0.2 | 45.0 | 4.3 | 45.0 | 100.0 |
| Example 5 | 5.2 | 0.5 | 120.3 | 4.3 | 45.0 | 101.7 |
| Example 6 | 7.0 | 0.3 | 44.0 | 4.2 | 45.0 | 100.0 |
| Example 7 | 6.0 | 0.5 | 60.0 | 3.8 | 45.0 | 106.0 |
| Example 8 | 17.0 | 0.9 | 143.0 | 8.9 | 45.0 | 100.0 |
| Example 9 | 5.0 | 0.1 | 40.0 | 4.1 | 45.0 | 100.0 |
| Example 10 | 8.0 | 1.0 | 229.0 | 25.9 | 45.0 | 100.0 |
| Example 11 |  | 0.9 |  | 69.5 | 45.0 | 106.0 |
| Example 12 | 6.0 | 0.7 | 83.0 | 20.3 | 45.0 | 100.0 |
| Example 13 |  | 0.5 |  | 56.0 | 45.0 | 100.0 |
| Example 14 |  | 3.2 |  | 31.1 | 2.7 | 43.0 |
| Example 15 |  | 1.9 |  | 80.2 | 45.0 | 50.0 |
| Example 16 |  | 13.1 |  | 51.0 | 45.0 | 50.0 |
| Example 17 |  | 19.0 |  | 43.4 | 0.0 | 89.0 |
| Example 18 | 8.0 | 2.2 | 1290.0 | 126.0 | 45.0 | 56.0 |
| Example 19 | 7.0 | 2.9 | 143.0 | 21.2 | 45.0 | 75.0 |
| Example 20 | 12.0 | 0.3 | 28.0 | 7.2 | 45.0 | 100.0 |
| Example 21 | 3.0 | 1.4 | 78.0 | 6.9 | 45.0 | 100.0 |
| Example 22 | 3.0 | 0.9 | 71.0 | 5.6 | 11.7 | 94.0 |
| Example 23 | 7.0 | 2.3 | 84.0 | 11.7 | 13.3 | 53.0 |
| Example 24 | 8.0 | 1.8 | 54.0 | 8.6 | 45.0 | 100.0 |
| Example 25 |  | 6.9 |  | 18.8 | 45.0 | 100.0 |
| Example 26 | 16.0 | 7.3 | 222.5 | 22.5 | 45.0 | 102.0 |
| Example 27 | 5.5 | 2.3 | 84.5 | 11.9 | 45.0 | 100.0 |
| Example 28 | 18.5 | 6.8 | 225.5 | 36.7 | 45.0 | 86.5 |
| Example 29 |  | 4.6 |  | 28.1 | 45.0 | 100.0 |
| Example 30 | 5.0 | 0.4 | 111.0 | 6.0 | 45.0 | 94.0 |
| Example 31 | 2.2 | 0.3 | 39.4 | 3.7 | 45.0 | 101.7 |
| Example 32 |  | 0.2 |  | 14.1 |  |  |
| Example 33 |  | 0.2 |  | 17.9 |  |  |
| Example 34 | 3.0 | 0.6 | 21.0 | 1.7 | 45.0 | 100.0 |
| Example 35 | 3.0 | 1.0 | 248.0 | 18.8 | 45.0 | 95.0 |
| Example 36 | 6.0 | 1.7 | 158.0 | 11.4 | 45.0 | 100.0 |
| Example 37 | 8.0 | 3.2 | 459.1 | 9.6 | 45.0 | 100.0 |
| Example 38 | 12.0 | 1.5 | 52.6 | 3.7 |  |  |
| Example 39 | 60.7 | 1.3 | 46.1 | 4.0 |  |  |
| Example 40 | 62.9 | 0.4 | 917.4 | 10.1 |  |  |
| Example 41 | 14.7 | 1.1 | 54.2 | 5.1 |  |  |
| Example 42 | 18.3 | 0.2 | 105.6 | 11.8 |  |  |

The results in Table 1 show GLP-1 derivatives that are GLP-1/glucagon receptor co-agonists. In addition, the results show that most GLP-1 derivatives exhibit unexpected high physical stability assessed by the lag time and/or recovery in the ThT fibrillation assay.

Example 44: Chemical Stability of GLP-1 Derivatives

Chemical stability of selected GLP-1 derivatives of the invention was determined according to the method described in Assay (V) herein. Assay (V) was carried out at pH 7.3. The results are shown in Table 2.

TABLE 2

Chemical stability of GLP-1/glucagon receptor co-agonists. Data show chemical degradation in % after incubation over 14 days at 37° C. in phosphate buffer (pH 7.3).

| Compound of Example no. | Chemical stability: Chemical degradation over 14 days at 37° C. [%] |
| --- | --- |
| Example 1 | 1.5 |
| Example 3 | −0.3 |
| Example 4 | 0.2 |
| Example 5 | 0.4 |
| Example 6 | 0.1 |
| Example 7 | 0.0 |
| Example 8 | 1.6 |
| Example 9 | 0.2 |
| Example 10 | 2.0 |
| Example 12 | 4.4 |
| Example 20 | 0.4 |
| Example 21 | 1.6 |
| Example 24 | 2.2 |
| Example 31 | 0.1 |

The results in Table 2 show that the GLP-1/glucagon receptor co-agonists unexpectedly have good to excellent chemical stability.

While certain features of the invention have been illustrated and described herein, many modifications, substitutions, changes, and equivalents will now occur to those of ordinary skill in the art. It is, therefore, to be understood that the appended claims are intended to cover all such modifications and changes as fall within the true spirit of the invention.

The invention claimed is:

1. A GLP-1 derivative comprising:
   (i) a polypeptide consisting of the amino acid sequence of SEQ ID NO:5; and
   (ii) a substituent comprising a lipophilic moiety and at least two negatively charged moieties, wherein one of the negatively charged moieties is distal of the lipophilic moiety;
   wherein the polypeptide optionally comprises a C-terminal amide;
   or a pharmaceutically acceptable salt and/or ester thereof.

2. The GLP-1 derivative according to claim 1, wherein the substituent is covalently attached to the polypeptide via an amino acid residue in the polypeptide at position.

3. The GLP-1 derivative according to claim 1, wherein the substituent comprises at least three negatively charged moieties.

4. The GLP-1 derivative according to claim 1, wherein the lipophilic moiety comprises an alkyl group of at least 12 carbon atoms.

5. The GLP-1 derivative according to claim 4, wherein the lipophilic moiety comprises an alkyl group has 12-20 carbon atoms.

6. The GLP-1 derivative according to claim 5, wherein the lipophilic moiety comprises an alkyl group has 14-18 carbon atoms.

7. The GLP-1 derivative according to claim 6, wherein the lipophilic moiety comprises an alkyl group has 16 carbon atoms.

8. The GLP-1 derivative according to claim 1, wherein the substituent is covalently attached to the side chain of an amino acid.

9. The GLP-1 derivative according to claim 8, wherein the substituent is covalently attached to the nitrogen atom of the side chain of a lysine.

10. The GLP-1 derivative according to claim 1, wherein the structure of the substituent is $Z_1-Z_2-Z_3-Z_4-Z_5-Z_6-Z_7-Z_8-Z_9-Z_{10}-$,
    wherein the lipophilic moiety is $Z_1$ and consists of:

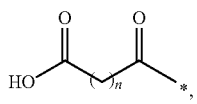

wherein n is 6-20 and the symbol * represents the attachment point to the nitrogen of a neighbouring group;
wherein $Z_2$, $Z_3$, $Z_4$, $Z_5$, $Z_6$, $Z_7$, $Z_8$, $Z_9$, and $Z_{10}$ individually are absent or are amino acids selected from the group consisting of Glu, γGlu, Gly, Ser, Ala, Thr, and Ado; and
wherein $Z_1-Z_2-Z_3-Z_4-Z_5-Z_6-Z_7-Z_8-Z_9-Z_{10}$ together comprise at least two negatively charged moieties.

11. The GLP-1 derivative according to claim 10, wherein $Z_2-Z_3-Z_4-Z_5-Z_6-Z_7-Z_8-Z_9-Z_{10}$ is selected from the group consisting of:
    γGlu-γGlu-Ado-Ado-;
    γGlu-γGlu-Ado-Ado-γGlu-;
    γGlu-γGlu-Ado-γGlu-γGlu-;
    γGlu-γGlu-Ado-γGlu-Ado-γGlu-Ado-γGlu-;
    γGlu-γGlu-Ser-Gly-;
    γGlu-γGlu-Ser-Gly-Glu-Ser-Gly-;
    γGlu-γGlu-γGlu-Ado-Ado-;
    γGlu-γGlu-γGlu-γGlu-;
    γGlu-Ado-Ado-;
    γGlu-Ado-Ado-γGlu-γGlu-; and
    Gly-Ser-Glu-Gly-Ser-γGlu-γGlu-.

12. The GLP-1 derivative according to claim 11, wherein n is 12-20.

13. The GLP-1 derivative according to claim 12, wherein n is 14-18.

14. The GLP-1 derivative according to claim 13, wherein n is 16.

15. A pharmaceutical composition comprising the GLP-1 derivative according to claim 1 and one or more pharmaceutically acceptable excipients.

16. A method for treating a disease, comprising administering the GLP-1 derivative according to claim 1 to a subject in need thereof, wherein the disease is selected from the group consisting of obesity, hyperglycaemia, type 2 diabetes, impaired glucose tolerance, and type 1 diabetes.

17. The GLP-1 derivative according to claim 1, wherein the GLP-1 derivative is $N^{\varepsilon34}$-[2-[[(2S)-2-[[(2S)-4-carboxy-2-[[2-[[(2S)-2-[[(4S)-4-carboxy-4-[[(4S)-4-carboxy-4-(17-carboxyheptadecanoylamino)butanoyl]amino]butanoyl]amino]-3-hydroxypropanoyl]amino]acetyl]amino]butanoyl]amino]-3-hydroxypropanoyl]amino]acetyl]-[Imp7,Aib8,His9,Lys18,Glu22,Arg26,Leu33,Thr35]-GLP-1-(7-35)-peptide amide (SEQ ID NO: 5)

(Chem. 3)

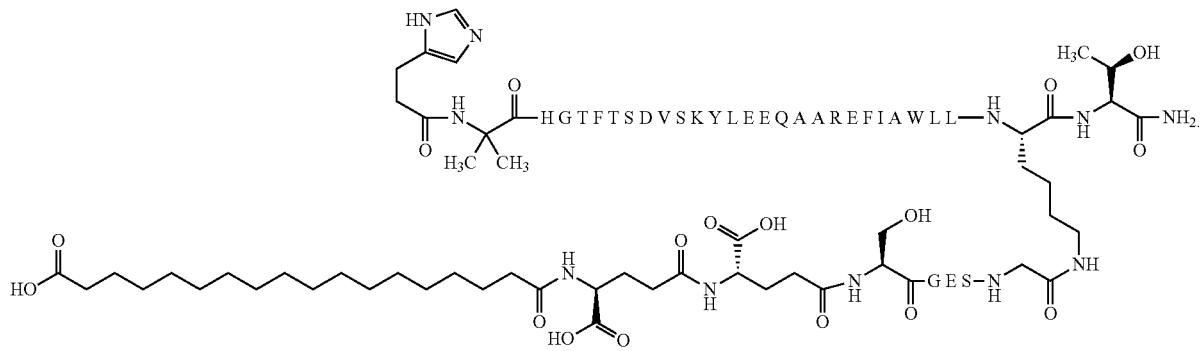

18. The GLP-1 derivative according to claim 1, wherein the GLP-1 derivative is $N^{\varepsilon 34}$-[2-[[(2S)-2-[[(4S)-4-carboxy-4-[[(4S)-4-carboxy-4-(17-carboxyheptadecanoylamino)butanoyl]amino]butanoyl]amino]-3-hydroxypropanoyl]amino]acetyl]-[Imp7,Aib8,His9,Lys18,Glu22,Arg26,Leu33,Thr35]-GLP-1-(7-35)-peptide amide (SEQ ID NO: 5)

(Chem. 4)

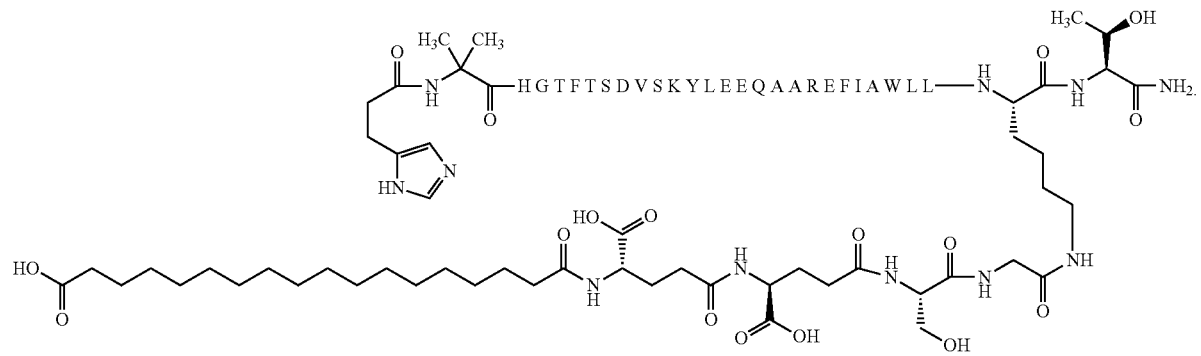

19. The GLP-1 derivative according to claim 1, wherein the GLP-1 derivative is $N^{\varepsilon 34}$-[2-[2-[2-[[2-[2-[2-[[(4S)-4-carboxy-4-[[(4S)-4-carboxy-4-(17-carboxyheptadecanoylamino)butanoyl]amino]butanoyl]amino]ethoxy]ethoxy]acetyl]amino]ethoxy]ethoxy]acetyl]-[Imp7,Aib8,His9,Lys18,Glu22,Arg26,Leu33,Thr35]-GLP-1-(7-35)-peptide amide (SEQ ID NO: 5)

(Chem. 5)

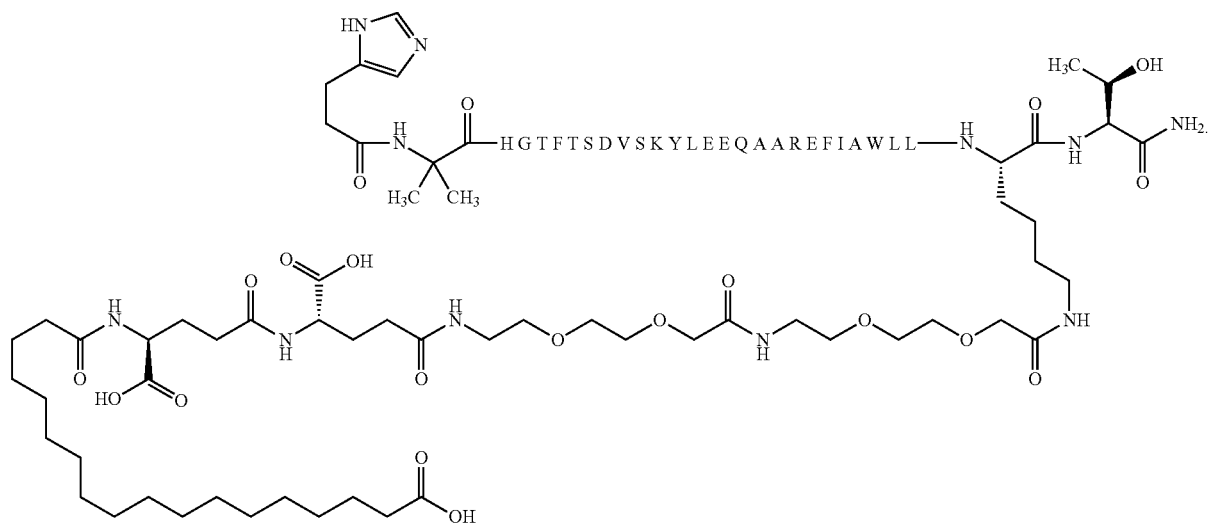

20. The GLP-1 derivative according to claim 1, wherein the GLP-1 derivative is $N^{\varepsilon 34}$-[(4S)-4-carboxy-4-[[(4S)-4-carboxy-4-[[(4S)-4-carboxy-4-[[(4S)-4-carboxy-4-(17-carboxyheptadecanoylamino)butanoyl]amino]butanoyl]amino]butanoyl]amino]butanoyl]-[Imp7,Aib8,His9,Lys18,Glu22,Arg26,Leu33,Thr35]-GLP-1-(7-35)-peptide amide (SEQ ID NO: 5)

(Chem. 6)

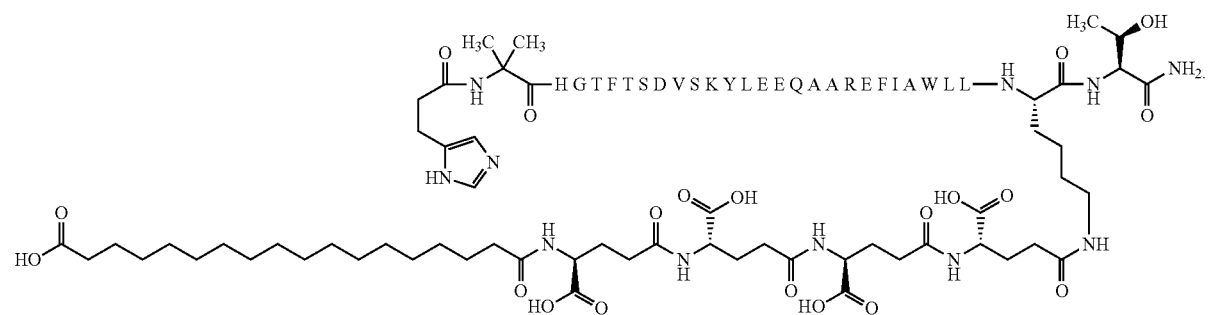

21. The GLP-1 derivative according to claim 1, wherein the GLP-1 derivative is $N^{\varepsilon 34}$-[2-[2-[2-[[2-[2-[2-[[(4S)-4-carboxy-4-(17-carboxyheptadecanoylamino)butanoyl]amino]ethoxy]ethoxy]acetyl]amino]ethoxy]ethoxy]acetyl]-[Imp7,Aib8,His9,Lys18,Glu22,Arg26,Leu33,Thr35]-GLP-1-(7-35)-peptide amide (SEQ ID NO: 5)

(Chem. 12)

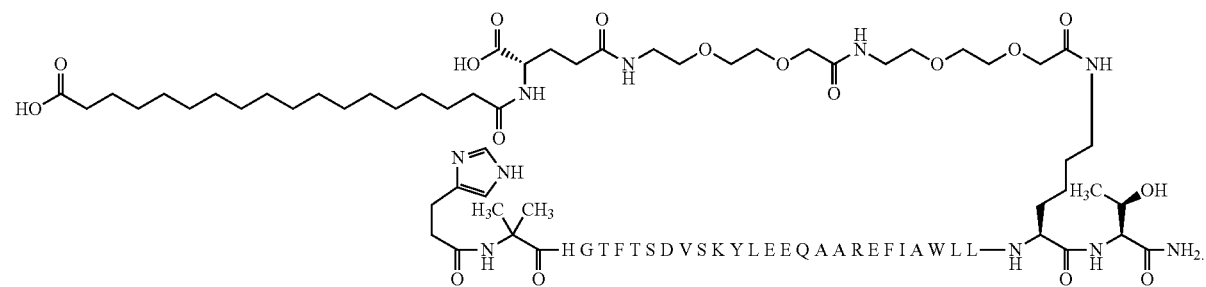

22. The GLP-1 derivative according to claim 1, wherein the GLP-1 derivative is N^ε34-[2-[[(2S)-2-[[(2S)-4-carboxy-2-[[2-[[(2S)-2-[[(4S)-4-carboxy-4-[[(4S)-4-carboxy-4-(17-carboxyheptadecanoylamino)butanoyl]amino]butanoyl]amino]-3-hydroxypropanoyl]amino]acetyl]amino]butanoyl]amino]-3-hydroxypropanoyl]amino]acetyl]-[Imp7,Aib8,His9,Lys18,Glu22,Arg26,Leu33,Thr35]-GLP-1-(7-35)-peptide (SEQ ID NO: 5)

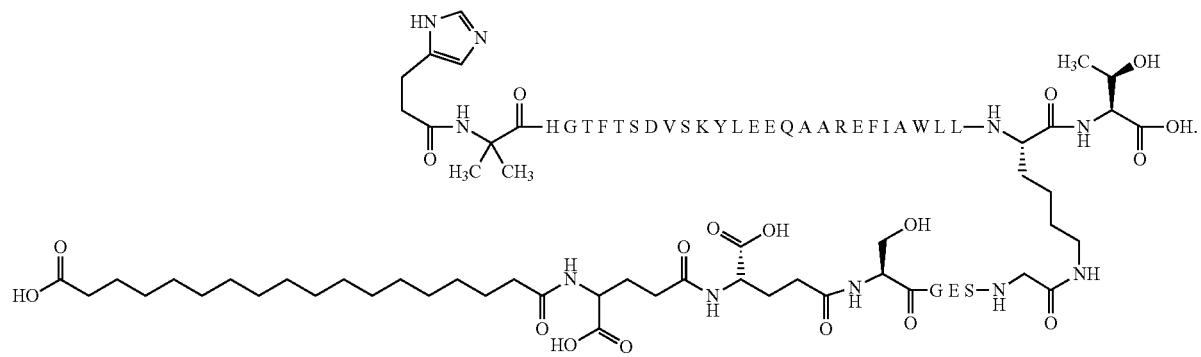

(Chem. 25)

23. The GLP-1 derivative according to claim 1, wherein the GLP-1 derivative is N^ε34-[(4S)-4-carboxy-4-[[(4S)-4-carboxy-4-[[(2S)-2-[[2-[[(2S)-4-carboxy-2-[[(2S)-2-[[2-(17-carboxyheptadecanoylamino)acetyl]amino]-3-hydroxypropanoyl]amino]butanoyl]amino]acetyl]amino]-3-hydroxypropanoyl]amino]butanoyl]amino]butanoyl]-[Imp7,Aib8,His9,Lys18,Glu22,Arg26,Leu33,Thr35]-GLP-1-(7-35)-peptide (SEQ ID NO: 5)

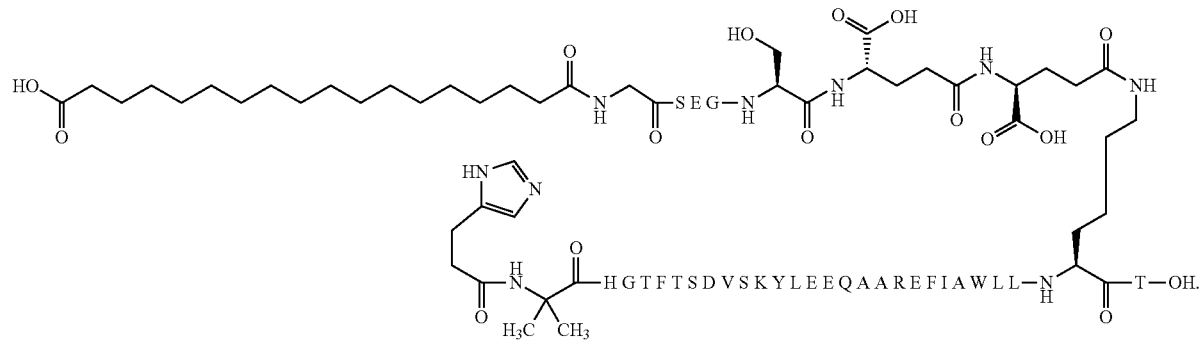

(Chem. 27)

24. The GLP-1 derivative according to claim 1, wherein the GLP-1 derivative is N^ε34-[2-[2-[2-[[2-[2-[2-[[(4S)-4-carboxy-4-[[(4S)-4-carboxy-4-[[(4S)-4-carboxy-4-(17-carboxyheptadecanoylamino)butanoyl]amino]butanoyl]amino]butanoyl]amino]ethoxy]ethoxy]acetyl]amino]ethoxy]ethoxy]acetyl]-[Imp7,Aib8,His9,Lys18,Glu22,Arg26,Leu33,Thr35]-GLP-1-(7-35)-peptide (SEQ ID NO: 5)

(Chem. 29)

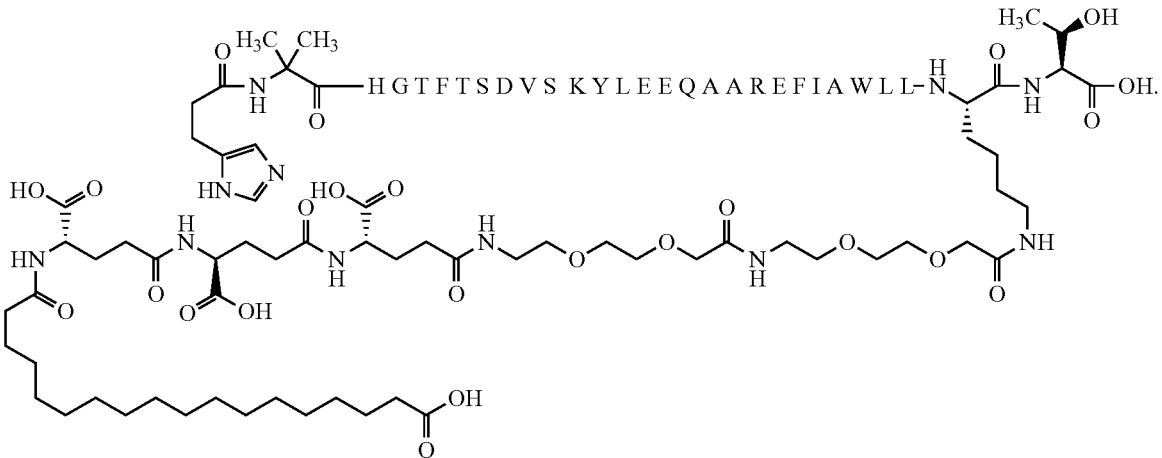

25. The GLP-1 derivative according to claim 1, wherein the GLP-1 derivative is N$^{\epsilon 34}$-[2-[[(2S)-2-[[(2S)-4-carboxy-2-[[2-[[(2S)-2-[[(4S)-4-carboxy-4-[[(4S)-4-carboxy-4-(19-carboxynonadecanoylamino)butanoyl]amino]butanoyl]amino]-3-hydroxypropanoyl]amino]acetyl]amino]butanoyl]amino]-3-hydroxypropanoyl]amino]acetyl]-[Imp7,Aib8,His9,Lys18,Glu22,Arg26,Leu33,Thr35]-GLP-1-(7-35)-peptide amide (SEQ ID NO: 5)

(Chem. 30)

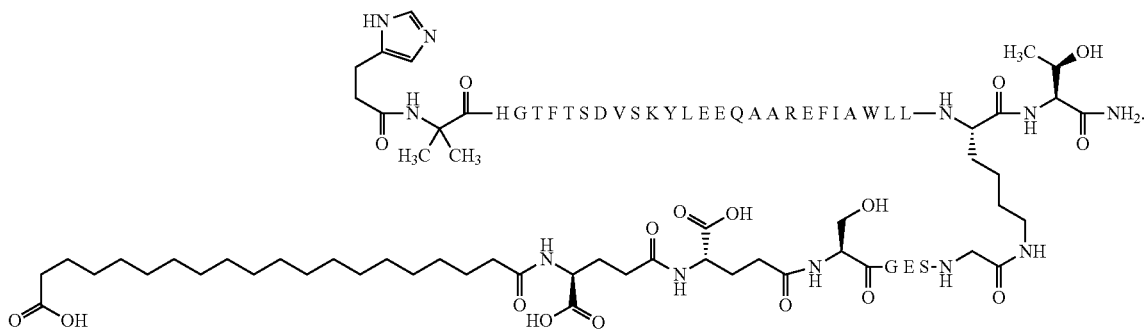

26. The GLP-1 derivative according to claim 1, wherein the GLP-1 derivative is N$^{\epsilon 34}$-[2-[2-[2-[[2-[2-[2-[[(4S)-4-carboxy-4-[[(4S)-4-carboxy-4-(13-carboxytridecanoylamino)butanoyl]amino]butanoyl]amino]ethoxy]ethoxy]acetyl]amino]ethoxy]ethoxy]acetyl]-[Imp7,Aib8,His9,Lys8,Glu22,Arg26,Leu33,Thr35]-GLP-1-(7-35)-peptide amide (SEQ ID NO: 5)

(Chem. 38)

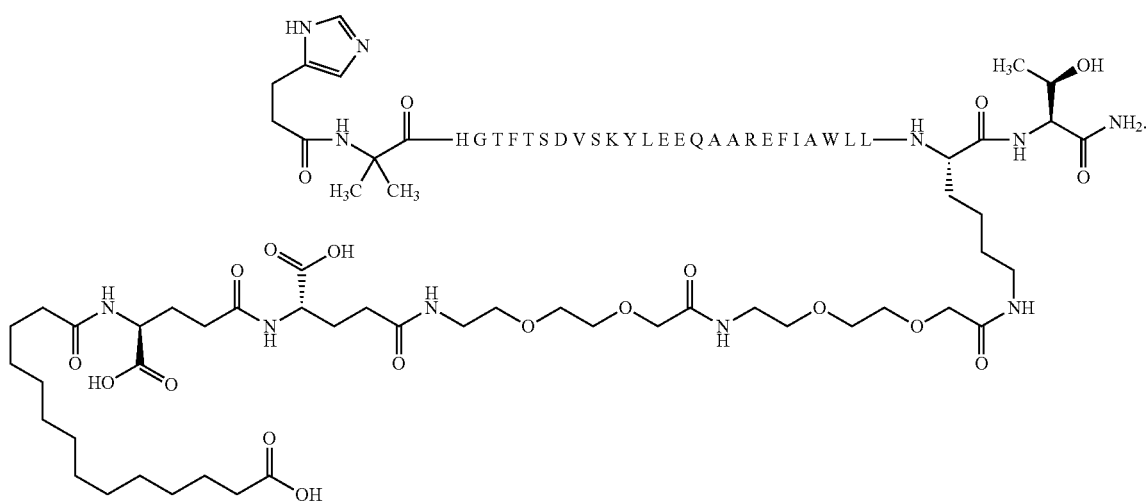

27. The GLP-1 derivative according to claim 1, wherein the GLP-1 derivative is $N^{\varepsilon 34}$-[2-[2-[2-[[2-[2-[2-[[(4S)-4-carboxy-4-[[(4S)-4-carboxy-4-(15-carboxypentadecanoylamino)butanoyl]amino]butanoyl]amino]ethoxy]ethoxy]acetyl]amino]ethoxy]ethoxy]acetyl]-[Imp7,Aib8,His9,Lys18,Glu22,Arg26,Leu33,Thr35]-GLP-1-(7-35)-peptide amide (SEQ ID NO: 5)

(Chem. 39)

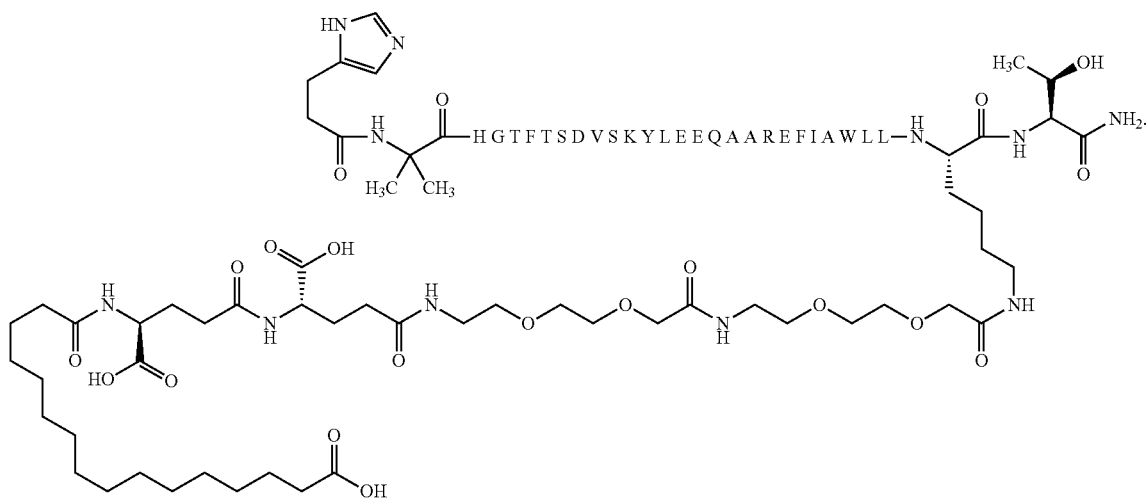

28. The GLP-1 derivative according to claim 1, wherein the GLP-1 derivative is $N^{\varepsilon 34}$-[2-[2-[2-[[2-[2-[2-[[(4S)-4-carboxy-4-[[(4S)-4-carboxy-4-(19-carboxypentadecanoylamino)butanoyl]amino]butanoyl]amino]ethoxy]ethoxy]acetyl]amino]ethoxy]thoxy]acetyl]-[Imp7,Aib8,His9,Lys18,Glu22,Arg26,Leu33,Thr35]-GLP-1-(7-35)-peptide amide (SEQ ID NO: 5)

(Chem. 40)
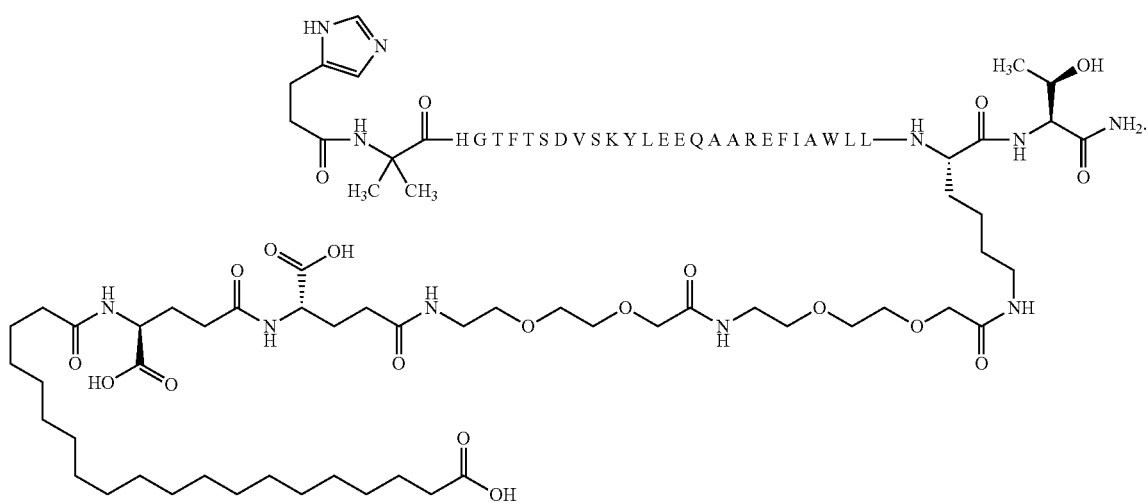
29. A GLP-1 analogue consisting of the amino acid sequence of SEQ ID NO: 5; or a pharmaceutically acceptable salt, amide or ester thereof.
* * * * *

UNITED STATES PATENT AND TRADEMARK OFFICE
CERTIFICATE OF CORRECTION

PATENT NO. : 9,988,430 B2
APPLICATION NO. : 14/879428
DATED : June 5, 2018
INVENTOR(S) : Steffen Reedtz-Runge et al.

It is certified that error appears in the above-identified patent and that said Letters Patent is hereby corrected as shown below:

In the Claims

At Column 229, Claim 2, Line 34, please make the following change:
"... in polypeptide at position 34."

At Column 239, Claim 28, Line 63, please make the following change:
"... 19-carboxynonadecanoy ..."

At Column 239, Claim 28, Line 65, please make the following change:
"... ethoxy]ethoxy] ..."

Signed and Sealed this
Twelfth Day of March, 2019

Andrei Iancu
*Director of the United States Patent and Trademark Office*

SEQUENCE LISTING

```
<160> NUMBER OF SEQ ID NOS: 45

<210> SEQ ID NO 1
<211> LENGTH: 31
<212> TYPE: PRT
<213> ORGANISM: HOMO SAPIENS

<400> SEQUENCE: 1

His Ala Glu Gly Thr Phe Thr Ser Asp Val Ser Ser Tyr Leu Glu Gly
1               5                   10                  15

Gln Ala Ala Lys Glu Phe Ile Ala Trp Leu Val Lys Gly Arg Gly
            20                  25                  30

<210> SEQ ID NO 2
<211> LENGTH: 31
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: Xaa = Imp
<220> FEATURE:
<221> NAME/KEY: MISC_FEATURE
<222> LOCATION: (2)..(2)
<223> OTHER INFORMATION: Xaa = Ala, Aib, Acb, or Gly
<220> FEATURE:
<221> NAME/KEY: MISC_FEATURE
<222> LOCATION: (10)..(10)
<223> OTHER INFORMATION: Xaa = Val, Leu, Ile, or Tyr
<220> FEATURE:
<221> NAME/KEY: MISC_FEATURE
<222> LOCATION: (12)..(12)
<223> OTHER INFORMATION: Xaa = Lys or Arg
<220> FEATURE:
<221> NAME/KEY: MISC_FEATURE
<222> LOCATION: (16)..(16)
<223> OTHER INFORMATION: Xaa = Gly, Ala, Glu, Lys, Arg, Ser, or Aib
```

```
<220> FEATURE:
<221> NAME/KEY: MISC_FEATURE
<222> LOCATION: (17)..(17)
<223> OTHER INFORMATION: Xaa = Gln, Arg, or Lys
<220> FEATURE:
<221> NAME/KEY: MISC_FEATURE
<222> LOCATION: (20)..(20)
<223> OTHER INFORMATION: Xaa = Lys or Arg
<220> FEATURE:
<221> NAME/KEY: MISC_FEATURE
<222> LOCATION: (21)..(21)
<223> OTHER INFORMATION: Xaa = Glu or Lys
<220> FEATURE:
<221> NAME/KEY: MISC_FEATURE
<222> LOCATION: (27)..(27)
<223> OTHER INFORMATION: Xaa = Val, Leu, or Ile
<220> FEATURE:
<221> NAME/KEY: MISC_FEATURE
<222> LOCATION: (28)..(28)
<223> OTHER INFORMATION: Xaa = Lys or Arg
<220> FEATURE:
<221> NAME/KEY: MISC_FEATURE
<222> LOCATION: (29)..(29)
<223> OTHER INFORMATION: Xaa = Gly, Thr, Lys, or is absent
<220> FEATURE:
<221> NAME/KEY: MISC_FEATURE
<222> LOCATION: (30)..(30)
<223> OTHER INFORMATION: Xaa = Ala, Gly, Lys, Ser, or is absent
<220> FEATURE:
<221> NAME/KEY: MISC_FEATURE
<222> LOCATION: (31)..(31)
<223> OTHER INFORMATION: Xaa = Gly or is absent

<400> SEQUENCE: 2

His Xaa His Gly Thr Phe Thr Ser Asp Xaa Ser Xaa Tyr Leu Glu Xaa
 1               5                  10                  15

Xaa Ala Ala Xaa Xaa Phe Ile Ala Trp Leu Xaa Xaa Xaa Xaa Xaa
            20                  25                  30

<210> SEQ ID NO 3
<211> LENGTH: 29
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: Xaa= Imp
<220> FEATURE:
<221> NAME/KEY: MISC_FEATURE
<222> LOCATION: (2)..(2)
<223> OTHER INFORMATION: Xaa= Acb

<400> SEQUENCE: 3

Xaa Xaa His Gly Thr Phe Thr Ser Asp Tyr Ser Lys Tyr Leu Glu Glu
 1               5                  10                  15

Gln Ala Ala Arg Glu Phe Ile Ala Trp Leu Leu Lys Lys
            20                  25

<210> SEQ ID NO 4
<211> LENGTH: 29
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: Xaa = Imp
<220> FEATURE:
<221> NAME/KEY: MISC_FEATURE
<222> LOCATION: (2)..(2)
```

-continued

<223> OTHER INFORMATION: Xaa = Acb

<400> SEQUENCE: 4

Xaa Xaa His Gly Thr Phe Thr Ser Asp Val Ser Lys Tyr Leu Glu Glu
1               5                   10                  15

Gln Ala Ala Arg Glu Phe Ile Ala Trp Leu Leu Lys Lys
            20                  25

<210> SEQ ID NO 5
<211> LENGTH: 29
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: Xaa = Imp
<220> FEATURE:
<221> NAME/KEY: MISC_FEATURE
<222> LOCATION: (2)..(2)
<223> OTHER INFORMATION: Xaa = Aib

<400> SEQUENCE: 5

Xaa Xaa His Gly Thr Phe Thr Ser Asp Val Ser Lys Tyr Leu Glu Glu
1               5                   10                  15

Gln Ala Ala Arg Glu Phe Ile Ala Trp Leu Leu Lys Thr
            20                  25

<210> SEQ ID NO 6
<211> LENGTH: 29
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: Xaa = Imp
<220> FEATURE:
<221> NAME/KEY: MISC_FEATURE
<222> LOCATION: (2)..(2)
<223> OTHER INFORMATION: Xaa = Aib

<400> SEQUENCE: 6

Xaa Xaa His Gly Thr Phe Thr Ser Asp Val Ser Lys Tyr Leu Glu Glu
1               5                   10                  15

Gln Ala Ala Lys Glu Phe Ile Ala Trp Leu Leu Lys Thr
            20                  25

<210> SEQ ID NO 7
<211> LENGTH: 29
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: Xaa = Imp
<220> FEATURE:
<221> NAME/KEY: MISC_FEATURE
<222> LOCATION: (2)..(2)
<223> OTHER INFORMATION: Xaa = Aib

<400> SEQUENCE: 7

Xaa Xaa His Gly Thr Phe Thr Ser Asp Val Ser Arg Tyr Leu Glu Glu
1               5                   10                  15

Gln Ala Ala Arg Glu Phe Ile Ala Trp Leu Leu Lys Thr
            20                  25

<210> SEQ ID NO 8
<211> LENGTH: 29
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: Xaa = Imp
<220> FEATURE:
<221> NAME/KEY: MISC_FEATURE
<222> LOCATION: (2)..(2)
<223> OTHER INFORMATION: Xaa = Aib

<400> SEQUENCE: 8

Xaa Xaa His Gly Thr Phe Thr Ser Asp Val Ser Arg Tyr Leu Glu Gly
1               5                   10                  15

Gln Ala Ala Arg Glu Phe Ile Ala Trp Leu Leu Lys Thr
            20                  25

<210> SEQ ID NO 9
<211> LENGTH: 29
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: Xaa = Imp
<220> FEATURE:
<221> NAME/KEY: MISC_FEATURE
<222> LOCATION: (2)..(2)
<223> OTHER INFORMATION: Xaa = Acb

<400> SEQUENCE: 9

Xaa Xaa His Gly Thr Phe Thr Ser Asp Val Ser Lys Tyr Leu Glu Glu
1               5                   10                  15

Gln Ala Ala Arg Glu Phe Ile Ala Trp Leu Leu Lys Thr
            20                  25

<210> SEQ ID NO 10
<211> LENGTH: 29
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: Xaa = Imp

<400> SEQUENCE: 10

Xaa Ala His Gly Thr Phe Thr Ser Asp Val Ser Lys Tyr Leu Glu Gly
1               5                   10                  15

Arg Ala Ala Arg Glu Phe Ile Ala Trp Leu Leu Lys Thr
            20                  25

<210> SEQ ID NO 11
<211> LENGTH: 31
<212> TYPE: PRT
<213> ORGANISM: Artificial Sequence
<220> FEATURE:
<223> OTHER INFORMATION: Synthetic
<220> FEATURE:

<221> NAME/KEY: MISC_FEATURE
<222> LOCATION: (1)..(1)
<223> OTHER INFORMATION: Xaa = Imp
<220> FEATURE:
<221> NAME/KEY: MISC_FEATURE
<222> LOCATION: (2)..(2)
<223> OTHER INFORMATION: Xaa = Imp

<400> SEQUENCE: 11

Xaa Xaa His Gly Thr Phe Thr Ser Asp Val Ser Lys Tyr Leu Glu Gly
1               5                   10                  15

Arg Ala Ala Arg Glu Phe Ile Ala Trp Leu Leu Lys Gly Gly Gly
            20                  25                  30

<210> SEQ ID NO 12
<211> LENGTH: 31
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: Xaa = Imp
<220> FEATURE:
<221> NAME/KEY: MISC_FEATURE
<222> LOCATION: (2)..(2)
<223> OTHER INFORMATION: Xaa = Aib

<400> SEQUENCE: 12

Xaa Xaa His Gly Thr Phe Thr Ser Asp Val Ser Lys Tyr Leu Glu Lys
1               5                   10                  15

Gln Ala Ala Arg Glu Phe Ile Ala Trp Leu Leu Lys Gly Gly Gly
            20                  25                  30

<210> SEQ ID NO 13
<211> LENGTH: 31
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: Xaa = Imp
<220> FEATURE:
<221> NAME/KEY: MISC_FEATURE
<222> LOCATION: (2)..(2)
<223> OTHER INFORMATION: Xaa = Aib

<400> SEQUENCE: 13

Xaa Xaa His Gly Thr Phe Thr Ser Asp Tyr Ser Lys Tyr Leu Glu Glu
1               5                   10                  15

Gln Ala Ala Arg Glu Phe Ile Ala Trp Leu Leu Lys Gly Lys Gly
            20                  25                  30

<210> SEQ ID NO 14
<211> LENGTH: 29
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: Xaa = Imp
<220> FEATURE:
<221> NAME/KEY: MISC_FEATURE
<222> LOCATION: (2)..(2)
<223> OTHER INFORMATION: Xaa = Aib

<400> SEQUENCE: 14

Xaa Xaa His Gly Thr Phe Thr Ser Asp Val Ser Lys Tyr Leu Glu Gly
1               5                   10                  15

Lys Ala Ala Arg Glu Phe Ile Ala Trp Leu Leu Lys Thr
            20                  25

<210> SEQ ID NO 15
<211> LENGTH: 29
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: Xaa = Imp
<220> FEATURE:
<221> NAME/KEY: MISC_FEATURE
<222> LOCATION: (2)..(2)
<223> OTHER INFORMATION: Xaa = Aib

<400> SEQUENCE: 15

Xaa Xaa His Gly Thr Phe Thr Ser Asp Tyr Ser Lys Tyr Leu Glu Gly
1               5                   10                  15

Lys Ala Ala Arg Glu Phe Ile Ala Trp Leu Leu Lys Thr
            20                  25

<210> SEQ ID NO 16
<211> LENGTH: 28
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: Xaa = Imp

<400> SEQUENCE: 16

Xaa Ala His Gly Thr Phe Thr Ser Asp Val Ser Arg Tyr Leu Glu Gly
1               5                   10                  15

Arg Ala Ala Lys Glu Phe Ile Ala Trp Leu Leu Lys
            20                  25

<210> SEQ ID NO 17
<211> LENGTH: 28
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: Xaa = Imp

<400> SEQUENCE: 17

Xaa Ala His Gly Thr Phe Thr Ser Asp Val Ser Arg Tyr Leu Glu Glu
1               5                   10                  15

Gln Ala Ala Arg Lys Phe Ile Ala Trp Leu Leu Arg
            20                  25

<210> SEQ ID NO 18
<211> LENGTH: 29
<212> TYPE: PRT
<213> ORGANISM: Artificial Sequence
<220> FEATURE:

```
<223> OTHER INFORMATION: Synthetic
<220> FEATURE:
<221> NAME/KEY: MISC_FEATURE
<222> LOCATION: (1)..(1)
<223> OTHER INFORMATION: Xaa = Imp
<220> FEATURE:
<221> NAME/KEY: MISC_FEATURE
<222> LOCATION: (2)..(2)
<223> OTHER INFORMATION: Xaa = Aib

<400> SEQUENCE: 18

Xaa Xaa His Gly Thr Phe Thr Ser Asp Val Ser Arg Tyr Leu Glu Glu
1               5                   10                  15

Gln Ala Ala Arg Lys Phe Ile Ala Trp Leu Leu Lys Arg
            20                  25

<210> SEQ ID NO 19
<211> LENGTH: 29
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: Xaa = Imp
<220> FEATURE:
<221> NAME/KEY: MISC_FEATURE
<222> LOCATION: (2)..(2)
<223> OTHER INFORMATION: Xaa = Acb

<400> SEQUENCE: 19

Xaa Xaa His Gly Thr Phe Thr Ser Asp Val Lys Tyr Leu Glu Gly
1               5                   10                  15

Arg Ala Ala Arg Glu Phe Ile Ala Trp Leu Leu Lys Thr
            20                  25

<210> SEQ ID NO 20
<211> LENGTH: 29
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: Xaa = Imp
<220> FEATURE:
<221> NAME/KEY: MISC_FEATURE
<222> LOCATION: (2)..(2)
<223> OTHER INFORMATION: Xaa = Acb

<400> SEQUENCE: 20

Xaa Xaa His Gly Thr Phe Thr Ser Asp Tyr Ser Arg Tyr Leu Glu Glu
1               5                   10                  15

Gln Ala Ala Arg Glu Phe Ile Ala Trp Leu Leu Arg Lys
            20                  25

<210> SEQ ID NO 21
<211> LENGTH: 29
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: Xaa = Imp
<220> FEATURE:
<221> NAME/KEY: MISC_FEATURE
```

```
<222> LOCATION: (2)..(2)
<223> OTHER INFORMATION: Xaa = Acb

<400> SEQUENCE: 21

Xaa Xaa His Gly Thr Phe Thr Ser Asp Tyr Ser Lys Tyr Leu Glu Arg
1               5                   10                  15

Gln Ala Ala Arg Glu Phe Ile Ala Trp Leu Leu Lys Lys
            20                  25

<210> SEQ ID NO 22
<211> LENGTH: 29
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: Xaa = Imp
<220> FEATURE:
<221> NAME/KEY: MISC_FEATURE
<222> LOCATION: (2)..(2)
<223> OTHER INFORMATION: Xaa = Acb

<400> SEQUENCE: 22

Xaa Xaa His Gly Thr Phe Thr Ser Asp Tyr Ser Lys Tyr Leu Glu Arg
1               5                   10                  15

Arg Ala Ala Arg Glu Phe Ile Ala Trp Leu Leu Lys Lys
            20                  25

<210> SEQ ID NO 23
<211> LENGTH: 29
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: Xaa = Imp
<220> FEATURE:
<221> NAME/KEY: MISC_FEATURE
<222> LOCATION: (2)..(2)
<223> OTHER INFORMATION: Xaa = Acb

<400> SEQUENCE: 23

Xaa Xaa His Gly Thr Phe Thr Ser Asp Tyr Ser Lys Tyr Leu Glu Gly
1               5                   10                  15

Arg Ala Ala Arg Glu Phe Ile Ala Trp Leu Leu Lys Lys
            20                  25

<210> SEQ ID NO 24
<211> LENGTH: 29
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: Xaa = Imp
<220> FEATURE:
<221> NAME/KEY: MISC_FEATURE
<222> LOCATION: (2)..(2)
<223> OTHER INFORMATION: Xaa = Acb

<400> SEQUENCE: 24

Xaa Xaa His Gly Thr Phe Thr Ser Asp Tyr Ser Arg Tyr Leu Glu Gly
1               5                   10                  15
```

Arg Ala Ala Arg Glu Phe Ile Ala Trp Leu Leu Arg Lys
            20                  25

<210> SEQ ID NO 25
<211> LENGTH: 31
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: Xaa = Imp
<220> FEATURE:
<221> NAME/KEY: MISC_FEATURE
<222> LOCATION: (2)..(2)
<223> OTHER INFORMATION: Xaa = Aib

<400> SEQUENCE: 25

Xaa Xaa His Gly Thr Phe Thr Ser Asp Val Ser Lys Tyr Leu Glu Ala
1               5                   10                  15
Arg Ala Ala Arg Glu Phe Ile Ala Trp Leu Leu Lys Gly Gly Gly
            20                  25                  30

<210> SEQ ID NO 26
<211> LENGTH: 29
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: Xaa = Imp
<220> FEATURE:
<221> NAME/KEY: MISC_FEATURE
<222> LOCATION: (2)..(2)
<223> OTHER INFORMATION: Xaa = Acb

<400> SEQUENCE: 26

Xaa Xaa His Gly Thr Phe Thr Ser Asp Val Ser Lys Tyr Leu Glu Lys
1               5                   10                  15
Arg Ala Ala Arg Glu Phe Ile Ala Trp Leu Leu Lys Thr
            20                  25

<210> SEQ ID NO 27
<211> LENGTH: 29
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: Xaa = Imp
<220> FEATURE:
<221> NAME/KEY: MISC_FEATURE
<222> LOCATION: (2)..(2)
<223> OTHER INFORMATION: Xaa = Acb

<400> SEQUENCE: 27

Xaa Xaa His Gly Thr Phe Thr Ser Asp Val Ser Lys Tyr Leu Glu Lys
1               5                   10                  15
Gln Ala Ala Arg Glu Phe Ile Ala Trp Leu Leu Lys Thr
            20                  25

<210> SEQ ID NO 28
<211> LENGTH: 29

```
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: Xaa = Imp
<220> FEATURE:
<221> NAME/KEY: MISC_FEATURE
<222> LOCATION: (2)..(2)
<223> OTHER INFORMATION: Xaa = Aib

<400> SEQUENCE: 28

Xaa Xaa His Gly Thr Phe Thr Ser Asp Val Ser Lys Tyr Leu Glu Ala
1               5                   10                  15
Gln Ala Ala Arg Glu Phe Ile Ala Trp Leu Leu Lys Thr
            20                  25

<210> SEQ ID NO 29
<211> LENGTH: 31
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: Xaa = Imp
<220> FEATURE:
<221> NAME/KEY: MISC_FEATURE
<222> LOCATION: (2)..(2)
<223> OTHER INFORMATION: Xaa = Aib

<400> SEQUENCE: 29

Xaa Xaa His Gly Thr Phe Thr Ser Asp Val Ser Arg Tyr Leu Glu Gly
1               5                   10                  15
Arg Ala Ala Arg Glu Phe Ile Ala Trp Leu Leu Lys Gly Ala Gly
            20                  25                  30

<210> SEQ ID NO 30
<211> LENGTH: 31
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: Xaa = Imp
<220> FEATURE:
<221> NAME/KEY: MISC_FEATURE
<222> LOCATION: (2)..(2)
<223> OTHER INFORMATION: Xaa = Aib

<400> SEQUENCE: 30

Xaa Xaa His Gly Thr Phe Thr Ser Asp Val Ser Arg Tyr Leu Glu Gly
1               5                   10                  15
Arg Ala Ala Arg Glu Phe Ile Ala Trp Leu Leu Lys Gly Ser Gly
            20                  25                  30

<210> SEQ ID NO 31
<211> LENGTH: 29
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(1)
```

<223> OTHER INFORMATION: Xaa = Imp

<400> SEQUENCE: 31

Xaa Gly His Gly Thr Phe Thr Ser Asp Val Ser Arg Tyr Leu Glu Glu
1               5                   10                  15

Gln Ala Ala Arg Glu Phe Ile Ala Trp Leu Leu Lys Thr
            20                  25

<210> SEQ ID NO 32
<211> LENGTH: 29
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: Xaa = Imp
<220> FEATURE:
<221> NAME/KEY: MISC_FEATURE
<222> LOCATION: (2)..(2)
<223> OTHER INFORMATION: Xaa = Aib

<400> SEQUENCE: 32

Xaa Xaa His Gly Thr Phe Thr Ser Asp Leu Ser Lys Tyr Leu Glu Glu
1               5                   10                  15

Gln Ala Ala Arg Glu Phe Ile Ala Trp Leu Leu Lys Thr
            20                  25

<210> SEQ ID NO 33
<211> LENGTH: 29
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: Xaa = Imp
<220> FEATURE:
<221> NAME/KEY: MISC_FEATURE
<222> LOCATION: (2)..(2)
<223> OTHER INFORMATION: Xaa = Aib

<400> SEQUENCE: 33

Xaa Xaa His Gly Thr Phe Thr Ser Asp Val Ser Lys Tyr Leu Glu Glu
1               5                   10                  15

Gln Ala Ala Arg Glu Phe Ile Ala Trp Leu Ile Leu Thr
            20                  25

<210> SEQ ID NO 34
<211> LENGTH: 31
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: Xaa = Imp

```
<400> SEQUENCE: 34

Xaa Ala Glu Gly Thr Phe Thr Ser Asp Val Ser Ser Tyr Leu Glu Glu
1               5                   10                  15

Gln Ala Ala Arg Glu Phe Ile Ala Trp Leu Val Arg Gly Arg Lys
            20                  25                  30

<210> SEQ ID NO 35
<211> LENGTH: 31
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (2)..(2)
<223> OTHER INFORMATION: Xaa = Aib

<400> SEQUENCE: 35

His Xaa Glu Gly Thr Phe Thr Ser Asp Val Ser Ser Tyr Leu Glu Gly
1               5                   10                  15

Gln Ala Ala Lys Glu Phe Ile Ala Trp Leu Val Arg Gly Arg Gly
            20                  25                  30

<210> SEQ ID NO 36
<211> LENGTH: 31
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (2)..(2)
<223> OTHER INFORMATION: Xaa = Aib
<220> FEATURE:
<221> NAME/KEY: MISC_FEATURE
<222> LOCATION: (16)..(16)
<223> OTHER INFORMATION: Xaa = Aib
<220> FEATURE:
<221> NAME/KEY: MISC_FEATURE
<222> LOCATION: (29)..(29)
<223> OTHER INFORMATION: Xaa = Aib

<400> SEQUENCE: 36

His Xaa Glu Gly Thr Phe Thr Ser Asp Val Ser Ser Tyr Leu Glu Xaa
1               5                   10                  15

Gln Ala Ala Lys Glu Phe Ile Ala Trp Leu Val Lys Xaa Arg Lys
            20                  25                  30

<210> SEQ ID NO 37
<211> LENGTH: 31
<212> TYPE: PRT
<213> ORGANISM: Artificial Sequence
<220> FEATURE:
<223> OTHER INFORMATION: Synthetic

<400> SEQUENCE: 37

His Ala Glu Gly Thr Phe Thr Ser Asp Val Ser Ser Tyr Leu Glu Gly
1               5                   10                  15

Gln Ala Ala Lys Glu Phe Ile Ala Trp Leu Val Lys Gly Arg Arg
            20                  25                  30

<210> SEQ ID NO 38
<211> LENGTH: 31
<212> TYPE: PRT
<213> ORGANISM: Artificial Sequence
<220> FEATURE:
```

```
<223> OTHER INFORMATION: Synthetic
<220> FEATURE:
<221> NAME/KEY: MISC_FEATURE
<222> LOCATION: (1)..(1)
<223> OTHER INFORMATION: Xaa = Imp

<400> SEQUENCE: 38

Xaa Ala His Gly Thr Phe Thr Ser Asp Val Ser Lys Tyr Leu Glu Gly
1               5                   10                  15

Arg Ala Ala Arg Glu Phe Ile Ala Trp Leu Leu Lys Gly Gly Gly
            20                  25                  30

<210> SEQ ID NO 39
<211> LENGTH: 31
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: Xaa = Imp
<220> FEATURE:
<221> NAME/KEY: MISC_FEATURE
<222> LOCATION: (2)..(2)
<223> OTHER INFORMATION: Xaa = Aib

<400> SEQUENCE: 39

Xaa Xaa His Gly Thr Phe Thr Ser Asp Val Ser Lys Tyr Leu Glu Lys
1               5                   10                  15

Gln Ala Ala Arg Glu Phe Ile Ala Trp Leu Leu Lys Gly Gly Gly
            20                  25                  30

<210> SEQ ID NO 40
<211> LENGTH: 28
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: Xaa = Imp

<400> SEQUENCE: 40

Xaa Ala His Gly Thr Phe Thr Ser Asp Val Ser Lys Tyr Leu Glu Gly
1               5                   10                  15

Arg Ala Ala Arg Glu Phe Ile Ala Trp Leu Leu Lys
            20                  25

<210> SEQ ID NO 41
<211> LENGTH: 28
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: Xaa = Imp
<220> FEATURE:
<221> NAME/KEY: MISC_FEATURE
<222> LOCATION: (2)..(2)
<223> OTHER INFORMATION: Xaa = Aib

<400> SEQUENCE: 41

Xaa Xaa His Gly Thr Phe Thr Ser Asp Val Ser Arg Tyr Leu Glu Glu
1               5                   10                  15
```

Gln Ala Ala Arg Lys Phe Ile Ala Trp Leu Leu Arg
            20                  25

<210> SEQ ID NO 42
<211> LENGTH: 29
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: Xaa = Imp
<220> FEATURE:
<221> NAME/KEY: MISC_FEATURE
<222> LOCATION: (2)..(2)
<223> OTHER INFORMATION: Xaa = Acb

<400> SEQUENCE: 42

Xaa Xaa His Gly Thr Phe Thr Ser Asp Tyr Ser Lys Tyr Leu Glu Gly
1               5                   10                  15

Arg Ala Ala Arg Glu Phe Ile Ala Trp Leu Leu Lys Lys
            20                  25

<210> SEQ ID NO 43
<211> LENGTH: 29
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: Xaa = Imp
<220> FEATURE:
<221> NAME/KEY: MISC_FEATURE
<222> LOCATION: (2)..(2)
<223> OTHER INFORMATION: Xaa = Aib

<400> SEQUENCE: 43

Xaa Xaa His Gly Thr Phe Thr Ser Asp Val Ser Lys Tyr Leu Glu Glu
1               5                   10                  15

Gln Ala Ala Arg Glu Phe Ile Ala Trp Leu Ile Lys Thr
            20                  25

<210> SEQ ID NO 44
<211> LENGTH: 31
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: Xaa = Imp

<400> SEQUENCE: 44

Xaa Ala His Gly Thr Phe Thr Ser Asp Val Ser Ser Tyr Leu Glu Gly
1               5                   10                  15

Gln Ala Ala Lys Glu Phe Ile Ala Trp Leu Val Lys Gly Arg Gly
            20                  25                  30

<210> SEQ ID NO 45
<211> LENGTH: 31
<212> TYPE: PRT
<213> ORGANISM: Artificial Sequence
<220> FEATURE:
<223> OTHER INFORMATION: Synthetic
<220> FEATURE:

```
<221> NAME/KEY: MISC_FEATURE
<222> LOCATION: (1)..(1)
<223> OTHER INFORMATION: Xaa = Imp
<220> FEATURE:
<221> NAME/KEY: MISC_FEATURE
<222> LOCATION: (30)..(30)
<223> OTHER INFORMATION: Xaa = Imp
<220> FEATURE:
<221> NAME/KEY: MISC_FEATURE
<222> LOCATION: (31)..(31)
<223> OTHER INFORMATION: Xaa = Imp

<400> SEQUENCE: 45

Xaa Ala His Gly Thr Phe Thr Ser Asp Val Ser Ser Tyr Leu Glu Gly
1               5                   10                  15

Gln Ala Ala Lys Glu Phe Ile Ala Trp Leu Val Lys Gly Xaa Xaa
            20                  25                  30
```